US008946426B2

(12) United States Patent
Gijsen et al.

(10) Patent No.: US 8,946,426 B2
(45) Date of Patent: Feb. 3, 2015

(54) SUBSTITUTED BICYCLIC HETEROCYCLIC COMPOUNDS AS GAMMA SECRETASE MODULATORS

(75) Inventors: Henricus Jacobus Maria Gijsen, Breda (NL); Adriana Ingrid Velter, Antwerp (BE); Gregor James MacDonald, Zoersel (BE); François Paul Bischoff, Vosselaar (BE); Tongfei Wu, Turnhout (BE); Sven Franciscus Anna Van Brandt, Nijlen (BE); Michel Surkyn, Merksplas (BE); Mirko Zaja, München (DE); Serge Maria Aloysius Pieters, Hulst (NL); Didier Jean-Claude Berthelot, Antwerp (BE); Michel Anna Jozef De Cleyn, Lille (BE); Daniel Oehlrich, Malle (BE)

(73) Assignees: Janssen Pharmaceuticals, Inc., Titusville, NJ (US); Cellzome Limited, Brentford, Middlesex (GB)

( * ) Notice: Subject to any disclaimer, the term of this patent is extended or adjusted under 35 U.S.C. 154(b) by 6 days.

(21) Appl. No.: 13/144,554

(22) PCT Filed: Feb. 2, 2010

(86) PCT No.: PCT/EP2010/051244
§ 371 (c)(1),
(2), (4) Date: Jul. 14, 2011

(87) PCT Pub. No.: WO2010/089292
PCT Pub. Date: Aug. 12, 2010

(65) Prior Publication Data
US 2011/0281881 A1 Nov. 17, 2011

(30) Foreign Application Priority Data
Feb. 6, 2009 (EP) ..................... 09152254

(51) Int. Cl.
A61K 31/437 (2006.01)
C07D 471/04 (2006.01)
C07D 487/04 (2006.01)
C07D 403/10 (2006.01)
C07D 413/10 (2006.01)

(52) U.S. Cl.
CPC ............ *C07D 487/04* (2013.01); *C07D 403/10* (2013.01); *C07D 413/10* (2013.01)
USPC .......... 546/118; 546/119; 546/121; 546/256; 546/269.4; 546/269.7; 546/271.4; 546/272.4; 546/273.4; 548/143; 548/205; 548/238; 548/255; 548/262.2; 514/300; 514/303; 514/333; 514/339; 514/340; 514/341; 514/342; 514/364; 514/365; 514/374; 514/383; 514/387

(58) Field of Classification Search
USPC .......... 546/273.4, 118, 119, 121, 256, 269.7, 546/271.4, 272.4; 514/338, 300, 303, 333, 514/339, 340, 341, 342, 364, 365, 374, 383, 514/387; 548/143, 205, 238, 255, 262.2
See application file for complete search history.

(56) References Cited

U.S. PATENT DOCUMENTS

| 5,767,144 | A | 6/1998 | Winn et al. |
| 6,114,334 | A | 9/2000 | Kerrigan et al. |
| 7,923,563 | B2 | 4/2011 | Kushida et al. |
| 2002/0128319 | A1 | 9/2002 | Koo et al. |
| 2006/0004013 | A1 | 1/2006 | Kimura et al. |
| 2008/0280948 | A1 | 11/2008 | Baumann et al. |
| 2009/0062529 | A1 | 3/2009 | Kimura et al. |
| 2010/0137320 | A1 | 6/2010 | Huang et al. |

FOREIGN PATENT DOCUMENTS

| EP | 1757591 A1 | 2/2007 |
| JP | 2003/502313 | 1/2003 |
| WO | WO 01/78721 A1 | 10/2001 |
| WO | 01/87845 A2 | 11/2001 |
| WO | WO 02/069946 | 9/2002 |
| WO | WO 2004/017963 A1 | 3/2004 |

(Continued)

OTHER PUBLICATIONS

Garofalo, Albert, "Patents targeting gamma-secretase inhibition and modulation for the treatment of Alzheimer's disease: 2004-2008", Expert Opinion Ther. Patents (2008) 18 (7): 693-703.*
Citron, M., et al. "Mutant Presenilins of Alzheimer's Disease Increase Production of 42-Residue Amyloid β- Protein in Both Transfected Cells and Transgenic Mice", Nature Medicine, vol. 3,No. 1, pp. 67-72 (1997).
Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.

(Continued)

*Primary Examiner* — David K O'Dell
(74) *Attorney, Agent, or Firm* — Baker & Hostetler LLP

(57) ABSTRACT

The present invention is concerned with substituted bicyclic heterocyclic compounds of Formula (I)

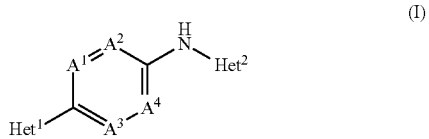

wherein $Het^1$, $Het^2$, $A^1$, $A^2$, $A^3$ and $A^4$ have the meaning defined in the claims. The compounds according to the present invention are useful as gamma secretase modulators. The invention further relates to processes for preparing such novel compounds, pharmaceutical compositions comprising said compounds as an active ingredient as well as the use of said compounds as a medicament.

9 Claims, No Drawings

(56) References Cited

FOREIGN PATENT DOCUMENTS

| WO | WO 2004/076448 | | 9/2004 |
|---|---|---|---|
| WO | 2004/110350 | A2 | 12/2004 |
| WO | WO 2004/110350 | A1 | 12/2004 |
| WO | 2005/016892 | A1 | 2/2005 |
| WO | 2005/085245 | A1 | 9/2005 |
| WO | WO 2005/115990 | A1 | 12/2005 |
| WO | 2006/135667 | A1 | 12/2006 |
| WO | WO 2007/034252 | | 3/2007 |
| WO | 2007/044895 | A2 | 4/2007 |
| WO | WO 2007/038314 | | 4/2007 |
| WO | WO 2007/043786 | | 4/2007 |
| WO | 2007/105053 | A1 | 9/2007 |
| WO | 2007/113276 | A1 | 10/2007 |
| WO | WO 2007/131991 | A1 | 11/2007 |
| WO | 2008/065199 | A1 | 6/2008 |
| WO | WO 2008/073370 | | 6/2008 |
| WO | WO 2008/082490 | | 7/2008 |
| WO | 2008/097538 | A1 | 8/2008 |
| WO | WO 2008/099210 | | 8/2008 |
| WO | WO 2008/100412 | | 8/2008 |
| WO | WO 2008/137139 | A1 | 11/2008 |
| WO | 2008/156580 | A1 | 12/2008 |
| WO | 2009/005729 | A1 | 3/2009 |
| WO | 2009/032277 | A1 | 3/2009 |
| WO | 2009/050227 | A1 | 4/2009 |
| WO | 2009/073777 | A1 | 6/2009 |
| WO | 2009/076352 | A1 | 6/2009 |
| WO | 2009/103652 | A1 | 8/2009 |
| WO | 2010/010188 | A1 | 1/2010 |
| WO | 2010/137320 | A1 | 2/2010 |
| WO | WO 2010/052199 | | 5/2010 |
| WO | WO 2010/054067 | | 5/2010 |
| WO | 2010/065310 | A1 | 6/2010 |
| WO | 2010/070008 | A1 | 6/2010 |
| WO | 2010/083141 | A1 | 7/2010 |
| WO | 2010/089292 | A1 | 8/2010 |
| WO | 2010/094647 | A1 | 8/2010 |
| WO | 2010/098495 | A1 | 9/2010 |
| WO | 2010/100606 | A1 | 9/2010 |
| WO | WO 2010/098487 | | 9/2010 |
| WO | WO 2010/098488 | | 9/2010 |
| WO | 2010/106745 | A1 | 11/2010 |
| WO | 2010/126745 | A1 | 11/2010 |
| WO | 2010/145883 | A1 | 12/2010 |
| WO | 2011/006903 | A1 | 1/2011 |
| WO | 2011/086098 | A1 | 7/2011 |
| WO | WO 2011/086099 | | 7/2011 |
| WO | 2012/126984 | A1 | 9/2012 |
| WO | 2012/131539 | A1 | 10/2012 |
| WO | 2013/010904 | A1 | 1/2013 |

OTHER PUBLICATIONS

Greene, T., et al. "Protective Groups in Organic Synthesis", John Wiley & Sons, Inc. (1999).

Larner, A., "Secretases as Therapeutic Targets in Alzheimer's Disease: Patents 2000-2004", Exp. Opinion Ther. Patents 14, p. 1403 (2004).

Marjaux, E., et al. "γ-Secretase Inhibitors: Still in the Running as Alzheimer's Therapeutics", Drug Discovery Today: Therapeutics Strategies 1, p. 1 (2004).

Moechars, D., et al., "Early Phenotypic Changes in Transgenic Mice That Overexpress Different Mutants of Amyloi Precursor Protein in Brain", Journal of Biological Chemistry, vol. 274, No. 10, pp. 6483-6492 (1999).

Morihara, T., et al. "Selective Inhibition of Aβ42 Production b NSAID R-Enantiomer", J., Neurochem. 83, p. 1009 (2002).

Oumata, N., et al. "Roscovitine-Derived, Dual-Specificity Inhibitors of Cyclin-Dependent Kinases and Casein Kinases 1", Journal Medicinal Chemistry, vol. 51, pp. 5229-5242 (2008).

Peretto, D., et al. "Synthesis and Biological Activity of Fluriprofen Analogues as Selective Inhibitors of β-Amylid 1-42 Secretion", J. Med. Chem. 48 p. 5705 (2005).

Schweisguth, F., et al. Regulation of Notch Signaling Activity, Curr. Biol. 14, p. R129 (2004).

Steiner, H., "Uncovering γ-Sucretase", Curr. Alzheimer Research 1(3), p. 175 (2004).

Tanzi, R., et al. "Twenty Years of the Alzheimer's Disease Amyloid Hypothesis: A Genetic Perspective", Cell, vol. 120, (2005), p. 545-555.

Weggen, S., et al. "A Subset of NSAIDs Lower Amylidogenic Aβ42 Independently of Cyclooxygenase Activity", Nature 414, p. 212 (2001).

Jadhav, G., et al. "Amonium Metavanadate: A Novel Catalyst for Synthesis of 2-Substituted Benzimidazole Derivatives", Chinese Chemical Letters, vol. 20 (2009) pp. 292-295.

Matthews, D., et al. 'A Convenient Procedure for the Preparation of 4(5)-Cyanoimidazoles, Journal of Organic Chemistry, vol. 51 (1986), pp. 3228-3231.

Dyatkin A. et al. "Determination of the Absolute configuration of a Key Tricyclic Component of a Novel Vasopressin Receptor Antagonist by Use of Vibrational Circular Dichroism", Chirality, vol. 14, No. 215, pp. 215-219 (2002).

Sechi, M. et al. "Design and Synthesis of Novel Indole β—Diketo Acid Derivatives as HIV-1 Integrase Inhibitors" J. Medicinal Chemistry, 2004, vol. 47, pp. 5298-5310.

West, Anthony R., Solid State Chemistry and its Applications, Wiley, New York, 1988, pp. 358-365.

Zettl et al. "Exploring the Chemical Space of Gamma-Secretase Modulators" Trends in Pharmacological Sciences, vol. 31, No. 9, pp. 402-410, 2010.

"Crystallization", Kirk-Othmer Encyclopedia of Chemical Technology, 2002, 8, 95-147.

Dörwald, "Side Reactions in Organic Synthesis", Wiley: VCH Weinheim, 2005, Preface, Chapter 8, 45 pages.

Guillory (Brittain, Ed.), "Polymorphism in Pharmaceutical Solids", Marcel Dekker. Inc., NY, 1999, 50 pages.

Jain et al., "Polymorphism in Pharmacy", Indian Drugs 1986, 23(6), 315-329.

Vippagunta et al., "Crystalline Solids", Advanced Drug Delivery Reviews, 2001, 48, 3-26.

Wang et al., "Preparation of a-Chloroketones by the Chloracetate Claisen Reaction", Synlett, 2000, 6, 902-904.

Yu et al., "Physical Characterization of Polymorphic Drugs: An Integrated Characterization Strategy", PSTT, 1998, 1(3), 118-127.

* cited by examiner

US 8,946,426 B2

SUBSTITUTED BICYCLIC HETEROCYCLIC COMPOUNDS AS GAMMA SECRETASE MODULATORS

CROSS REFERENCE TO RELATED APPLICATIONS

This application is a national stage application of Patent Application No. PCT/EP2010/051244, filed Feb. 2, 2010, which in turn claims the benefit of EPO Patent Application No. 09152254.0 filed Feb. 6, 2009. The complete disclosures of the aforementioned related patent applications are hereby incorporated herein by reference for all purposes.

FIELD OF THE INVENTION

The present invention is concerned with novel substituted bicyclic heterocyclic compounds useful as gamma secretase modulators. The invention further relates to processes for preparing such novel compounds, pharmaceutical compositions comprising said compounds as an active ingredient as well as the use of said compounds as a medicament.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history and (3) head trauma; other factors include environmental toxins and low levels of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleavage at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single protein, but is in fact associated with an assembly of different proteins.

The gamma (γ)-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until now, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Larner, 2004. Secretases as therapeutics targets in Alzheimer's disease: patents 2000-2004. Expert Opin. Ther. Patents 14, 1403-1420).

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of COX enzymes, which can lead to unwanted side effects, and their low CNS penetration (Peretto et al., 2005, J. Med. Chem. 48, 5705-5720).

WO-2008/137139 relates to heterocyclic derivatives and their use as gamma secretase modulators.

WO-2005/115990 discloses cinnamide compounds that are useful for the treatment of neurodegenerative diseases caused by amyloid β proteins such as Alzheimer's disease, senile dementia, Down's syndrome and amyloidosis.

WO-2004/110350 relates to aryl compounds and their use in modulating amyloid β.

WO-2007/131991 discloses imidazopyrazine compounds as MAPKAPK5 inhibitors useful for the treatment of degenerative and inflammatory diseases.

WO-2004/017963 relates to benzimidazoles as coagulation factor Xa inhibitors for the treatment of thromboembolic illnesses.

There is a strong need for novel compounds which modulate γ-secretase activity thereby opening new avenues for the treatment of Alzheimer's disease. It is an object of the present invention to overcome or ameliorate at least one of the disadvantages of the prior art, or to provide a useful alternative. It is accordingly an object of the present invention to provide such novel compounds.

SUMMARY OF THE INVENTION

It has been found that the compounds of the present invention are useful as gamma secretase modulators. The compounds according to the invention and the pharmaceutically acceptable compositions thereof, may be useful in the treatment or prevention of Alzheimer's disease.

The present invention concerns novel compounds of Formula (I):

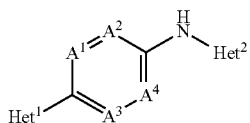
(I)

and stereoisomeric forms thereof, wherein
Het$^1$ is a 5-membered or 6-membered aromatic heterocycle, having formula (a-1), (a-2), (a-3), (a-4) or (a-5):

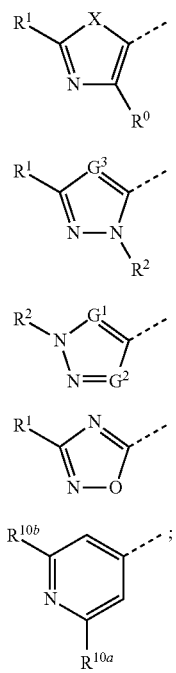

R$^0$ is H or C$_{1-4}$alkyl;
R$^1$ is H, C$_{1-4}$alkyl or C$_{1-4}$alkyloxyC$_{1-4}$alkyl;
R$^2$ is C$_{1-4}$alkyl;
X is O or S;
G$^1$ is CH or N;
G$^2$ is CH, N or C substituted with C$_{1-4}$alkyl;

provided that G$^1$ and G$^2$ are not simultaneously N;
G$^3$ is CH or N;
R$^{10a}$ and R$^{10b}$ each independently are hydrogen or C$_{1-4}$alkyl;
A$^1$ is CR$^3$ or N; wherein R$^3$ is H, halo or C$_{1-4}$alkyloxy;
A$^2$, A$^3$ and A$^4$ each independently are CH, CF or N; provided that maximum two of A$^1$, A$^2$, A$^3$ and A$^4$ are N;
Het$^2$ is a 9-membered bicyclic aromatic heterocycle, having formula (b-1) or (b-2):

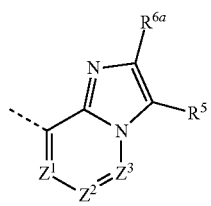
(b-1)

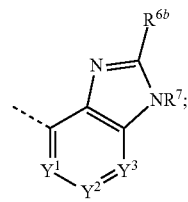
(b-2)

Z$^1$ is CH or N;
Z$^2$ is CR$^{4a}$ or N;
Z$^3$ is CH or N; provided that maximum one of Z$^1$, Z$^2$ and Z$^3$ is N;
Y$^1$ is CH or N;
Y$^2$ is CR$^{4b}$ or N;
Y$^3$ is CH or N; provided that maximum one of Y$^1$, Y$^2$ and Y$^3$ is N;
R$^{4a}$ is H; halo; C$_{1-4}$alkyloxy; cyano; cycloC$_{3-7}$alkyl; C$_{1-4}$alkylcarbonyl;
C$_{1-4}$alkyloxycarbonyl; or C$_{1-4}$alkyl optionally substituted with one or more substituents each independently selected from the group consisting of halo and amino;
R$^{4b}$ is H; H halo; C$_{1-4}$alkyloxy; cyano; cycloC$_{3-7}$alkyl; or C$_{1-4}$alkyl optionally substituted with one or more substituents each independently selected from the group consisting of halo and amino;
R$^5$ is H; halo; cyano; C$_{1-4}$alkyloxy; C$_{2-6}$alkenyl; or C$_{1-6}$alkyl optionally substituted with one or more substituents each independently selected from the group consisting of C$_{1-4}$alkyloxy and halo;
R$^{6a}$ is C$_{2-6}$alkyl substituted with one or more halo substituents; C$_{1-6}$alkyl optionally substituted with one or more substituents each independently selected from the group consisting of piperidinyl, Ar, C$_{1-6}$alkyloxy, tetrahydropyranyl, cycloC$_{3-7}$alkyloxy, and cycloC$_{3-7}$alkyl; cycloC$_{3-7}$alkyl; C$_{1-4}$alkylcarbonyl; tetrahydropyranyl; Ar; R$^8$R$^9$N-carbonyl; or CH$_2$—O—Ar;
R$^{6b}$ is C$_{2-6}$alkyl substituted with one or more halo substituents; C$_{1-6}$alkyl optionally substituted with one or more substituents each independently selected from the group consisting of piperidinyl, Ar, C$_{1-6}$alkyloxy, tetrahydropyranyl, cycloC$_{3-7}$alkyloxy, and cycloC$_{3-7}$alkyl; cycloC$_{3-7}$alkyl; cycloC$_{3-7}$alkyl substituted with one or more phenyl substituents optionally substituted with one or more halo substituents; piperidinyl; morpholinyl; pyrrolidinyl; NR$^8$R$^9$; tetrahydropyranyl; O—Ar; C$_{1-6}$alkyloxy; C$_{1-6}$alkylthio; Ar; CH$_2$—O—Ar; S—Ar; NCH$_3$—Ar; or NH—Ar;

wherein each piperidinyl, morpholinyl, and pyrrolidinyl may optionally be substituted with one or more substituents each independently selected from the group consisting of $C_{1-4}$alkyl, $C_{2-6}$alkenyl, $C_{1-4}$alkylcarbonyl, halo, and $C_{1-4}$alkyloxycarbonyl;

wherein each Ar independently is phenyl optionally substituted with one or more substituents each independently selected from the group consisting of halo, $C_{1-4}$alkyloxy, cyano, $NR^8R^9$, morpholinyl, $C_{1-4}$alkyl, and $C_{1-4}$alkyl substituted with one or more halo substituents; pyridinyl optionally substituted with one or more substituents each independently selected from the group consisting of halo, $C_{1-4}$alkyloxy, cyano, $C_{1-4}$alkyl, and $C_{1-4}$alkyl substituted with one or more halo substituents; oxazolyl optionally substituted with one or more $C_{1-4}$alkyl substituents; or thienyl optionally substituted with one or more halo substituents;

each $R^8$ independently is H or $C_{1-4}$alkyl;
each $R^9$ independently is H or $C_{1-4}$alkyl;
$R^7$ is H, $C_{1-6}$alkyl optionally substituted with one or more substituents each independently selected from the group consisting of halo, phenyl, and $C_{1-4}$alkyloxy; and the pharmaceutically acceptable addition salts, and the solvates thereof.

The present invention also concerns methods for the preparation of compounds of Formula (I) and pharmaceutical compositions comprising them.

The present compounds surprisingly were found to modulate the γ-secretase activity in vitro and in vivo, and are therefore useful in the treatment or prevention of Alzheimer's disease (AD), traumatic brain injury, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably Alzheimer's disease and other disorders with Beta-amyloid pathology (eg glaucoma).

In view of the aforementioned pharmacology of the compounds of Formula (I), it follows that they are suitable for use as a medicament.

More especially the compounds are suitable in the treatment or prevention of Alzheimer's disease, cerebral amyloid angiopathy, multi-infarct dementia, dementia pugilistica or Down syndrome.

The present invention also concerns to the use of a compound according to the general Formula (I), the stereoisomeric forms thereof and the pharmaceutically acceptable acid or base addition salts and the solvates thereof, for the manufacture of a medicament for the modulation of γ-secretase activity.

Use of a compound of Formula (I) for the modulation of γ-secretase activity resulting in a decrease in the relative amount of Aβ42-peptides produced are preferred.

One advantage of the compounds or a part of the compounds of the present invention may lie in their enhanced CNS-penetration.

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION

When describing the compounds of the invention, the terms used are to be construed in accordance with the following definitions, unless a context dictates otherwise.

When indicating the number of substituents, the term "one or more" means from one substituent to the highest possible number of substitution, i.e. replacement of one hydrogen up to replacement of all hydrogens by substituents each individually selected from the indicated groups, provided that the normal valency is not exceeded, and that the substitution results in a chemically stable compound, i.e. a compound that is sufficiently robust to survive isolation to a useful degree of purity from a reaction mixture, and formulation into a therapeutic agent. Thereby, one, two, three or four substituents are preferred. In particular one, two or three substituents are preferred. More in particular one substituent is preferred.

The term "halo", "Halo" or "halogen" as a group or part of a group is generic for fluoro, chloro, bromo, iodo unless otherwise is indicated.

The term "$C_{1-6}$alkyl" as a group or part of a group refers to a hydrocarbyl radical of Formula $C_nH_{2n+1}$ wherein n is a number ranging from 1 to 6. $C_{1-6}$alkyl groups comprise from 1 to 6 carbon atoms, in particular from 1 to 4 carbon atoms, more in particular from 1 to 3 carbon atoms, still more in particular 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes such as for example methyl, ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{2-6}$alkyl" as a group or part of a group refers to a hydrocarbyl radical of Formula $C_nH_{2n+1}$ wherein n is a number ranging from 2 to 6. $C_{2-6}$alkyl groups comprise from 2 to 6 carbon atoms, in particular from 2 to 4 carbon atoms, more in particular from 2 to 3 carbon atoms. Alkyl groups may be linear or branched and may be substituted as indicated herein. When a subscript is used herein following a carbon atom, the subscript refers to the number of carbon atoms that the named group may contain. Thus, for example, $C_{2-6}$alkyl includes all linear, or branched alkyl groups with between 2 and 6 carbon atoms, and thus includes such as for example ethyl, n-propyl, i-propyl, 2-methyl-ethyl, butyl and its isomers (e.g. n-butyl, isobutyl and tert-butyl), pentyl and its isomers, hexyl and its isomers, and the like.

The term "$C_{1-4}$alkyl" as a group or part of a group refers to a hydrocarbyl radical of Formula $C_nH_{2n+1}$ wherein n is a number ranging from 1 to 4. $C_{1-4}$alkyl groups comprise from 1 to 4 carbon atoms, in particular from 1 to 3 carbon atoms, more in particular 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl includes all linear, or branched alkyl groups with between 1 and 4 carbon atoms, and thus includes such as for example methyl, ethyl, n-propyl, i-propyl, 2-methyl-ethyl, butyl and its isomers (e.g. n-butyl, isobutyl and tert-butyl), and the like.

The term "$C_{1-6}$alkyloxy" as a group or part of a group refers to a radical having the Formula $OR^b$ wherein $R^b$ is $C_{1-6}$alkyl. Non-limiting examples of suitable $C_{1-6}$alkyloxy include methyloxy, ethyloxy, propyloxy, isopropyloxy, butyloxy, isobutyloxy, sec-butyloxy, tert-butyloxy, pentyloxy, and hexyloxy.

The term "$C_{1-4}$alkyloxy" as a group or part of a group refers to a radical having the Formula $OR^c$ wherein $R^c$ is $C_{1-4}$alkyl. Non-limiting examples of suitable $C_{1-4}$alkyloxy include methyloxy, ethyloxy, propyloxy, isopropyloxy, butyloxy, isobutyloxy, sec-butyloxy and tert-butyloxy.

In the framework of this application, $C_{2-6}$alkenyl is a straight or branched hydrocarbon radical having from 2 to 6 carbon atoms containing a double bond such as ethenyl, propenyl, butenyl, pentenyl, 1-propen-2-yl, hexenyl and the like.

The term "cyclo$C_{3-7}$alkyl" alone or in combination, refers to a cyclic saturated hydrocarbon radical having from 3 to 7 carbon atoms. Non-limiting examples of suitable cyclo$C_{3-7}$alkyl include cyclopropyl, cyclobutyl, cyclopentyl, cyclohexyl and cycloheptyl.

The term "cyclo$C_{3-7}$alkyloxy" alone or in combination, refers to a radical having the Formula $OR^d$, wherein $R^d$ is cyclo$C_{3-7}$alkyl. Non-limiting examples of suitable cyclo$C_{3-7}$alkyloxy include cyclopropyloxy, cyclobutyloxy, cyclopentyloxy, cyclohexyloxy and cycloheptyloxy.

The chemical names of the compounds of the present invention were generated according to the nomenclature rules agreed upon by the Chemical Abstracts Service.

In case of tautomeric forms, it should be clear that the other non-depicted tautomeric form is also included within the scope of the present invention.

When any variable occurs more than one time in any constituent, each definition is independent.

It will be appreciated that some of the compounds of Formula (I) and their pharmaceutically acceptable addition salts and stereoisomeric forms may contain one or more centers of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

When a specific regioisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s).

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the hydrates and solvent addition forms which the compounds of formula (I) are able to form, as well as the salts thereof. Examples of such forms are e.g. hydrates, alcoholates and the like.

The compounds of Formula (I) as prepared in the processes described below may be synthesized in the form of racemic mixtures of enantiomers that can be separated from one another following art-known resolution procedures. A manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound would be synthesized by stereospecific methods of preparation. These methods will advantageously employ enantiomerically pure starting materials.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element. For example, when hydrogen is mentioned, it is understood to refer to $^1H$, $^2H$, $^3H$ and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (I), or a pharmaceutically acceptable salt thereof, which contains at least one radioactive atom. For example, a compound can be labelled with positron or with gamma emitting radioactive isotopes. For radioligand-binding techniques, the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. In particular, the radioactive isotope is selected from the group of $^{3}$H, $^{11}$C, $^{18}$F, $^{122}$I, $^{123}$I, $^{125}$I, $^{131}$I, $^{75}$Br, $^{76}$Br, $^{77}$Br and $^{82}$Br.

As used in the specification and the appended claims, the singular forms "a", "an," and "the" also include plural referents unless the context clearly dictates otherwise. By way of example, "a compound" means one compound or more than one compound.

The terms described above and others used in the specification are well understood to those in the art.

Preferred features of the compounds of this invention are now set forth.

The present invention concerns novel compounds of Formula (I):

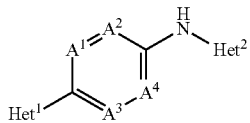

and stereoisomeric forms thereof, wherein
Het$^1$ is a 5-membered or 6-membered aromatic heterocycle, having formula (a-1), (a-2), (a-3), (a-4) or (a-5):

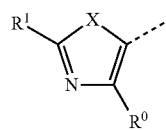

(a-1)

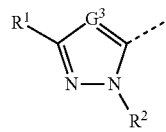

(a-2)

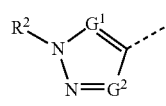

(a-3)

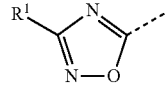

(a-4)

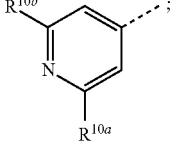

(a-5)

$R^0$ is H or $C_{1-4}$alkyl;
$R^1$ is H, $C_{1-4}$alkyl or $C_{1-4}$alkyloxy$C_{1-4}$alkyl;
$R^2$ is $C_{1-4}$alkyl;
X is O or S;
$G^1$ is CH or N;
$G^2$ is CH, N or C substituted with $C_{1-4}$alkyl;
provided that $G^1$ and $G^2$ are not simultaneously N;
$G^3$ is CH or N;
$R^{10a}$ and $R^{10b}$ each independently are hydrogen or $C_{1-4}$alkyl;
$A^1$ is CR$^3$ or N; wherein R$^3$ is H, halo or $C_{1-4}$alkyloxy;
$A^2$, $A^3$ and $A^4$ each independently are CH, CF or N; provided that maximum two of $A^1$, $A^2$, $A^3$ and $A^4$ are N;
Het$^2$ is a 9-membered bicyclic aromatic heterocycle, having formula (b-1) or (b-2):

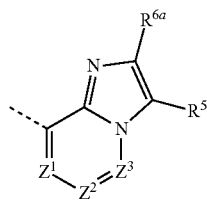

(b-1)

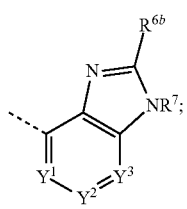

(b-2)

$Z^1$ is CH or N;
$Z^2$ is CR$^{4a}$ or N;
$Z^3$ is CH or N; provided that maximum one of $Z^1$, $Z^2$ and $Z^3$ is N;
$Y^1$ is CH or N;
$Y^2$ is CR$^{4b}$ or N;
$Y^3$ is CH or N; provided that maximum one of $Y^1$, $Y^2$ and $Y^3$ is N;
$R^{4a}$ is H; halo; $C_{1-4}$alkyloxy; cyano; cycloC$_{3-7}$alkyl; $C_{1-4}$alkylcarbonyl; $C_{1-4}$alkyloxycarbonyl; or $C_{1-4}$alkyl optionally substituted with one or more substituents each independently selected from the group consisting of halo and amino;
$R^{4b}$ is H; H halo; $C_{1-4}$alkyloxy; cyano; cycloC$_{3-7}$alkyl; or $C_{1-4}$alkyl optionally substituted with one or more substituents each independently selected from the group consisting of halo and amino;
$R^5$ is H; halo; cyano; $C_{1-4}$alkyloxy; $C_{2-6}$alkenyl; or $C_{1-6}$alkyl optionally substituted with one or more substituents each independently selected from the group consisting of $C_{1-4}$alkyloxy and halo;
$R^{6a}$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl, cycloC$_{3-7}$alkyloxy, and cycloC$_{3-7}$alkyl; cycloC$_{3-7}$alkyl; $C_{1-4}$alkylcarbonyl; tetrahydropyranyl; Ar; R$^8$R$^9$N-carbonyl; or CH$_2$—O—Ar;
$R^{6b}$ is $C_{2-6}$alkyl substituted with one or more halo substituents; $C_{1-6}$alkyl optionally substituted with one or more substituents each independently selected from the group consisting of piperidinyl, Ar, $C_{1-6}$alkyloxy, tetrahydropyranyl, cycloC$_{3-7}$alkyloxy, and cycloC$_{3-7}$alkyl; cycloC$_{3-7}$ alkyl; cycloC$_{3-7}$alkyl substituted with one or more phenyl substituents optionally substituted with one or more halo substituents; piperidinyl; morpholinyl; pyrrolidinyl; NR$^8$R$^9$; tetrahydropyranyl; O—Ar; C$_{1-6}$alkyloxy; C$_{1-6}$alkylthio; Ar; CH$_2$—O—Ar; S—Ar; NCH$_3$—Ar; or NH—Ar;

wherein each piperidinyl, morpholinyl, and pyrrolidinyl may optionally be substituted with one or more substituents each independently selected from the group consisting of C$_{1-4}$alkyl, C$_{2-6}$alkenyl, C$_{1-4}$alkylcarbonyl, halo, and C$_{1-4}$alkyloxycarbonyl;

wherein each Ar independently is phenyl optionally substituted with one or more substituents each independently selected from the group consisting of halo, C$_{1-4}$alkyloxy, cyano, NR$^8$R$^9$, morpholinyl, C$_{1-4}$alkyl, and C$_{1-4}$alkyl substituted with one or more halo substituents; pyridinyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents; oxazolyl optionally substituted with one or more C$_{1-4}$alkyl substituents; or thienyl optionally substituted with one or more halo substituents;

each R$^8$ independently is H or C$_{1-4}$alkyl;
each R$^9$ independently is H or C$_{1-4}$alkyl;
R$^7$ is H, C$_{1-6}$alkyl optionally substituted with one or more substituents each independently selected from the group consisting of halo, phenyl, and C$_{1-4}$alkyloxy;
and the pharmaceutically acceptable addition salts, and the solvates thereof.

In an embodiment, the invention relates to compounds of Formula (I) and stereoisomeric forms thereof, or any subgroup thereof as mentioned in any of the other embodiments, wherein one or more, preferably all, of the following restrictions apply:

(a) A$^2$, A$^3$ and A$^4$ each independently are CH or N; provided that maximum two of A$^1$, A$^2$, A$^3$ and A$^4$ are N;
(b) Z$^2$ is CR$^{4a}$;
(c) R$^{4a}$ is H; halo; cyano; cycloC$_{3-7}$alkyl; C$_{1-4}$alkylcarbonyl; C$_{1-4}$alkyloxycarbonyl; or C$_{1-4}$alkyl optionally substituted with one or more substituents each independently selected from the group consisting of halo and amino;
(d) R$^5$ is H; halo; C$_{1-4}$alkyloxy; C$_{2-6}$alkenyl; or C$_{1-6}$alkyl optionally substituted with one or more C$_{1-4}$alkyloxy substituents;
(e) R$^{6a}$ is C$_{1-6}$alkyl optionally substituted with one or more substituents each independently selected from the group consisting of Ar, C$_{1-6}$alkyloxy, and tetrahydropyranyl; cycloC$_{3-7}$alkyl; C$_{1-4}$alkylcarbonyl; tetrahydropyranyl; Ar; or R$^8$R$^9$N-carbonyl;
(f) R$^{6b}$ is C$_{2-6}$alkyl substituted with one or more halo substituents; C$_{1-6}$alkyl optionally substituted with one or more substituents each independently selected from the group consisting of Ar, C$_{1-6}$alkyloxy, tetrahydropyranyl, and cycloC$_{3-7}$alkyl; cycloC$_{3-7}$alkyl; cycloC$_{3-7}$alkyl substituted with one phenyl substituent optionally substituted with one or more halo substituents; unsubstituted pyrrolidinyl; NR$^8$R$^9$; tetrahydropyranyl; Ar; or CH$_2$—O—Ar;
(g) each Ar independently is phenyl optionally substituted with one or more substituents each independently selected from the group consisting of halo, C$_{1-4}$alkyloxy, C$_{1-4}$alkyl, and C$_{1-4}$alkyl substituted with one or more halo substituents; oxazolyl optionally substituted with one or more C$_{1-4}$alkyl substituents; or thienyl optionally substituted with one or more halo substituents;
(h) each R$^8$ independently is C$_{1-4}$alkyl;
(i) each R$^9$ independently is C$_{1-4}$alkyl;
(j) R$^7$ is C$_{1-6}$alkyl optionally substituted with one or more C$_{1-4}$alkyloxy substituents;
and the pharmaceutically acceptable addition salts, and the solvates thereof.

In an embodiment, the invention relates to compounds of Formula (I) and stereoisomeric forms thereof, or any subgroup thereof as mentioned in any of the other embodiments, wherein one or more, preferably all, of the following restrictions apply:

(a) R$^0$ is H or methyl;
(b) R$^1$ is H, methyl, isopropyl or methoxymethyl;
(c) R$^2$ is methyl;
(d) G$^2$ is CH, N or C substituted with methyl; provided that G$^1$ and G$^2$ are not simultaneously N;
(e) R$^{10a}$ and R$^{10b}$ each independently are hydrogen or methyl;
(f) A$^1$ is CR$^3$ or N; wherein R$^3$ is H, F or methoxy;
(g) A$^2$ is CH or N;
(h) A$^3$ is CH;
(i) A$^4$ is CH or N;
(j) Z$^2$ is CR$^{4a}$;
(k) R$^{4a}$ is H; Br; Cl; F; cyano; cyclopropyl; methylcarbonyl; methoxycarbonyl; or C$_{1-4}$alkyl optionally substituted with one or more substituents each independently selected from the group consisting of F and amino;
(l) R$^{4b}$ is H; F; methoxy; cyano; cyclopropyl; or C$_{1-4}$alkyl optionally substituted with one or more substituents each independently selected from the group consisting of F and amino;
(m) R$^5$ is H; I; methoxy; 1-propen-2-yl; or C$_{1-6}$alkyl optionally substituted with one or more methoxy substituents;
(n) R$^{6a}$ is C$_{1-6}$alkyl optionally substituted with one or more substituents each independently selected from the group consisting of Ar, ethoxy, and tetrahydropyranyl; cyclopropyl; methylcarbonyl; tetrahydropyranyl; Ar; or R$^8$R$^9$N-carbonyl;
(o) R$^{6b}$ is C$_{2-6}$alkyl substituted with one or more F substituents; C$_{1-6}$alkyl optionally substituted with one or more substituents each independently selected from the group consisting of Ar, isopropyloxy, tetrahydropyranyl, and cyclopropyl; cyclopropyl; cyclopropyl substituted with one phenyl substituent which is further substituted with one or more Cl substituents; unsubstituted pyrrolidinyl; NR$^8$R$^9$; tetrahydropyranyl; Ar; or CH$_2$—O—Ar;
(p) wherein each Ar independently is phenyl optionally substituted with one or more substituents each independently selected from the group consisting of F, Cl, C$_{1-4}$alkyloxy, C$_{1-4}$alkyl, and C$_{1-4}$alkyl substituted with one or more F substituents; oxazolyl optionally substituted with one or more methyl substituents; or thienyl optionally substituted with one or more Cl substituents;
(q) each R$^8$ is methyl;
(r) each R$^9$ is methyl or 2-methyl-propyl;
(s) R$^7$ is C$_{1-6}$alkyl optionally substituted with one or more methoxy substituents;
and the pharmaceutically acceptable addition salts, and the solvates thereof.

In an embodiment, the invention relates to compounds of Formula (I) and stereoisomeric forms thereof, or any subgroup thereof as mentioned in any of the other embodiments, wherein one or more, preferably all, of the following restrictions apply:

(a) Het$^1$ is a 5-membered or 6-membered aromatic heterocycle, having formula (a-1) or (a-5); in particular (a-1);
(b) R$^0$ is H or C$_{1-4}$alkyl; in particular H or methyl;
(c) R$^1$ is H or C$_{1-4}$alkyl; in particular H or methyl;
(d) X is O;

(e) R$^{10a}$ and R$^{10b}$ each independently are hydrogen or C$_{1-4}$alkyl; in particular R$^{10a}$ is H and R$^{10b}$ is C$_{1-4}$alkyl; more in particular R$^{10a}$ is H and R$^{10b}$ is methyl;

(f) A$^1$ is CR$^3$ or N; wherein R$^3$ is C$_{1-4}$alkyloxy; in particular R$^3$ is methoxy;

(g) A$^2$, A$^3$ and A$^4$ are CH;

(h) Het$^2$ is a 9-membered bicyclic aromatic heterocycle, having formula (b-1) or (b-2); in particular (b-2);

(i) Z$^1$ and Z$^3$ are CH;

(j) Z$^2$ is CR$^{4a}$;

(k) R$^{4a}$ is H or halo; in particular halo; more in particular fluoro;

(l) Y$^1$ and Y$^3$ are CH;

(m) Y$^2$ is CR$^{4b}$;

(n) R$^{4b}$ is H or C$_{1-4}$alkyloxy; in particular H or methoxy;

(o) R$^5$ is H or methyl; in particular H;

(p) R$^{6a}$ is C$_{1-6}$alkyl;

(q) R$^{6b}$ is phenyl optionally substituted with one or more halo substituents; in particular phenyl substituted with one halo substituent; more in particular phenyl substituted with one F substituent; most in particular phenyl substituted with one F substituent in the para position.

(r) R$^7$ is C$_{1-6}$alkyl; in particular methyl or isopropyl;

and the pharmaceutically acceptable addition salts, and the solvates thereof.

In an embodiment, the present invention concerns novel compounds of Formula (I), and stereoisomeric forms thereof, wherein Het$^1$ is a 5-membered aromatic heterocycle, having formula (a-1), (a-2), (a-3) or (a-4)

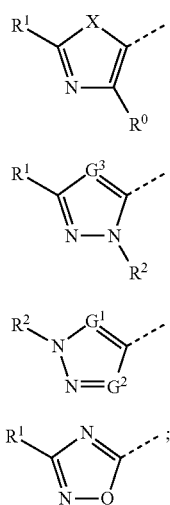

R$^0$ is H or C$_{1-4}$alkyl;
R$^1$ is H or C$_{1-4}$alkyl;
R$^2$ is C$_{1-4}$alkyl;
X is O or S;
G$^1$ is CH or N; G$^2$ is CH, N or C substituted with C$_{1-4}$alkyl; provided that G$^1$ and G$^2$ are not simultaneously N;
G$^3$ is CH or N;
A$^1$ is CR$^3$ or N; wherein R$^3$ is H, halo or C$_{1-4}$alkyloxy;
A$^2$, A$^3$ and A$^4$ each independently are CH, CF or N; provided that maximum two of A$^1$, A$^2$, A$^3$ and A$^4$ are N;
Het$^2$ is a 9-membered bicyclic aromatic heterocycle, having formula (b-1) or (b-2):

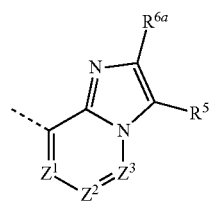

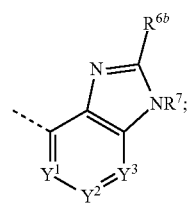

Z$^1$ is CH or N; Z$^2$ is CR$^{4a}$; Z$^3$ is CH;
Y$^1$ is CH or N; Y$^2$ is CR$^{4b}$; Y$^3$ is CH;
R$^{4a}$ is H; halo; C$_{1-4}$alkyloxy; cyano; or C$_{1-4}$alkyl optionally substituted with one or more halo substituents;
R$^{4b}$ is H; halo; C$_{1-4}$alkyloxy; cyano; or C$_{1-4}$alkyl optionally substituted with one or more halo substituents;
R$^5$ is H; halo; cyano; or C$_{1-6}$alkyl optionally substituted with one or more substituents each independently selected from the group consisting of C$_{1-4}$alkyloxy and halo;
R$^{6a}$ is C$_{2-6}$alkyl substituted with one or more halo substituents; C$_{1-6}$alkyl optionally substituted with one or more substituents each independently selected from the group consisting of piperidinyl, Ar, C$_{1-6}$alkyloxy, tetrahydropyranyl, cycloC$_{3-7}$alkyloxy, and cycloC$_{3-7}$alkyl; cycloC$_{3-7}$alkyl; tetrahydropyranyl; Ar; or CH$_2$—O—Ar;
R$^{6b}$ is C$_{2-6}$alkyl substituted with one or more halo substituents; C$_{1-6}$alkyl optionally substituted with one or more substituents each independently selected from the group consisting of piperidinyl, Ar, C$_{1-6}$alkyloxy, tetrahydropyranyl, cycloC$_{3-7}$alkyloxy, and cycloC$_{3-7}$alkyl; cycloC$_{3-7}$alkyl; piperidinyl; morpholinyl; pyrrolidinyl; NR$^8$R$^9$; tetrahydropyranyl; O—Ar; C$_{1-6}$alkyloxy; C$_{1-6}$alkylthio; Ar; CH$_2$—O—Ar; S—Ar; NCH$_3$—Ar or NH—Ar;
wherein each piperidinyl, morpholinyl, and pyrrolidinyl may optionally be substituted with one or more substituents each independently selected from the group consisting of C$_{1-4}$alkyl, C$_{2-6}$alkenyl, C$_{1-4}$alkylcarbonyl, halo, and C$_{1-4}$alkyloxycarbonyl;
wherein each Ar independently is phenyl optionally substituted with one or more substituents each independently selected from the group consisting of halo, C$_{1-4}$alkyloxy, cyano, NR$^8$R$^9$, morpholinyl, C$_{1-4}$alkyl, and C$_{1-4}$alkyl substituted with one or more halo substituents; or pyridinyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents;
each R$^8$ independently is H or C$_{1-4}$alkyl;
each R$^9$ independently is H or C$_{1-4}$alkyl;
R$^7$ is H, C$_{1-6}$alkyl optionally substituted with one or more substituents each independently selected from the group consisting of halo, phenyl, and C$_{1-4}$alkyloxy;
and the pharmaceutically acceptable addition salts, and the solvates thereof.

In an embodiment, the present invention concerns novel compounds of Formula (I):

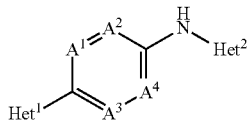
(I)

and stereoisomeric forms thereof, wherein
Het¹ is a 5-membered aromatic heterocycle, having formula (a-1), (a-2), (a-3) or (a-4)

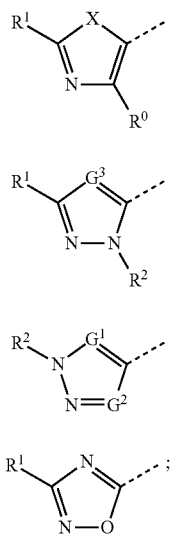

$R^0$ is H or $C_{1-4}$alkyl;
$R^1$ is H or $C_{1-4}$alkyl;
$R^2$ is $C_{1-4}$alkyl;
X is O or S;
$G^1$ is CH or N;
$G^2$ is CH, N or C substituted with $C_{1-4}$alkyl; provided that $G^1$ and $G^2$ are not simultaneously N;
$G^3$ is CH or N;
$A^1$ is $CR^3$ or N; wherein $R^3$ is H, halo or $C_{1-4}$alkyloxy;
$A^2$, $A^3$ and $A^4$ each independently are CH, CF or N; provided that no more than two of $A^1$, $A^2$, $A^3$ and $A^4$ are N;
Het² is a 9-membered bicyclic aromatic heterocycle, having formula (b-1a) or (b-2a)

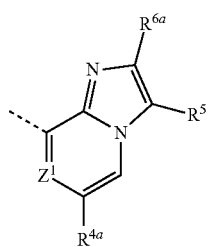
(b-1a)

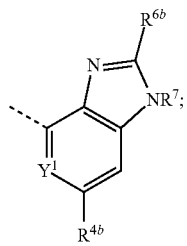
(b-2a)

$R^{4a}$ is H, halo, $C_{1-4}$alkyloxy, cyano, or $C_{1-4}$alkyl optionally substituted with one or more substituents selected from halo;

$R^{4b}$ is H, halo, $C_{1-4}$alkyloxy, cyano, or $C_{1-4}$alkyl optionally substituted with one or more substituents selected from halo;

$R^5$ is H; halo; cyano; or $C_{1-6}$alkyl optionally substituted with one or more substituents selected from $C_{1-4}$alkyloxy and halo;

$R^{6a}$ is $C_{2-6}$alkyl substituted with one or more substituents selected from halo; $C_{1-6}$alkyl optionally substituted with one or more substituents selected from piperidinyl, Ar, $C_{1-6}$alkyloxy, tetrahydropyranyl, cycloC$_{3-7}$alkyloxy, and cycloC$_{3-7}$alkyl; cycloC$_{3-7}$alkyl; tetrahydropyranyl; Ar; or CH$_2$—O—Ar;

$R^{6b}$ is $C_{2-6}$alkyl substituted with one or more substituents selected from halo; $C_{1-6}$alkyl optionally substituted with one or more substituents selected from piperidinyl, Ar, $C_{1-6}$alkyloxy, tetrahydropyranyl, cycloC$_{3-7}$alkyloxy, and cycloC$_{3-7}$alkyl; cycloC$_{3-7}$alkyl; piperidinyl; morpholinyl; pyrrolidinyl; NR$^8$R$^9$; tetrahydropyranyl; O—Ar; $C_{1-6}$alkyloxy; $C_{1-6}$alkylthio; Ar; CH$_2$—O—Ar; S—Ar; NCH$_3$—Ar or NH—Ar;

wherein each piperidinyl, morpholinyl, and pyrrolidinyl may optionally be substituted with one or more substituents selected from $C_{1-4}$alkyl, $C_{2-6}$alkenyl, $C_{1-4}$alkylcarbonyl, halo, and $C_{1-4}$alkyloxycarbonyl;

wherein each Ar independently is phenyl optionally substituted with one or more substituents each independently selected from halo, $C_{1-4}$alkyloxy, cyano, NR$^8$R$^9$, morpholinyl, $C_{1-4}$alkyl, and $C_{1-4}$alkyl substituted with one or more substituents selected from halo; or pyridinyl optionally substituted with 1 or more substituents each independently selected from halo, $C_{1-4}$alkyloxy, cyano, $C_{1-4}$alkyl, and $C_{1-4}$alkyl substituted with one or more substituents selected from halo;

wherein $R^8$ is H or $C_{1-4}$alkyl;
wherein $R^9$ is H or $C_{1-4}$alkyl;
$R^7$ is H, $C_{1-6}$alkyl optionally substituted with one or more substituents selected from halo, phenyl and $C_{1-4}$alkyloxy;
$Z^1$ is CH or N;
$Y^1$ is CH or N;
and the pharmaceutically acceptable addition salts, and the solvates thereof.

In another embodiment, the invention relates to compounds of Formula (I) and stereoisomeric forms thereof, wherein
Het¹ is a 5-membered aromatic heterocycle, having formula (a-1), (a-2), (a-3) or (a-4)

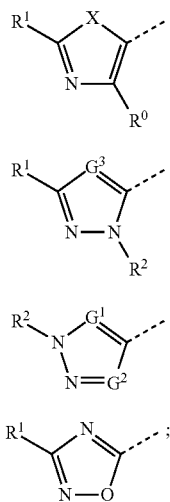

(a-1)
(a-2)
(a-3)
(a-4)

$R^0$ is H or $C_{1-4}$alkyl;
$R^1$ is H or $C_{1-4}$alkyl;
$R^2$ is $C_{1-4}$alkyl;
X is O or S;
$G^1$ is CH;
$G^2$ is CH, or C substituted with $C_{1-4}$alkyl;
$G^3$ is CH;
$A^1$ is $CR^3$ or N; wherein $R^3$ is H, halo or $C_{1-4}$alkyloxy;
$A^2$, $A^3$ and $A^4$ each independently are CH or N; provided that maximum two of $A^1$, $A^2$, $A^3$ and $A^4$ are N;
$Het^2$ is a 9-membered bicyclic aromatic heterocycle, having formula (b-1) or (b-2);
wherein $Z^1$ is CH or N; $Z^2$ is $CR^{4a}$; $Z^3$ is CH; $Y^1$ is CH or N; $Y^2$ is $CR^{4b}$; $Y^3$ is CH;
$R^{4a}$ is H; halo; cyano; or $C_{1-4}$alkyl optionally substituted with one or more halo substituents;
$R^{4b}$ is H; halo; cyano; or $C_{1-4}$alkyl optionally substituted with one or more halo substituents;
$R^5$ is H or $C_{1-4}$alkyl;
$R^{6a}$ is Ar; $C_{2-6}$alkyl substituted with one or more halo substituents; or $C_{1-6}$alkyl optionally substituted with one or more substituents each independently selected from the group consisting of Ar, $C_{1-6}$alkyloxy, and cyclo$C_{3-7}$alkyl;
$R^{6b}$ is Ar; $C_{2-6}$alkyl substituted with one or more halo substituents;
$C_{1-6}$alkyl optionally substituted with one or more substituents each independently selected from the group consisting of Ar, $C_{1-6}$alkyloxy, and cyclo$C_{3-7}$alkyl; or $CH_2$—O—Ar;
wherein each Ar independently is phenyl optionally substituted with one or more substituents each independently selected from the group consisting of halo, cyano, $C_{1-4}$alkyloxy, $C_{1-4}$alkyl, and $C_{1-4}$alkyl substituted with one or more halo substituents;
$R^7$ is $C_{1-6}$alkyl optionally substituted with one or more substituents each independently selected from the group consisting of halo and $C_{1-4}$alkyloxy;
and the pharmaceutically acceptable addition salts, and the solvates thereof.

In another embodiment, the invention relates to compounds of Formula (I) and stereoisomeric forms thereof, wherein
$Het^1$ is a 5-membered aromatic heterocycle, having formula (a-1), (a-2), (a-3) or (a-4);
$R^0$ is H or $C_{1-4}$alkyl;
$R^1$ is H or $C_{1-4}$alkyl;
$R^2$ is $C_{1-4}$alkyl;
X is O or S;
$G^1$ is CH;
$G^2$ is CH or C substituted with $C_{1-4}$alkyl;
$G^3$ is CH;
$A^1$ is $CR^3$ or N; wherein $R^3$ is H, halo or $C_{1-4}$alkyloxy;
$A^2$ is CH or N;
$A^3$ and $A^4$ are CH;
$Het^2$ is a 9-membered bicyclic aromatic heterocycle, having formula (b-1) or (b-2);
wherein $Z^1$ is CH or N; $Z^2$ is $CR^{4a}$; $Z^3$ is CH; $Y^1$ is CH or N; $Y^2$ is $CR^{4b}$; $Y^3$ is CH;
$R^{4a}$ is H or halo;
$R^{4b}$ is H, halo or $C_{1-4}$alkyl optionally substituted with one or more halo substituents;
$R^5$ is H, or $C_{1-4}$alkyl;
$R^{6a}$ is Ar; or $C_{1-6}$alkyl optionally substituted with one Ar;
$R^{6b}$ is Ar; $C_{2-6}$alkyl substituted with one or more halo substituents; $C_{1-6}$alkyl optionally substituted with one or more Ar substituents; or $CH_2$—O—Ar;
wherein each Ar independently is phenyl optionally substituted with one or more substituents each independently selected from the group consisting of halo, $C_{1-4}$alkyloxy, $C_{1-4}$alkyl, and $C_{1-4}$alkyl substituted with one or more halo substituents;
$R^7$ is $C_{1-6}$alkyl optionally substituted with one or more $C_{1-4}$alkyloxy substituents;
and the pharmaceutically acceptable addition salts, and the solvates thereof.

In another embodiment, the invention relates to compounds of Formula (I) and stereoisomeric forms thereof, wherein
$Het^1$ is a 5-membered aromatic heterocycle, having formula (a-1), (a-2), (a-3) or (a-4);
$R^0$ is H or methyl;
$R^1$ is H or methyl;
$R^2$ is methyl;
X is O or S;
$G^1$ is CH;
$G^2$ is CH, or C substituted with methyl;
$G^3$ is CH;
$A^1$ is $CR^3$ or N; wherein $R^3$ is H, F or methoxy;
$A^2$ and $A^3$ are CH or N; provided that maximum two of $A^1$, $A^2$ and $A^3$ are N;
$A^4$ is CH;
$Het^2$ is a 9-membered bicyclic aromatic heterocycle, having formula (b-1) or (b-2);
wherein $Z^1$ is CH or N; $Z^2$ is $CR^{4a}$; $Z^3$ is CH; $Y^1$ is CH or N; $Y^2$ is $CR^{4b}$; $Y^3$ is CH;
$R^{4a}$ is H, Br, F, cyano or $CF_3$;
$R^{4b}$ is H, F, cyano, $CH_3$ or $CF_3$;
$R^5$ is H or $CH_3$;
$R^{6a}$ is Ar; ethyl; or methyl optionally substituted with one or more substituents each independently selected from the group consisting of $C_{1-3}$alkyloxy and Ar;
$R^{6b}$ is Ar; 3,3,3-trifluoropropyl; cyclopropylmethyl; methyl optionally substituted with one or more Ar substituents; or $CH_2$—O—Ar;
wherein each Ar independently is phenyl optionally substituted with one or more substituents each independently selected from the group consisting of F, Cl, CN, methyl, 2-propyl, methoxy, ethoxy, and trifluoromethyl;
$R^7$ is methyl, 2-propyl, tert-butyl, or ethyl optionally substituted with one methoxy;
and the pharmaceutically acceptable addition salts, and the solvates thereof.

In another embodiment, the invention relates to compounds of Formula (I) and stereoisomeric forms thereof, wherein
Het$^1$ is a 5-membered aromatic heterocycle, having formula (a-1), (a-2), (a-3) or (a-4);
R$^0$ is H or methyl;
R$^1$ is H or methyl;
R$^2$ is methyl;
X is O or S;
G$^1$ is CH;
G$^2$ is CH, or C substituted with methyl;
G$^3$ is CH;
A$^1$ is CR$^3$ or N; wherein R$^3$ is H, F or methoxy;
A$^2$ is CH or N
A$^3$ and A$^4$ are CH;
Het$^2$ is a 9-membered bicyclic aromatic heterocycle, having formula (b-1) or (b-2);
wherein Z$^1$ is CH or N; Z$^2$ is CR$^{4a}$; Z$^3$ is CH; Y$^1$ is CH or N; Y$^2$ is CR$^{4b}$; Y$^3$ is CH;
R$^{4a}$ is H or Br;
R$^{4b}$ is H, F, CH$_3$ or CF$_3$;
R$^5$ is H, or CH$_3$;
R$^{6a}$ is Ar; or methyl optionally substituted with one Ar;
R$^{6b}$ is Ar; 3,3,3-trifluoropropyl; cyclopropylmethyl; methyl optionally substituted with one or more Ar substituents; or CH$_2$—O—Ar;
wherein each Ar independently is phenyl optionally substituted with one or more substituents each independently selected from the group consisting of F, Cl, methyl, 2-propyl, methoxy, ethoxy, and trifluoromethyl;
R$^7$ is methyl, 2-propyl, tert-butyl, or ethyl optionally substituted with one methoxy;
and the pharmaceutically acceptable addition salts, and the solvates thereof.

In another embodiment, the invention relates to compounds of Formula (I) and stereoisomeric forms thereof, wherein
Het$^1$ is a 5-membered aromatic heterocycle, having formula (a-1);
R$^0$ is H or C$_{1-4}$alkyl;
R$^1$ is H or C$_{1-4}$alkyl;
X is O;
A$^1$ is CR$^3$ or N; wherein R$^3$ is H, F or C$_{1-4}$alkyloxy;
A$^2$, A$^3$ and A$^4$ are CH;
Het$^2$ is a 9-membered bicyclic aromatic heterocycle, having formula (b-2); wherein Y$^1$ is CH or N; Y$^2$ is CR$^{4b}$; Y$^3$ is CH;
R$^{4b}$ is H, F or CF$_3$;
R$^{6b}$ is phenyl optionally substituted with one or more substituents each independently selected from the group consisting of halo, methyl, and methoxy;
R$^7$ is C$_{1-4}$alkyl;
and the pharmaceutically acceptable addition salts, and the solvates thereof.

In another embodiment, the invention relates to compounds of Formula (I) and stereoisomeric forms thereof, wherein
Het$^1$ is a 5-membered aromatic heterocycle, having formula (a-1);
R$^0$ is H or C$_{1-4}$alkyl;
R$^1$ is H or C$_{1-4}$alkyl;
X is O;
A$^1$ is CR$^3$; wherein R$^3$ is C$_{1-4}$alkyloxy;
A$^2$, A$^3$ and A$^4$ are CH;
Het$^2$ is a 9-membered bicyclic aromatic heterocycle, having formula (b-2); wherein Y$^1$ is CH; Y$^2$ is CH; Y$^3$ is CH;
R$^{6b}$ is phenyl optionally substituted with one or more halo substituents;
R$^7$ is C$_{1-4}$alkyl;
and the pharmaceutically acceptable addition salts, and the solvates thereof.

In another embodiment, the invention relates to compounds according to any of the other embodiments, wherein R$^{6a}$ is C$_{2-6}$alkyl substituted with one or more halo substituents; C$_{1-6}$alkyl optionally substituted with one or more substituents each independently selected from the group consisting of Ar, C$_{1-6}$alkyloxy, cycloC$_{3-7}$alkyloxy, and cycloC$_{3-7}$alkyl; Ar; or CH$_2$—O—Ar;
wherein each Ar independently is phenyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents.

In another embodiment, the invention relates to compounds according to any of the other embodiments, wherein R$^{6b}$ is C$_{2-6}$alkyl substituted with one or more halo substituents; C$_{1-6}$alkyl optionally substituted with one or more substituents each independently selected from the group consisting of Ar, C$_{1-6}$alkyloxy, cycloC$_{3-7}$alkyloxy, and cycloC$_{3-7}$alkyl; Ar; or CH$_2$—O—Ar;
wherein each Ar independently is phenyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents.

In another embodiment, the invention relates to compounds according to any of the other embodiments, wherein R$^{6a}$ is isobutyl; cyclopropylmethyl; 3,3,3-trifluoropropyl; C$_{2-4}$alkyl substituted with methoxy; CH$_2$—O—Ar; or Ar;
wherein each Ar independently is phenyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents.

In another embodiment, the invention relates to compounds according to any of the other embodiments, wherein R$^{6b}$ is isobutyl; cyclopropylmethyl; 3,3,3-trifluoropropyl; C$_{2-4}$alkyl substituted with methoxy; CH$_2$—O—Ar; or Ar;
wherein each Ar independently is phenyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents.

In another embodiment, the invention relates to compounds according to any of the other embodiments, wherein R$^{6a}$ is Ar;
wherein each Ar independently is phenyl optionally substituted with one or more substituents each independently selected from the group consisting of halo, C$_{1-4}$alkyloxy, cyano, C$_{1-4}$alkyl, and C$_{1-4}$alkyl substituted with one or more halo substituents.

In another embodiment, the invention relates to compounds according to any of the other embodiments, wherein R$^{6a}$ is C$_{2-6}$alkyl substituted with one or more halo substituents; or phenyl optionally substituted with one or more substituents each independently selected from the group consisting of halo, C$_{1-4}$alkyloxy, C$_{1-4}$alkyl, and C$_{1-4}$alkyl substituted with one or more halo substituents;
in particular phenyl optionally substituted with one or more substituents each independently selected from the group consisting of halo, methoxy, methyl, and trifluoromethyl.

In another embodiment, the invention relates to compounds according to any of the other embodiments, wherein R$^{6b}$ is Ar;

wherein each Ar independently is phenyl optionally substituted with one or more substituents each independently selected from the group consisting of halo, $C_{1-4}$alkyloxy, cyano, $C_{1-4}$alkyl, and $C_{1-4}$alkyl substituted with one or more halo substituents.

In another embodiment, the invention relates to compounds according to any of the other embodiments, wherein $R^{6b}$ is $C_{2-6}$alkyl substituted with one or more halo substituents; or phenyl optionally substituted with one or more substituents each independently selected from the group consisting of halo, $C_{1-4}$alkyloxy, $C_{1-4}$alkyl, and $C_{1-4}$alkyl substituted with one or more halo substituents;

in particular $C_{2-6}$alkyl substituted with one or more halo substituents; or phenyl optionally substituted with one or more substituents each independently selected from the group consisting of halo, methoxy, methyl, and trifluoromethyl.

In another embodiment, the invention relates to compounds according to any of the other embodiments, wherein $R^{4a}$ is H, halo, $C_{1-4}$alkyloxy, or methyl optionally substituted with one or more halo substituents; in particular H or halo; more in particular H or F.

In another embodiment, the invention relates to compounds according to any of the other embodiments, wherein $R^{4a}$ is H, halo, methyl, cyano or trifluoromethyl.

In another embodiment, the invention relates to compounds according to any of the other embodiments, wherein $R^{4b}$ is H, halo, $C_{1-4}$alkyloxy, or methyl optionally substituted with one or more halo substituents; in particular H, halo or $C_{1-4}$alkyloxy; more in particular H, F or methoxy.

In another embodiment, the invention relates to compounds according to any of the other embodiments, wherein $R^{4b}$ is H, halo, methyl, cyano or trifluoromethyl.

In another embodiment, the invention relates to compounds according to any of the other embodiments, wherein $R^7$ is $C_{1-6}$alkyl optionally substituted with one or more substituents each independently selected from the group consisting of halo and $C_{1-4}$alkyloxy.

In another embodiment, the invention relates to compounds according to any of the other embodiments, wherein $R^7$ is $C_{1-4}$alkyl.

In another embodiment, the invention relates to compounds according to any of the other embodiments, wherein $R^8$ is H or $C_{1-4}$alkyl; and wherein $R^9$ is H or $C_{1-4}$alkyl.

In an embodiment, the invention relates to compounds according to any of the other embodiments, wherein
$R^5$ is H or methyl;
$R^{6a}$ is phenyl substituted in a meta position and optionally further substituted in other positions.

In an embodiment, the invention relates to compounds according to any of the other embodiments, wherein
$R^5$ is H or methyl;
$R^{6a}$ is phenyl substituted in an ortho position and optionally further substituted in other positions.

In an embodiment, the invention relates to compounds according to any of the other embodiments, wherein
$R^5$ is H or methyl;
$R^{6a}$ is phenyl substituted in the para position and optionally further substituted in other positions.

In an embodiment, the invention relates to compounds according to any of the other embodiments, wherein
$R^5$ is H or methyl;
$R^{6a}$ is phenyl substituted with F in the para position and optionally further substituted in other positions.

In an embodiment, the invention relates to compounds according to any of the other embodiments, wherein
$R^5$ is H;
$R^{6a}$ is methyl substituted with phenyl, wherein phenyl is optionally substituted with one or more substituents each independently selected from the group consisting of halo, $C_{1-4}$alkyloxy, cyano, $NR^8R^9$, morpholinyl, $C_{1-4}$alkyl, and $C_{1-4}$alkyl substituted with one or more halo substituents.

In an embodiment, the invention relates to compounds according to any of the other embodiments, wherein $R^{6b}$ is phenyl substituted in a meta position and optionally further substituted in other positions.

In an embodiment, the invention relates to compounds according to any of the other embodiments, wherein $R^{6b}$ is phenyl substituted in an ortho position and optionally further substituted in other positions.

In an embodiment, the invention relates to compounds according to any of the other embodiments, wherein $R^{6b}$ is phenyl substituted in the para position and optionally further substituted in other positions.

In an embodiment, the invention relates to compounds according to any of the other embodiments, wherein $R^{6b}$ is phenyl substituted with F in the para position and optionally further substituted in other positions.

In an embodiment, the invention relates to compounds according to any of the other embodiments, wherein $R^{6b}$ is methyl substituted with phenyl, wherein phenyl is optionally substituted with one or more substituents each independently selected from the group consisting of halo, $C_{1-4}$alkyloxy, cyano, $NR^8R^9$, morpholinyl, $C_{1-4}$alkyl, and $C_{1-4}$alkyl substituted with one or more halo substituents.

In an embodiment, the invention relates to compounds according to any of the other embodiments, wherein one of $R^0$ and $R^1$ is $C_{1-4}$alkyl, and one of $R^0$ and $R^1$ is H; in particular one of $R^0$ and $R^1$ is methyl, and one of $R^0$ and $R^1$ is H.

In a further embodiment, the invention relates to compounds according to any of the other embodiments, wherein X is O.

In a further embodiment, the invention relates to compounds according to any of the other embodiments, wherein $Het^1$ is (a-1) and X is O.

In a further embodiment, the invention relates to compounds according to any of the other embodiments, wherein X is S.

In a further embodiment, the invention relates to compounds according to any of the other embodiments, wherein $Het^1$ is (a-1) and X is S.

In a further embodiment, the invention relates to compounds according to any of the other embodiments, wherein $A^1$ is $CR^3$ or N; wherein $R^3$ is H, F or methoxy.

In a next embodiment, the invention relates to compounds according to any of the other embodiments, wherein
$A^1$ is $CR^3$ or N; wherein $R^3$ is H, halo or $C_{1-4}$alkyloxy; in particular $R^3$ is H, F or $C_{1-4}$alkyloxy; more in particular $R^3$ is H, F or methoxy; most in particular $R^3$ is methoxy;
$A^2$ is CH, CF or N; in particular CH or N;
$A^3$ and $A^4$ are CH or N; provided that maximum two of $A^1$, $A^2$, $A^3$ and $A^4$ are N.

In a next embodiment, the invention relates to compounds according to any of the other embodiments, wherein
$A^1$ is $CR^3$ or N; wherein $R^3$ is H, halo or $C_{1-4}$alkyloxy;
$A^2$ is CH, CF or N; in particular CH or CF; more in particular CH;
$A^3$ and $A^4$ are CH.

In a next embodiment, the invention relates to compounds according to any of the other embodiments, wherein $A^1$ is N and $A^2$ is CH.

In a next embodiment, the invention relates to compounds according to any of the other embodiments, wherein $A^2$ is CH when $A^1$ is N.

In a next embodiment, the invention relates to compounds according to any of the other embodiments, wherein maximum one of $A^1$, $A^2$, $A^3$ and $A^4$ is N.

In a further embodiment, the invention relates to compounds according to any of the other embodiments, wherein $Het^1$ has formula (a-1).

In a further embodiment, the invention relates to compounds according to any of the other embodiments, wherein $Het^1$ has formula (a-2).

In a further embodiment, the invention relates to compounds according to any of the other embodiments, wherein $Het^1$ has formula (a-3).

In a further embodiment, the invention relates to compounds according to any of the other embodiments, wherein $Het^1$ has formula (a-4).

In a further embodiment, the invention relates to compounds according to any of the other embodiments, wherein $Het^1$ has formula (a-5).

In a further embodiment, the invention relates to compounds according to any of the other embodiments, wherein $Het^2$ has formula (b-1).

In a further embodiment, the invention relates to compounds according to any of the other embodiments, wherein $Het^2$ has formula (b-2).

In a further embodiment, the invention relates to compounds according to any of the other embodiments, wherein $Y^1$ is CH.

In a further embodiment, the invention relates to compounds according to any of the other embodiments, wherein $Y^1$ is N.

In a further embodiment, the invention relates to compounds according to any of the other embodiments, wherein $Z^1$ is CH.

In a further embodiment, the invention relates to compounds according to any of the other embodiments, wherein $Z^1$ is N.

In a further embodiment, the invention relates to compounds according to any of the other embodiments, wherein $Z^2$ is $CR^{4a}$.

In a further embodiment, the invention relates to compounds according to any of the other embodiments, wherein $Z^2$ is N.

In a further embodiment, the invention relates to compounds according to any of the other embodiments, wherein one of $Z^2$ and $Z^3$ is N, or wherein one of $Y^2$ and $Y^3$ is N.

In a further embodiment, the invention relates to compounds according to any of the other embodiments, wherein $C_{1-6}$alkyl is restricted to $C_{1-4}$alkyl.

In an embodiment the compound of Formula (I) is selected from the group comprising:

2-(4-fluorophenyl)-N-[3-methoxy-4-(5-oxazolyl)phenyl]-imidazo[1,2-c]pyridin-8-amine,
N-[4-(2,4-dimethyl-5-oxazolyl)-3-methoxyphenyl]-2-(4-fluorophenyl)-imidazo[1,2-a]pyridin-8-amine,
N-[4-(2,4-dimethyl-5-oxazolyl)-3-methoxyphenyl]-3-methyl-2-phenyl-imidazo[1,2-a]pyridin-8-amine,
2-(4-fluorophenyl)-N-[3-methoxy-4-(4-methyl-5-oxazolyl)phenyl]-imidazo[1,2-a]pyridin-8-amine,
2-(4-fluorophenyl)-N-[3-methoxy-4-(4-methyl-5-oxazolyl)phenyl]-1-methyl-1H-benzimidazol-4-amine,
2-(4-fluorophenyl)-N-[3-methoxy-4-(1-methyl-1H-pyrazol-4-yl)phenyl]-1-methyl-1H-benzimidazol-4-amine,
N-[4-(2,4-dimethyl-5-thiazolyl)-3-methoxyphenyl]-2-(3-methoxyphenyl)-3-methyl-imidazo[1,2-a]pyridin-8-amine,
N-[4-(1,3-dimethyl-1H-pyrazol-4-yl)-3-methoxyphenyl]-2-(3-methoxyphenyl)-3-methyl-imidazo[1,2-a]pyridin-8-amine,
N-[3-methoxy-4-(4-methyl-5-oxazolyl)phenyl]-2-(3-methoxyphenyl)-3-methyl-imidazo[1,2-a]pyridin-8-amine,
N-[3-methoxy-4-(2-methyl-5-thiazolyl)phenyl]-2-(3-methoxyphenyl)-3-methyl-imidazo[1,2-a]pyridin-8-amine,
N-[4-(2,4-dimethyl-5-oxazolyl)-3-methoxyphenyl]-2-(4-fluorophenyl)-1-methyl-1H-benzimidazol-4-amine,
2-(4-fluorophenyl)-N-[3-methoxy-4-(1-methyl-1H-pyrazol-5-yl)phenyl]-1-methyl-1H-benzimidazol-4-amine,
2-(4-fluorophenyl)-N-[3-methoxy-4-(3-methyl-1,2,4-oxadiazol-5-yl)phenyl]-1-methyl-1H-benzimidazol-4-amine,
2-(4-fluorophenyl)-N-[3-methoxy-4-(2-methyl-5-oxazolyl)phenyl]-1-methyl-1H-benzimidazol-4-amine,
2-(4-fluorophenyl)-1-methyl-N-[5-(4-methyl-5-oxazolyl)-2-pyridinyl]-1H-benzimidazol-4-amine,
N-[3-methoxy-4-(4-methyl-5-oxazolyl)phenyl]-1-methyl-2-(3,3,3-trifluoropropyl)-1H-benzimidazol-4-amine,
N-[3-methoxy-4-(4-methyl-5-oxazolyl)phenyl]-2-(3-methoxyphenyl)-1-methyl-1H-benzimidazol-4-amine,
2-(3-chlorophenyl)-1-methyl-N-[5-(4-methyl-5-oxazolyl)-2-pyridinyl]-1H-benzimidazol-4-amine,
2-(4-chloro-3-methoxyphenyl)-1-methyl-N-[5-(4-methyl-5-oxazolyl)-2-pyridinyl]-1H-benzimidazol-4-amine,
2-[4-ethoxy-2-methyl-5-(1-methylethyl)phenyl]-N-[3-methoxy-4-(4-methyl-5-oxazolyl)phenyl]-1-methyl-1H-benzimidazol-4-amine,
2-(4-fluorophenyl)-N-[3-methoxy-4-(2-methyl-5-oxazolyl)phenyl]-imidazo[1,2-a]pyridin-8-amine,
2-(4-fluorophenyl)-N-[4-(2-methyl-5-oxazolyl)phenyl]-imidazo[1,2-a]pyridin-8-amine,
1-(1,1-dimethylethyl)-2-(4-fluorophenyl)-N-[6-(4-methyl-5-oxazolyl)-3-pyridinyl]-1H-benzimidazol-4-amine,
2-(4-fluorophenyl)-1-methyl-N-[6-(4-methyl-5-oxazolyl)-3-pyridinyl]-1H-benzimidazol-4-amine,
2-(4-fluorophenyl)-1-(1-methylethyl)-N-[4-(2-methyl-5-oxazolyl)phenyl]-1H-benzimidazol-4-amine,
N-[4-(2-methyl-5-oxazolyl)phenyl]-2-(2-methylphenyl)-imidazo[1,2-a]pyridin-8-amine,
2-(4-fluoro-2-methylphenyl)-N-[6-(4-methyl-5-oxazolyl)-3-pyridinyl]-imidazo[1,2-a]pyridin-8-amine,
2-(2-fluoro-4-methylphenyl)-N-[6-(4-methyl-5-oxazolyl)-3-pyridinyl]-imidazo[1,2-a]pyridin-8-amine,
N-[4-(2-methyl-5-oxazolyl)phenyl]-2-[2-methyl-5-(trifluoromethyl)phenyl]-imidazo[1,2-a]pyridin-8-amine,
2-(2,4-difluorophenyl)-N-[3-methoxy-4-(2-methyl-5-oxazolyl)phenyl]-1-methyl-1H-imidazo[4,5-a]pyridin-4-amine,
1-(2-methoxyethyl)-N-[3-methoxy-4-(2-methyl-5-thiazolyl)phenyl]-2-methyl-1H-benzimidazol-4-amine,
N-[3-methoxy-4-(2-methyl-5-thiazolyl)phenyl]-2-(2-methylphenyl)-imidazo[1,2-a]pyridin-8-amine,
2-(4-fluorophenyl)-1-methyl-N-[4-(2-methyl-5-oxazolyl)phenyl]-1H-imidazo[4,5-c]pyridin-4-amine,
2-(4-fluorophenyl)-N-[3-methoxy-4-(2-methyl-5-oxazolyl)phenyl]-1-(1-methylethyl)-1H-benzimidazol-4-amine,
2-(4-fluorophenyl)-N-[3-methoxy-4-(2-methyl-5-oxazolyl)phenyl]-1-methyl-1H-imidazo[4,5-c]pyridin-4-amine,
2-(4-fluoro-2-methylphenyl)-N-[4-(2-methyl-5-oxazolyl)phenyl]-imidazo[1,2-a]pyridin-8-amine,
2-(2-fluoro-4-methylphenyl)-N-[4-(2-methyl-5-oxazolyl)phenyl]-imidazo[1,2-a]pyridin-8-amine, 2-(4-fluorophenyl)-1-methyl-N-[6-(2-methyl-5-oxazolyl)-3-pyridinyl]-1H-benzimidazol-4-amine,
2-(2-chlorophenyl)-3-methyl-N-[4-(2-methyl-5-oxazolyl)phenyl]-imidazo[1,2-a]pyridin-8-amine,
2-(5-methoxy-2-methylphenyl)-N-[4-(2-methyl-5-oxazolyl)phenyl]-imidazo[1,2-a]pyridin-8-amine,
2-[(4-fluorophenyl)methyl]-N-[4-(2-methyl-5-oxazolyl)phenyl]-imidazo[1,2-a]pyridin-8-amine,
N-[3-fluoro-4-(2-methyl-5-oxazolyl)phenyl]-2-(4-fluorophenyl)-1-methyl-1H-imidazo[4,5-c]pyridin-4-amine,
2-(5-fluoro-2-methylphenyl)-N-[3-methoxy-4-(2-methyl-5-oxazolyl)phenyl]-imidazo[1,2-a]pyridin-8-amine,
N-[6-(4-methyl-5-oxazolyl)-3-pyridinyl]-2-[2-methyl-5-(trifluoromethyl)phenyl]-imidazo[1,2-a]pyridin-8-amine,
2-(3-methoxyphenyl)-1-(1-methylethyl)-N-[4-(2-methyl-5-oxazolyl)phenyl]-1H-benzimidazol-4-amine,
2-(4-fluorophenyl)-1-(1-methylethyl)-N-[5-(2-methyl-5-oxazolyl)-2-pyridinyl]-1H-benzimidazol-4-amine,
2-(4-fluorophenyl)-N-[3-methoxy-4-(2-methyl-5-oxazolyl)phenyl]-1-methyl-6-(trifluoromethyl)-1H-benzimidazol-4-amine,
2-(4-fluorophenyl)-1-(1-methylethyl)-N-[4-(2-methyl-5-oxazolyl)phenyl]-1H-imidazo[4,5-c]pyridin-4-amine,
2-(4-fluorophenyl)-N-[3-methoxy-4-(2-methyl-5-oxazolyl)phenyl]-1-(1-methylethyl)-1H-imidazo[4,5-c]pyridin-4-amine,
N-[3-fluoro-4-(2-methyl-5-oxazolyl)phenyl]-2-(5-methoxy-2-methylphenyl)-imidazo[1,2-a]pyridin-8-amine,
N-[3-fluoro-4-(2-methyl-5-oxazolyl)phenyl]-2-(4-fluorophenyl)-1-(1-methylethyl)-1H-benzimidazol-4-amine,
2-(4-fluorophenyl)-1-(1-methylethyl)-N-[6-(2-methyl-5-oxazolyl)-3-pyridinyl]-1H-benzimidazol-4-amine,
2-(2,4-difluorophenyl)-1-methyl-N-[4-(2-methyl-5-oxazolyl)phenyl]-1H-imidazo[4,5-c]pyridin-4-amine,
2-(2,4-difluorophenyl)-N-[3-methoxy-4-(4-methyl-5-oxazolyl)phenyl]-1-methyl-1H-imidazo[4,5-c]pyridin-4-amine,
2-(2,4-difluorophenyl)-N-[3-fluoro-4-(2-methyl-5-oxazolyl)phenyl]-1-methyl-1H-imidazo[4,5-c]pyridin-4-amine,
6-fluoro-2-(3-methoxyphenyl)-1-methyl-N-[4-(2-methyl-5-oxazolyl)phenyl]-1H-benzimidazol-4-amine,
2-(4-fluoro-2-methylphenyl)-N-[4-(2-methyl-5-oxazolyl)phenyl]-imidazo[1,2-a]pyrazin-8-amine,
2-(4-fluorophenyl)-1,6-dimethyl-N-[4-(2-methyl-5-oxazolyl)phenyl]-1H-imidazo[4,5-c]pyridin-4-amine,
2-(4-fluorophenyl)-N-[3-methoxy-4-(2-methyl-5-oxazolyl)phenyl]-1,6-dimethyl-1H-imidazo[4,5-c]pyridin-4-amine,
6-bromo-2-(4-fluoro-2-methylphenyl)-N-[4-(2-methyl-5-oxazolyl)phenyl]-imidazo[1,2-a]pyrazin-8-amine,
1-methyl-N-[6-(4-methyl-5-oxazolyl)-3-pyridinyl]-2-(phenoxymethyl)-1H-benzimidazol-4-amine,
2-(4-chloro-3-methoxyphenyl)-N-[3-methoxy-4-(2-methyl-5-oxazolyl)phenyl]-1-methyl-1H-benzimidazol-4-amine,
N-[3-methoxy-4-(2-methyl-5-oxazolyl)phenyl]-2-(3-methoxyphenyl)-1-methyl-1H-benzimidazol-4-amine,
2-(cyclopropylmethyl)-1-ethyl-N-[3-methoxy-4-(2-methyl-5-oxazolyl)phenyl]-1H-benzimidazol-4-amine,
N-[3-fluoro-4-(4-methyl-5-oxazolyl)phenyl]-2-(4-fluorophenyl)-1-(1-methylethyl)-1H-benzimidazol-4-amine,
2-(cyclopropylmethyl)-N-[3-fluoro-4-(2-methyl-5-oxazolyl)phenyl]-1-methyl-1H-imidazo[4,5-c]pyridin-4-amine,
2-(4-fluorophenyl)-N-[3-methoxy-4-(2-methyl-5-thiazolyl)phenyl]-1-(1-methylethyl)-1H-benzimidazol-4-amine,
N-[3-fluoro-4-(2-methyl-5-oxazolyl)phenyl]-2-(3-methoxyphenyl)-1-methyl-1H-imidazo[4,5-c]pyridin-4-amine,
2-(2,4-difluorophenyl)-N-[3-methoxy-4-(2-methyl-5-thiazolyl)phenyl]-1-methyl-1H-imidazo[4,5-c]pyridin-4-amine,
N-[3-fluoro-4-(2-methyl-5-oxazolyl)phenyl]-2-(4-fluorophenyl)-3-methyl-3H-imidazo[4,5-b]pyridin-7-amine,
N-[3-methoxy-4-(4-methyl-5-oxazolyl)phenyl]-1-methyl-6-(trifluoromethyl)-2-(3,3,3-trifluoropropyl)-1H-benzimidazol-4-amine,
N-[3-methoxy-4-(4-methyl-5-oxazolyl)phenyl]-2-methyl-6-(trifluoromethyl)-imidazo[1,2-a]pyridin-8-amine,
2-(4-fluorophenyl)-1-methyl-N-[4-(1-methyl-1H-pyrazol-4-yl)phenyl]-1H-benzimidazol-4-amine,
8-[[3-fluoro-4-(2-methyl-5-oxazolyl)phenyl]amino]-N,N-dimethyl-6-(trifluoromethyl)-imidazo[1,2-a]pyridine-2-carboxamide,
6-fluoro-2-(3-methoxyphenyl)-1-methyl-N-[6-(2-methyl-5-oxazolyl)-3-pyridinyl]-1H-benzimidazol-4-amine,
N-[3-methoxy-4-(4-methyl-5-oxazolyl)phenyl]-2,3-dimethyl-6-(trifluoromethyl)-imidazo[1,2-a]pyridin-8-amine,
N-[3-methoxy-4-(2-methyl-5-oxazolyl)phenyl]-2-methyl-6-(trifluoromethyl)-imidazo[1,2-a]pyrazin-8-amine,
6-bromo-2-methyl-N-[4-(2-methyl-5-oxazolyl)phenyl]-imidazo[1,2-a]pyrazin-8-amine,
8-[[3-methoxy-4-(4-methyl-5-oxazolyl)phenyl]amino]-N,N-dimethyl-6-(trifluoromethyl)-imidazo[1,2-a]pyridine-2-carboxamide,
2-(4-fluorophenyl)-1-methyl-N-[6-(2-methyl-5-oxazolyl)-3-pyridinyl]-6-(trifluoromethyl)-1H-benzimidazol-4-amine,
1-methyl-2-[(1-methylethoxy)methyl]-N-[4-(2-methyl-5-oxazolyl)phenyl]-1H-benzimidazol-4-amine,
2-(4-fluorophenyl)-1-methyl-N-[6-(1-methyl-1H-pyrazol-4-yl)-3-pyridinyl]-1H-benzimidazol-4-amine,
2,3-dimethyl-N-[4-[2-(1-methylethyl)-5-oxazolyl]phenyl]-imidazo[1,2-a]pyridin-8-amine,
N-[3-methoxy-4-(4-methyl-5-oxazolyl)phenyl]-2,3-dimethyl-imidazo[1,2-a]pyridin-8-amine,
1-[8-[[3-methoxy-4-(4-methyl-5-oxazolyl)phenyl]amino]-6-(trifluoromethyl)imidazo[1,2-a]pyridin-2-yl]-ethanone,
N-[3-methoxy-4-(2-methyl-5-oxazolyl)phenyl]-1-methyl-2-(3,3,3-trifluoropropyl)-1H-imidazo[4,5-c]pyridin-4-amine,
2-(4-fluorophenyl)-N-[3-methoxy-4-(4-methyl-5-oxazolyl)phenyl]-1,6-dimethyl-1H-imidazo[4,5-c]pyridin-4-amine,
8-[[3-methoxy-4-(4-methyl-5-oxazolyl)phenyl]amino]-2-methyl-imidazo[1,2-a]pyridine-6-carbonitrile,
N-[3-methoxy-4-(2-methyl-5-oxazolyl)phenyl]-2-methyl-6-(trifluoromethyl)-imidazo[1,2-b]pyridazin-8-amine,
N-[3-methoxy-4-(4-methyl-5-oxazolyl)phenyl]-2-methyl-6-(trifluoromethyl)-imidazo[1,2-b]pyridazin-8-amine,
6-fluoro-N-[3-methoxy-4-(2-methyl-5-oxazolyl)phenyl]-1-methyl-2-(1-pyrrolidinyl)-1H-benzimidazol-4-amine,
2-(4-fluorophenyl)-N-[3-methoxy-4-(1-methyl-1H-1,2,4-triazol-5-yl)phenyl]-1-methyl-1H-benzimidazol-4-amine,
6-fluoro-1-methyl-N-[4-(2-methyl-5-oxazolyl)phenyl]-2-(1-pyrrolidinyl)-1H-benzimidazol-4-amine,
6-fluoro-2-(4-fluoro-2-methylphenyl)-N-[3-methoxy-4-(4-methyl-5-oxazolyl)phenyl]-imidazo[1,2-a]pyridin-8-amine,
2-(4-fluoro-2-methylphenyl)-8-[[3-methoxy-4-(4-methyl-5-oxazolyl)phenyl]amino]-imidazo[1,2-a]pyridine-6-carbonitrile,
2-(4-fluorophenyl)-N-[3-methoxy-4-(4-methyl-5-oxazolyl)phenyl]-3-methyl-3H-imidazo[4,5-c]pyridin-7-amine, 2-(4-fluorophenyl)-N-[3-methoxy-4-(2-methyl-5-oxazolyl)phenyl]-3-methyl-3H-imidazo[4,5-c]pyridin-7-amine,
N-[3-methoxy-4-(2-methyl-5-oxazolyl)phenyl]-2-(3-methoxyphenyl)-1,6-dimethyl-1H-imidazo[4,5-c]pyridin-4-amine,
1-methyl-2-(4-methyl-5-oxazolyl)-N-[4-(2-methyl-5-oxazolyl)phenyl]-6-(trifluoromethyl)-1H-benzimidazol-4-amine,
2-(3-methoxyphenyl)-1,6-dimethyl-N-[4-(2-methyl-5-oxazolyl)phenyl]-1H-imidazo[4,5-c]pyridin-4-amine,
2-(4-fluorophenyl)-1-methyl-N-[5-(2-methyl-5-oxazolyl)-2-pyrimidinyl]-1H-benzimidazol-4-amine,
N-[3-methoxy-4-(4-methyl-5-oxazolyl)phenyl]-2-(3-methoxyphenyl)-1,6-dimethyl-1H-imidazo[4,5-c]pyridin-4-amine,
2-(3-methoxyphenyl)-1-methyl-4-[[6-(2-methyl-5-oxazolyl)-3-pyridinyl]amino]-1H-benzimidazole-6-carbonitrile,
N-[3-methoxy-4-(4-methyl-5-oxazolyl)phenyl]-2-methyl-imidazo[1,2-a]pyrazin-8-amine,
6-fluoro-N-[3-methoxy-4-(4-methyl-5-oxazolyl)phenyl]-2-(2-methylpropyl)-imidazo[1,2-a]pyridin-8-amine,
2-(4-fluorophenyl)-7-[[3-methoxy-4-(2-methyl-5-oxazolyl)phenyl]amino]-3-methyl-3H-imidazo[4,5-b]pyridine-5-carbonitrile,
1-methyl-N-[4-(2-methyl-5-oxazolyl)phenyl]-2-(tetrahydro-2H-pyran-4-yl)-6-(trifluoromethyl)-1H-benzimidazol-4-amine,
2-(4-fluorophenyl)-1-methyl-N-[4-(1-methyl-1H-pyrazol-5-yl)phenyl]-1H-benzimidazol-4-amine,
2-(4-fluorophenyl)-6-methoxy-N-[3-methoxy-4-(2-methyl-5-oxazolyl)phenyl]-1-methyl-1H-benzimidazol-4-amine,
N-[3-methoxy-4-(2-methyl-5-oxazolyl)phenyl]-1-(1-methylethyl)-2-(tetrahydro-2H-pyran-4-yl)-1H-benzimidazol-4-amine,
2-(4-fluorophenyl)-N-[3-methoxy-4-(2-methyl-5-oxazolyl)phenyl]-3,5-dimethyl-3H-imidazo[4,5-b]pyridin-7-amine,
4-[[3-methoxy-4-(4-methyl-5-oxazolyl)phenyl]amino]-2-(3-methoxyphenyl)-1-methyl-1H-benzimidazole-6-carbonitrile,
2-(4-fluorophenyl)-1-methyl-N-[5-(1-methyl-1H-pyrazol-5-yl)-2-pyridinyl]-1H-benzimidazol-4-amine,
2-(ethoxymethyl)-N-[3-methoxy-4-(4-methyl-5-oxazolyl)phenyl]-6-(trifluoromethyl)-imidazo[1,2-a]pyridin-8-amine,
2-(4-fluoro-2-methylphenyl)-8-[[3-methoxy-4-(4-methyl-5-oxazolyl)phenyl]amino]-imidazo[1,2-a]pyridine-6-methanamine,
N-[3-methoxy-4-(2-methyl-5-oxazolyl)phenyl]-1,6-dimethyl-2-(tetrahydro-2H-pyran-4-yl)-1H-imidazo[4,5-c]pyridin-4-amine,
5-cyclopropyl-2-(4-fluorophenyl)-N-[3-methoxy-4-(2-methyl-5-oxazolyl)phenyl]-3-methyl-3H-imidazo[4,5-b]pyridin-7-amine,
2-(4-fluorophenyl)-3-(1-methylethenyl)-N-[4-(2-methyl-5-oxazolyl)phenyl]-imidazo[1,2-a]pyridin-8-amine,
6-cyclopropyl-2-(4-fluorophenyl)-N-[3-methoxy-4-(2-methyl-5-oxazolyl)phenyl]-1-methyl-1H-imidazo[4,5-c]pyridin-4-amine,
2-(4-fluorophenyl)-3-(1-methylethyl)-N-[4-(2-methyl-5-oxazolyl)phenyl]-imidazo[1,2-a]pyridin-8-amine,
2-(4-fluorophenyl)-4-[[3-methoxy-4-(4-methyl-5-oxazolyl)phenyl]amino]-1-methyl-1H-benzimidazole-6-carbonitrile,
8-[[3-methoxy-4-(4-methyl-5-oxazolyl)phenyl]amino]-2-(2-methylpropyl)-imidazo[1,2-a]pyridine-6-carbonitrile,
N-[3-methoxy-4-(2-methyl-5-oxazolyl)phenyl]-1,6-dimethyl-2-[3-(1-methylethoxy)phenyl]-1H-imidazo[4,5-c]pyridin-4-amine,
6-fluoro-N-[4-(2-methyl-5-oxazolyl)phenyl]-2-(2-methylpropyl)-imidazo[1,2-a]pyridin-8-amine,
2-(4-fluorophenyl)-1-methyl-N-[6-(2-methyl-5-thiazolyl)-3-pyridinyl]-1H-benzimidazol-4-amine,
6-fluoro-2-(4-fluoro-2-methylphenyl)-N-[4-(2-methyl-5-oxazolyl)phenyl]-imidazo[1,2-a]pyridin-8-amine,
2-(4-fluoro-2-methylphenyl)-N-[3-methoxy-4-(4-methyl-5-oxazolyl)phenyl]-6-methyl-imidazo[1,2-a]pyridin-8-amine,
2-(4-fluorophenyl)-1-methyl-N-[4-(4-methyl-5-oxazolyl)phenyl]-1H-benzimidazol-4-amine,
2-(3-methoxyphenyl)-3-methyl-N-[4-(4-methyl-5-oxazolyl)phenyl]-imidazo[1,2-a]pyridin-8-amine,
6-fluoro-$N^4$-[3-methoxy-4-(2-methyl-5-oxazolyl)phenyl]-$N^2$,1-dimethyl-$N^2$-(2-methylpropyl)-1H-benzimidazole-2,4-diamine,
N-[3-methoxy-4-(4-methyl-5-oxazolyl)phenyl]-2-(tetrahydro-2H-pyran-4-yl)-imidazo[1,2-a]pyridin-8-amine,
2-(4-fluorophenyl)-4-[[3-methoxy-4-(4-methyl-5-oxazolyl)phenyl]amino]-1-methyl-1H-benzimidazole-6-methanamine,
N-[6-(4-methyl-5-oxazolyl)-3-pyridinyl]-2-(tetrahydro-2H-pyran-4-yl)-imidazo[1,2-a]pyridin-8-amine,
2-(4-fluorophenyl)-1-methyl-4-[[6-(4-methyl-5-oxazolyl)-3-pyridinyl]amino]-1H-benzimidazole-6-carbonitrile,
6-cyclopropyl-N-[3-methoxy-4-(4-methyl-5-oxazolyl)phenyl]-2-methyl-imidazo[1,2-a]pyrazin-8-amine,
2-(3-chlorophenyl)-1-(1-methylethyl)-N-[6-(4-methyl-5-oxazolyl)-3-pyridinyl]-1H-benzimidazol-4-amine,
2-(4-fluorophenyl)-1-(1-methylethyl)-N-[6-(4-methyl-5-oxazolyl)-3-pyridinyl]-1H-benzimidazol-4-amine,
2-(2-chlorophenyl)-6-fluoro-1-methyl-N-[6-(4-methyl-5-oxazolyl)-3-pyridinyl]-1H-benzimidazol-4-amine,
2-(2-chlorophenyl)-1-methyl-N-[6-(4-methyl-5-oxazolyl)-3-pyridinyl]-1H-imidazo[4,5-c]pyridin-4-amine,
N-[4-(2,4-dimethyl-5-oxazolyl)phenyl]-2-(4-fluorophenyl)-1-methyl-1H-benzimidazol-4-amine,
2-(4-fluorophenyl)-1-methyl-4-[[6-(2-methyl-5-oxazolyl)-3-pyridinyl]amino]-1H-benzimidazole-6-carbonitrile,
6-fluoro-2-(4-fluoro-2-methylphenyl)-N-[6-(2-methyl-5-oxazolyl)-3-pyridinyl]-imidazo[1,2-a]pyridin-8-amine,
2-(2-chlorophenyl)-1-methyl-N-[6-(2-methyl-5-oxazolyl)-3-pyridinyl]-1H-imidazo[4,5-c]pyridin-4-amine,
2-(4-fluorophenyl)-N-[3-methoxy-4-(2-methyl-5-oxazolyl)phenyl]-3-methyl-5-(1-methylethyl)-3H-imidazo[4,5-b]pyridin-7-amine,
6-fluoro-2-(4-fluorophenyl)-1-methyl-N-[6-(4-methyl-5-oxazolyl)-3-pyridinyl]-1H-benzimidazol-4-amine,
6-fluoro-2-(4-fluorophenyl)-1-methyl-N-[6-(2-methyl-5-oxazolyl)-3-pyridinyl]-1H-benzimidazol-4-amine,
2-(2-chlorophenyl)-6-fluoro-1-methyl-N-[6-(2-methyl-5-oxazolyl)-3-pyridinyl]-1H-benzimidazol-4-amine,
6-chloro-N-[3-methoxy-4-(4-methyl-5-oxazolyl)phenyl]-2-(tetrahydro-2H-pyran-4-yl)-imidazo[1,2-a]pyridin-8-amine,
2-(5-chloro-2-thienyl)-1-(1-methylethyl)-N-[6-(4-methyl-5-oxazolyl)-3-pyridinyl]-1H-benzimidazol-4-amine,
N-[6-(2,4-dimethyl-5-oxazolyl)-3-pyridinyl]-2-(4-fluorophenyl)-1-(1-methylethyl)-1H-benzimidazol-4-amine,
2-(2-chlorophenyl)-N-[6-(2,4-dimethyl-5-oxazolyl)-3-pyridinyl]-6-fluoro-1-methyl-1H-benzimidazol-4-amine,
N-[3-methoxy-4-(2-methyl-5-oxazolyl)phenyl]-3-(3-methoxypropyl)-2-[2-(trifluoromethyl)phenyl]-imidazo[1,2-a]pyridin-8-amine, 2-(4-fluorophenyl)-3-methyl-N-[6-(2-methyl-5-oxazolyl)-3-pyridinyl]-3H-imidazo[4,5-c]pyridin-7-amine,
2-(4-fluorophenyl)-3-iodo-N-[4-(2-methyl-5-oxazolyl)phenyl]-imidazo[1,2-a]pyridin-8-amine,
3-methyl-N-[6-(2-methyl-5-oxazolyl)-3-pyridinyl]-2-[2-(trifluoromethyl)phenyl]-imidazo[1,2-a]pyridin-8-amine,
8-[[3-methoxy-4-(4-methyl-5-oxazolyl)phenyl]amino]-2-(2-methylpropyl)-imidazo[1,2-a]pyridine-6-carboxylic acid methyl ester,
N-[4-(2,4-dimethyl-5-oxazolyl)-3-methoxyphenyl]-2-(4-fluorophenyl)-1-(1-methylethyl)-1H-benzimidazol-4-amine,
N-[4-(2,4-dimethyl-5-oxazolyl)phenyl]-2-(4-fluorophenyl)-1-(1-methylethyl)-1H-benzimidazol-4-amine,
2-cyclopropyl-N-[6-(4-methyl-5-oxazolyl)-3-pyridinyl]-imidazo[1,2-a]pyridin-8-amine,
2-cyclopropyl-N-[4-(2-methyl-5-oxazolyl)phenyl]-imidazo[1,2-a]pyridin-8-amine,
6-fluoro-2-(4-fluorophenyl)-1-(1-methylethyl)-N-[6-(2-methyl-5-oxazolyl)-3-pyridinyl]-1H-benzimidazol-4-amine,
6-fluoro-N-[3-methoxy-4-(4-methyl-5-oxazolyl)phenyl]-2-(tetrahydro-2H-pyran-4-yl)-imidazo[1,2-a]pyridin-8-amine,
2-(4-fluorophenyl)-3-(methoxymethyl)-N-[3-methoxy-4-(2-methyl-5-oxazolyl)phenyl]-imidazo[1,2-a]pyridin-8-amine,
2-[1-(4-chlorophenyl)cyclopropyl]-1-methyl-N-[6-(2-methyl-5-oxazolyl)-3-pyridinyl]-1H-benzimidazol-4-amine,
N-[6-(4-methyl-5-oxazolyl)-3-pyridinyl]-2-[(tetrahydro-2H-pyran-4-yl)methyl]-imidazo[1,2-a]pyridin-8-amine,
2-[1-(4-chlorophenyl)ethyl]-1-methyl-N-[6-(2-methyl-5-oxazolyl)-3-pyridinyl]-1H-benzimidazol-4-amine,
2-(2-chlorophenyl)-N-[3-methoxy-4-(4-methyl-5-oxazolyl)phenyl]-1,6-dimethyl-1H-imidazo[4,5-c]pyridin-4-amine,
2-(2-chlorophenyl)-1,6-dimethyl-N-[6-(4-methyl-5-oxazolyl)-3-pyridinyl]-1H-imidazo[4,5-c]pyridin-4-amine,
6-chloro-2-(5-fluoro-2-methylphenyl)-N-[6-(5-methyl-4-oxazolyl)-3-pyridinyl]-imidazo[1,2-b]pyridazin-8-amine,
1-[8-[[3-methoxy-4-(4-methyl-5-oxazolyl)phenyl]amino]-2-(2-methylpropyl)imidazo[1,2-a]pyridin-6-yl]-ethanone,
2-(4-fluorophenyl)-3-(2-methoxyethyl)-N-[3-methoxy-4-(2-methyl-5-oxazolyl)phenyl]-imidazo[1,2-a]pyridin-8-amine,
2-(4-fluorophenyl)-N-[4-[2-(methoxymethyl)-5-oxazolyl]phenyl]-1-(1-methylethyl)-1H-benzimidazol-4-amine,
2-(2-chlorophenyl)-3-methyl-N-[6-(2-methyl-5-oxazolyl)-3-pyridinyl]-imidazo[1,2-a]pyridin-8-amine,
2-methyl-N-[6-(2-methyl-5-oxazolyl)-3-pyridinyl]-imidazo[1,2-a]pyridin-8-amine,
2-(4-fluorophenyl)-3-methyl-5-(1-methylethyl)-N-[6-(2-methyl-5-oxazolyl)-3-pyridinyl]-3H-imidazo[4,5-b]pyridin-7-amine,
2-(4-fluorophenyl)-3-methoxy-N-[6-(4-methyl-5-oxazolyl)-3-pyridinyl]-imidazo[1,2-a]pyridin-8-amine,
2-(5-fluoro-2-methylphenyl)-N-[6-(4-methyl-5-oxazolyl)-3-pyridinyl]-imidazo[1,2-b]pyridazin-8-amine,
2-(4-fluorophenyl)-N-[3-methoxy-4-(1-methyl-1H-1,2,3-triazol-4-yl)phenyl]-1-methyl-1H-benzimidazol-4-amine,
2-(4-fluorophenyl)-N-[3-methoxy-4-(2-methyl-2H-1,2,3-triazol-4-yl)phenyl]-1-methyl-1H-benzimidazol-4-amine,
2-(4-fluorophenyl)-N-[3-methoxy-4-(2-methyl-4-pyridinyl)phenyl]-1-methyl-1H-benzimidazol-4-amine,
2-(4-fluorophenyl)-N-[3-methoxy-4-(2-methyl-4-pyridinyl)phenyl]-1,6-dimethyl-1H-imidazo[4,5-c]pyridin-4-amine,
2-(4-fluorophenyl)-1-methyl-N-[4-(2-methyl-4-pyridinyl)phenyl]-1H-benzimidazol-4-amine,
2-(2-chlorophenyl)-N-[3-methoxy-4-(2-methyl-4-pyridinyl)phenyl]-3-methyl-imidazo[1,2-a]pyridin-8-amine,
2-(4-fluorophenyl)-N-[3-methoxy-4-(2-methyl-4-pyridinyl)phenyl]-1-(1-methylethyl)-1H-benzimidazol-4-amine,
2-(4-fluorophenyl)-1,6-dimethyl-N-[4-(2-methyl-4-pyridinyl)phenyl]-1H-imidazo[4,5-c]pyridin-4-amine,
2-(4-fluorophenyl)-1-(1-methylethyl)-N-[4-(2-methyl-4-pyridinyl)phenyl]-1H-benzimidazol-4-amine,
2-(2-chlorophenyl)-3-methyl-N-[4-(2-methyl-4-pyridinyl)phenyl]-imidazo[1,2-a]pyridin-8-amine,
2-(4-fluorophenyl)-N-(2-methoxy-2'-methyl[3,4'-bipyridin]-6-yl)-1-(1-methylethyl)-1H-benzimidazol-4-amine,
2-(4-fluorophenyl)-N-(2-methoxy-2'-methyl[3,4'-bipyridin]-6-yl)-1-methyl-1H-benzimidazol-4-amine,
2-(2-chlorophenyl)-N-(2-methoxy-2'-methyl[3,4'-bipyridin]-6-yl)-3-methyl-imidazo[1,2-a]pyridin-8-amine,
2-(4-fluorophenyl)-N-[6-methoxy-5-(1-methyl-1H-pyrazol-4-yl)-2-pyridinyl]-1-(1-methylethyl)-1H-benzimidazol-4-amine,
2-(4-fluorophenyl)-N-[6-methoxy-5-(1-methyl-1H-pyrazol-4-yl)-2-pyridinyl]-1-methyl-1H-benzimidazol-4-amine,
N-[4-(2,6-dimethyl-4-pyridinyl)phenyl]-2-(4-fluorophenyl)-1-(1-methylethyl)-1H-benzimidazol-4-amine,
N-[3-fluoro-4-(2-methyl-4-pyridinyl)phenyl]-2-(4-fluorophenyl)-1-methyl-1H-benzimidazol-4-amine,
N-[3-fluoro-4-(2-methyl-4-pyridinyl)phenyl]-2-(4-fluorophenyl)-1-(1-methylethyl)-1H-benzimidazol-4-amine,
2-(2-chlorophenyl)-N-[3-fluoro-4-(2-methyl-4-pyridinyl)phenyl]-3-methyl-imidazo[1,2-a]pyridin-8-amine,
N-[3-fluoro-4-(2-methyl-4-pyridinyl)phenyl]-2-(4-fluorophenyl)-1,6-dimethyl-1H-imidazo[4,5-c]pyridin-4-amine,
2-(4-fluorophenyl)-1-methyl-N-[6-(2-methyl-4-pyridinyl)-3-pyridazinyl]-1H-benzimidazol-4-amine,
2-(4-fluorophenyl)-1,6-dimethyl-N-[6-(2-methyl-4-pyridinyl)-3-pyridazinyl]-1H-imidazo[4,5-c]pyridin-4-amine, and
2-(4-fluorophenyl)-1-methyl-N-[4-(4-pyridinyl)phenyl]-1H-benzimidazol-4-amine, including any stereochemically isomeric form thereof,
and the pharmaceutically acceptable addition salts and the solvates thereof.

In an embodiment preferably said compound of Formula (I) is 2-(4-fluorophenyl)-N-[3-methoxy-4-(4-methyl-5-oxazolyl)phenyl]-1-methyl-1H-benzimidazol-4-amine, including any stereochemically isomeric forms thereof, and the pharmaceutically acceptable addition salts and the solvates thereof.

In an embodiment preferably said compound of Formula (I) is 2-(4-fluorophenyl)-N-[3-methoxy-4-(2-methyl-5-oxazolyl)phenyl]-1-methyl-1H-benzimidazol-4-amine, including any stereochemically isomeric forms thereof, and the pharmaceutically acceptable addition salts and the solvates thereof.

In an embodiment preferably said compound of Formula (I) is 2-(4-fluorophenyl)-1-(1-methylethyl)-N-[6-(2-methyl-5-oxazolyl)-3-pyridinyl]-1H-benzimidazol-4-amine, including any stereochemically isomeric forms thereof, and the pharmaceutically acceptable addition salts and the solvates thereof.

In an embodiment preferably said compound of Formula (I) is 2-(4-fluorophenyl)-1-(1-methylethyl)-N-[6-(2-methyl-5-oxazolyl)-3-pyridinyl]-1H-benzimidazol-4-amine In an embodiment the compound of Formula (I) is selected from the group consisting of:

2-(4-fluorophenyl)-1-(1-methylethyl)-N-[6-(2-methyl-5-ox-azolyl)-3-pyridinyl]-1H-benzimidazol-4-amine,
6-fluoro-N-[3-methoxy-4-(4-methyl-5-oxazolyl)phenyl]-2-(2-methylpropyl)-imidazo[1,2-a]pyridin-8-amine .HCl,
2-(4-fluorophenyl)-6-methoxy-N-[3-methoxy-4-(2-methyl-5-oxazolyl)phenyl]-1-methyl-1H-benzimidazol-4-amine,
2-(4-fluorophenyl)-N-[3-methoxy-4-(4-methyl-5-oxazolyl)phenyl]-1-methyl-1H-benzimidazol-4-amine,
2-(4-fluorophenyl)-N-[3-methoxy-4-(2-methyl-4-pyridinyl)phenyl]-1-(1-methylethyl)-1H-benzimidazol-4-amine,
including any stereochemically isomeric forms thereof, and the pharmaceutically acceptable addition salts and the solvates thereof.

In the passages above, the features of an embodiment can be combined with the features of another embodiment or combinations of embodiments.

The present invention also encompasses processes for the preparation of compounds of Formula (I) and subgroups thereof. In the reactions described, it can be necessary to protect reactive functional groups, for example hydroxy, amino, or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1999.

The compounds of Formula (I) and the subgroups thereof can be prepared by a succession of steps as described hereunder. They are generally prepared from starting materials which are either commercially available or prepared by standard means obvious to those skilled in the art. The compounds of the present invention can be also prepared using standard synthetic processes commonly used by those skilled in the art of organic chemistry.

The general preparation of some typical examples is shown below:

EXPERIMENTAL PROCEDURE 1

In general, compounds of formula (I), can be prepared as set out below in Scheme 1 wherein all variables are defined as hereabove:

Compounds of formula (I) can be prepared via a coupling reaction between intermediates of formula (II-a) and (III-a) or between intermediates of formula (II-b) and (III-b), wherein Halo is defined as Cl, Br or I and wherein all other variables are as defined hereinbefore. This reaction may be performed in the presence of a suitable base such as, for example, $Cs_2CO_3$ or sodium tert-butoxide. The reaction can be performed in a reaction-inert solvent such as, for example, toluene, N,N-dimethylformamide (DMF), tert-butanol or dioxane. The reaction typically is performed in the presence of a catalyst system comprising of a suitable catalyst such as palladium(II) acetate $(Pd(OAc)_2)$ or tris(dibenzylideneacetone)dipalladium $(Pd_2(dba)_3)$ and a ligand such as (9,9-dimethyl-9H-xanthene-4,5-diyl)bis[diphenylphosphine] (Xantphos), [1,1'-binaphthalene]-2,2'-diylbis[diphenylphosphine] (BINAP), or dicyclohexyl[2',4',6'-tris(1-methylethyl)[1,1'-biphenyl]-2-yl]-phosphine (X-phos). Preferably this reaction is carried out under an inert atmosphere, such as a nitrogen or an argon atmosphere. Reaction rate and yield may be enhanced by microwave assisted heating.

In an alternative procedure, that is only valid when $Y^1$, $Y^3$, $Z^1$ or $Z^3$ is N in the definition of $Het^2$, a compound of formula (I) wherein $Y^1$, $Y^3$, $Z^1$ or $Z^3$ is N, can be prepared via an aromatic nucleophilic substitution between intermediates of formula (II-a) and (III-a). This reaction may be performed in the presence of a suitable base such as, for example, $K_2CO_3$ or diisopropylethylamine. The reaction can be performed in a reaction-inert solvent such as, for example, DMF or $CH_3CN$. This reaction may also be performed under acidic conditions, for example, in the presence of HCl or methanesulfonic acid. This reaction can be performed in a reaction-inert solvent such as, for example, 2-propanol. Reaction rate and yield may be enhanced by microwave assisted heating.

EXPERIMENTAL PROCEDURE 2

Compounds of formula (I), can also be prepared via a coupling reaction between an intermediate of formula (IV) and an intermediate of formula (V) according to Scheme 2 wherein Halo is defined as Cl, Br or I and wherein all other variables are as defined before.

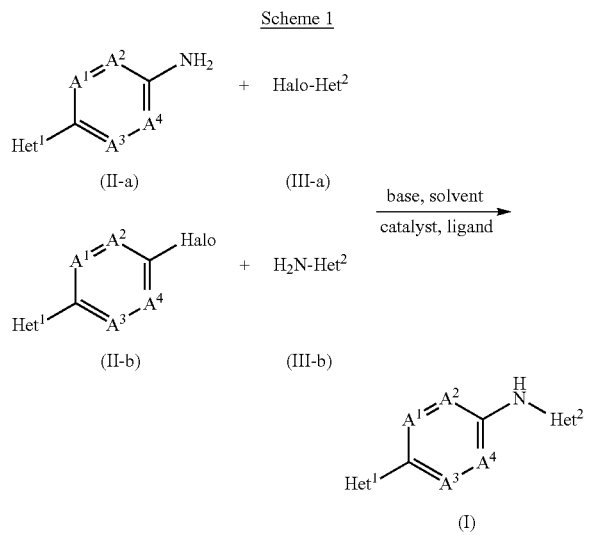

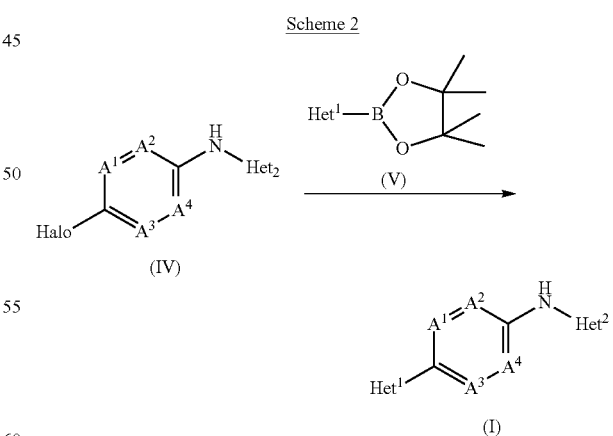

In Scheme 2, intermediate of formula (V) may be commercially available or may be prepared according to conventional reaction procedures generally know in the art. The coupling reaction is performed in the presence of a suitable base such as, for example, $Cs_2CO_3$, $Na_2CO_3$ or NaOH. The reaction can be performed in a reaction-inert solvent such as, for example, toluene, DMF or dioxane. The reaction typically is performed in the presence of a catalyst such as tetrakis(triphenylphosphine)palladium (Pd(PPh$_3$)$_4$). Stirring, elevated temperatures (for example between 70-140° C.) and/or pressure may enhance the rate of the reaction. Preferably this reaction is carried out under an inert atmosphere, such as a nitrogen or argon atmosphere.

Alternatively, the boronic acid picanol ester derivative of formula (V) can be replaced by the corresponding boronic acid derivative.

EXPERIMENTAL PROCEDURE 3

Alternatively compounds of formula (I), can also be prepared via a coupling reaction between an intermediate of formula (VI) and an intermediate of formula (VII) according to Scheme 3 wherein Halo is defined as Cl, Br or I and wherein all other variables are as defined before.

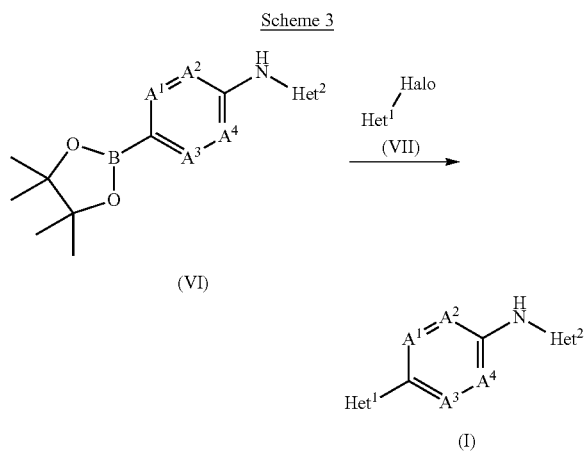

In Scheme 3 intermediates of formula (VII) may be commercially available or may be prepared according to conventional reaction procedures generally know in the art. The reaction conditions are analogous to the reaction conditions described in experimental procedure 2.

EXPERIMENTAL PROCEDURE 4

An intermediate of formula (II-a) can be prepared by reduction of an intermediate of formula (VIII) as is shown in Scheme 4, wherein all variables are as defined before.

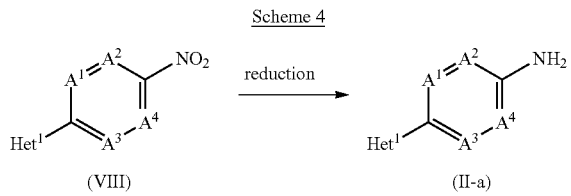

The reduction of (VIII) to (II-a) can be conducted by conventional methods such as, for example, a reductive hydrogenation or reduction with a metal or a metal salt and an acid [for example a metal such as iron or a metal salt such as SnCl$_2$ and acid such as an inorganic acid (hydrochloric acid, sulfuric acid or the like) or an organic acid (acetic acid or the like)], or other well-known methods for converting a nitro-group to the corresponding amine

EXPERIMENTAL PROCEDURE 5

An intermediate of formula (VIII) wherein Het$^1$ is restricted to oxazole substituted with R$^0$ in the 4-position, hereby named intermediate of formula (XI), can be prepared by a condensation reaction of an intermediate of formula (X) with an intermediate of formula (IX) as is illustrated in Scheme 5. Intermediate (IX) may be commercially available or may be prepared according to conventional reaction procedures generally know in the art. This condensation reaction is performed in the presence of a suitable base such as, for example, K$_2$CO$_3$ or sodium ethoxide (NaOEt). The reaction can be performed in a protic solvent such as, for example, methanol (MeOH) or ethanol (EtOH). Stirring and/or elevated temperatures (for example between 70-110° C.) may enhance the rate of the reaction. In Scheme 5, all variables are defined as mentioned hereabove.

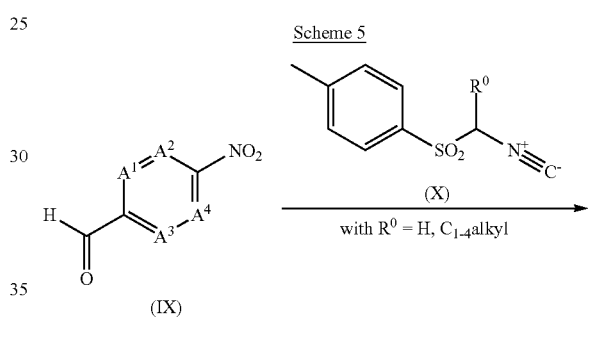

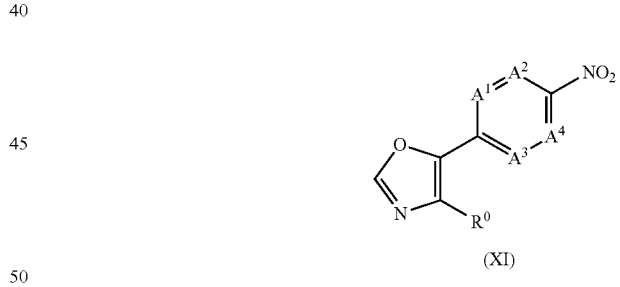

Alternatively, the reaction described in Scheme 5 may also be performed with a benzaldehyde derivative of the intermediate of formula (IX) wherein NO$_2$ is replaced by Cl, Br, I, or NH-Het$^2$.

EXPERIMENTAL PROCEDURE 6

An intermediate of formula (II-a) can also be prepared by conversion of the Halo-substitutent in an intermediate of formula (II-b) into an amino-group, or a masked or protected amino functionality which can subsequently be converted into an amino-group, according to Scheme 6 by using reaction conditions well known to those skilled in the art. In Scheme 6, Halo is defined as Cl, Br or I, and all other variables are defined as mentioned hereabove.

Scheme 6

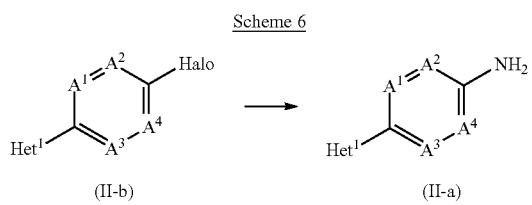

The intermediate of formula (II-b), wherein Het[1] is limited to oxazole substituted with R[0], hereby named intermediate of formula (XII-b), can be prepared according to the synthesis protocol that was used for the synthesis of intermediate (XI), starting from an intermediate of formula (XII):

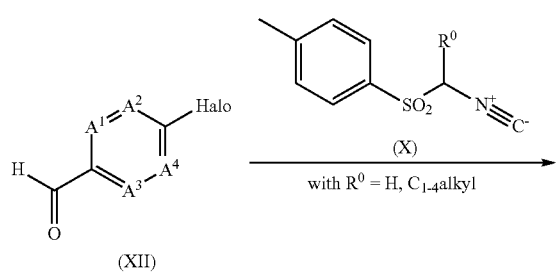

The intermediate of formula (XII) is commercially available or may be prepared according to conventional reaction procedures generally known in the art.

EXPERIMENTAL PROCEDURE 7

An intermediate of formula (VIII) wherein Het[1] is restricted to oxazole substituted with R[1] in the 2-position and CH$_3$ in the 4-position, hereby named an intermediate of formula (XIII), can be prepared by a condensation reaction of an intermediate of formula (XIV) with an intermediate of formula (IX) according to Scheme 7 wherein all variables are defined as hereinbefore. Both intermediates may be commercially available or may be prepared according to conventional reaction procedures generally know in the art. This condensation reaction typically can be performed in a solvent such as pyridine. Stirring and/or elevated temperatures (for example between 70-110° C.) may enhance the rate of the reaction.

Scheme 7

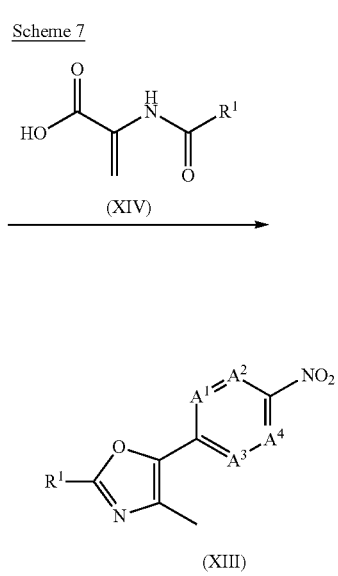

EXPERIMENTAL PROCEDURE 8

An intermediate of formula (IV) can be prepared via a coupling reaction between an intermediate of formula (XV) and an intermediate of formula (III-a), as is shown in Scheme 8 wherein Halo is defined as Cl, Br or I and wherein all other variables are defined as hereinbefore. This reaction may be performed in analogy to the synthesis protocol described in Experimental procedure 1.

Scheme 8

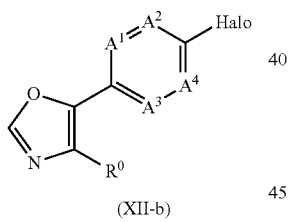

EXPERIMENTAL PROCEDURE 9

An intermediate of formula (VIII) wherein Het[1] is restricted as shown in Scheme 9, hereby named an intermediate of formula (XVIII), can be prepared by condensation of an intermediate of formula (XVII) with an intermediate of formula (XVI) which is activated with iodobenzene diacetate in the presence of trifluoromethanesulfonic acid. Stirring and/or elevated temperatures (for example between 70-100° C.) may enhance the rate of reaction. In Scheme 9, R[1a] a is defined as C$_{1-4}$alkyl and all other variables in are defined as hereinbefore.

Scheme 9

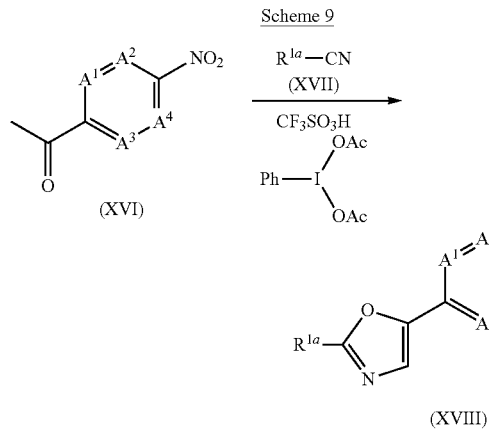

An intermediate of formula (XVIII) wherein NO$_2$ is replaced by Cl or Br, can be prepared from an intermediate of formula (XVI) wherein NO$_2$ is replaced by the corresponding halogen (Cl or Br respectively).

EXPERIMENTAL PROCEDURE 10

An intermediate of formula (VIII) wherein Het$^1$ is restricted as shown in Scheme 10, hereby named an intermediate of formula (XXI), can be prepared via the condensation of an intermediate of formula (XIX) with an intermediate of formula (XX) as shown in Scheme 10 wherein all variables are as defined before. Typically the reaction can be performed in acetic acid. Stirring and/or elevated temperatures (up to 90° C.) may enhance the rate of the reaction.

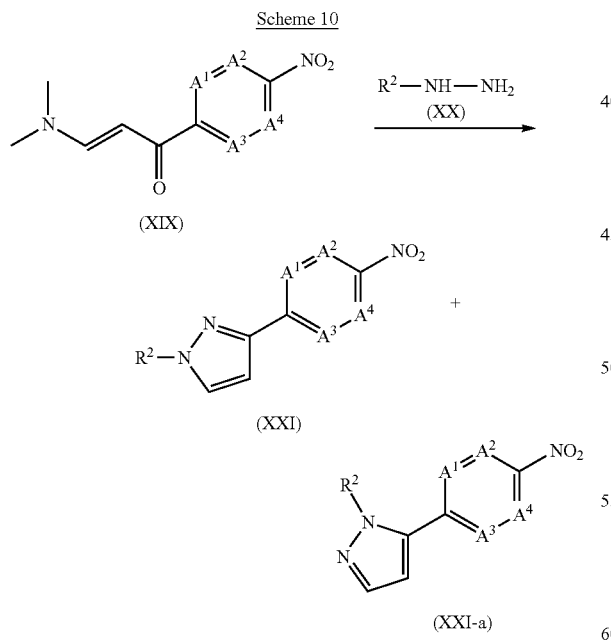

EXPERIMENTAL PROCEDURE 11

An intermediate of formula (XIX) can be prepared by the condensation of dimethylformamide dimethyl acetal (DMF-DMA) with an intermediate of formula (XVI) as depicted in Scheme 11. Stirring and/or elevated temperatures (for example between 70-110° C.) may enhance the rate of the reaction.

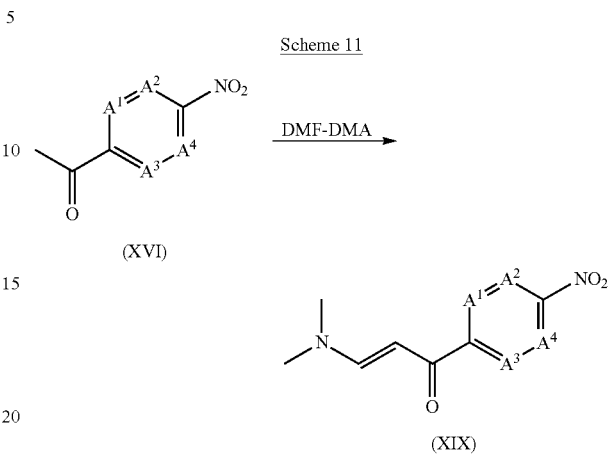

EXPERIMENTAL PROCEDURE 12

An intermediate of formula (III-a) wherein Het$^2$ is restricted to result in an intermediate of formula (XXIV), can be prepared via a condensation reaction between an intermediate of formula (XXII) and an intermediate of formula (XXIII) as is illustrated in Scheme 12, wherein Halo is restricted to Br and Cl, and wherein all other variables are defined as hereabove. The reaction may be performed in a reaction-inert solvent such as, for example, EtOH or n-butanol, or by mixing the reagents without the presence of a solvent. The reaction may conveniently be carried out at elevated temperatures ranging between 50° C. and the reflux temperature of the reaction mixture. Reaction rate and yield may be enhanced by microwave assisted heating.

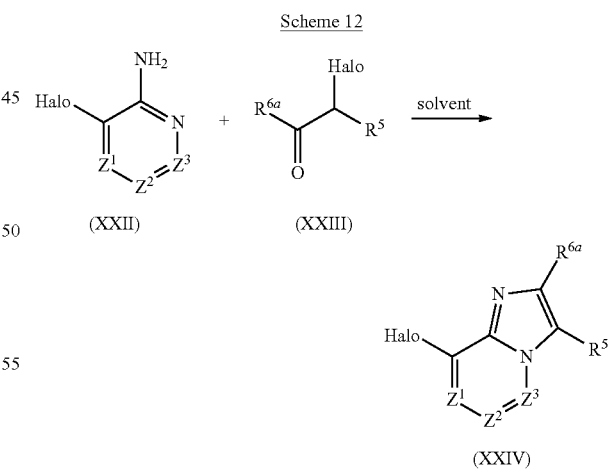

EXPERIMENTAL PROCEDURE 13

An intermediate of formula (III-a) wherein Het$^2$ is restricted to result in an intermediate of formula (XXVII) wherein R$^{6b}$ is carbon-linked to the benzimidazole heterocycle, can be prepared by an acylation of an intermediate of formula (XXV) with an intermediate of formula (XXVI) followed by a condensation reaction to yield (XXVII), according to Scheme 13 wherein Halo is restricted to Br, Cl and I and wherein all other substituents are as defined hereinbefore. The acylation reaction can be carried out in a solvent such as pyridine or a reaction inert solvent such as DMF in the presence of a base such as triethylamine ($Et_3N$). The subsequent condensation reaction can be carried out by heating the crude acylated product in a solvent such as acetic acid.

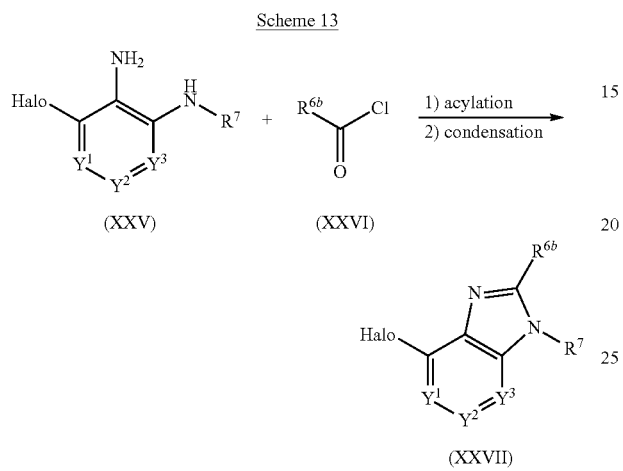

EXPERIMENTAL PROCEDURE 14

Alternatively, an intermediate of formula (XXVII) wherein $R^{6b}$ is carbon-linked to the benzimidazole heterocycle can also be prepared by treatment of an intermediate (XXV) with an aldehyde of formula (XXVIII). The reaction can be performed in the presence of sodium metabisulfite in a reaction inert solvent such as N,N-dimethylacetamide (DMA) according to Scheme 14 wherein Halo is restricted to Br, Cl and I and wherein all other substituents are as defined hereinbefore.

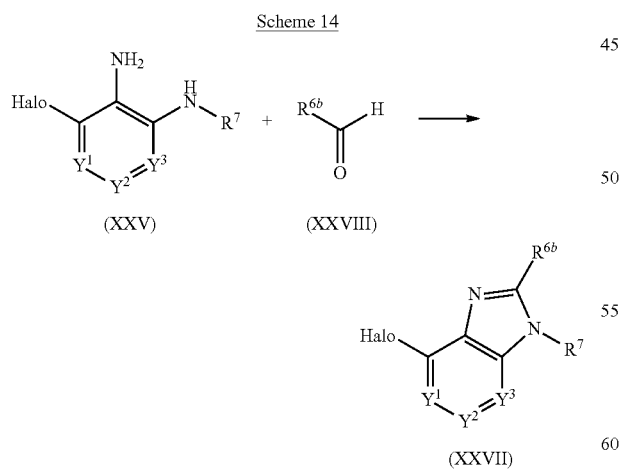

EXPERIMENTAL PROCEDURE 15

Alternatively, an intermediate of formula (XXVII) wherein $R^{6b}$ is carbon-linked to the benzimidazole heterocycle can also be prepared by treatment of an intermediate (XXIX) with an aldehyde of formula (XXVIII) in the presence of sodium dithionite in a reaction inert solvent such as EtOH according to Scheme 15 wherein Halo is restricted to Br, Cl and I and wherein all other substituents are as defined hereinbefore.

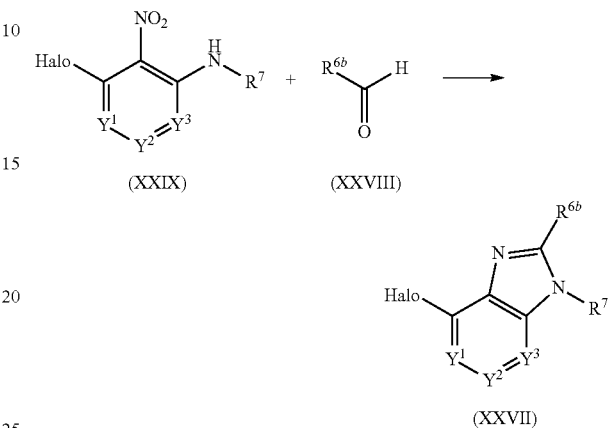

For an intermediate of formula (XXVII) wherein $R^7$ is H, an alternative $R^7$ can be introduced via N-alkylation, leading predominantly to an intermediate of formula (XXVII) wherein $R^7$ is a substituent as defined before, except hydrogen.

EXPERIMENTAL PROCEDURE 16

An intermediate of formula (XXV) can be prepared via reduction of an intermediate (XXIX) as shown in Scheme 16 below, wherein Halo is restricted to Br, Cl and I and wherein all other substituents are as defined hereinbefore. The reduction of (XXIX) to (XXV) can be conducted by a conventional method such as, for example, a reductive hydrogenation or reduction with a metal or a metal salt and an acid [for example a metal such as iron, or a metal salt such as $SnCl_2$ and acid such as an inorganic acid (hydrochloric acid, sulfuric acid or the like) or an organic acid (acetic acid or the like)], or other well-known methods for converting a nitro-group to the corresponding amine

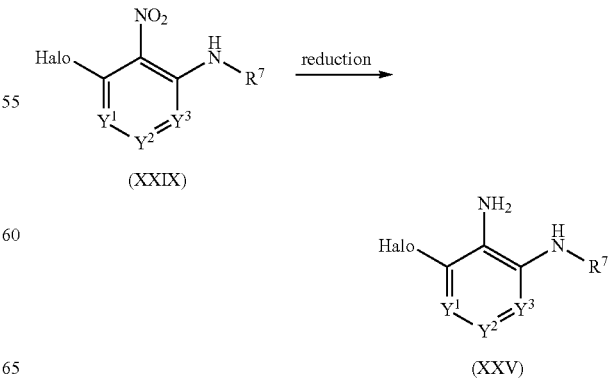

EXPERIMENTAL PROCEDURE 17

An intermediate of formula (XXIX) can be prepared via a substitution reaction of an intermediate of formula (XXX) with an intermediate of formula (XLV) as is shown in Scheme 17 below, wherein Halo is restricted to Br, Cl and I, Halo-b is defined as F, Cl, or Br, and wherein all other substituents are as defined hereinbefore. Intermediates of formula (XLV) are commercially available or may be prepared according to conventional reaction procedures generally known in the art.

Scheme 17

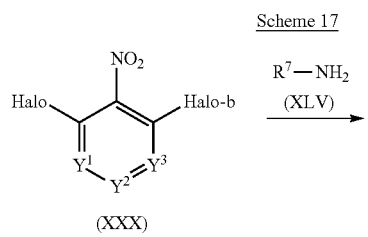

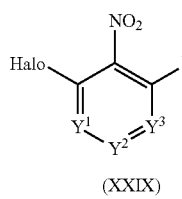

(XXIX)

EXPERIMENTAL PROCEDURE 18

An intermediate of formula (VIII), can be prepared via a coupling reaction between intermediates of formula (XXXI-a) and (XXXII-a) or between intermediates of formula (XXXI-b) and (XXXII-b). This reaction is shown in Scheme 18 wherein Halo is restricted to Br, Cl and I and wherein all other variables are defined as hereinbefore. In Scheme 18, intermediates of formula (XXXI-a), (XXXI-b), (XXXII-a) and (XXXII-b) may be commercially available or may be prepared according to conventional reaction procedures generally know in the art. The coupling reaction is performed in the presence of a suitable base such as, for example, $Cs_2CO_3$, $Na_2CO_3$ or NaOH. The reaction can be performed in a reaction-inert solvent such as, for example, toluene, DMF or tetrahydrofuran (THF). The reaction typically is performed in the presence of a catalyst system comprising of a suitable catalyst such as palladium(II) acetate ($Pd(OAc)_2$) and a ligand such as triphenylphosphine. Stirring, elevated temperatures (for example between 70-140° C.) and/or pressure may enhance the rate of the reaction. Preferably this reaction is carried out under an inert atmosphere, such as a nitrogen or argon atmosphere. Instead of boronic acids (XXXII-a) or (XXXI-b), the corresponding boronate esters, such as pinacol esters can be used.

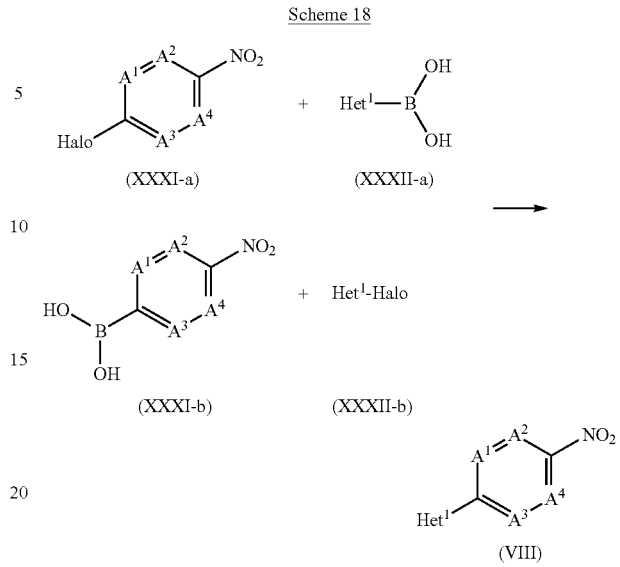

EXPERIMENTAL PROCEDURE 19

An intermediate of formula (XVI) can be prepared via a coupling reaction between an intermediate of formula (XXXI-a) and tributyl(1-ethoxyvinyl)tin according to Scheme 19 wherein Halo is defined as Br, Cl or I and wherein all other variables are as defined before. In Scheme 19, an intermediate of formula (XXXI-a) may be commercially available or may be prepared according to conventional reaction procedures generally know in the art. The reaction can be performed in a reaction-inert solvent such as, for example, toluene or DMF. The reaction typically is performed in the presence of a catalyst such as $Pd(PPh_3)_4$. Stirring, elevated temperatures (for example between 70-140° C.) and/or pressure may enhance the rate of the reaction. Preferably this reaction is carried out under an inert atmosphere, such as a nitrogen or an argon atmosphere. Subsequently, the obtained ethanol can be hydrolysed in acidic conditions such as, for example, by using hydrochloric acid, to yield the acetyl derivative of formula (XVI).

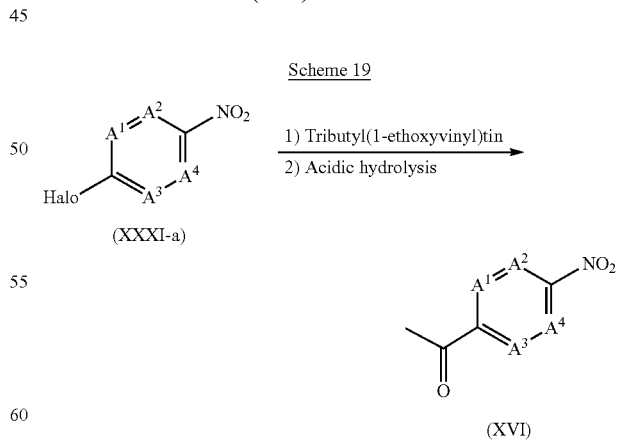

EXPERIMENTAL PROCEDURE 20

An intermediate of formula (XXXV) can be prepared via a condensation reaction between an intermediate of formula (XXXIV) and an intermediate of formula (XXXIII) as shown in Scheme 20 wherein $R^{1a}$ is defined as $C_{1-4}$alkyl and wherein all other substituents are defined as hereabove. The reaction can be performed in a solvent such as, for example, pyridine. Stirring, elevated temperatures (for example between 70 and 100° C.) may enhance the rate of the reaction.

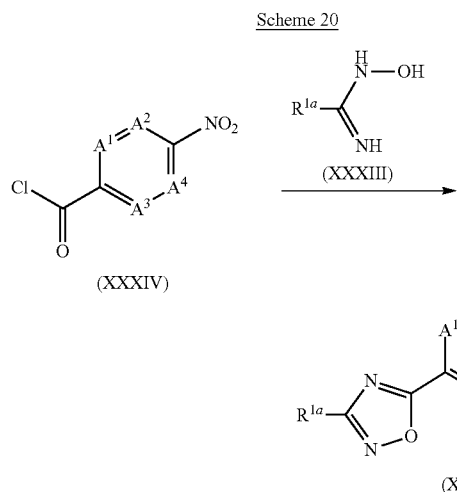

EXPERIMENTAL PROCEDURE 21

An intermediate of formula (XXXIV) can be prepared via an activation reaction of an intermediate of formula (XXXVI) as is shown in Scheme 21 wherein all variables are defined as hereabove. The reaction can be performed in a reaction-inert solvent such as, for example, chloroform, in the presence of DMF. The reaction typically is performed in the presence of an activating reagent such as, for example, $SOCl_2$. Stirring, elevated temperatures (for example between 50 and 80° C.) may enhance the rate of the reaction.

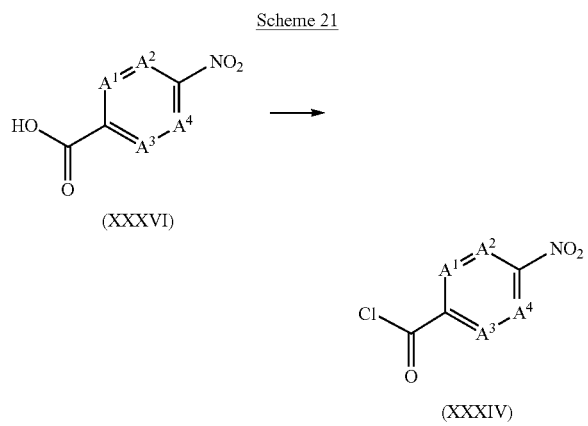

EXPERIMENTAL PROCEDURE 22

An intermediate of formula (XXXIX) can be prepared via a coupling reaction between an intermediate of formula (XXXVII) and an intermediate of formula (XXXVIII) according to Scheme 22 wherein Halo is defined as I or Br, and wherein all other variables are defined as before. In Scheme 22, intermediates of formula (XXXVII) and (XXXVIII) may be commercially available or may be prepared according to conventional reaction procedures generally know in the art. The coupling reaction is performed in the presence of a suitable base such as, for example, $Cs_2CO_3$, or $Ag_2CO_3$. The reaction can be performed in a reaction-inert solvent such as, for example, $H_2O$, $CH_3CN$ or DMF. The reaction typically is performed in the presence of a catalyst system comprising of a suitable catalyst such as palladium(II) acetate ($Pd(OAc)_2$) or 1.1-bis(diphenylphosphinoferrocene-dichloropalladiumII) ($Pd(dppf)Cl_2$), and a ligand such as triphenylphosphine. Stirring, elevated temperatures (for example between 60 an 140° C.) may enhance the rate of the reaction.

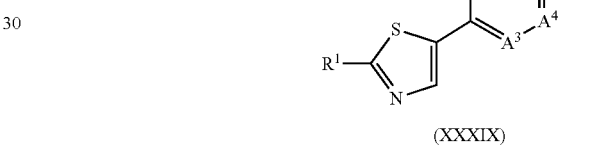

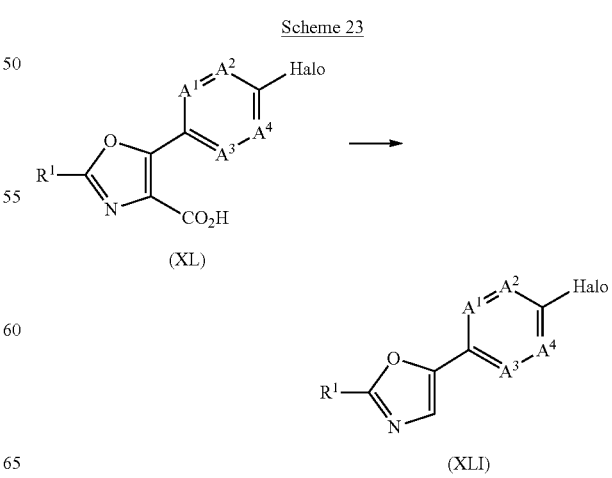

EXPERIMENTAL PROCEDURE 23

An intermediate of formula (XLI) can be prepared via a decarboxylation reaction of a compound of formula (XL) as depicted in Scheme 23 wherein Halo is defined as Br, I or Cl, and wherein all other variables are defined as hereinabove. The reaction can be performed in a solvent such as quinoline or DMF in the presence of copper(II) oxide (CuO). The reaction typically requires high temperature (up to 150° C.).

EXPERIMENTAL PROCEDURE 24

An intermediate of formula (XL) can be prepared via hydrolysis of the carboxylic ester function of a compound of formula (XLII) as depicted in Scheme 24 wherein Halo is defined as Br, I or Cl, and wherein all other variables are defined as before. This reaction can be performed either in acidic conditions or in basic conditions. It will be preferably performed in basic conditions in the presence of a base such as NaOH or LiOH in a mixture of dioxane and water at room temperature.

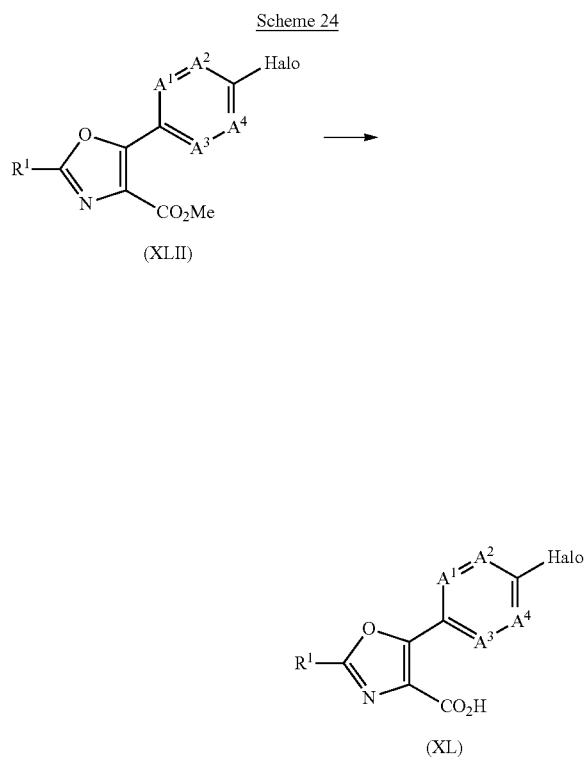

Scheme 24

(XLII)

(XL)

EXPERIMENTAL PROCEDURE 25

An intermediate of formula (XLII) can be prepared via a coupling reaction between an intermediate of formula (XLIII) and an intermediate of formula (XLIV) as depicted in Scheme 25 wherein Halo is defined as Br, I or Cl, wherein Halo-c is defined as Br or I, and wherein all other variables are defined as hereinbefore. Intermediates of formula (XLIII) and (XLIV) may be commercially available or may be prepared according to conventional reaction procedures generally know in the art. The coupling reaction is performed in the presence of a suitable base such as, for example, $Cs_2CO_3$ or $Ag_2CO_3$. The reaction can be performed in a reaction-inert solvent such as, for example, $CH_3CN$, toluene or DMF. The reaction typically is performed in the presence of a catalyst system comprising of a suitable catalyst such as palladium(II) acetate ($Pd(OAc)_2$) or [1,1'-Bis(diphenylphosphino)ferrocene]dichloropalladium(II) ($Pd(dppf)Cl_2$), and a ligand such as, for instance, triphenylphosphine or tri-o-toluoylphosphine. Stirring, elevated temperatures (for example between 60 an 140° C.) may enhance the rate of the reaction.

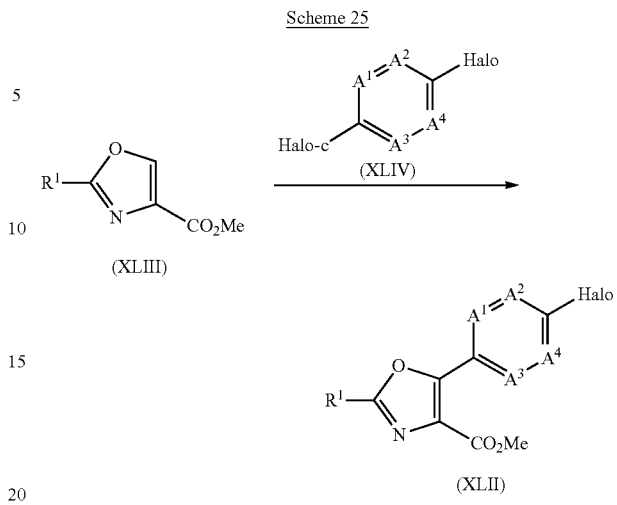

Scheme 25

(XLIII)

(XLIV)

(XLII)

Where necessary or desired, any one or more of the following further steps in any order may be performed:

Compounds of Formula (I), any subgroup thereof, addition salts, solvates, and stereochemical isomeric forms thereof can be converted into further compounds according to the invention using procedures known in the art. In a particular case, a compound of formula (I), wherein $R^{4a}$ or $R^{4b}$ is defined as Cl, Br or I can be further derivatized to a compound of formula (I) wherein $R^{4a}$ or $R^{4b}$ is H, under reductive conditions well known by those skilled in the art.

It will be appreciated by those skilled in the art that in the processes described above the functional groups of intermediate compounds may need to be blocked by protecting groups. In case the functional groups of intermediate compounds were blocked by protecting groups, they can be deprotected after a reaction step.

Pharmacology

It has been found that the compounds of the present invention modulate the γ-secretase activity. The compounds according to the invention and the pharmaceutically acceptable compositions thereof are therefore useful in the treatment or prevention of Alzheimer's disease (AD), traumatic brain injury, mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid, preferably Alzheimer's disease.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

It has been previously shown that the γ-secretase complex is also involved in the processing of the Notch-protein. Notch is a signaling protein which plays a crucial role in developmental processes (e.g. reviewed in Schweisguth F (2004)

Curr. Biol. 14, R129). With respect to the use of γ-secretase modulators in therapy, it seems particularly advantageous not to interfere with the Notch-processing activity of the γ-secretase activity in order to avoid putative undesired side-effects. While γ-secretase inhibitors show side effects due to concomitant inhibition of Notch processing, γ-secretase modulators may have the advantage of selectively decreasing the production of highly aggregatable and neurotoxic forms of Aβ, i.e. Aβ42, without decreasing the production of smaller, less aggregatable forms of Aβ, i.e. Aβ38 and without concomitant inhibition of Notch processing. Thus, compounds are preferred which do not show an effect on the Notch-processing activity of the γ-secretase-complex.

As used herein, the term "treatment" is intended to refer to all processes, wherein there may be a slowing, interrupting, arresting, or stopping of the progression of a disease, but does not necessarily indicate a total elimination of all symptoms.

The invention relates to a compound according to the general Formula (I), the stereoisomeric forms thereof and the pharmaceutically acceptable acid or base addition salts and the solvates thereof, for use as a medicament.

The invention also relates to a compound according to the general Formula (I), the stereoisomeric forms thereof and the pharmaceutically acceptable acid or base addition salts and the solvates thereof, for the treatment or prevention of diseases or conditions selected from Alzheimer's disease (AD), traumatic brain injury, mild cognitive impairment (MCI), senility, dementia, dementia with Lewy bodies, cerebral amyloid angiopathy, multi-infarct dementia, or Down's syndrome.

In an embodiment, said disease or condition is selected from Alzheimer's disease, mild cognitive impairment, senility, dementia, dementia with Lewy bodies, cerebral amyloid angiopathy, multi-infarct dementia, or Down's syndrome.

In an embodiment, said disease or condition is preferably Alzheimer's disease.

The invention also relates to a compound according to the general Formula (I), the stereoisomeric forms thereof and the pharmaceutically acceptable acid or base addition salts and the solvates thereof, for the treatment of said diseases.

The invention also relates to a compound according to the general formula (I), the stereoisomeric forms thereof and the pharmaceutically acceptable acid or base addition salts and the solvates thereof, for the treatment or prevention, in particular treatment, of γ-secretase mediated diseases or conditions.

The invention also relates to the use of a compound according to the general Formula (I), the stereoisomeric forms thereof and the pharmaceutically acceptable acid or base addition salts and the solvates thereof, for the manufacture of a medicament.

The invention also relates to the use of a compound according to the general Formula (I), the stereoisomeric forms thereof and the pharmaceutically acceptable acid or base addition salts and the solvates thereof, for the manufacture of a medicament for the modulation of γ-secretase activity.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

In the invention, particular preference is given to compounds of Formula (I), or any subgroup thereof with a $IC_{50}$ value for the inhibition of the production of Aβ42-peptide of less than 1000 nM, preferably less than 100 nM, more preferably less than 50 nM, even more preferably less than 20 nM as determined by a suitable assay, such as the assays used in the Examples below.

The compounds of the present invention can be administered to mammals, preferably humans for the treatment or prevention of any one of the diseases mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof and a pharmaceutically acceptable addition salt or solvate thereof, to warm-blooded animals, including humans.

Those of skill in the treatment of such diseases could determine the effective therapeutic daily amount from the test results presented hereinafter. An effective therapeutic daily amount would be from about 0.005 mg/kg to 50 mg/kg, in particular 0.01 mg/kg to 50 mg/kg body weight, more in particular from 0.01 mg/kg to 25 mg/kg body weight, preferably from about 0.01 mg/kg to about 15 mg/kg, more preferably from about 0.01 mg/kg to about 10 mg/kg, even more preferably from about 0.01 mg/kg to about 1 mg/kg, most preferably from about 0.05 mg/kg to about 1 mg/kg body weight. The amount of a compound according to the present invention, also referred to here as the active ingredient, which is required to achieve a therapeutically effect will of course, vary on case-by-case basis, for example with the particular compound, the route of administration, the age and condition of the recipient, and the particular disorder or disease being treated.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that are suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

While it is possible for the active ingredient to be administered alone, it is preferable to present it as a pharmaceutical composition.

Accordingly, the present invention further provides a pharmaceutical composition comprising a pharmaceutically acceptable carrier and, as active ingredient, a therapeutically effective amount of a compound according to Formula (I).

The carrier or diluent must be "acceptable" in the sense of being compatible with the other ingredients of the composition and not deleterious to the recipients thereof.

For ease of administration, the subject compounds may be formulated into various pharmaceutical forms for administration purposes. The compounds according to the invention, in particular the compounds according to Formula (I), a pharmaceutically acceptable acid or base addition salt thereof, a stereochemically isomeric form thereof, or any subgroup or combination thereof may be formulated into various pharmaceutical forms for administration purposes. As appropriate compositions there may be cited all compositions usually employed for systemically administering drugs.

To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable solutions, for example, may be prepared in which the carrier comprises saline solution, glucose solution or a mixture of saline and glucose solution. Injectable solutions containing compounds of Formula (I) may be formulated in an oil for prolonged action. Appropriate oils for this purpose are, for example, peanut oil, sesame oil, cottonseed oil, corn oil, soybean oil, synthetic glycerol esters of long chain fatty acids and mixtures of these and other oils. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. Acid or base addition salts of compounds of Formula (I) due to their increased water solubility over the corresponding base or acid form, are more suitable in the preparation of aqueous compositions.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are potent orally administrable compounds, pharmaceutical compositions comprising said compounds for administration orally are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

Depending on the mode of administration, the pharmaceutical composition will preferably comprise from 0.05 to 99% by weight, more preferably from 0.1 to 70% by weight, even more preferably from 0.1 to 50% by weight of the compound of formula (I), and, from 1 to 99.95% by weight, more preferably from 30 to 99.9% by weight, even more preferably from 50 to 99.9% by weight of a pharmaceutically acceptable carrier, all percentages being based on the total weight of the composition.

The following examples illustrate the present invention.

EXAMPLES

Hereinafter, the term "DCM" means dichloromethane; "MeOH" means methanol; "LCMS" means Liquid Chromatography/Mass spectrometry; "aq." means aqueous; "sat." means saturated; "sol." means solution; "HPLC" means high-performance liquid chromatography; "r.t." means room temperature; "AcOH" means acetic acid; "m.p." means melting point; "Et$_2$O" means diethyl ether; "BDS" means base deactivated silica; "RP" means reversed phase; "min" means minute(s); "h" means hour(s); "I.D." means internal diameter; "Pd(OAc)$_2$" means palladium(II) acetate; "LiHMDS" means lithium hexamethyldisilazane; "HBTU" means 1-[bis(dimethylamino)methylene]-1H-benzotriazol-1-ium 3-oxide hexafluorophosphate; "Xantphos" means (9,9-dimethyl-9H-xanthene-4,5-diyl)bis[diphenylphosphine]; "X-Phos" means dicyclohexyl[2',4',6'-tris(1-methylethyl)[1,1'-biphenyl]-2-yl]-phosphine; "NH$_4$OAc" means ammonium acetate; "NMP" means 1-methyl-2-pyrrolidinone; "SFC" means Supercritical Fluid Chromatography; "iPrNH$_2$" means isopropylamine; "DME" means 1,2-dimethoxyethane; "EtOAc" means ethyl acetate; "BINAP" means [1,1'-binaphthalene]-2,2'-diylbis[diphenylphosphine] (racemic); "Et$_3$N" means triethylamine; "EtOH" means ethanol; "Pd(PPh$_3$)$_4$ means tetrakis(triphenylphosphine)palladium; "PPh$_3$" means triphenylphosphine; "eq" means equivalent; "r.m." means reaction mixture(s); "DIPE" means diisopropyl ether; "DIPEA" means diisopropylethylamine; "DMA" means N,N-dimethylacetamide; "THF" means tetrahydrofuran, "DMSO" means dimethyl sulfoxide; "DMF" means N,N-dimethyl formamide; "DMF-DMA" means dimethylformamide dimethyl acetal; "PdCl$_2$(PPh$_3$)$_2$ means dichlorobis(triphenylphosphine)palladium; "KOtBu" means potassium tert-butoxide; "Ph(Ph$_3$)$_4$" means tetrakis(triphenylphosphine)palladium and "Pd$_2$(dba)$_3$" means tris[μ-[(1,2-η:4,5-η)-(1E,4E)-1,5-diphenyl-1,4-pentadien-3-one]]dipalladium.

A. Preparation of the Intermediates

Example A1 a) Preparation of Intermediate 1

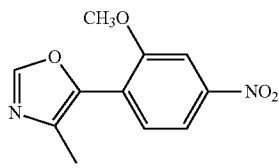

K$_2$CO$_3$ (9.6 g, 69.5 mmol) and 1-methyl-1-tosylmethylisocyanide (8 g, 38.2 mmol) were added to a sol. of 2-formyl-5-nitroanisole (6.29 g, 34.7 mmol) in MeOH (150 ml) and the r.m. was refluxed for 4 h. The r.m. was concentrated under reduced pressure, the residue was dissolved in DCM and the organic phase was washed with H$_2$O, dried (MgSO$_4$), filtered and the solvent was evaporated in vacuo. The residue was purified by flash chromatography over Silica gel (eluent: n-heptane/EtOAc from 100/0 to 50/50). The product fractions were collected and the solvent was evaporated. Yield: 6.24 g of intermediate 1 (77%).

b) Preparation of Intermediate 2

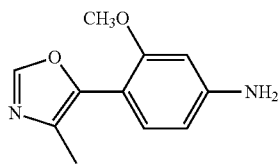

MeOH (150 ml) was added to Pd/C 10% (1 g) under a N$_2$ atmosphere. Subsequently, a 0.4% thiophene sol. in DIPE (1 ml) and intermediate 1 (6.24 g, 26.6 mmol) were added. The r.m. was stirred at 25° C. under a H$_2$ atmosphere until 3 eq of H$_2$ was absorbed. The catalyst was filtered off over diatomaceous earth and the filtrate was evaporated. Yield: 5.4 g of intermediate 2 (99%).

Example A2 a) Preparation of Intermediate 3

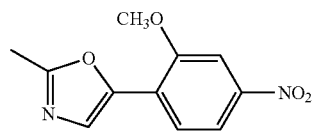

Iodobenzene diacetate (5.49 g, 18.44 mmol) and trifluoromethanesulfonic acid (6.08 ml, 69.17 mmol) were stirred in CH$_3$CN (100 ml) at r.t. for 1 h under N$_2$. 2'-Methoxy-4'-nitroacetophenone (3.0 g, 15.37 mmol) was added at once at r.t. to the sol. and the r.m. was then refluxed for 2 h, then cooled to r.t. and carefully added to a stirred sat. aq. sol. of Na$_2$CO$_3$ (500 ml). The product was extracted with DCM and the organic phase was dried (MgSO$_4$), filtered and the solvent was evaporated under reduced pressure. The resulting dark brown oil was purified by flash column chromatography over Silica gel (eluent: DCM/MeOH isocratic 95/5). The product fractions were collected and the solvent was evaporated under reduced pressure. Yield: 3.0 g of intermediate 3 (75%).

b) Preparation of Intermediate 4

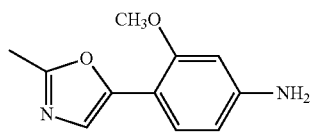

MeOH (50 ml) was added to Pd/C 10% (0.250 g) under a N$_2$ atmosphere. Subsequently, a 0.4% thiophene sol. in DIPE (2 ml) and intermediate 3 (0.946 g, 4.04 mmol) were added. The r.m. was stirred at 25° C. under a H$_2$ atmosphere until 3 eq of H$_2$ was absorbed. The catalyst was filtered off over diatomaceous earth and the filtrate was evaporated. The product was triturated in DIPE, filtered off and dried under vacuum. Yield: 0.66 g of intermediate 4 (80%).

Example A3

Preparation of Intermediate 5

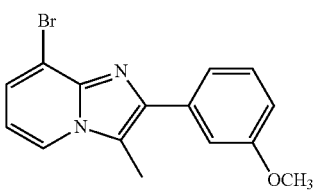

3-Bromo-2-pyridinamine (24.9 g, 144 mmol), 2-bromo-1-(3-methoxyphenyl)-1-propanone (42 g, 172.8 mmol) and 250 ml n-butanol were heated at reflux temperature for 3 nights. The mixture was separated between DCM and water. The organic layer was dried (MgSO$_4$), filtered and the solvent was evaporated in vacuo. The residue was purified by column chromatography over Silica gel (eluent: DCM/MeOH(NH$_3$) from 100/0 to 98/2. The purest fractions were concentrated under reduced pressure and the residue was crystallized from DIPE. Yield: 19 g of intermediate 5 (42%).

Example A4

Preparation of Intermediate 6

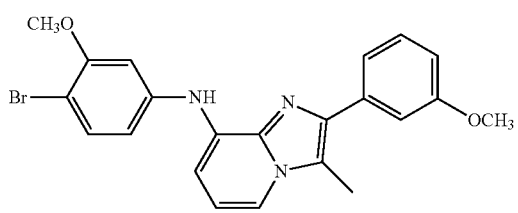

To a sol. of intermediate 5 (2 g, 6.3 mmol) and 4-bromo-3-methoxyaniline (1.40 g, 6.93 mmol) in DMF (40 ml) were added $Cs_2CO_3$ (4.1 g, 12.61 mmol), $Pd_2(dba)_3$ (0.144 g, 0.158 mmol) and BINAP (0.196 g, 0.315 mmol) and the mixture was purged with $N_2$ for 5 min. The r.m. was heated at 120° C. for 2 h then cooled to r.t. To the r.m. $H_2O$ (300 ml) and EtOAc (300 ml) were added and the mixture was stirred at r.t. for 15 min. The organic phase was separated, washed with $H_2O$ and brine, dried ($MgSO_4$), filtered and evaporated till dryness. The residue was crystallized from EtOH, filtered and dried. Yield: 1.8 g of intermediate 6 (65%).

Example A5

Preparation of Intermediate 7

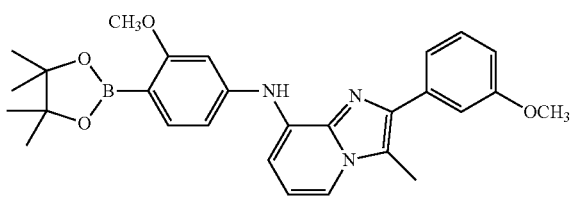

Bis(pinacolato)diborane (0.191 g, 0.753 mmol), [1,1'-Bis(diphenylphosphino) ferrocene]dichloropalladium (0.020 g, 0.025 mmol) and potassium acetate (0.049 g, 0.502 mmol) were added to a sol. of intermediate 6 (0.110 g, 0.251 mmol) in DMF (10 ml) and the mixture was purged with $N_2$ for 10 min. The r.m. was heated at 120° C. for 5 h. The r.m. was cooled to r.t. and the solvent was removed under reduced pressure.

The residue was dissolved in DCM. The organic phase was washed with $H_2O$ and brine, dried ($MgSO_4$), filtered and evaporated till dryness. The residue was purified by flash chromatography over Silica gel (eluent: DCM/MeOH from 100/0 to 90/10). The product fractions were collected and the solvent was evaporated. Yield: 0.070 g of intermediate 7 (57%).

Example A6 a) Preparation of Intermediate 8

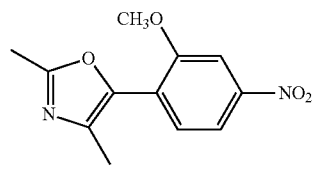

2-Methoxy-4-nitrobenzaldehyde (4.677 g, 25.817 mmol) and 2-acetamidoacrylic acid (5 g, 38.725 mmol) were added to pyridine (50 ml) and the r.m. was stirred at 120° C. overnight. After cooling the r.m. was poured into $H_2O$ and the product was extracted with EtOAc. The organic phase was separated, dried ($MgSO_4$), filtered and evaporated under reduced pressure. The residue was purified by flash chromatography over Silica gel (eluent: n-heptane/EtOAc from 100/0 to 75/25). The product fractions were collected and the solvent was evaporated. Yield: 0.9 g of intermediate 8 (14%).

b) Preparation of Intermediate 9

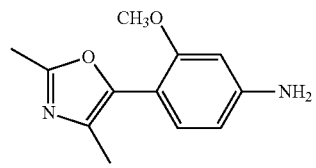

MeOH (50 ml) was added to Pd/C 10% (0.2 g) under a $N_2$ atmosphere. Subsequently, a 0.4% thiophene sol. in DIPE (0.5 ml) and intermediate 8 (0.9 g, 3.62 mmol) were added. The r.m. was stirred at 25° C. under a $H_2$ atmosphere until 3 eq of $H_2$ was absorbed. The catalyst was filtered off over diatomaceous earth and the filtrate was evaporated. Yield: 5.4 g of intermediate 9 (88%).

Example A7 a) Preparation of Intermediate 10

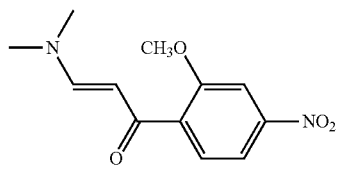

2'-Methoxy-4'-nitro-acetophenone (90564-14-0, 3.07 g, 15.73 mmol) in DMF-DMA was refluxed for 6 h. The r.m. was cooled to r.t. and concentrated under reduced pressure.

The residue was triturated in DIPE and the precipitate was filtered. Yield: 3.63 g of intermediate 10 (92%).

b) Preparation of Intermediates 11 and 12

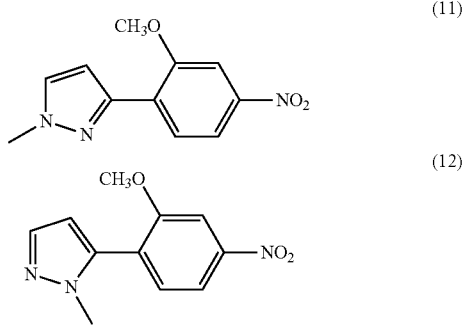

Intermediate 10 (3.63 g, 14.505 mmol) was added to a sol. of methylhydrazine (0.84 ml, 15.956 mmol) in AcOH (20 ml) and the resulting mixture was stirred at 90° C. for 3 h. The r.m. was cooled to r.t. and concentrated under reduced pressure. The residue was purified by flash chromatography over Silica gel (eluent: DCM/n-heptane from 50/50 to 70/30). The product fractions were collected and the solvent was evaporated. Yield: 1.44 g of intermediate 11 (42%) and 0.83 g of intermediate 12 (24%).

c) Preparation of Intermediate 13

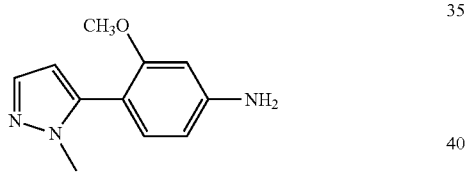

MeOH (50 ml) was added to Pd/C 10% (0.2 g) under a $N_2$ atmosphere. Subsequently, a 0.4% thiophene sol. in DIPE (1 ml) and intermediate 12 (0.83 g, 3.57 mmol) were added. The r.m. was stirred at 25° C. under a $H_2$ atmosphere until 3 eq of $H_2$ was absorbed. The catalyst was filtered off over diatomaceous earth and the filtrate was evaporated. Yield: 0.72 g of intermediate 13 (98%).

Example A8 a) Preparation of Intermediate 14

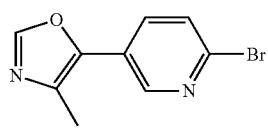

First $K_2CO_3$ (14.84 g, 107.5 mmol) and then 1-methyl-1-tosylmethylisocyanide (13.5 g, 64.5 mmol) were added to a sol. of 6-bromopyridine-3-carbaldehyde (10.0 g, 53.76 mmol) in 200 ml MeOH. The r.m. was refluxed for 1 h. The r.m. was concentrated under reduced pressure, the residue was dissolved in DCM and the organic phase was washed with $H_2O$, dried ($MgSO_4$), filtered and the solvent was evaporated in vacuo. The residue was purified by flash chromatography over Silica gel (eluent: n-heptane/EtOAc from 100/0 to 50/50). The product fractions were collected and the solvent was evaporated. The residue was suspended in DIPE, the precipitate was filtered off and dried under vacuum at 50° C. Yield: 6.8 g of intermediate 14 (53%).

b) Preparation of Intermediate 15

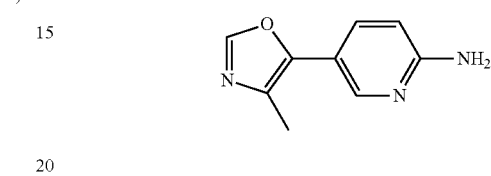

2-Methyl-2-propanol, sodium salt (0.804 g, 8.36 mmol), BINAP (0.521 g, 0.837 mmol), $Pd_2(dba)_3$ (0.383 g, 0.418 mmol) and benzophenone imine (0.948 g, 5.23 mmol) were added to a sol. of intermediate 14 (1.0 g, 4.18 mmol) in toluene (20 ml). The r.m. was degassed and put under a $N_2$ atmosphere. The r.m. was stirred at 100° C. for 2 h in the microwave. After cooling most of the solvent was evaporated (almost dry) and a 1 N HCl:THF sol. (1/1, 100 ml) was added. The r.m. was stirred at r.t. for 1 h. The r.m. was treated with a 10% $Na_2CO_3$ sol. and the product was extracted with EtOAc. The organic phase was dried ($MgSO_4$), filtered and the solvent was evaporated. The residue was purified by column chromatography over Silica gel (eluent: DCM/MeOH from 100/0 to 95/5). The product fractions were collected and the solvent was evaporated. Yield: 0.29 g of intermediate 15 (39%).

Example A9

Preparation of Intermediate 16

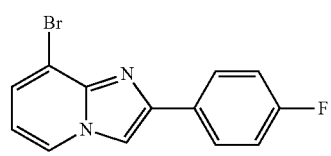 [SMILES: Fc1ccc(-c2cn3cccc(Br)c3n2)cc1]

A mixture of 3-bromo-2-pyridinamine (50 g, 289 mmol) and 2-bromo-1-(4-fluorophenyl)ethanone (75.3 g, 346.8 mmol) in EtOH (300 ml) was heated at 75° C. for 17 h. The r.m. was cooled to r.t. The formed precipitate was filtered off, washed with EtOH (50 ml) and dried in vacuo, yielding fraction 1. The corresponding filtrate was concentrated to a volume of 100 ml. EtOH (20 ml) and DIPE (100 ml) were added to the concentrate resulting in precipitation of the product. The solids were filtered off, washed with a mixture of DIPE (50 ml) and EtOH (10 ml), and dried in vacuo, yielding fraction 2. Fractions 1 and 2 were combined and stirred for 30 min in a sat. aq. $NaHCO_3$ sol. (500 ml). This mixture was extracted with DCM (500 ml). The separated organic layer was dried ($Na_2SO_4$), filtered and the solvent was evaporated in vacuo. The residue was recrystallized from EtOAc. The solid was filtered off and dried in vacuo. Yield: 46.5 g of intermediate 16 (55%).

Example A10 a) Preparation of Intermediate 17

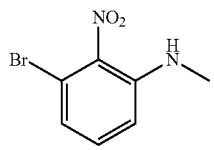

An 8 M methylamine sol. in ethanol (100 ml, 0.8 mol) was added to 1-bromo-3-fluoro-2-nitro-benzene (19.8 g, 90 mmol). The mixture was cooled on a water bath and was stirred overnight at r.t. Then, the solvent was evaporated and the residue was partitioned between water and DCM. The combined organic layers were dried ($MgSO_4$), filtered and concentrated in vacuo. Yield: 20 g of intermediate 17 (96%), which was used as such in the next step.

b) Preparation of Intermediate 18

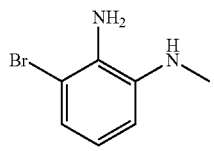

Intermediate 17 (20 g, 86.6 mmol) and iron powder (15 g, 269 mmol) were added to acetic acid (150 ml), and the resulting suspension was stirred and heated at 60° C. for 1 h. The r.m. was concentrated in vacuo and the residue was partitioned between DCM and a sat. aq. $NaHCO_3$ sol. The organic layer was dried ($MgSO_4$), filtered and concentrated in vacuo. Yield: 14 g of intermediate 18 (80%), which was used as such in the next step.

c) Preparation of Intermediate 19

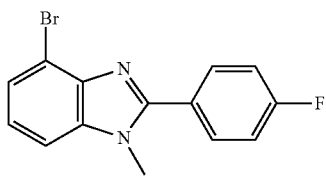 [SMILES: Cn1c(-c2ccc(F)cc2)nc2c(Br)cccc21]

$Et_3N$ (8.1 g, 80 mmol) was added to a sol. of intermediate 18 (10 g, 39.8 mmol) in DCM (250 ml). Subsequently, 4-fluoro-benzoylchloride (5.5 g, 34.7 mmol) was added dropwise at r.t., and the r.m. was stirred at r.t. overnight. The r.m. was washed with water, and the organic layers was dried ($MgSO_4$), filtered and concentrated in vacuo. The residue was dissolved in AcOH (100 ml), and a concentrated aq. HCl sol. (3 ml) was added. The r.m. was stirred at 100° C. for 2 h. The r.m. was concentrated in vacuo and the residue was dissolved in DCM and washed with a sat. aq. $NaHCO_3$ sol. and water.

The organic layer was dried ($MgSO_4$), filtered and concentrated in vacuo. Yield: 12 g of intermediate 19, which was used as such in the next step.

Example A11

Preparation of Intermediate 20

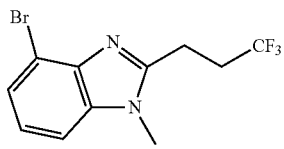 [SMILES: Cn1c(CCC(F)(F)F)nc2c(Br)cccc21]

4,4,4-Trifluorobutyraldehyde (1.891 g, 15 mmol) was dropwise added at r.t. to a sol. of intermediate 18 (3.015 g, 15 mmol) and sodium metabisulfite (3.707 g, 19.5 mmol) in DMA (80 ml). The reaction was preformed in the microwave at 220° C. for 45 min. The r.m. was diluted in EtOAc and the organic layer was washed with $H_2O$, dried ($MgSO_4$), filtered and the solvent was evaporated. The residue was purified by RP preparative HPLC [RP Shandon Hyperprep® C18 BDS (8 μm, 250 g, I.D. 5 cm); mobile phase: a gradient of (0.25% $NH_4HCO_3$ sol. in water)/MeOH]. The product fractions were collected and worked up. Yield: 0.670 g of intermediate 20 (14.5%).

Example A12

Preparation of Intermediate 21

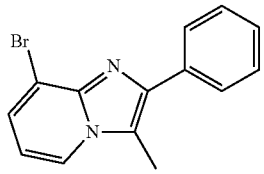 [SMILES: Cc1c(-c2ccccc2)nc2c(Br)cccn12]

A mixture of 3-bromo-2-pyridinamine (1 g, 5.78 mmol) and 2-bromo-1-phenyl-1-propanone (1.48 g, 6.94 mmol) in EtOH (20 ml) was stirred and heated at 100° C. for 2 days. The solvent was evaporated in vacuo and the residue was purified by flash chromatography (eluent: DCM/MeOH($NH_3$) from 100/0 to 98/2). The product fractions were collected and the solvent was evaporated. The residue was purified by RP preparative HPLC [RP Shandon Hyperprep® C18 BDS (8 μm, 250 g, I.D. 5 cm); mobile phase: a gradient of (0.25%

NH$_4$HCO$_3$ sol. in water)/MeOH]. The product fractions were collected and worked up. Yield: 0.850 g of intermediate 21 (51%).

Example A13 a) Preparation of Intermediate 22

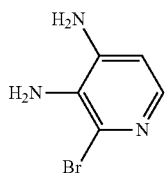

MeOH (100 ml) was added to Pt/C$_5$% (1 g) under N$_2$ atmosphere. Subsequently, a 0.4% thiophene sol. in DIPE (2 ml) and 4-amino-2-bromo-3-nitro-pyridine (3.5 g, 16 mmol) were added. The r.m. was stirred at 25° C. under H$_2$ atmosphere until 3 eq of H$_2$ was absorbed. The catalyst was filtered off over diatomaceous earth and the filtrate was concentrated in vacuo. Yield: 1.8 g of intermediate 22 (63%), which was used as such in the next step.

b) Preparation of Intermediate 23

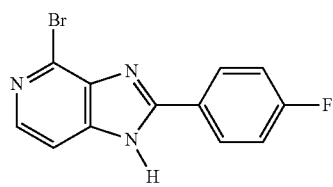 [SMILES: Fc1ccc(-c2nc3c(Br)nccc3[nH]2)cc1]

A mixture of intermediate 22 (1.8 g, 9.57 mmol) and 4-fluoro-benzoic acid (1.34 g, 9.57 mmol) in polyphosphoric acid (25 g) was stirred and heated at 180° C. for 1 h. The r.m. was cooled to r.t, and water was added. The resulting sol. was neutralized with K$_2$CO$_3$, and the resulting precipitate was filtered off and washed with water. Yield: 1 g of crude intermediate 23, which was used as such in the next step.

c) Preparation of Intermediate 24

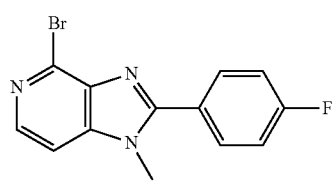 [SMILES: Cn1c(-c2ccc(F)cc2)nc2c(Br)nccc21]

Intermediate 23 (825 mg, 2.8 mmol), CH$_3$I (400 mg, 2.8 mmol), and K$_2$CO$_3$ (830 mg, 6 mmol) were added to DMF (25 ml). The resulting mixture was stirred at 50° C. for 1 h. The r.m. was cooled to r.t., and concentrated in vacuo. The residue was partitioned between DCM and water. The organic layer was dried (MgSO$_4$), filtered and concentrated in vacuo. The residue was purified by RP preparative HPLC [RP Shandon Hyperprep® C18 BDS (8 μm, 250 g, I.D. 5 cm); mobile phase: a gradient of (0.25% NH$_4$HCO$_3$ sol. in water)/MeOH]. The product fractions were collected and worked up. Yield: 180 mg of intermediate 24 (21%).

Example A14 a) Preparation of Intermediate 25

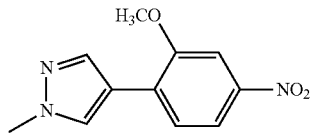

1-Methyl-4-pyrazoyl boronic acid (0.63 g, 4.99 mmol) and Cs$_2$CO$_3$ (3.257 g, 9.99 mmol) were added to a sol. of 2-bromo-5-nitroanisole (1.16 g, 4.99 mmol), palladium(II) acetate (0.112 g, 0.5 mmol) and triphenylphosphine (0.262 g, 1 mmol) in THF (20 ml). After stirring for 10 min, a 3 N NaOH sol. (1.6 ml) was added and the mixture was purged with N$_2$ for 2 min. The r.m. was stirred at r.t. overnight and the product was extracted with EtOAc. The organic layer was washed with H$_2$O dried (MgSO$_4$), filtered and evaporated off. The residue was purified by flash chromatography over Silica gel (eluent: DCM/MeOH from 100/0 to 96/4). The product fractions were collected and the solvent was evaporated. Yield: 0.630 g of intermediate 25 (54%).

b) Preparation of Intermediate 26

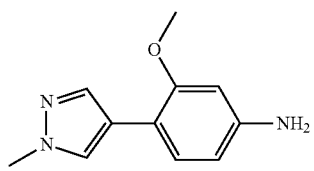

MeOH (100 ml) was added to Pd/C 10% (0.2 g) under a N$_2$ atmosphere. Subsequently, a 0.4% thiophene sol. in DIPE (0.5 ml) and intermediate 25 (0.926 g, 3.97 mmol) were added. The r.m. was stirred at 50° C. under a H$_2$ atmosphere until 3 eq of H$_2$ was absorbed. The catalyst was filtered off over diatomaceous earth and the filtrate was evaporated. The residue was diluted in DCM and the organic layer was washed with H$_2$O, dried (MgSO$_4$), filtered and concentrated under reduced pressure. The residue was purified by flash chromatography over Silica gel (eluent: DCM/MeOH from 100/0 to 90/10). The product fractions were collected and the solvent was evaporated. Yield: 0.82 g of intermediate 26 (100%).

Example A15 a) Preparation of Intermediate 27

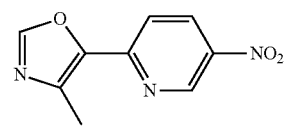

First K$_2$CO$_3$ (36 g, 262 mmol) and then 1-methyl-1-tosyl-methylisocyanide (35 g, 167 mmol) were added to a sol. of 5-nitropyridine-2-carboxaldehyde (131 mmol) in MeOH (500 ml) and the r.m. was refluxed for 4 h. The r.m. was concentrated under reduced pressure, the residue was dissolved in DCM and the organic phase was washed with H$_2$O, dried (Na$_2$SO$_4$), filtered and the solvent was evaporated in vacuo. The residue was purified by flash chromatography over Silica gel (eluent: petroleum ether/EtOAc 4/1). The product fractions were collected and the solvent was evaporated. Yield: 15 g of intermediate 27 (56%).

b) Preparation of Intermediate 28

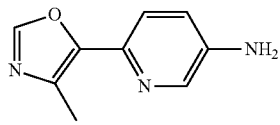

A sol. of intermediate 27 (10 g, 48.7 mmol) in THF (300 ml) was added to a sol. of ammonium chloride (2.6 g, 48.7 mmol) in H$_2$O (100 ml). Iron (16.3 g, 292 mmol) was then added and the r.m. was refluxed for 4 h. The precipitate was removed by filtration and the filtrate evaporated in vacuo. The residue was dissolved in EtOAc and the organic layer was washed with H$_2$O, dried (Na$_2$SO$_4$), filtered and the solvent was evaporated in vacuo. The residue was dissolved in a 2 N HCl sol. and the aq. phase was washed with DCM, made basic by addition of a 2 N NaOH sol. and the product was extracted by EtOAc. The organic layer was washed, dried (Na$_2$SO$_4$), filtered and the solvent was evaporated in vacuo to yield 6 g of intermediate 28 (71%).

Example A16 a) Preparation of Intermediate 29

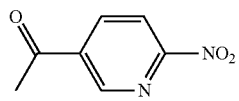

A mixture of 5-bromo-2-nitropyridine (5 g, 24.63 mmol), tributyl(1-ethoxyvinyl)tin (9.785 g, 27.1 mmol) and Ph(PPh$_3$)$_4$ (0.284 g, 0.246 mmol) in DMF (100 ml) were stirred at 120° C. for 3 h. After cooling, a 1 N HCl sol. was added and the r.m. was stirred at r.t. for 18 h. The r.m. was neutralized with a sat. aq. NaHCO$_3$ sol. and the product was extracted with DCM. The organic phase was dried (Na$_2$SO$_4$), filtered and the solvent was evaporated in vacuo. The residue was purified by flash chromatography over Silica gel (eluent: DCM/MeOH from 100/0 to 98/2). The product fractions were collected and the solvent was evaporated. Yield: 3.44 g of intermediate 29 (83%).

b) Preparation of Intermediate 30

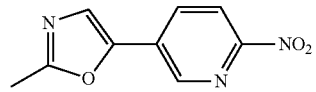

Iodobenzene diacetate (2.327 g, 7.2 mmol) and trifluoromethanesulfonic acid (2.397 ml, 27.1 mmol) were stirred in CH$_3$CN (50 ml) at r.t. for 20 min under N$_2$. Intermediate 29 (1 g, 6.0 mmol) in CH$_3$CN (10 ml) was added at once at r.t. to the sol. and the r.m. was then refluxed for 2 h. After cooling the excess of CH$_3$CN was removed under reduced pressure and the crude product was extracted with DCM. The organic layer was washed with a sat. aq. sol. of Na$_2$CO$_3$, dried (MgSO$_4$), filtered and the solvent was evaporated under reduced pressure. The residue was purified by flash chromatography over Silica gel (eluent: DCM/MeOH from 100/0 to 99/1). The product fractions were collected and the solvent was evaporated under reduced pressure. Yield: 0.73 g of intermediate 30 (47%).

c) Preparation of Intermediate 31

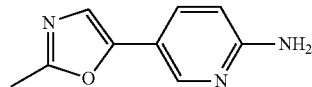

MeOH (150 ml) was added to Pd/C 10% (0.5 g) under a N$_2$ atmosphere. Subsequently, a 0.4% thiophene sol. in DIPE (2 ml) and intermediate 30 (2.2 g, 10.7 mmol) were added. The r.m. was stirred at 50° C. under a H$_2$ atmosphere until 3 eq of H$_2$ was absorbed. The catalyst was filtered off over diatomaceous earth and the filtrate was evaporated. Yield: 1.6 g of intermediate 31 (68%).

Example A17 a) Preparation of Intermediate 32

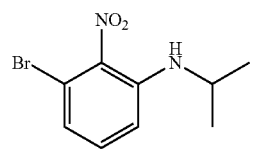

Isopropylamine (12.9 g, 218 mmol) was added to a sol. of 1-bromo-3-fluoro-2-nitro-benzene (8.0 g, 36 mmol) in EtOH (40 mL). The r.m. was stirred at r.t. overnight. Then, the solvent was evaporated and the residue was partitioned between water and DCM. The combined organic layers were dried (MgSO$_4$), filtered and concentrated in vacuo. Yield: 8.3 g of intermediate 32 (88%), which was used as such in the next step.

b) Preparation of Intermediate 33

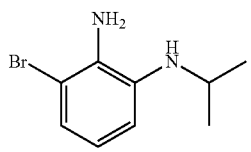

Intermediate 32 (8.3 g, 32 mmol) and iron powder (8.95 g, 160 mmol) were added to acetic acid (50 ml), and the resulting suspension was stirred and heated at 60° C. for 1 h. The r.m. was concentrated in vacuo and the residue was partitioned between DCM and a sat. aq. NaHCO$_3$ sol. The organic layer was dried (MgSO$_4$), filtered and concentrated in vacuo. Yield: 7.5 g of intermediate 33 (100%), which was used as such in the next step.

c) Preparation of Intermediate 34

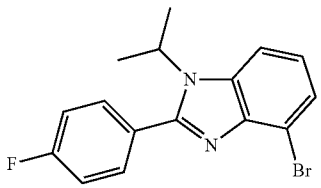 [SMILES: CC(C)n1c(-c2ccc(F)cc2)nc2c(Br)cccc21]

4-Fluoro-benzaldehyde (2.28 g, 18.3 mmol) and Na$_2$S$_2$O$_5$ (3.73 g, 19.6 mmol) were added to a sol. of intermediate 33 (3 g, 13.1 mmol) in DMA (50 ml). The r.m. was stirred at r.t. overnight. Then, the r.m. was poured into water, resulting in the precipitation of a solid. The solid was filtered off, washed with water, and suspended in DIPE. The resulting solid was filtered off, washed with DIPE, and dried. Yield: 2.3 g of intermediate 34 (53%).

Example A18 a) Preparation of Intermediate 35

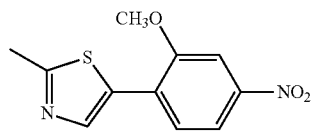

2-Iodo-5-nitroanisole (0.675 g, 2.42 mmol), Ag$_2$CO$_3$ (1.11 g, 4.0 mmol), [1,1'-Bis(diphenylphosphino)ferrocene]dichloropalladium(II) (0.073 g, 0.101 mmol) and PPh$_3$ (0.053 g, 0.20 mmol) were thoroughly mixed. 2-Methythiazole (0.2 g, 2.02 mmol) was added followed by CH$_3$CN (10 ml) and the mixture was purged with N$_2$ for 2 min. The r.m. was stirred at 60° C. overnight. After cooling DCM (20 ml) and acetone (10 ml) were added and the suspension was filtered over diatomaceous earth and extensively washed with DCM. The filtrate was concentrated under reduced pressure and the residue was purified by flash chromatography over Silica gel (eluent: DCM). The product fractions were collected and the solvent was evaporated under reduced pressure. Yield: 0.257 g of intermediate 35 (51%).

b) Preparation of Intermediate 36

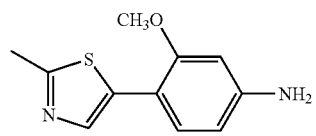

Intermediate 35 (0.25 g, 1 mmol) and iron (0.278 g, 5 mmol) were shaken in AcOH (6 ml) for 1.5 h. The solvent was evaporated. The residue was taken up in DCM and the organic layer was washed with a 1 N NaOH sol., dried (MgSO$_4$), filtered and concentrated under reduced pressure. Yield: 0.220 g of intermediate 36 (100%).

Example A19 a) Preparation of Intermediate 37

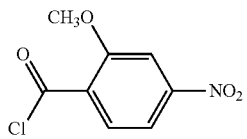

A suspension of 2-methoxy-4-nitro-benzoic acid (4.0 g, 20.3 mmol), SOCl$_2$ (4.72 ml, 64.9 mmol), CHCl$_3$ (20 ml) and a drop of DMF was refluxed for 6 h. After cooling, the solvents were removed under reduced pressure and the crude residual oil was used in the next step without purification. Yield: 4.4 g of intermediate 37 (100%).

b) Preparation of Intermediate 38

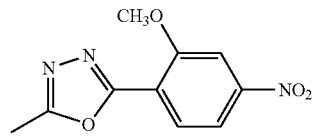

A sol. of intermediate 37 (4.374 g, 20.3 mmol) and acetamide oxime (1.653 g, 22.32 mmol) in pyridine (50 ml) was refluxed overnight. After cooling the solvent was evaporated and the residue was dissolved in DCM. The organic layer was washed with H$_2$O, dried (MgSO$_4$), filtered and the solvent was evaporated under reduced pressure. The residue was purified by flash chromatography over Silica gel (eluent:

DCM). The product fractions were collected and the solvent was evaporated under reduced pressure. Yield: 3.8 g of intermediate 38 (79%).

c) Preparation of Intermediate 39

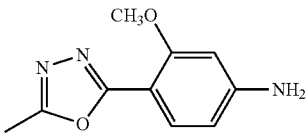

Intermediate 38 (0.2 g, 0.85 mmol) and tin(II) chloride dihydrate (0.959 g, 4.25 mmol) in EtOH (5 ml) were stirred at 60° C. for 1.5 h. After cooling the r.m. was poured into a mixture of a sat. Na$_2$CO$_3$ sol. (15 ml) and DCM (8 ml). The 2 phases were separated and the aq. phase was extracted with DCM. The combined organic layers were dried (MgSO4), filtered and concentrated under reduced pressure. Yield: 0.153 g of intermediate 39 (87%).

Example A20 a) Preparation of Intermediate 40

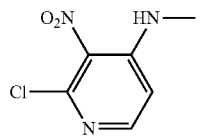

A 2 M sol. of methylamine in THF (0.80 g, 25.9 mmol) was added at 0° C. to a mixture of 2,4-dichloro-3-nitropyridine (5.0 g, 25.9 mmol) and Et$_3$N (4 ml, 28.9 mmol) in DMF (15 ml). The r.m. was stirred at r.t. for 1 h, then poured into ice water and the resulting solid was filtered, washed with H$_2$O and dried under vacuum. Yield: 3.0 g of intermediate 40 (62%).

b) Preparation of Intermediate 41

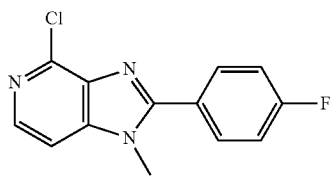

4-Fluorobenzaldehyde (1.74 g, 14.08 mmol) and Na$_2$S$_2$O$_4$ (8.3 g, 47.7 mmol) were added to a sol. of intermediate 40 (2.5 g, 13.32 mmol) in EtOH (60 ml). The r.m. was heated under microwave conditions at 150° C. for 45 min. The r.m. was cooled to r.t. and filtered through diatomaceous earth. The filtrate was evaporated and the residue was purified by flash column chromatography over Silica gel (eluent: DCM/MeOH(NH$_3$) 99/1). The product fractions were collected and the solvent was evaporated. Yield: 0.44 g of intermediate 41 (13%).

Example A21 a) Preparation of Intermediate 42

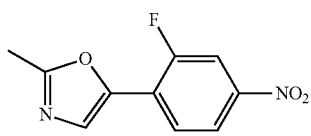 [SMILES: Cc1ncc(-c2ccc([N+](=O)[O-])cc2F)o1]

Trifluoromethanesulfonic acid (2.39 ml, 27.0 mmol) was added to a sol. of iodobenzene diacetate (2.32 g, 7.21 mmol) in CH$_3$CN (60 ml) and the r.m. was stirred at r.t. for 20 min under N$_2$. A sol. of 2'-fluoro-4'-nitro-acetophenone (1.1 g, 6.0 mmol) in CH$_3$CN (10 ml) was added at once at r.t. to the sol. and the r.m. was then refluxed for 2 h and subsequently cooled to r.t. CH$_3$CN was evaporated and the residue was extracted with DCM. The organic phase was washed with a sat. aq. NaHCO$_3$ sol., dried (MgSO$_4$), filtered and the solvent was evaporated under reduced pressure. The residue was purified by flash column chromatography over Silica gel (eluent: DCM). The product fractions were collected and the solvent was evaporated under reduced pressure. Yield: 0.75 g of intermediate 42 (53%).

b) Preparation of Intermediate 43

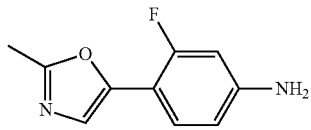

MeOH (50 ml) was added to Pd/C 10% (0.2 g) under a N$_2$ atmosphere. Subsequently, a 0.4% thiophene sol. in DIPE (1 ml) and intermediate 42 (0.7 g, 3.15 mmol) were added. The r.m. was stirred at 25° C. under a H$_2$ atmosphere until 3 eq of H$_2$ was absorbed. The catalyst was filtered off over diatomaceous earth and the filtrate was evaporated. Yield: 0.6 g of intermediate 43 (77%).

Example A22 a) Preparation of Intermediate 44

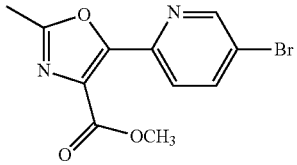 [SMILES: COC(=O)c1nc(C)oc1-c1ccc(Br)cn1]

A sol. of 2-iodo-5-bromopyridine (13.7 g, 48.2 mmol), 2-methyl-4-oxazole carboxylic acid methyl ester (3.4 g, 24.1 mmol), palladium(II)acetate (0.54 g, 2.41 mmol), tri-o-toluoylphosphine (1.47 g, 4.81 mmol) and Cs$_2$CO$_3$ (15.7 g, 48.2 mmol) in toluene (75 ml) was flushed with N₂, sealed and stirred at 110° C. overnight. The catalyst was filtered over diatomaceous earth and the filtrate was evaporated. The crude product was purified by flash column chromatography over Silica gel (eluent: DCM/MeOH(NH₃) from 100/0 to 98/2). The product fractions were collected and the solvent was evaporated. Yield: 5.64 g of intermediate 44 (13%).

b) Preparation of Intermediate 45

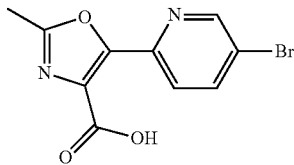 [SMILES: Cc1nc(C(=O)O)c(-c2ccc(Br)cn2)o1]

Intermediate 44 (5.64 g, 15.4 mmol) and LiOH (0.91 g, 38 mmol) were dissolved in a mixture of dioxane (40 ml) and H₂O (10 ml). The r.m. was stirred at r.t. for 5 h, then treated with a 1 M HCl sol. until pH=2. The obtained precipitate was filtered and dried under vacuum. The filtrate was extracted with CHCl₃ and the organic layer was dried (MgSO₄), filtered and the solvent was removed under reduced pressure to afford a solid. The two solid fractions were combined. Yield: 4.75 g of intermediate 45 (97%).

c) Preparation of Intermediate 46

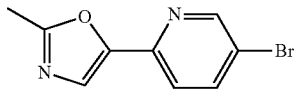

Copper(II) oxide (1.33 g, 16.8 mmol) was added to a sol. of intermediate 45 (4.75 g, 16.8 mmol) in DMF (75 ml). The r.m. was heated at 150° C. for 15 h. After cooling, the catalyst was filtered over diatomaceous earth and the filtrate was evaporated. The residue was triturated in DIPE/CH₃CN and the resulting solid was filtered off. The filtrate was evaporated and the residue was used as such in the next step. Yield: 1 g of intermediate 46 (14.5%).

d) Preparation of Intermediate 47

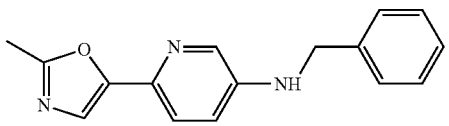 [SMILES: Cc1ncc(-c2ccc(NCc3ccccc3)cn2)o1]

Intermediate 46 (0.53 g, 2.23 mmol), Pd₂(dba)₃ (0.204 g, 0.223 mmol), dicyclohexyl[2',4',6'-tris(1-methylethyl)[1,1'-biphenyl]-2-yl]phosphine (0.212 g, 0.446 mmol) and Cs₂CO₃ (2.18 g, 6.69 mmol) were added to a sol. N-benzylamine (0.239 g, 2.23 mmol) in 2-methyl-2-propanol (20 ml), and the r.m. was heated at 110° C. overnight. After cooling, H₂O was added and the product was extracted with DCM. The organic phase was dried (MgSO4) filtered and concentrated under reduced pressure. The residue was purified by flash column chromatography over Silica gel (eluent: DCM/MeOH (NH₃) from 100/0 to 98/2) and the product fractions were collected and the solvent was evaporated. Yield: 0.15 g of intermediate 47 (21%).

e) Preparation of Intermediate 48

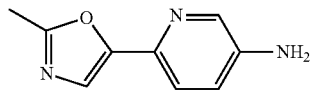

MeOH (50 ml) was added to Pd/C 10% (0.05 g) under a N₂ atmosphere. Subsequently, intermediate 47 (0.15 g, 0.565 mmol) was added. The r.m. was stirred at 50° C. under a H₂ atmosphere until 1 eq of H₂ was absorbed. The catalyst was filtered off over diatomaceous earth and the filtrate was evaporated. Yield: 0.105 g of intermediate 48 (95%).

Example A23 a) Preparation of Intermediate 49

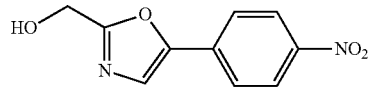 [SMILES: O=[N+]([O-])c1ccc(-c2cnc(CO)o2)cc1]

A 1 M sol. of LiHMDS in THF (47 ml, 47 mmol) was added dropwise at 0° C. under a N₂ atmosphere to a sol. of 5-(4-nitrophenyl)-oxazole (6.0 g, 31.6 mmol) in THF (100 ml). The r.m. was stirred at 0° C. for 30 min, and then DMF (3.67 ml, 47 mmol) was added and the mixture was allowed to warm to r.t. The r.m. was stirred at r.t. for 1 h and then MeOH (100 ml) and NaBH₄ (1.55 g, 41 mmol) were added. The r.m. was stirred at r.t. for 16 h, and then the solvents were partially removed in vacuo. H₂O was added, and the mixture was neutralized by adding AcOH. The mixture was extracted with DCM. The organic phase was separated, dried (MgSO₄), filtered and the solvent was evaporated in vacuo. The residue was triturated with DIPE. Yield: 4.6 g of intermediate 49 (61%).

b) Preparation of Intermediate 50

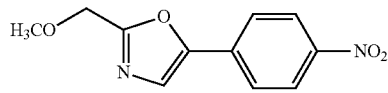

A suspension of 60% NaH in mineral oil (600 mg, 15 mmol) was added under a N₂ atmosphere to a sol. of intermediate 49 (1.79 g, 7.5 mmol) in THF (61 ml). The r.m. was stirred at r.t. for 30 min, and then CH₃I (1.87 ml, 30 mmol) was added. The r.m. was stirred at 60° C. for 4 h, and then brine was added. The organic phase was separated, dried (MgSO₄), filtered and the solvent was evaporated in vacuo. The residue was purified by flash column chromatography over silica gel (eluent: DCM/MeOH(NH₃) 100/0 to 98/2).

The product fractions were collected and the solvent was evaporated. Yield: 790 mg of intermediate 50 (41%).

c) Preparation of Intermediate 51

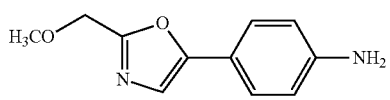 [SMILES: COCc1ncc(-c2ccc(N)cc2)o1]

MeOH (100 ml) was added to Pd/C 10% (0.2 g) under a N$_2$ atmosphere. Subsequently, a 0.4% thiophene sol. in DIPE (0.5 ml) and intermediate 50 (0.79 g, 3.1 mmol) were added. The r.m. was stirred at 25° C. under a H$_2$ atmosphere until 3 eq of H$_2$ was absorbed. The catalyst was filtered off over diatomaceous earth and the filtrate was evaporated. Yield: 0.65 g of intermediate 51 (quantitative).

Example A24 a) Preparation of Intermediate 52

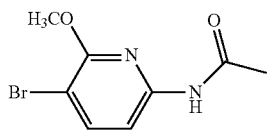

A mixture of N-(5-bromo-1,6-dihydro-6-oxo-2-pyridinyl)-acetamide (8.6 g, 37.2 mmol), CH$_3$I (13.2 g, 93 mmol), and Ag$_2$CO$_3$ (10.2 g, 3.2 mmol) in toluene (275 ml) was stirred at 60° C. for 48 h. The r.m. was cooled to r.t., and the solvent was removed in vacuo. The residue was partitioned between DCM and H$_2$O. The organic phase was separated, dried (MgSO$_4$), filtered and the solvent was evaporated in vacuo. The residue was triturated with DIPE. Yield: 5.7 g of intermediate 52 (62%).

b) Preparation of Intermediate 53

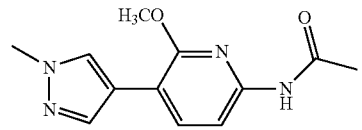

1-Methyl-4-pyrazoyl boronic acid pinacol ester (1.96 g, 9.4 mmol) and Pd(PPh$_3$)$_4$ (0.835 g, 0.72 mmol) were added to a solution of intermediate 52 (1.77 g, 7.2 mmol) in DMF (15 ml), H$_2$O (5 ml) and K$_2$CO$_3$ (2.0 g, 14.4 mmol). The r.m. was degassed, put under N$_2$, stirred and heated for 30 min at 140° C. under microwave irradiation. The r.m. was cooled to r.t. and partitioned between H$_2$O and DCM. The organic phase was separated, dried (MgSO$_4$), filtered and the solvent was evaporated in vacuo. The residue was triturated with CH$_3$CN. Yield: 1.35 g of intermediate 53 (76%).

c) Preparation of Intermediate 54

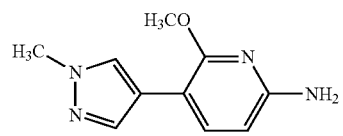

An aq. 10% NaOH sol. (50 ml) was added to a solution of intermediate 53 (1.3 g, 5.28 mmol) in MeOH (100 ml), and the r.m. was stirred at 80° C. for 18 h. The organic solvent was removed in vacuo and DCM and H$_2$O were added. The organic phase was separated, dried (MgSO$_4$), filtered and the solvent was evaporated in vacuo. The residue was triturated with DIPE. Yield: 0.95 g of intermediate 54 (88%).

Example A25 a) Preparation of Intermediate 55

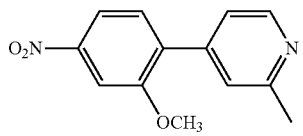 [SMILES: COc1cc([N+](=O)[O-])ccc1-c1ccnc(C)c1]

2-Methylpyridine-4-boronic acid pinacol ester (3178 mg, 14.5 mmol) and Pd(PPh$_3$)$_4$ (1.22 g, 1.06 mmol) were added to a solution of 2-bromo-5-nitroanisole (3.06 g, 13.2 mmol) in DME (40 ml), water (16 ml) and Cs$_2$CO$_3$ (1.33 g, 40.9 mmol). The resulting mixture was stirred and heated at reflux temperature for 16 h. The r.m. was cooled to r.t. and partitioned between H$_2$O and DCM. The organic phase was separated, dried (MgSO$_4$), filtered and the solvent was evaporated in vacuo. The residue was purified by flash column chromatography over silica gel (eluent: DCM/MeOH from 100/0 to 98/2). The product fractions were collected and concentrated in vacuo, yielding 2.04 g of intermediate 55 (63%).

b) Preparation of Intermediate 56

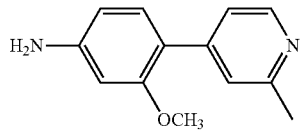

Intermediate 55 (2.04 g, 9.50 mmol) was added to a stirring mixture of 10% Pd/C (500 mg) and a 4% thiophene solution in MeOH (1 ml). The r.m. was heated at 50° C. under a H$_2$ atmosphere. After 3 eq. of H$_2$ were absorbed, the catalyst was removed by filtration over diatomaceous earth. The filtrate was evaporated under reduced pressure and the crude product was purified by column chromatography on silica gel (eluent:

MeOH/DCM 10/90). The product fractions were combined and evaporated to yield a light-brown solid. Yield: 1700 mg of intermediate 56 (95%).

Example A26

Preparation of Intermediate 57

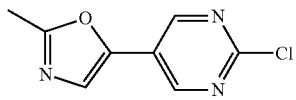

Trifluoromethanesulfonic acid (7.63 ml, 86 mmol) was added to a sol. of iodobenzene diacetate (7.41 g, 23 mmol) in $CH_3CN$ (50 ml) and the r.m. was stirred at r.t. for 20 min under $N_2$. A sol. of 1-(2-chloro-5-pyrimidinyl)-ethanone (3 g, 19.2 mmol) in $CH_3CN$ (10 ml) was added at once at r.t. to the sol. and the r.m. was then refluxed for 2 h and subsequently cooled to r.t. $CH_3CN$ was evaporated and the residue was extracted with DCM. The organic phase was washed with a sat. aq. $NaHCO_3$ sol., dried ($MgSO_4$), filtered and the solvent was evaporated under reduced pressure. The residue was purified by flash column chromatography over Silica gel (eluent: DCM). The product fractions were collected and the solvent was evaporated under reduced pressure. Yield: 1.6 g of intermediate 57 (43%).

Example A27 a) Preparation of Intermediate 58

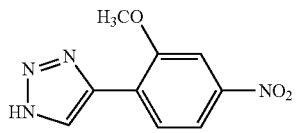

A mixture of 1-ethynyl-2-methoxy-4-nitro-benzene (785 mg, 4.43 mmol) and trimethylsilyl azide (1.75 ml, 13.3 mmol) was divided over 6 microwave vials and heated at 150° C. for 2 h under microwave irradiation. The r.m. was cooled to r.t. and filtered over diatomaceous earth using DCM. The filtrate was washed with $H_2O$. The organic phase was separated, dried ($MgSO_4$), filtered and the solvent was evaporated in vacuo. The residue was purified by flash column chromatography over silica gel (eluent: DCM/MeOH from 100/0 to 96/4). The product fractions were collected and concentrated in vacuo, yielding 344 mg of intermediate 58 (35%).

b) Preparation of Intermediate 59 and Intermediate 60

Intermediate 59

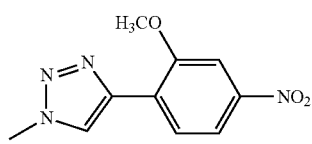

Intermediate 60

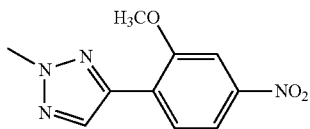

$K_2CO_3$ (580 mg, 4.2 mmol) was added to a sol. of intermediate 58 (462 mg, 2.1 mmol) in THF (10 ml). The mixture was cooled to 0-5° C., and $CH_3I$ (0.131 ml, 2.1 mmol) was added. The r.m. was stirred at r.t. for 3 h. The r.m. was filtered over diatomaceous earth using DCM. The filtrate was washed with water. The organic phase was separated, dried ($MgSO_4$), filtered and the solvent was evaporated in vacuo. The residue was purified by Preparative SFC (Chiralpak Diacel AD 20×250 mm; Mobile phase $CO_2$, MeOH with 0.2% $iPrNH_2$). The product fractions were collected and concentrated in vacuo. Yield: 214 mg of intermediate 59 (43%); 70 mg of intermediate 60 (14%).

c) Preparation of Intermediate 61

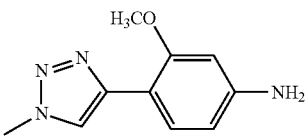

MeOH (40 ml) was added to Pd/C 10% (0.05 g) under a $N_2$ atmosphere. Subsequently, a 0.4% thiophene sol. in DIPE (0.1 ml) and intermediate 59 (0.214 g, 0.91 mmol) were added. The r.m. was stirred at 25° C. under a $H_2$ atmosphere until 3 eq of $H_2$ was absorbed. The catalyst was filtered off over diatomaceous earth and the filtrate was evaporated. The residue was partitioned between DCM and $H_2O$. The organic phase was separated, dried ($MgSO_4$), filtered and the solvent was evaporated in vacuo. Yield: 0.198 g of intermediate 61 (98%).

d) Preparation of Intermediate 62

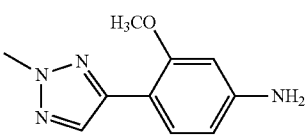

MeOH (40 ml) was added to Pd/C 10% (0.05 g) under a $N_2$ atmosphere. Subsequently, a 0.4% thiophene sol. in DIPE (0.1 ml) and intermediate 60 (0.070 g, 0.3 mmol) were added. The r.m. was stirred at 25° C. under a $H_2$ atmosphere until 3 eq of $H_2$ was absorbed. The catalyst was filtered off over diatomaceous earth and the filtrate was evaporated. The residue was partitioned between DCM and water. The organic phase

Example A28

Preparation of Intermediate 63

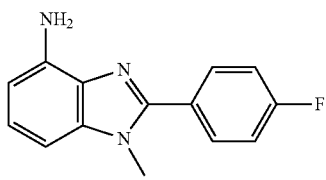 [SMILES: Cn1c(-c2ccc(F)cc2)nc2c(N)cccc21]

A stainless steel autoclave was loaded with intermediate 19 (370 mg, 1.21 mmol), copper(I)oxide (10 mg), and a 0.5 M sol. of $NH_3$ in dioxane (30 ml, 15 mmol). The autoclave was closed and the r.m. was heated at 150° C. for 18 h. Then, the r.m. was cooled, a sat. aq. $NH_4OH$ sol. (5 ml) was added, and the r.m. was heated at 150° C. for another 18 h. The r.m. was cooled, and the r.m. was concentrated in vacuo. The residue was partitioned between DCM and a saturated aq. $NH_4Cl$ sol. The organic layer was dried ($MgSO_4$), filtered and concentrated in vacuo. Yield: 240 mg of intermediate 63 (82%), which was used as such in the next reaction step.

Example A29 a) Preparation of Intermediate 64

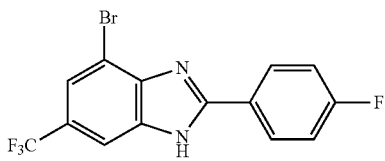 [SMILES: Fc1ccc(-c2nc3c(Br)cc(C(F)(F)F)cc3[nH]2)cc1]

$Na_2S_2O_5$ (1.64 g, 8.62 mmol) and 4-fluoro-benzaldehyde (891 mg, 7.18 mmol) were added to a sol. of 3-bromo-5-trifluoromethyl-1,2-diaminobenzene (1.65 g, 6.47 mmol) in DMA (40 ml). The r.m. was stirred overnight at 70° C. Then, the r.m. was cooled to r.t. and poured into water. The solid was filtered off, washed with water, and suspended in DIPE and some drops of 2-propanol. The resulting solid was filtered off, washed with DIPE, and dried. Yield: 1.95 g of intermediate 64 (84%).

b) Preparation of Intermediate 65

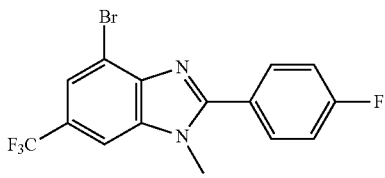 [SMILES: Cn1c(-c2ccc(F)cc2)nc2c(Br)cc(C(F)(F)F)cc21]

A 1 M sol. of LiHMDS in THF (9.2 ml, 9.2 mmol) was added dropwise at r.t. under a $N_2$ atmosphere to a sol. of intermediate 64 (1.65 g, 4.6 mmol) in THF (50 ml). The r.m. was stirred at r.t. for 30 min, and then $CH_3I$ (3.26 g, 23 mmol) was added. The r.m. was stirred at r.t. for 1 h and then washed with a sat. aq. $NaHCO_3$ sol. and brine. The organic phase was separated, dried ($MgSO_4$), filtered and the solvent was evaporated in vacuo. The residue was purified by RP preparative HPLC [RP Shandon Hyperprep® C18 BDS (8 µm, 250 g, I.D. 5 cm); mobile phase: a gradient of (0.25% $NH_4HCO_3$ sol. in water)/MeOH/$CH_3CN$]. The product fractions were collected and worked up. Yield: 720 mg of intermediate 65 (42%).

Example A30 a) Preparation of Intermediate 66

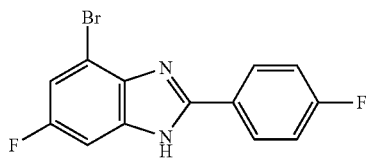 [SMILES: Fc1ccc(-c2nc3c(Br)cc(F)cc3[nH]2)cc1]

$Na_2S_2O_5$ (5.56 g, 29.2 mmol) and 4-fluoro-benzaldehyde (2.91 g, 23.4 mmol) were added to a sol. of 3-bromo-5-fluoro-1,2-diaminobenzene (4.0 g, 19.5 mmol) in DMA (80 ml). The r.m. was stirred overnight at 70° C. Then, the r.m. was cooled to r.t. and poured into water. The solid was filtered off, washed with water, and dried. Yield: 6 g of intermediate 66, used as such in the next reaction step.

b) Preparation of Intermediate 67

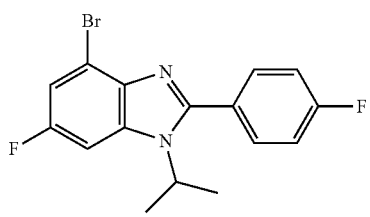 [SMILES: CC(C)n1c(-c2ccc(F)cc2)nc2c(Br)cc(F)cc21]

A suspension of 60% NaH in mineral oil (233 mg, 5.82 mmol) was added under a $N_2$ atmosphere to a cooled (5° C.) sol. of intermediate 66 (900 mg, 2.91 mmol) in THF (5 ml). The r.m. was stirred at 5° C. for 30 min, and then isopropyliodide (1.98 g, 11.6 mmol) was added. The r.m. was stirred at 130° C. for 2 h under microwave irradiation. The r.m. was cooled, extra THF was added and the mixture was washed with brine. The organic phase was separated, dried ($MgSO_4$), filtered and the solvent was evaporated in vacuo. The residue was purified by flash column chromatography over silica gel (eluent: heptane/DCM 50/50 to 0/100). The product fractions were collected and the solvent was evaporated. Yield: 350 mg of intermediate 67 (34%).

Example A31 a) Preparation of Intermediate 68

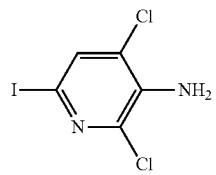

N-Iodosuccinimide (26.7 g, 119 mmol) and TFA (2.5 mL, 32.4 mmol) were added to a suspension of 2,4-dichloro-pyridin-3-ylamine (17.6 g, 108 mmol) in $CH_3CN$ (150 ml). The reaction mixture was stirred at r.t. for 16 h., and then heated to 40° C. for 6 h. The r.m. was diluted with EtOAc and washed with a sat. aq. $Na_2S_2O_3$ sol. The aq. phase was extracted with EtOAc, and the combined organic layers were dried ($MgSO_4$), filtered and the solvent was evaporated in vacuo. The residue was purified by flash column chromatography over silica gel (eluent: DCM). The product fractions were collected and the solvent was evaporated. Yield: 22 g of intermediate 68 (71%).

b) Preparation of Intermediate 69 and Intermediate 70 intermediate 69

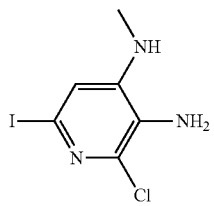

intermediate 70

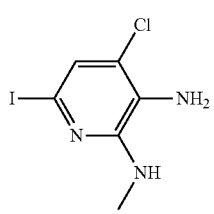

A sol. of methylamine in THF (2 M, 25 ml, 50 mmol) was added to a sol. of intermediate 68 (4.8 g, 16.6 mmol) in EtOH (20 ml). The r.m. was stirred at 160° C. under microwave irradiation for 8 h. Then, the solvent was evaporated and the residue was partitioned between aq. $NaHCO_3$ sol. and DCM. The combined organic layers were dried ($Na_2SO_4$), filtered and concentrated in vacuo. The residue was purified by flash column chromatography over silica gel (eluent: heptane/DCM 100/0 to 0/100). The product fractions were collected and the solvent was evaporated. Yield: 950 mg of intermediate 69 (20%) and 2900 mg of intermediate 70 (62%).

c) Preparation of Intermediate 71

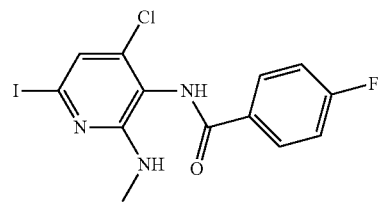 [SMILES: CNc1nc(I)cc(Cl)c1NC(=O)c1ccc(F)cc1]

$Et_3N$ (3.61 ml, 26.5 mmol) and 4-fluoro-benzoylchloride (1.68 g, 10.6 mmol) were added to a sol. of intermediate 70 (2.5 g, 8.8 mmol) in DCM (100 ml), and the r.m. was stirred at r.t. for 4 h. The r.m. was concentrated in vacuo. Yield: 2.7 g of crude intermediate 71 (75%), which was used as such in the next step.

d) Preparation of Intermediate 72

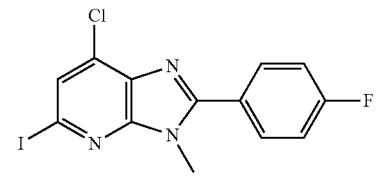

Phosphoroxychloride (907 mg, 5.9 mmol) was added to a sol. of intermediate 71 (2.0 g, 4.93 mmol) in dichloroethane (15 ml), and the resulting mixture was stirred and heated at 150° C. for 0.25 h under microwave irradiation. The r.m. was concentrated in vacuo, and the residue was purified by flash column chromatography over silica gel (eluent: DCM/MeOH ($NH_3$) from 100/0 to 97/3). The product fractions were collected and the solvent was evaporated. Yield: 1.56 g of intermediate 72 (81%).

e) Preparation of Intermediate 73

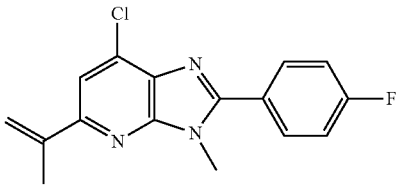 [SMILES: C=C(C)c1cc(Cl)c2nc(-c3ccc(F)cc3)n(C)c2n1]

Isopropenylboronic acid pinacol ester (867 mg, 5.16 mmol) and $Pd(PPh_3)_4$ (298 mg, 0.258 mmol) was added to a sol. of intermediate 72 (2.0 g, 5.16 mmol) in dioxane (8 ml) and an aq. $NaHCO_3$ sol. (4 ml), and the resulting mixture was stirred and heated at 160° C. for 10 min. under microwave irradiation. The r.m. was cooled to r.t. and filtered over diatomaceous earth using EtOAc, and the filtrate was evaporated. The residue was purified by flash column chromatography over silica gel (eluent: DCM/MeOH($NH_3$) from 100/0 to 97/3). The product fractions were collected and the solvent was evaporated. Yield: 1.25 g of intermediate 73 (80%).

f) Preparation of Intermediate 74

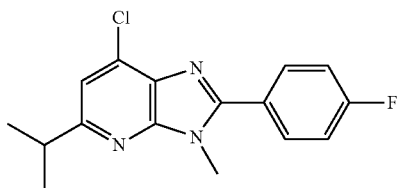 [SMILES: CC(C)c1cc(Cl)c2nc(-c3ccc(F)cc3)n(C)c2n1]

MeOH (40 ml) was added to Pt/C$_5$% (100 mg) under N$_2$ atmosphere. Subsequently, intermediate 73 (1.25 g, 4.14 mmol) was added. The r.m. was stirred at 25° C. under H$_2$ atmosphere until 1 eq of H$_2$ was absorbed. The catalyst was filtered off over diatomaceous earth and the filtrate was evaporated. Yield: 0.9 g of crude intermediate 74 (71%), which was used as such in the next reaction step.

g) Preparation of Intermediate 75

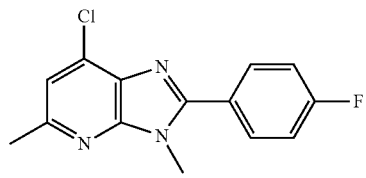 [SMILES: Cc1cc(Cl)c2nc(-c3ccc(F)cc3)n(C)c2n1]

Methylboronic acid (93 mg, 1.55 mmol) and Pd(PPh$_3$)$_4$ (71 mg, 0.062 mmol) was added to a sol. of intermediate 72 (600 mg, 0.31 mmol) in dioxane (10 ml) and an aq. NaHCO$_3$ sol. (5 ml). The resulting mixture was stirred and heated at 150° C. for 20 min. under microwave irradiation. The r.m. was cooled to r.t. and partitioned between water and DCM. The organic phase was separated, dried (MgSO$_4$), filtered and the solvent was evaporated in vacuo. Yield: 180 mg of crude intermediate 75 which was used as such in the next reaction step.

h) Preparation of Intermediate 76

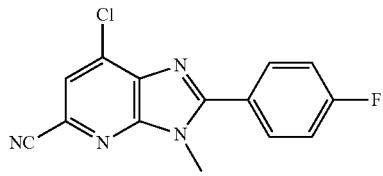 [SMILES: Cn1c(-c2ccc(F)cc2)nc2c(Cl)cc(C#N)nc21]

Zn(CN)$_2$ (36 mg, 0.31 mmol) and Pd(PPh$_3$)$_4$ (30 mg, 0.026 mmol) were added to a solution of intermediate 72 (200 mg, 0.52 mmol) in DMF (5.1 L). The resulting mixture was stirred and heated at 160° C. for 10 min. under microwave irradiation. The r.m. was cooled to r.t. and filtered through diatomaceous earth. The filtrate was conc. in vacuo and the residue was purified by flash column chromatography over silica gel (eluent: DCM/MeOH(NH$_3$) 100/0 to 97/3). The product fractions were collected and the solvent was evaporated. Yield: 0.14 g of intermediate 76 (95%).

Example A32 a) Preparation of Intermediate 77

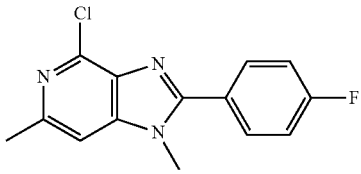 [SMILES: Cc1cc2c(nc(-c3ccc(F)cc3)n2C)c(Cl)n1]

4-Fluorobenzaldehyde (1.11 g, 8.93 mmol) and Na$_2$S$_2$O$_4$ (3.89 g, 22.3 mmol) were added to a sol. of 2-chloro-N-6-dimethyl-3-nitro-pyridin-4-amine (1.5 g, 7.44 mmol) in EtOH (15 ml). The r.m. was heated under microwave conditions for 1 h at 160° C. The r.m. was cooled to r.t. and filtered through diatomaceous earth using EtOAc. This was repeated 3×. The combined filtrates were evaporated and the residue was purified by RP preparative HPLC [RP Vydec Denali C18 (10 μm, 250 g, I.D. 5 cm); mobile phase: a gradient of (0.25% NH$_4$HCO$_3$ sol. in water)/CH$_3$CN]. The product fractions were collected and worked up. Yield: 1.95 g of intermediate 77 (32%).

Example A33 a) Preparation of Intermediate 78

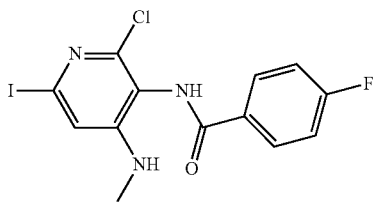 [SMILES: CNc1cc(I)nc(Cl)c1NC(=O)c1ccc(F)cc1]

Et$_3$N (1.87 ml, 13.8 mmol) and 4-fluoro-benzoylchloride (873 mg, 5.5 mmol) were added to a sol. of intermediate 69 (1.3 g, 4.6 mmol) in DCM (80 ml), and the r.m. was stirred at r.t. for 4 h. The r.m. was concentrated in vacuo. Yield: 1.5 g of crude intermediate 78 (81%), which was used as such in the next reaction step.

b) Preparation of Intermediate 79

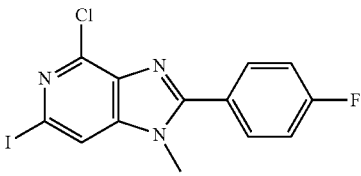 [SMILES: Cn1c(-c2ccc(F)cc2)nc2c(Cl)nc(I)cc21]

Phosphoroxychloride (121 mg, 0.79 mmol) was added to a sol. of intermediate 78 (267 mg, 0.66 mmol) in dichloroethane (2 ml), and the mixture was stirred and heated at 150° C.

for 0.25 h under microwave irradiation. The r.m. was concentrated in vacuo, and the residue was purified by flash column chromatography over silica gel (eluent: DCM/MeOH(NH$_3$) from 100/0 to 97/3). The product fractions were collected and the solvent was evaporated. Yield: 215 mg of intermediate 79 (84%).

c) Preparation of Intermediate 80

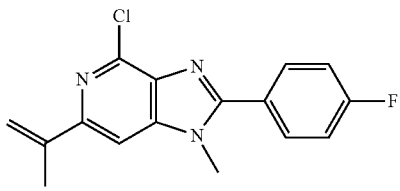 [SMILES: C=C(C)c1cc2c(nc(-c3ccc(F)cc3)n2C)c(Cl)n1]

Isopropenylboronic acid pinacol ester (434 mg, 2.58 mmol) and Pd(PPh$_3$)$_4$ (149 mg, 0.129 mmol) was added to a sol. of intermediate 79 (1.0 g, 2.58 mmol) in dioxane (8 ml) and an aq. NaHCO$_3$ sol. (4 ml), and the resulting mixture was stirred and heated at 160° C. for 10 min. under microwave irradiation. The r.m. was cooled to r.t. and filtered over diatomaceous earth using EtOAc, and the filtrate was evaporated. The residue was purified by flash column chromatography over silica gel (eluent: DCM/MeOH(NH$_3$) from 100/0 to 97/3). The product fractions were collected and the solvent was evaporated. Yield: 0.72 g of intermediate 80 (92%).

d) Preparation of Intermediate 81

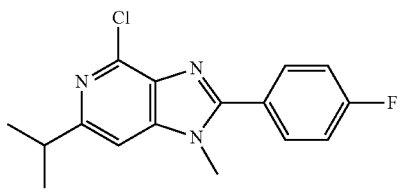 [SMILES: CC(C)c1cc2c(nc(-c3ccc(F)cc3)n2C)c(Cl)n1]

MeOH (40 ml) was added to Pt/C$_5$% (100 mg) under N$_2$ atmosphere. Subsequently, intermediate 80 (0.75 g, 2.49 mmol) was added. The r.m. was stirred at 25° C. under H$_2$ atmosphere until 1 eq of H$_2$ was absorbed. The catalyst was filtered off over diatomaceous earth and the filtrate was evaporated. Yield: 0.55 g of crude intermediate 81 (73%), which was used as such in the next reaction step.

e) Preparation of Intermediate 82

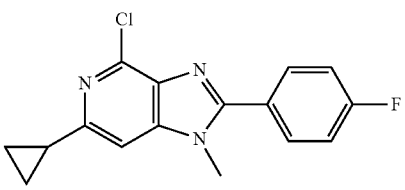 [SMILES: Cn1c(-c2ccc(F)cc2)nc2c(Cl)nc(C3CC3)cc21]

Cyclopropylboronic acid (86 mg, 1.0 mmol) and Pd(PPh$_3$)$_4$ (78 mg, 0.067 mmol) was added to a sol. of intermediate 79 (260 mg, 0.67 mmol) in dioxane (6 ml) and an aq. NaHCO$_3$ sol. (3 ml). The mixture was stirred and heated at 160° C. for 10 min. under microwave irradiation. The r.m. was cooled to r.t. and filtered over diatomaceous earth using EtOAc, and the filtrate was evaporated. The residue was purified by flash column chromatography over silica gel (eluent: DCM/MeOH(NH$_3$) from 100/0 to 97/3). The product fractions were collected and the solvent was evaporated. Yield: 0.15 g of intermediate 82 (74%).

Example A34 a) Preparation of Intermediate 83

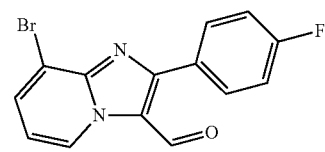 [SMILES: O=Cc1c(-c2ccc(F)cc2)nc2c(Br)cccn12]

Phosphoroxychloride (1.25 ml, 13.7 mmol) was added to DMF (3.5 ml) at 0° C. and the mixture was stirred for 0.5 h at this temperature. Intermediate 16 (1 g, 3.44 mmol) was added at 0° C., and the r.m. was stirred at r.t. and DMF (5 ml) was added. The r.m. was stirred at r.t. overnight. The r.m. was poured into on ice and the mixture was neutralized by adding NaHCO$_3$. The mixture was extracted with DCM. The organic layer was dried (MgSO$_4$), filtered and the solvent was evaporated in vacuo. The residue was triturated with DIPE. The solid was collected and dried. Yield: 0.625 g of intermediate 83 (57%).

b) Preparation of Intermediate 84

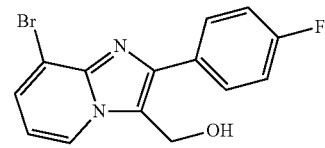 [SMILES: OCc1c(-c2ccc(F)cc2)nc2c(Br)cccn12]

NaBH$_4$ (28 mg, 0.75 mmol) was added to a solution of intermediate 83 (200 mg, 0.63 mmol) in MeOH (5 ml) and THF (2 ml). The r.m. was stirred at r.t for 15 min, then the solvents were removed in vacuo. The residue was partitioned between DCM and water. The organic layer was dried (MgSO$_4$), filtered and the solvent was evaporated in vacuo. Yield: 90 mg of intermediate 84 (45%).

c) Preparation of Intermediate 85

Thionylchloride (33 mg, 0.28 mmol) was added to intermediate 84 (90 mg, 0.28 mmol) in DCM (2 ml). The r.m. was stirred at r.t for 30 min and an aq. sat. NaHCO$_3$ sol. was added.

The organic layer was separated, filtered over diatomaceous earth and the filtrate was concentrated. Yield: 90 mg of intermediate 85 (95%).

d) Preparation of Intermediate 86

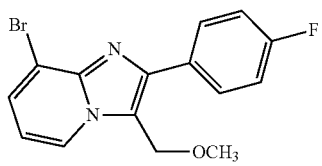 [SMILES: COCc1c(-c2ccc(F)cc2)nc2c(Br)cccn12]

A 0.5 M NaOMe solution in MeOH (0.64 ml, 0.32 mmol) was added to a sol. of intermediate 85 (90 mg, 0.265 mmol) in MeOH (2 ml). The r.m. was stirred at r.t for 30 min, then the solvents were removed in vacuo. The residue was partitioned between DCM and $H_2O$. The organic layer was filtered over diatomaceous earth and the filtrate was concentrated. The residue was triturated with DIPE and dried in vacuo. Yield: 60 mg of intermediate 86 (67%).

e) Preparation of Intermediate 87

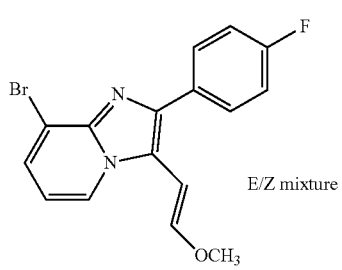 [SMILES: CO/C=C/c1c(-c2ccc(F)cc2)nc2c(Br)cccn12]

A solution of KOtBu (0.87 g, 7.74 mmol) in THF (7 ml) was added to a suspension of methoxymethylenetriphenylphosphonium chloride (1.53 g, 4.47 mmol) in THF (3 ml) at −15° C. The r.m. was stirred for 30 min. Subsequently, a solution of intermediate 83 (0.95 g, 3 mmol) in THF (3 ml) was added at 5° C., and the r.m. was stirred for 1 h at r.t. The r.m. was partitioned between DCM and $H_2O$. The organic layer was dried ($MgSO_4$), filtered and the solvent was evaporated in vacuo. The residue was purified by column chromatography over silica gel (eluent: DCM/MeOH 99/1). The product fractions were collected and the solvent was evaporated in vacuo. Yield: 700 mg of intermediate 87 as an E/Z mixture (68%).

Example A35 a) Preparation of Intermediate 88

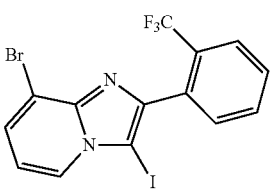 [SMILES: FC(F)(F)c1ccccc1-c1nc2c(Br)cccn2c1I]

1-Iodo-2,5-pyrrolidinedione (5.54 g, 24.6 mmol) was added to 8-bromo-2-(2-trifluoromethyl-phenyl)-imidazo[1,2-a]pyridine (prepared from 3-bromo-2-pyridinamine and 2-bromo-1-(2-trifluoromethyl-phenyl)ethanone, according to example A9; 5.6 g, 16.4 mmol) in DCM (50 ml). The r.m. was stirred at r.t. for 24 h, diluted with extra DCM, then washed with a 15% aq. NaOH solution, followed by a sat. aq. $NaHSO_3$ solution. The organic layer was dried ($MgSO_4$), filtered, concentrated in vacuo. Yield: 7.2 g of intermediate 88 (94%).

b) Preparation of Intermediate 89

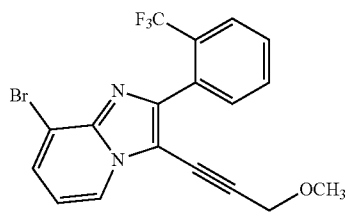 [SMILES: COCC#Cc1c(-c2ccccc2C(F)(F)F)nc2c(Br)cccn12]

A mixture of intermediate 88 (350 mg, 0.75 mmol), 3-methoxy-propyne (58 mg, 0.82 mmol), $PdCl_2(PPh_3)_2$ (20 mg, 0.028 mmol), CuI (5 mg, 0.027 mmol) in $Et_3N$ (3 ml) was stirred at 50° C. for 20 h under a $N_2$ atmosphere. The mixture was partitioned between DCM and $H_2O$. The organic layer was dried ($MgSO_4$), filtered, and concentrated in vacuo. The residue was purified by column chromatography over silica gel (eluent: DCM/MeOH 99/1). The product fractions were collected and the solvent was evaporated in vacuo. Yield: 100 mg of intermediate 89 (33%).

c) Preparation of Intermediate 90

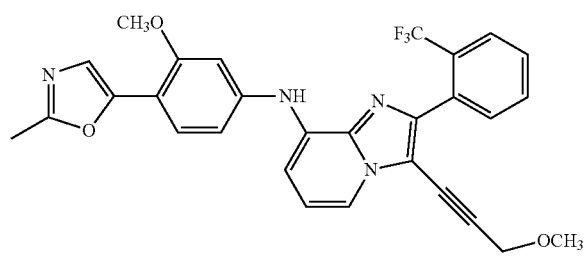

Intermediate 4 (50 mg, 0.24 mmol), Pd$_2$(dba)$_3$ (22 mg, 0.024 mmol), X-phos (23 mg, 0.049 mmol) and Cs$_2$CO$_3$ (240 mg, 0.73 mmol) were added to a solution of intermediate 89 (100 mg, 0.24 mmol) in 2-methyl-2-propanol (10 ml) under a N$_2$ atmosphere. The r.m. was heated at 100° C. for 20 h. Then, water was added and the mixture was extracted with DCM. The combined organic layers were dried (MgSO$_4$), filtered and the solvent was evaporated. The residue was purified by flash chromatography over silica gel (eluent: DCM/MeOH (NH$_3$) from 100/0 to 99/1). The product fractions were collected and the solvent was evaporated in vacuo. Yield: 30 mg of intermediate 90 (23%).

Example A36 a) Preparation of Intermediate 91

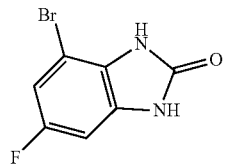 [SMILES: O=c1[nH]c2cc(F)cc(Br)c2[nH]1]

A mixture of 3-bromo-5-fluoro-1,2-diaminobenzene (10.5 g, 51 mmol) and urea (3.84 g, 64 mmol) in xylene (100 ml) was stirred at reflux overnight. Subsequently, the r.m. was cooled to r.t., and the resulting precipitate was filtered off. The solid was suspended in an aq. 1 N HCl sol., and filtered off again, then dried. The resulting solid was triturated with DIPE. Yield: 9.5 g of intermediate 91 (80%).

b) Preparation of Intermediate 92

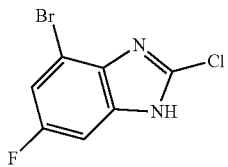 [SMILES: Fc1cc(Br)c2nc(Cl)[nH]c2c1]

Phosphoroxychloride (30 ml) was added slowly to intermediate 91 (3.0 g, 13 mmol), followed by an aq. conc. HCl sol. (1 ml). The r.m. was heated at reflux for 2 days. The r.m. was concentrated in vacuo. The residue was partitioned between DCM and an aq. NaHCO$_3$ sol. The organic layer was dried (MgSO$_4$), filtered and evaporated. Yield: 3.0 g (93%) of crude intermediate 92.

c) Preparation of Intermediate 93

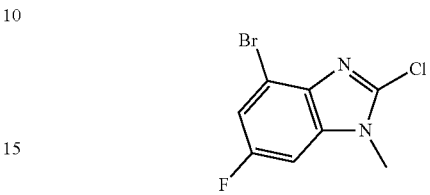

A suspension of 60% NaH in mineral oil (721 mg, 18 mmol) was added under a N$_2$ atmosphere to a cooled (5° C.) sol. of intermediate 92 (3.0 g, 12 mmol) in DMF (40 ml). The r.m. was stirred at 5° C. for 30 min, and then CH$_3$I (8.53 g, 60 mmol) was added. The r.m. was stirred at r.t. for 3 h, and then partitioned between water and EtOAc. The organic phase was separated, dried (MgSO$_4$), filtered and the solvent was evaporated in vacuo. The residue was purified by flash column chromatography over silica gel (eluent: heptane/EtOAc 80/20 to 50/50). The product fractions were collected and the solvent was evaporated. Yield: 850 mg of intermediate 93 (27%).

d) Preparation of Intermediate 94

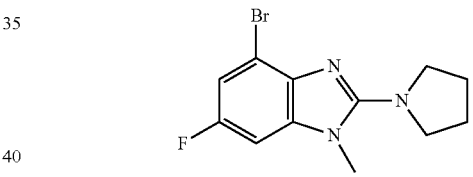

A mixture of intermediate 93 (760 mg, 2.88 mmol), and pyrrolidine (1.03 g, 14.4 mmol) in NMP (15 ml) was heated at 180° C. under microwave irradiation for 10 min. The r.m. was cooled to r.t., and poured into H$_2$O (100 ml). The resulting precipitate was filtered off, and washed with H$_2$O. The solid was dried and triturated with DIPE. Yield: 675 mg (78%) of intermediate 94.

Example A37 a) Preparation of Intermediate 95

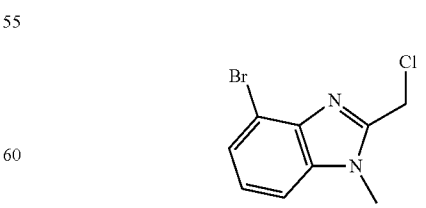

2-Chloro-aetaldehyde (6 M, 1.0 ml, 6.0 mmol) and Na$_2$S$_2$O$_5$ (1.14 g, 6.0 mmol) were added to a sol. of intermediate 18 (800 mg, 3.98 mmol) in DMA (10 ml). The r.m. was stirred at r.t. for 2 h. The r.m. was poured into H$_2$O. The solid was filtered off, washed with H₂O and suspended in DIPE. The solid was filtered off, washed with DIPE, and dried. Yield: 0.15 g of intermediate 95 (15%).

b) Preparation of Intermediate 96

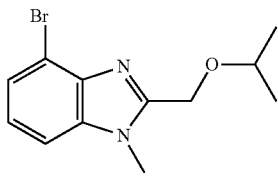 [SMILES: CC(C)OCc1nc2c(Br)cccc2n1C]

A suspension of 60% NaH in mineral oil (193 mg, 4.82 mmol) was added under a N₂ atmosphere to a sol. of 2-propanol (232 mg, 3.85 mmol) in DMF (10 ml). The r.m. was stirred at r.t. for 30 min, and then intermediate 95 (0.5 g, 1.93 mmol) was added. The r.m. was stirred at r.t. for 2 h, and then partitioned between H2O and EtOAc. The organic phase was separated, dried (MgSO₄), filtered and the solvent was evaporated in vacuo. The residue was purified by flash column chromatography over silica gel (eluent: DCM/MeOH(NH₃) 100/0 to 95/5). The product fractions were collected and the solvent was evaporated. Yield: 120 mg of intermediate 96 (15%).

Example A38 a) Preparation of Intermediate 97

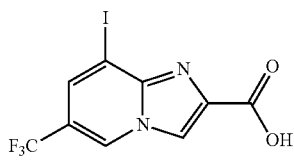 [SMILES: O=C(O)c1cn2cc(C(F)(F)F)cc(I)c2n1]

Ethyl 8-iodo-6-(trifluoromethyl)imidazo[1,2-a]pyridine-2-carboxylate (0.60 g 1.56 mmol) and LiOH (38 mg, 1.6 mmol) were dissolved in a mixture of THF/H₂O (10 ml/10 ml) and the mixture was stirred for 20 h at r.t. The mixture was acidified with an aq. 1 N HCl solution until the product precipitated. The precipitate was filtered off, and dried in vacuo. Yield: 0.5 g of intermediate 97 (90%).

b) Preparation of Intermediate 98

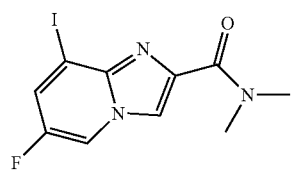 [SMILES: CN(C)C(=O)c1cn2cc(F)cc(I)c2n1]

A 2 M sol. of dimethylamine in THF (0.58 ml, 1.16 mmol) in THF (10 ml) was added to a mixture of intermediate 97 (500 mg, 1.4 mmol) and HBTU (533 mg, 1.4 mmol) in DMF (10 ml). Then DIPEA (0.98 ml, 5.62 mmol) was added, and the r.m. was stirred for 18 h at r.t. The mixture was diluted with DCM, and washed with an aq. 0.5 N NaOH sol. and H₂O. The organic layer was dried (MgSO₄), filtered and concentrated in vacuo. The residue was purified by flash column chromatography over silica gel (eluent: DCM/MeOH(NH₃) 99/1). The product fractions were collected and the solvent was evaporated in vacuo. Yield: 490 mg of intermediate 98 (90%).

Example A39 a) Preparation of Intermediate 99

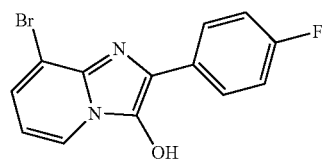 [SMILES: Oc1c(-c2ccc(F)cc2)nc2c(Br)cccn12]

BF₃ etherate (0.154 ml, 1.32 mmol) was added to a mixture of 4-fluorophenylglyoxal hydrate (4.5 g, 26.5 mmol) and 2-amino-3-bromopyridine (4.72 g, 26.5 mmol) in DCM (100 ml). The r.m. was stirred at r.t. for 6 h. The resulting precipitate was filtered off and dried in vacuo. Yield: 4 g of intermediate 99 (49%).

b) Preparation of Intermediate 100

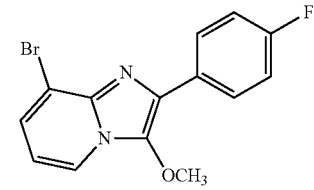 [SMILES: COc1c(-c2ccc(F)cc2)nc2c(Br)cccn12]

NaH (60% in mineral oil, 414 mg, 10.3 mmol) was added to an ice-cooled solution of intermediate 99 (1.06 g, 3.45 mmol) in DMF (50 ml). The r.m. was stirred at 0° C. for 15 min, then CH₃I (0.258 ml, 4.14 mmol) was added and the resulting r.m. was stirred at r.t. overnight. The r.m. was quenched with water, and then concentrated in vacuo. The residue was partitioned between DCM and H₂O. The organic layer was dried (MgSO₄), filtered and concentrated in vacuo. The residue was purified by flash column chromatography over silica gel (eluent: n-heptane/EtOAc 100/0 to 50/50). The product fractions were collected and the solvent was evaporated in vacuo. The residue was suspended in DIPE and dried in vacuo. Yield: 445 mg of intermediate 100 (40%).

Example A40

Preparation of Intermediate 101

3,5-Dibromo-pyrazin-2-ylamine (5 g, 19.8 mmol), 2-chloro-acetone (18.3 g, 198 mmol) and dioxane (40 ml) were heated at reflux temperature for 16 h. The r.m was concentrated under reduced pressure, and the residue was triturated with DIPE. Yield: 3.6 g of intermediate 101 (55%).

Example A41 a) Preparation of Intermediate 102

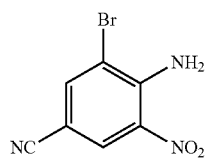

Bromine (3.15 ml, 61.3 mmol) was added dropwise at 15° C. to a solution of 4-amino-3-nitro-benzonitrile (10 g, 61.3 mmol) in AcOH (80 ml). The r.m was stirred at r.t overnight, and extra bromine (1.58 ml, 30.7 mmol) was added. After another 6 h at r.t., again bromine (0.79 ml, 15.3 mmol) was added, and stirring continued at r.t. over weekend. The r.m. was concentrated under reduced pressure, and the residue was triturated with water. The residue was purified by flash column chromatography over silica gel (eluent: DCM/MeOH 98/2). The product fractions were collected and the solvent was evaporated in vacuo. Yield: 6.24 g of intermediate 102 (35%).

b) Preparation of Intermediate 103

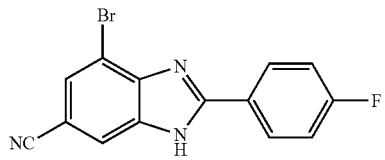 [SMILES: N#Cc1cc(Br)c2nc(-c3ccc(F)cc3)[nH]c2c1]

4-Fluorobenzaldehyde (0.96 ml, 9.1 mmol) and $Na_2S_2O_4$ (5.04 g, 28.9 mmol) were added to a sol. of intermediate 102 (2 g, 6.86 mmol) in EtOH (10 ml). The r.m. was heated under microwave conditions at 150° C. for 45 min. The r.m. was cooled to r.t. and filtered through diatomaceous earth. The filtrate was evaporated and the residue was dissolved in DMF. H2O was added. The resulting precipitate was filtered off and washed with $H_2O$. The residue was suspended in toluene, and the solvent was removed under reduced pressure. Yield: 1.6 g of intermediate 103 (70%).

c) Preparation of Intermediate 104

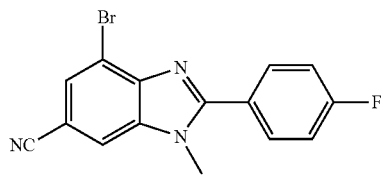 [SMILES: Cn1c(-c2ccc(F)cc2)nc2c(Br)cc(C#N)cc21]

A suspension of 60% NaH in mineral oil (569 mg, 14.2 mmol) was added under a $N_2$ atmosphere to a sol. of intermediate 103 (3 g, 9 mmol) in DMF (20 ml) at 5° C. The r.m. was stirred at 5° C. for 15 min, and then $CH_3I$ (1.48 ml, 23.7 mmol) was added. The r.m. was stirred at r.t. for 30 min, and partitioned between EtOAc and $H_2O$. The organic phase was separated, dried ($MgSO_4$), filtered and the solvent was evaporated in vacuo. The residue was purified by flash column chromatography over silica gel (eluent: DCM/MeOH 100/0 to 99/1). The product fractions were collected and the solvent was evaporated. The residue was purified further by preparative HPLC [RP Shandon Hyperprep C18 BDS (8 μm, 250 g, I.D. 5 cm); mobile phase: (0.25% $NH_4CO_3$ sol. in water, $CH_3CN$/MeOH)]. The product fractions were collected and concentrated under reduced pressure. Yield: 1.1 g of intermediate 104 (37%).

Example A42 a) Preparation of Intermediate 105

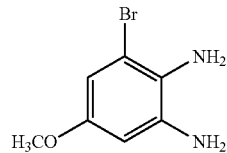

MeOH (150 ml) was added to Pt/$C_5$% (1 g) under $N_2$ atmosphere. Subsequently, a 0.4% thiophene sol. in DIPE (2 ml) and 2-bromo-4-methoxy-6-nitroaniline (5 g, 20.2 mmol) were added. The r.m. was stirred at 25° C. under $H_2$ atmosphere until 3 eq of $H_2$ was absorbed. The catalyst was filtered off over diatomaceous earth and the filtrate was concentrated in vacuo. Yield: 4.33 g of intermediate 105 (99%), which was used as such in the next step.

b) Preparation of Intermediate 106

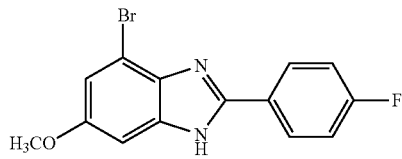 [SMILES: COc1cc(Br)c2nc(-c3ccc(F)cc3)[nH]c2c1]

4-Fluoro-benzaldehyde (1.17 ml, 11.1 mmol) and Na$_2$S$_2$O$_5$ (2.63 g, 13.8 mmol) were added to a sol. of intermediate 105 (2 g, 9.2 mmol) in DMA (40 ml). The r.m. was stirred at 90° C. overnight. Then, the r.m. was poured into water, resulting in the precipitation of a solid. The solid was filtered off, washed with water, and suspended in DIPE. The resulting solid was filtered off, washed with DIPE, and dried. Yield: 2.9 g of intermediate 106 (98%).

c) Preparation of Intermediate 107

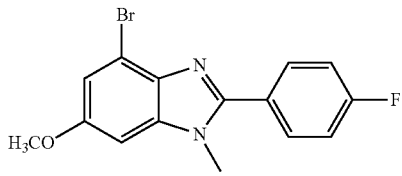 [SMILES: COc1cc(Br)c2nc(-c3ccc(F)cc3)n(C)c2c1]

A suspension of 60% NaH in mineral oil (486 mg, 12.1 mmol) was added under a N$_2$ atmosphere to a sol. of intermediate 106 (2.6 g, 8.1 mmol) in DMF (15 ml) at 5° C. The r.m. was stirred at 5° C. for 30 min, and then methyliodide (1.26 ml, 20.2 mmol) was added. The r.m. was stirred at r.t. for 3 h., and partitioned between EtOAc and water. The organic phase was separated, dried (MgSO$_4$), filtered and the solvent was evaporated in vacuo. The residue was purified by flash column chromatography over silica gel (eluent: DCM/MeOH 100/0 to 99/1). The product fractions were collected and the solvent was evaporated. Yield: 1.25 g of intermediate 107 (46%).

Example A43 a) Preparation of Intermediate 108

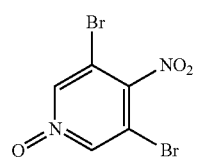 [SMILES: O=[N+]([O-])c1c(Br)c[n+]([O-])cc1Br]

Conc. HNO$_3$ (12.5 ml) was added to a sol. of 3,5-dibromo-pyridine N-oxide (4.5 g, 17.8 mmol) in conc. H$_2$SO$_4$ (16 ml). The r.m. was refluxed for 4 h., then cooled and poured onto ice-water. The resulting precipitate was collected by filtration and dried. Yield: 3.1 g of intermediate 108 (58%), which was used as such in the next step.

b) Preparation of Intermediate 109

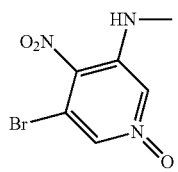

A 2 M sol. of methylamine in THF (7.15 ml, 14.3 mmol) was added to a mixture of intermediate 108 (2.66 g, 8.9 mmol) in THF (100 ml). The r.m. was stirred at 60° C. for 2 days, then conc. in vacuo. The residue was partitioned between DCM and an aq. NaHCO$_3$ sol. The organic phase was separated, dried (Na$_2$SO$_4$), filtered and the solvent was evaporated in vacuo. The residue was purified by flash column chromatography over silica gel (eluent: heptane/DCM/MeOH(NH$_3$) 100/0/0 to 0/100/0 to 0/70/30). The product fractions were collected and the solvent was evaporated. Yield: 1.2 g of intermediate 109 (54%).

c) Preparation of Intermediate 110

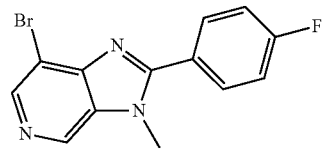 [SMILES: Cn1c(-c2ccc(F)cc2)nc2c(Br)cncc21]

4-Fluorobenzaldehyde (252 mg, 2.0 mmol) and Na$_2$S$_2$O$_4$ (1.18 g, 6.8 mmol) were added to a sol. of intermediate 109 (420 mg, 1.7 mmol) in EtOH (6 ml). The r.m. was heated under microwave conditions at 160° C. for 45 min. The r.m. was cooled to r.t. and diluted with EtOAc. The mixture was washed with an aq. NaHCO$_3$ sol. and brine. The organic phase was separated, dried (MgSO$_4$), filtered and the solvent was evaporated in vacuo. The residue was purified by flash column chromatography over silica gel (eluent: DCM/MeOH (NH$_3$) 100/0 to 97/3). The product fractions were collected and the solvent was evaporated. Yield: 0.35 g of intermediate 110 (68%).

Example A44

Preparation of Intermediate 111

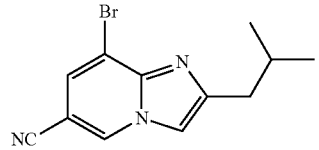 [SMILES: CC(C)Cc1cn2cc(C#N)cc(Br)c2n1]

A mixture of 6-amino-5-bromo-nicotinonitrile (4 g, 20.2 mmol) and 1-bromo-4-methyl-2-pentanone (5.43 g, 30.3 mmol) in NMP (40 ml) was heated at 150° C. for 2 h. The r.m. was cooled to r.t. and poured into an aq. 10% NaHCO$_3$ sol. The mixture was extracted with toluene. The organic layer was dried (MgSO$_4$), filtered and the solvent was evaporated in vacuo. The residue was purified by flash column chromatography over silica gel (eluent: n-heptane/EtOAc 100/0 to 50/50). The product fractions were collected and the solvent was evaporated. The residue was triturated with DIPE. Yield: 2.9 g of intermediate 111 (52%).

B. Preparation of the Compounds

Example B1

Preparation of Compound 1

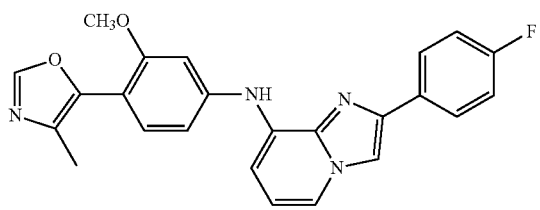

Cs$_2$CO$_3$ (0.56 g, 1.72 mmol), Pd$_2$(dba)$_3$ (0.039 g, 0.043 mmol) and BINAP (0.053 g, 0.086 mmol) were added to a sol. of intermediate 16 (0.25 g, 0.859 mmol) and intermediate 2 (0.184 g, 0.902 mmol) in DMF (80 ml). The r.m. was purged with N$_2$ for 5 min. and was then heated at 100° C. for 18 h. The r.m. was concentrated under reduced pressure. The residue was dissolved in DCM and the organic phase was washed with H$_2$O, dried (MgSO4), filtered and the solvent was evaporated in vacuo. The residue was purified by preparative HPLC [RP Shandon Hyperprep® C18 BDS (8 μm, 250 g, I.D. 5 cm); mobile phase: (0.25% NH$_4$CO$_3$ sol. in water, MeOH+CH$_3$CN). The product fractions were collected and concentrated under reduced pressure. The residue was suspended in DIPE and the precipitate was collected by filtration and dried under vacuum at 60° C. Yield: 0.068 g of compound 1 (19%).

Example B2

Preparation of Compound 2

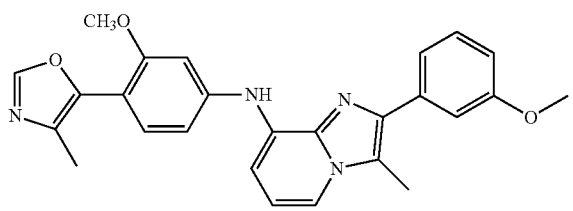

Cs$_2$CO$_3$ (0.616 g, 1.892 mmol), Pd$_2$(dba)$_3$ (0.043 g, 0.047 mmol) and BINAP (0.058 g, 0.094 mmol) were added to a sol. of intermediate 5 (0.3 g, 0.95 mmol) and intermediate 2 (0.203 g, 0.993 mmol) in DMF (20 ml). The mixture was purged with N$_2$ for 5 min. and was then heated at 100° C. for 18 h. The r.m. was concentrated under reduced pressure. The residue was dissolved in DCM and the organic phase was washed with H$_2$O, dried (MgSO4), filtered and the solvent was evaporated in vacuo. The residue was purified by preparative HPLC [RP Shandon Hyperprep® C18 BDS (8 μm, 250 g, I.D. 5 cm); mobile phase: (0.25% NH$_4$CO$_3$ sol. in water, MeOH+CH$_3$CN). The product fractions were collected and concentrated under reduced pressure. The solid product was dried under vacuum at 60° C. Yield: 0.129 g of compound 2 (30%).

Example B3

Preparation of Compound 3

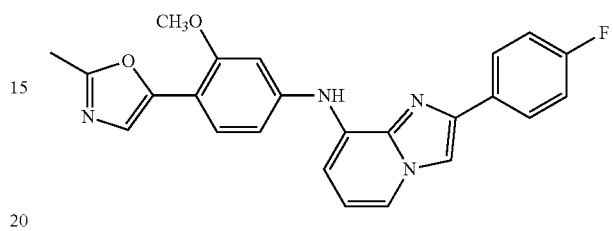

Intermediate 16 (0.230 g, 0.793 mmol), Pd$_2$(dba)$_3$ (0.060 g, 0.066 mmol), dicyclohexyl[2',4',6'-tris(1-methylethyl)[1,1'-biphenyl]-2-yl]phosphine (0.069 g, 0.145 mmol) and Cs$_2$CO$_3$ (0.646 g, 1.98 mmol) were added to a sol. of intermediate 4 (0.135 g, 0.661 mmol) in 2-methyl-2-propanol (10 ml), and the r.m. was heated at 110° C. overnight. After cooling, H$_2$O was added and the product was extracted with DCM. The organic phase was dried (MgSO4) filtered and concentrated under reduced pressure. The residue was purified by Flash column chromatography over Silica gel (eluent: DCM/MeOH from 100/0 to 98/2) and the product fractions were collected and worked up. The residue was crystallized from DIPE, filtered and dried under vacuum at 80° C. Yield: 0.032 g of compound 3 (11.7%).

Example B4 d) Preparation of Compound 4

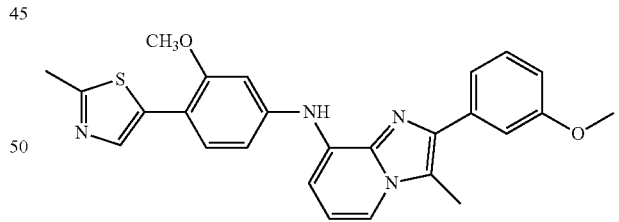

A sol. of intermediate 7 (0.070 g, 0.14 mmol), 5-bromo-2-methylthiazole (0.051 g, 0.29 mmol), Cs$_2$CO$_3$ (0.047 g, 0.14 mmol), Pd(PPh$_3$)$_4$ (0.033 g, 0.29 mmol) and a 3 N NaOH aq. sol. (0.024 ml, 0.07 mmol) in 1,4-dioxane (10 ml) was purged with N$_2$ for 2 min. The r.m. was stirred at 80° C. overnight. After cooling, H$_2$O was added and the product was extracted with DCM. The organic phase was washed with brine, dried (Na$_2$SO4) filtered and concentrated under reduced pressure. The residue was purified by preparative HPLC [RP Shandon Hyperprep® C18 BDS (8 μm, 250 g, I.D. 5 cm); mobile phase: (0.25% NH$_4$CO$_3$ sol. in water, MeOH+CH$_3$CN)]. The

Example B5

Preparation of Compound 5

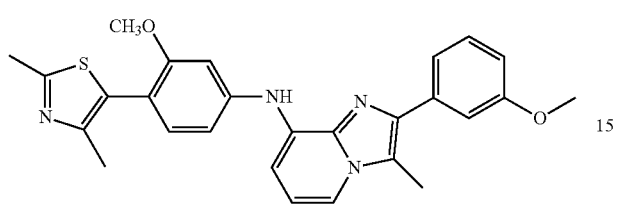

A sol. of intermediate 6 (0.220 g, 0.50 mmol), 2,4-dimethyl-5-(4,4,5,5-tetramethyl-1,3,2-dioxaborolan-2-yl)-1,3-thiazole (859833-13-9, 0.240 g, 1.0 mmol), Pd(PPh$_3$)$_4$ (0.116 g, 0.1 mmol), Cs$_2$CO$_3$ (0.163 g, 0.50 mmol) and a 3N NaOH aq. sol. (0.084 ml, 0.251 mmol) in 1,4-dioxane (20 ml) was purged with N$_2$ for 2 min. The r.m. was stirred at 80° C. overnight. After cooling, the r.m. was concentrated, H$_2$O was added and the product was extracted with EtOAc. The organic phase was washed with brine, dried (Na$_2$SO4) filtered and concentrated under reduced pressure. The residue was purified by preparative HPLC [RP Shandon Hyperprep® C18 BDS (8 µm, 250 g, I.D. 5 cm); mobile phase: (0.5% NH$_4$OAc sol. in water+10% CH$_3$CN, CH$_3$CN)]. The product fractions were collected and concentrated under reduced pressure. Yield: 0.078 g of compound 5 (33%).

Example B6

Preparation of Compound 6

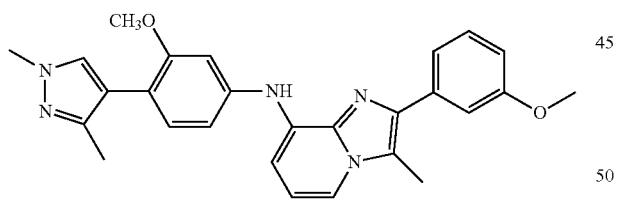

A sol. of intermediate 6 (0.220 g, 0.502 mmol), Pd(PPh$_3$)$_4$ (0.116 g, 0.1 mmol) in 1,4-dioxane (20 ml) was purged with N$_2$ for 2 min, and the r.m. was stirred at r.t. for 10 min. 1H-Pyrazole-1,3-dimethyl-4-(4,4,5,5-tetramethyl-1,3,2-dioxaborolan-2-yl) (0.223 g, 1.0 mmol), and Cs$_2$CO$_3$ (0.327 g, 1.0 mmol), were added into the r.m. After stirring for 10 min at r.t. a 3 N NaOH aq. sol. (0.084 ml, 0.251 mmol) was added. The r.m. was stirred at 80° C. overnight. After cooling, the r.m. was concentrated, H$_2$O was added and the product was extracted with EtOAc. The organic phase was washed with brine, dried (Na$_2$SO$_4$) filtered and concentrated under reduced pressure. The residue was purified by preparative HPLC [RP Shandon Hyperprep® C18 BDS (8 µm, 250 g, I.D. 5 cm); mobile phase: (0.25% NH$_4$CO$_3$ sol. in water, CH$_3$CN)]. The product fractions were collected and concentrated under reduced pressure. Yield: 0.013 g of compound 4 (19.7%).

Example B7

Preparation of Compound 7

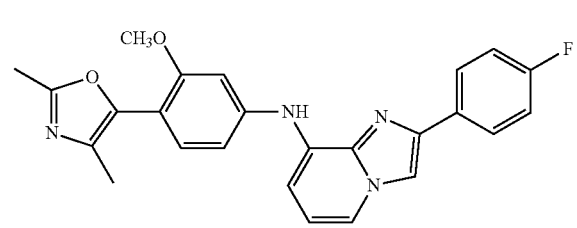

Cs$_2$CO$_3$ (1.137 g, 3.491 mmol), Pd$_2$(dba)$_3$ (0.080 g, 0.087 mmol) and BINAP (0.109 g, 0.175 mmol) were added to a sol. of intermediate 16 (0.508 g, 1.75 mmol) and intermediate 9 (0.400 g, 1.83 mmol) in DMF (30 ml). The mixture was purged with N$_2$ for 5 min. The r.m. was then heated at 100° C. for 18 h and subsequently concentrated under reduced pressure. The residue was dissolved in DCM and the organic phase was washed with H$_2$O, dried (MgSO4), filtered and the solvent evaporated in vacuo. The residue was purified by preparative HPLC [RP Shandon Hyperprep® C18 BDS (8 µm, 250 g, I.D. 5 cm); mobile phase: (0.25% NH$_4$CO$_3$ sol. in water, MeOH+CH$_3$CN)]. The product fractions were collected and evaporated off. The residue was re-purified by flash chromatography over Silica gel (eluent: DCM/MeOH from 100/0 to 95/5). The product fractions were collected and the solvent was evaporated. The residue was crystallized from n-heptane/DIPE, and the precipitate was filtered and dried under vacuum at 50° C. Yield: 0.099 g of compound 7 (13.2%).

Example B8

Preparation of Compound 8

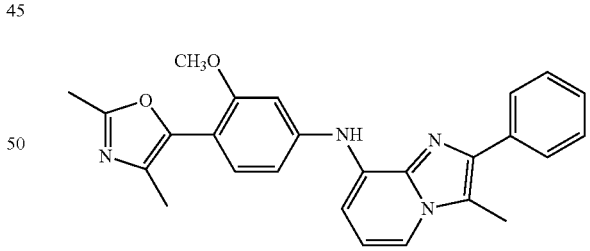

Cs$_2$CO$_3$ (0.261 g, 0.80 mmol), Pd$_2$(dba)$_3$ (0.018 g, 0.02 mmol) and BINAP (0.025 g, 0.04 mmol) were added to a sol. of intermediate 21 (0.115 g, 0.4 mmol) and intermediate 9 (0.091 g, 0.42 mmol) in DMF (20 ml) and the mixture was purged with N$_2$ for 5 min. The r.m. was heated at 100° C. for 18 h and then concentrated under reduced pressure. The residue was dissolved in DCM and the organic phase was washed with H$_2$O, dried (MgSO4), filtered and the solvent was evaporated in vacuo. The residue was purified by preparative HPLC [RP Shandon Hyperprep® C18 BDS (8 µm, 250 g, I.D. 5 cm); mobile phase: (0.25% NH$_4$CO$_3$ sol. in water, MeOH+CH$_3$CN)]. The product fractions were collected and concentrated under reduced pressure. The solid residue was dried under vacuum at 60° C. Yield: 0.043 g of compound 8 (25.3%).

Example B9

Preparation of Compound 9

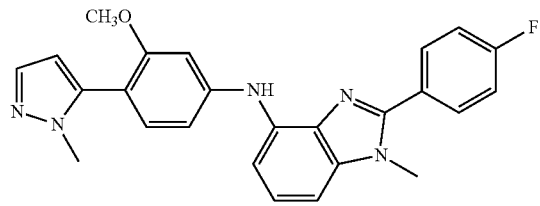

Intermediate 19 (0.305 g, 1 mmol), Pd$_2$(dba)$_3$ (0.091 g, 0.0.98 mmol), dicyclohexyl[2',4',6'-tris(1-methylethyl)[1,1'-biphenyl]-2-yl]phosphine (0.095 g, 0.2 mmol) and Cs$_2$CO$_3$ (0.978 g, 3.0 mmol) were added to a sol. of intermediate 13 (0.172 g, 0.983 mmol) in 2-methyl-2-propanol (20 ml), and the r.m. was heated at 110° C. overnight. The r.m. was then concentrated under reduced pressure. The residue was dissolved in DCM and the organic phase was washed with H$_2$O, dried (MgSO$_4$) filtered and concentrated under reduced pressure. The residue was purified by flash chromatography over Silica gel (eluent: DCM/MeOH(NH$_3$) from 100/0 to 98/2). The product fractions were collected and the solvent was evaporated. Yield: 0.160 g of compound 9 (37.4%).

Example B10

Preparation of Compound 10

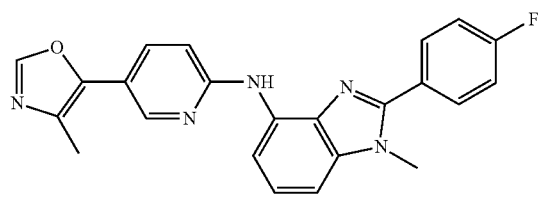 [SMILES: Cc1ncoc1-c1ccc(Nc2cccc3c2nc(-c2ccc(F)cc2)n3C)nc1]

Intermediate 19 (0.300 g, 0.983 mmol), Pd$_2$(dba)$_3$ (0.090 g, 0.098 mmol), dicyclohexyl[2',4',6'-tris(1-methylethyl)[1,1'-biphenyl]-2-yl]phosphine (0.103 g, 0.216 mmol) and Cs$_2$CO$_3$ (0.961 g, 2.95 mmol) were added to a sol. of intermediate 15 (0.172 g, 1 mmol) in 2-methyl-2-propanol (10 ml), and the r.m. was heated at 110° C. overnight. After cooling, H$_2$O was added and the mixture was stirred for 10 min prior to being diluted with DCM and filtered through diatomaceous earth. The filtrate was washed with H$_2$O and the organic phase was dried (MgSO$_4$) and concentrated under reduced pressure. The residue was purified by flash chromatography over Silica gel (eluent: DCM/MeOH from 100/0 to 95/5). The product fractions were collected and the solvent was evaporated. Yield: 0.169 g of compound 10 (43%).

Example B11

Preparation of Compound 11

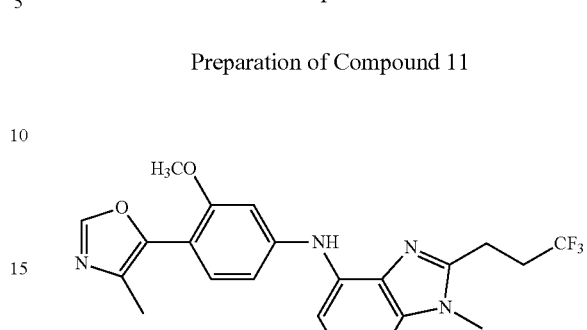

Intermediate 20 (0.210 g, 0.684 mmol), Pd$_2$(dba)$_3$ (0.062 g, 0.068 mmol), dicyclohexyl[2',4',6'-tris(1-methylethyl)[1,1'-biphenyl]-2-yl]phosphine (0.071 g, 0.15 mmol) and Cs$_2$CO$_3$ (0.688 g, 2.05 mmol) were added to a sol. of intermediate 2 (0.139 g, 0.684 mmol) in 2-methyl-2-propanol (10 ml), and the r.m. was heated at 110° C. for 6 h. After cooling, H$_2$O was added and the product was extracted with DCM. The organic phase was dried (MgSO4) and concentrated under reduced pressure. The residue was purified by preparative HPLC [RP Shandon Hyperprep® C18 BDS (8 μm, 250 g, I.D. 5 cm); mobile phase: (0.25% NH$_4$CO$_3$ sol. in water, CH$_3$CN)]. The product fractions were collected and concentrated under reduced pressure. Yield: 0.197 g of compound 11 (67%).

Example B12

Preparation of Compound 12

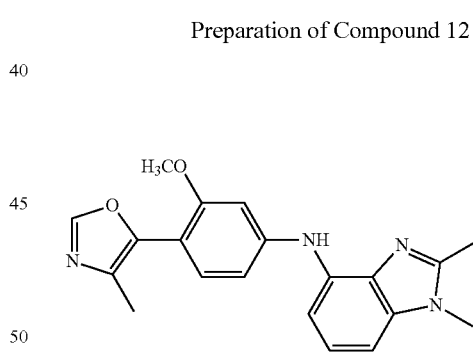

Intermediate 19 (0.660 g, 2.16 mmol), Pd$_2$(dba)$_3$ (0.198 g, 0.216 mmol), dicyclohexyl[2',4',6'-tris(1-methylethyl)[1,1'-biphenyl]-2-yl]phosphine (0.226 g, 0.476 mmol) and Cs$_2$CO$_3$ (2.115 g, 6.49 mmol) were added to a sol. of intermediate 2 (0.441 g, 2.16 mmol) in 2-methyl-2-propanol (30 ml), and the r.m. was heated at 90° C. for 72 hours. After cooling, the solvent was evaporated. H$_2$O was added and the mixture was extracted with DCM. The organic layer was separated, dried (MgSO$_4$) and concentrated under reduced pressure. The residue was purified by flash chromatography over Silica gel (eluent: DCM/MeOH(NH$_3$) from 100/0 to 99/1). The product fractions were collected and the solvent was evaporated. The product was crystallized from DIPE, filtered off and dried under vacuum. Yield: 0.465 g of compound 12 (50%).

Example B13

Preparation of Compound 13

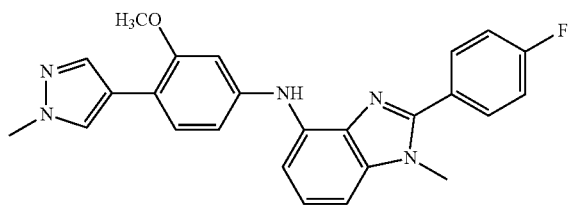 [SMILES: COc1cc(Nc2cccc3c2nc(-c2ccc(F)cc2)n3C)ccc1-c1cnn(C)c1]

Intermediate 19 (0.304 g, 0.99 mmol), Pd$_2$(dba)$_3$ (0.091 g, 0.099 mmol), dicyclohexyl[2',4',6'-tris(1-methylethyl)[1,1'-biphenyl]-2-yl]phosphine (0.104 g, 0.22 mmol) and Cs$_2$CO$_3$ (0.976 g, 3.0 mmol) were added to a sol. of intermediate 26 (0.203 g, 1.0 mmol) in 2-methyl-2-propanol (8 ml), and the r.m. was heated at 110° C. for 16 hours. After cooling, H$_2$O was added and the mixture was extracted with DCM. The organic layer was separated, dried (MgSO$_4$) and concentrated under reduced pressure. The residue was purified by flash chromatography over Silica gel (eluent: DCM isocratic). The product fractions were collected and the solvent was evaporated. The product was crystallized from DIPE, filtered off and dried under vacuum. Yield: 0.065 g of compound 13 (15.2%).

Example B14

Preparation of Compound 14

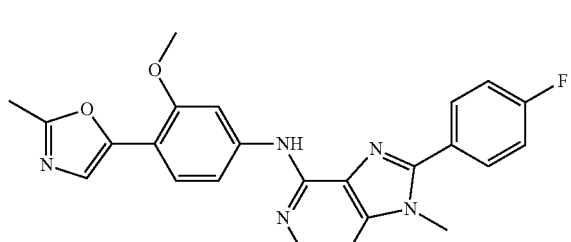

Intermediate 24 (0.298 g, 1.14 mmol), Pd$_2$(dba)$_3$ (0.104 g, 0.114 mmol), dicyclohexyl[2',4',6'-tris(1-methylethyl)[1,1'-biphenyl]-2-yl]phosphine (0.108 g, 0.228 mmol) and Cs$_2$CO$_3$ (1.108 g, 3.42 mmol) were added to a sol. of intermediate 4 (0.233 g, 1.14 mmol) in 2-methyl-2-propanol (15 ml), and the r.m. was heated at 110° C. overnight. After cooling, H$_2$O was added and the product was extracted with DCM. The organic phase was dried (MgSO4) filtered and concentrated under reduced pressure. The residue was crystallized in DIPE/CN$_3$CN and the precipitate was filtered and dried in vacuum. Yield: 0.246 g of compound 14 (50%).

Example B15

Preparation of Compound 15

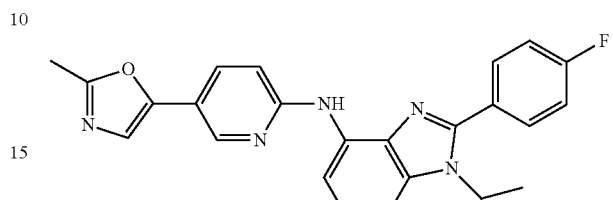

Intermediate 34 (0.320 g, 0.96 mmol), Pd$_2$(dba)$_3$ (0.088 g, 0.096 mmol), dicyclohexyl[2',4',6'-tris(1-methylethyl)[1,1'-biphenyl]-2-yl]phosphine (0.091 g, 0.192 mmol) and Cs$_2$CO$_3$ (0.939 g, 2.881 mmol) were added to a sol. of intermediate 31 (0.320 g, 0.96 mmol) in 2-methyl-2-propanol (15 ml), and the r.m. was heated at 100° C. overnight. After cooling, H$_2$O was added and the product was extracted with DCM. The organic phase was dried (MgSO$_4$) filtered and concentrated under reduced pressure. The residue was purified by flash chromatography over Silica gel (eluent: DCM/MeOH from 100/0 to 98/2). The product fractions were collected and the solvent was evaporated. Yield: 0.216 g of compound 15 (51.5%).

Example B16

Preparation of Compound 16

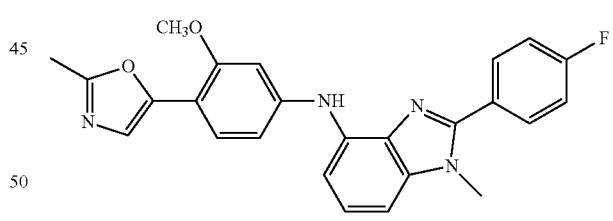

Intermediate 19 (0.336 g, 1.10 mmol), Pd$_2$(dba)$_3$ (0.101 g, 0.11 mmol), dicyclohexyl[2',4',6'-tris(1-methylethyl)[1,1'-biphenyl]-2-yl]phosphine (0.115 g, 0.242 mmol) and Cs$_2$CO$_3$ (1.077 g, 3.31 mmol) were added to a sol. of intermediate 4 (0.225 g, 1.10 mmol) in 2-methyl-2-propanol (15 ml), and the r.m. was heated at 90° C. for 72 h. After cooling, the solvent was evaporated, H$_2$O was added and the product was extracted with DCM. The organic phase was dried (MgSO4) filtered and concentrated under reduced pressure. The residue was purified by flash chromatography over Silica gel (eluent: DCM/MeOH from 100/0 to 99/1) and the product fractions were collected and the solvent was evaporated. The residue was crystallized from DIPE, filtered and dried under vacuum at 80° C. Yield: 0.220 g of compound 16 (46.6%).

Example B17

Preparation of Compound 17

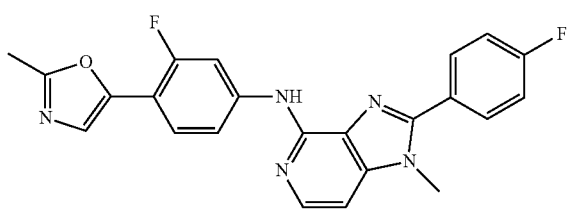 [SMILES: Cc1ncc(-c2ccc(Nc3nccc4c3nc(-c3ccc(F)cc3)n4C)cc2F)o1]

Intermediate 41 (0.22 g, 0.84 mmol), Pd$_2$(dba)$_3$ (0.077 g, 0.084 mmol), dicyclohexyl[2',4',6'-tris(1-methylethyl)[1,1'-biphenyl]-2-yl]phosphine (0.080 g, 0.168 mmol) and Cs$_2$CO$_3$ (0.822 g, 2.52 mmol) were added to a sol. of intermediate 43 (0.161 g, 0.841 mmol) in 2-methyl-2-propanol (15 ml), and the r.m. was heated at 100° C. for 20 h. After cooling, the solvent was evaporated, H$_2$O was added and the product was extracted with DCM. The organic phase was dried (MgSO4) filtered and the solvent was evaporated. The residue was purified by flash chromatography over Silica gel (eluent: DCM/MeOH(NH$_3$) 99/1) and the product fractions were collected and the solvent was evaporated. Yield: 0.20 g of compound 17 (57%).

Example B18

Preparation of Compound 18

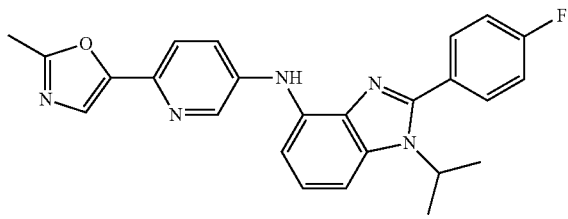 [SMILES: Cc1ncc(-c2ccc(Nc3cccc4c3nc(-c3ccc(F)cc3)n4C(C)C)cn2)o1]

Intermediate 34 (0.190 g, 0.57 mmol), Pd$_2$(dba)$_3$ (0.052 g, 0.057 mmol), dicyclohexyl[2',4',6'-tris(1-methylethyl)[1,1'-biphenyl]-2-yl]phosphine (0.054 g, 0.114 mmol) and Cs$_2$CO$_3$ (0.558 g, 1.71 mmol) were added to a sol. of intermediate 48 (0.100 g, 0.571 mmol) in 2-methyl-2-propanol (10 ml), and the r.m. was heated at 110° C. for 14 h. After cooling, H$_2$O was added and the product was extracted with DCM. The organic phase was dried (MgSO$_4$) filtered and concentrated under reduced pressure. The residue was purified by flash chromatography over silica gel (eluent: DCM/MeOH(NH$_3$) from 100/0 to 98/2). The product fractions were collected and the solvent was evaporated. Yield: 0.093 g of compound 18 (38%).

Example B19

Preparation of Compound 169

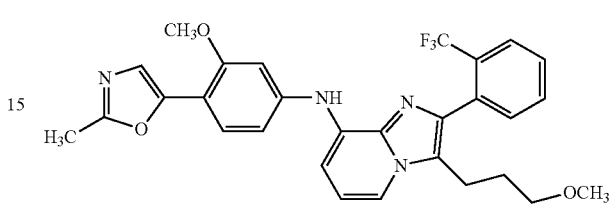

A mixture of intermediate 90 (30 mg, 0.056 mmol), and Raney nickel (20 mg), in THF (30 ml) was stirred at r.t. under H$_2$ (atmospheric pressure). After uptake of H$_2$ (2 eq), the catalyst was filtered off over diatomaceous earth. The solvent was evaporated and the residue was partitioned between DCM and H$_2$O. The organic layer was dried (MgSO$_4$), filtered and concentrated in vacuo. The residue was purified by preparative HPLC [RP Vydac Denali C18 (10 μm, 250 g, I.D. 5 cm); mobile phase: (0.25% NH$_4$CO$_3$ sol. in water, CH$_3$CN)]. The product fractions were collected and concentrated under reduced pressure. Yield: 1.1 mg of compound 169 (4%).

Example B20

Preparation of Compound 188

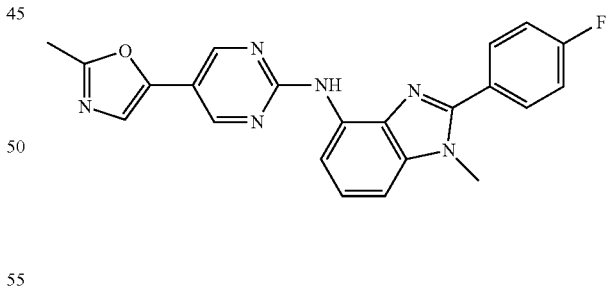

Intermediate 57 (0.224 g, 1.15 mmol), Pd(OAc)$_2$ (0.034 g, 0.15 mmol), Xantphos (0.133 g, 0.23 mmol) and Cs$_2$CO$_3$ (0.498 g, 1.53 mmol) were added to a sol. of intermediate 63 (0.185 g, 0.76 mmol) in dioxane (3 ml), and the r.m. was heated at 160° C. for 1 h under microwave irradiation. After cooling, H$_2$O was added and the product was extracted with DCM. The organic phase was dried (MgSO$_4$) and concentrated under reduced pressure. The residue was purified by preparative HPLC [RP Shandon Hyperprep® C18 BDS (8 μm, 250 g, I.D. 5 cm); mobile phase: (0.25% NH$_4$CO$_3$ sol. in water, MeOH)]. The product fractions were collected and concentrated under reduced pressure. Yield: 0.040 g of compound 188 (13%).

Example B21

Preparation of Compound 128

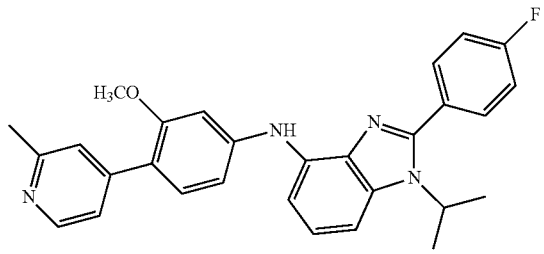 [SMILES: COc1cc(Nc2cccc3c2nc(-c2ccc(F)cc2)n3C(C)C)ccc1-c1ccnc(C)c1]

Intermediate 34 (0.405 g, 1.17 mmol), Pd$_2$(dba)$_3$ (0.107 g, 0.12 mmol), X-Phos (0.122 g, 0.26 mmol) and Cs$_2$CO$_3$ (1.14 g, 3.5 mmol) were added to a sol. of intermediate 56 (0.250 g, 1.17 mmol) in 2-methyl-2-propanol (10 ml), and the r.m. was heated at 100° C. for 4 h. After cooling, H$_2$O was added and the product was extracted with DCM. The organic phase was dried (MgSO$_4$) filtered and concentrated under reduced pressure. The residue was purified by flash chromatography over Silica gel (eluent: DCM/MeOH(NH$_3$) from 100/0 to 98/2). The product fractions were collected and the solvent was evaporated. The residue was triturated with DIPE/2-propanol. Yield: 0.284 g of compound 128 (52%).

Example B22

Preparation of Compound 165

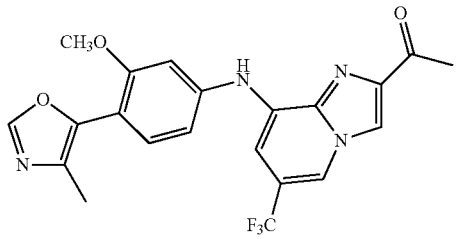

A solution of compound 143 (prepared form intermediate 98 and intermediate 2, according to example B3, 150 mg, 0.33 mmol) in THF (5 ml) was added slowly to a 1 M solution of CH$_3$Li in THF (1 ml, 1 mmol) at 0° C. The mixture was stirred at r.t. for 2 h, and then an additional 1 M sol. of CH$_3$Li in THF (1 ml, 1 mmol) was added and stirring was continued at r.t. for 1 h. An aq. 10% HCl solution was added and the mixture was extracted with DCM. The organic phase was dried (MgSO$_4$) filtered and concentrated under reduced pressure. The residue was purified by flash chromatography over Silica gel (eluent: DCM/MeOH(NH$_3$) from 100/0 to 99/1). The product fractions were collected and the solvent was evaporated. Yield: 21 mg of compound 165 (15%).

Example B23

Preparation of Compound 120

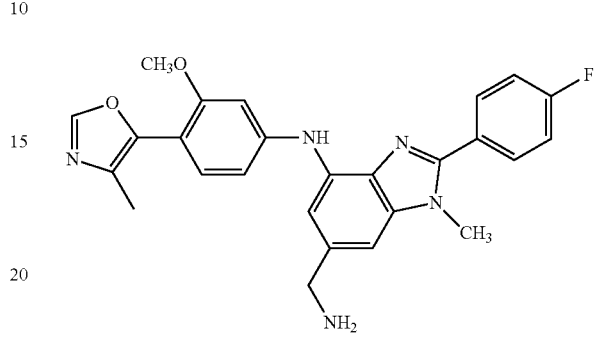

A mixture of compound 123 (prepared form intermediate 104 and intermediate 2, according to example B18, 40 mg, 0.088 mmol), and Raney nickel (20 mg), in MeOH(NH$_3$) (40 ml) was stirred at r.t. under H$_2$ (atmospheric pressure). After uptake of H$_2$ (2 eq), the catalyst was filtered off over diatomaceous earth. The solvent was evaporated and the residue was purified by flash chromatography over silica gel (eluent: DCM/MeOH(NH$_3$) 90/10). The product fractions were collected and the solvent was evaporated. Yield: 7 mg of compound 120 (17%).

Example B24

Preparation of Compound 197

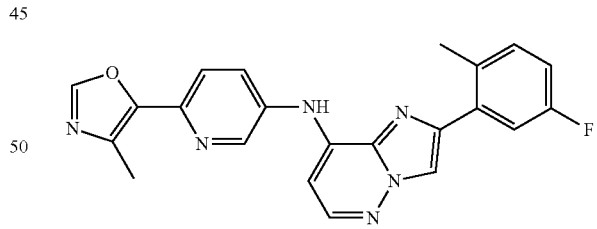

A 1:1 mixture of THF and MeOH (100 ml) was added to Pd/C (10%, 500 mg) under a N$_2$ atmosphere. Subsequently, a 0.4% thiophene solution in DIPE (0.5 ml), compound 198 (prepared according to example B3, 49 mg, 0.11 mmol), and KOAc (13 mg, 0.13 mmol) were added, and the r.m. was stirred at 25° C. under a H$_2$ atmosphere until 1 eq of H$_2$ was absorbed. The catalyst was filtered off over diatomaceous earth. The filtrate was evaporated and the residue was partitioned between DCM and a sat. aq. NaHCO$_3$ sol. The organic layer was dried (MgSO$_4$), filtered and the solvent was evaporated. The residue was purified by flash chromatography over silica gel (eluent: DCM/MeOH(NH$_3$) from 100/0 to 96/4).

Example B25

Preparation of Compound 179

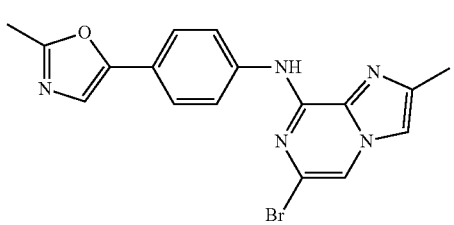

A mixture of 4-(2-methyl-oxazol-5-yl)-phenylamine (615 mg, 3.53 mmol), intermediate 101 (933 mg, 3.21 mmol), and DIPEA (1.24 g, 9.62 mmol) in CH$_3$CN (10 ml) were heated at 200° C. under microwave irradiation for 1.5 h. The volatiles were evaporated under reduced pressure and the residue was partitioned between DCM and H$_2$O. The organic layer was dried (MgSO$_4$), filtered and the solvent was evaporated. The residue was purified by flash chromatography over silica gel (eluent: DCM/MeOH(NH$_3$) 95/5). The fractions containing product were collected and the solvent was evaporated. The residue was purified further by preparative HPLC [RP Shandon Hyperprep® C18 BDS (8 µm, 250 g, I.D. 5 cm); mobile phase: (0.25% NH$_4$CO$_3$ sol. in water, MeOH)]. The product fractions were collected and concentrated under reduced pressure. Yield: 0.031 g of compound 179 (3%).

Example B26 a) Preparation of Compound 185

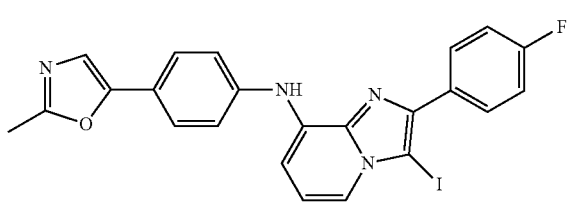 [SMILES: Cc1ncc(-c2ccc(Nc3cccn4c(I)c(-c5ccc(F)cc5)nc34)cc2)o1]

1-Iodo-2,5-pyrrolidinedione (837 mg, 3.72 mmol) was added to compound 42 (1.3 g, 3.38 mmol) in DCM (50 ml) and AcOH (5 ml). The r.m. was stirred at r.t. for 5 min., then washed with an aq. NaHCO$_3$ sol. The organic layer was dried (MgSO$_4$), filtered, concentrated in vacuo. The residue was purified by flash chromatography over silica gel (eluent: DCM/MeOH(NH$_3$) from 100/0 to 97/3). The product fractions were collected and the solvent was evaporated. Yield: 500 mg of compound 185 (29%).

b) Preparation of Compound 177

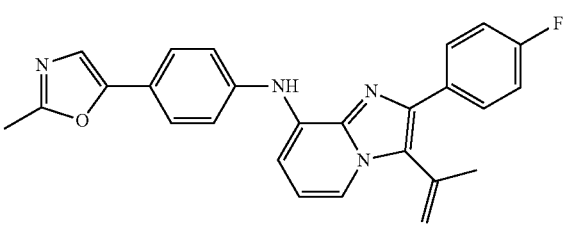 [SMILES: C=C(C)c1c(-c2ccc(F)cc2)nc2c(Nc3ccc(-c4cnc(C)o4)cc3)cccn12]

Isopropenylboronic acid pinacol ester (151 mg, 0.9 mmol) and Pd(PPh$_3$)$_4$ (52 mg, 0.045 mmol) was added to a sol. of compound 185 (230 mg, 0.45 mmol) in dioxane (2 ml) and an aq. NaHCO$_3$ sol. (2 ml), and the mixture was stirred and heated at 150° C. for 10 min. under microwave irradiation. The r.m. was cooled to r.t. and filtered over diatomaceous earth using EtOAc, and the filtrate was evaporated. The residue was purified by flash column chromatography over silica gel (eluent: DCM/MeOH(NH$_3$) from 100/0 to 97/3). The product fractions were collected and the solvent was evaporated. Yield: 14 mg of compound 177 (7%).

The product fractions were collected and the solvent was evaporated. Yield: 9.5 mg of compound 197 (21%).

c) Preparation of Compound 175

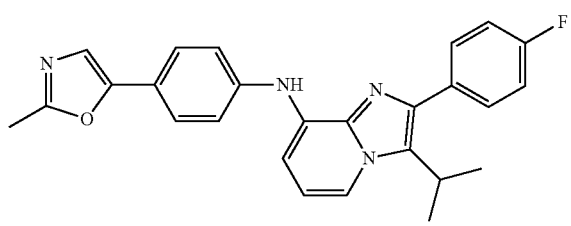 [SMILES: Cc1ncc(-c2ccc(Nc3cccn4c(C(C)C)c(-c5ccc(F)cc5)nc34)cc2)o1]

MeOH (40 ml) was added to Pt/C$_5$% (50 mg) under N$_2$ atmosphere. Subsequently, compound 177 (150 mg, 0.35 mmol) was added. The r.m. was stirred at 25° C. under H$_2$ atmosphere until 1 eq of H$_2$ was absorbed. The catalyst was filtered off over diatomaceous earth and the filtrate was evaporated. The residue was triturated with DIPE. Yield: 70 mg of crude compound 175 (46%).

Example B27 a) Preparation of Compound 156

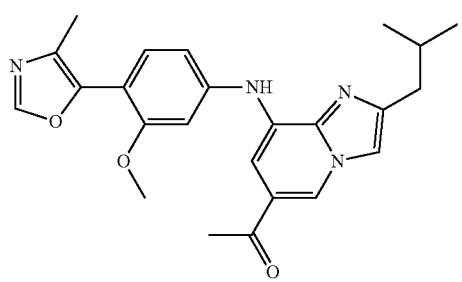 [SMILES: COc1cc(Nc2cc(C(C)=O)cn3cc(CC(C)C)nc23)ccc1-c1ocnc1C]

A 3 M CH$_3$MgBr sol. in Et$_2$O was added to a sol. of compound 151 (prepared from intermediate 2 and intermediate 111 according to example B3, 105 mg, 0.26 mmol) in THF (20 ml) at 0° C. Th r.m. was stirred at r.t. overnight, and then quenched with a sat. aq. NH$_4$Cl sol. Water was added, and the mixture was extracted with DCM. The organic layer was dried (MgSO$_4$), filtered, concentrated in vacuo. The residue was purified by flash chromatography over silica gel (eluent: DCM/MeOH from 100/0 to 95/5). The product fractions were collected and the solvent was evaporated. The residue was dissolved in DIPE/CH$_3$CN, and a 6 N HCl sol. in 2-propanol was added. The resulting precipitate was collected by filtration and dried. Yield: 3.2 mg of compound 156 as HCl salt (3%).

b) Preparation of Compound 162

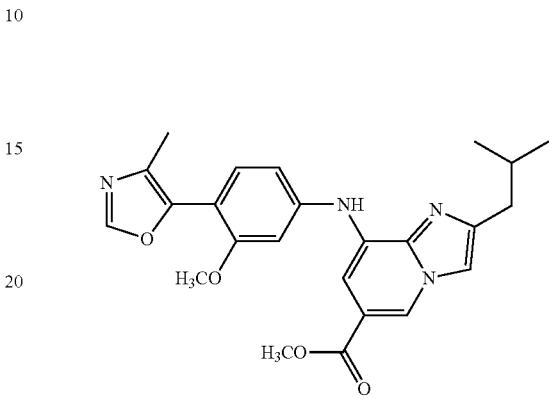

A solution of NaOH (2 g, 50 mmol) in H$_2$O (40 ml) was added to a sol. of compound 151 (0.4 g, 1 mmol) in dioxane (40 ml). The r.m. was stirred at reflux for 3 h, and was then cooled to r.t. and neutralized to pH 7 with aq. conc. HCl. The resulting precipitate was collected by filtration and dried. Part of the residue (213 mg, 0.51 mmol) was dissolved in DCM (13 ml), and oxalylchloride (0.13 ml, 1.52 mmol) and DMF (0.2 ml, 2.58 mmol) were subsequently added. The r.m. was stirred at r.t. overnight, then poured into MeOH (20 ml) and stirred at r.t. for 1 h. The mixture was partitioned between DCM and an aq. sat. NaHCO$_3$ sol. The organic layer was dried (MgSO$_4$), filtered, concentrated in vacuo. The residue was purified by flash chromatography over silica gel (eluent: DCM/MeOH from 100/0 to 95/5). The product fractions were collected and the solvent was evaporated. The residue was triturated with DIPE. Yield: 58 mg of compound 162 (20% yield over the 2 steps).

Compounds 1 to 202 in tables 1, 2, 3, 4 and 5 list the compounds that were prepared by analogy to one of the above Examples. In case no salt form is indicated, the compound was obtained as a free base. 'Pr.' refers to the Example number according to which protocol the compound was synthesized. 'Co. No.' means compound number. 'Bx' refers to the general Experimental Procedure 1 wherein sodium tert-butoxide, toluene, BINAP and Pd(OAc)$_2$ were used.

In order to obtain the HCl salt forms of the compounds, typical procedures known to those skilled in the art can be used. In a typical procedure, for example, the crude residue (free base) was dissolved in DIPE or Et$_2$O and subsequently, a 6 N HCl solution in 2-propanol or a 1 N HCl solution in Et$_2$O was added dropwise. The mixture was stirred for 10 minutes and the product was filtered off. The HCl salt was dried in vacuo.

TABLE 1
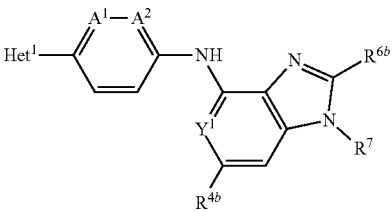
| Co. No. | Pr. | Het¹ | A¹ | A² | Y¹ | R⁴ᵇ | R⁶ᵇ | R⁷ | salt form |
|---|---|---|---|---|---|---|---|---|---|
| 13 | B13 | 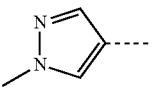 | COCH₃ | CH | CH | H | 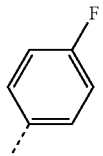 | CH₃ | |
| 9 | B9 | 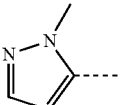 | COCH₃ | CH | CH | H | 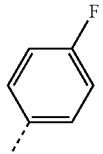 | CH₃ | |
| 19 | B3 | 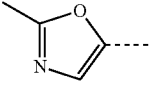 | CH | CH | CH | H | 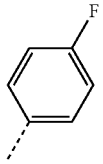 | CH(CH₃)₂ | •2 HCl |
| 11 | B11 | 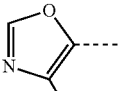 | COCH₃ | CH | CH | H | 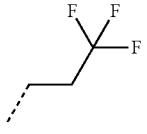 | CH₃ | |
| 20 | Bx | 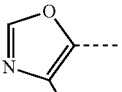 | COCH₃ | CH | CH | H | 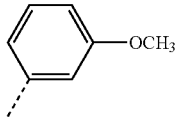 | CH₃ | |
| 21 | B3 | 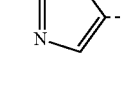 | CH | CH | CH | H | 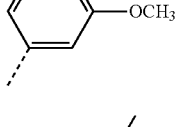 | CH(CH₃)₂ | |
| 22 | B3 | 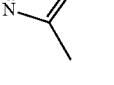 | COCH₃ | CH | CH | H | 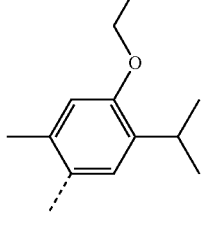 | CH₃ | |
| 23 | B3 | 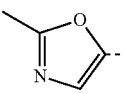 | CH | CH | N | H | 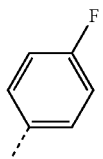 | CH₃ | |

TABLE 1-continued
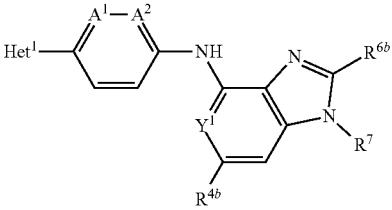
| Co. No. | Pr. | Het¹ | A¹ | A² | Y¹ | R⁴ᵇ | R⁶ᵇ | R⁷ | salt form |
|---|---|---|---|---|---|---|---|---|---|
| 15 | B15 | 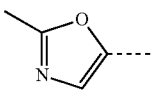 | CH | N | CH | H | 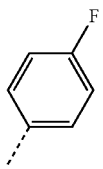 | CH(CH₃)₂ | |
| 12 | B12 |  | COCH₃ | CH | CH | H | 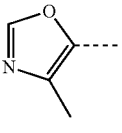 | CH₃ | |
| 16 | B16 | 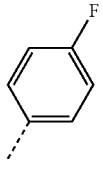 | COCH₃ | CH | CH | H |  | CH₃ | |
| 24 | B3 | 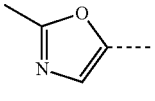 | COCH₃ | CH | CH | H | 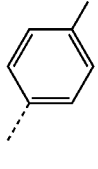 | CH₃ | |
| 14 | B14 |  | COCH₃ | CH | N | H | 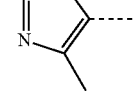 | CH₃ | |
| 25 | B3 | 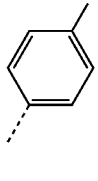 | COCH₃ | CH | CH | H |  | CH(CH₃)₂ | •2 HCl |
| 26 | B3 | 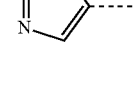 | CH | CH | N | H | 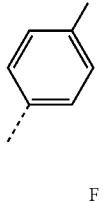 | CH(CH₃)₂ | |

TABLE 1-continued
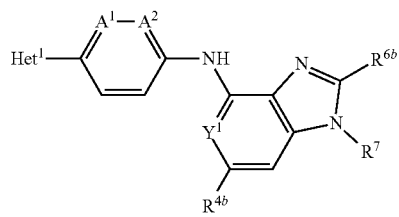
| Co. No. | Pr. | Het¹ | A¹ | A² | Y¹ | R⁴ᵇ | R⁶ᵇ | R⁷ | salt form |
|---|---|---|---|---|---|---|---|---|---|
| 27 | B3 | 2-oxazolyl | COCH₃ | CH | N | H | 4-F-phenyl | CH(CH₃)₂ | |
| 18 | B18 | 2-oxazolyl | N | CH | CH | H | 4-F-phenyl | CH(CH₃)₂ | |
| 28 | B3 | 2-oxazolyl | CF | CH | CH | H | 4-F-phenyl | CH(CH₃)₂ | |
| 17 | B17 | 2-oxazolyl | CF | CH | N | H | 4-F-phenyl | CH₃ | |
| 29 | B3 | 2-oxazolyl | N | CH | CH | H | 4-F-phenyl | CH₃ | |
| 10 | B10 | 4-methyl-5-oxazolyl | CH | N | CH | H | 4-F-phenyl | CH₃ | |
| 30 | B3 | 2-oxazolyl | COCH₃ | CH | CH | CF₃ | 4-F-phenyl | CH₃ | |

TABLE 1-continued
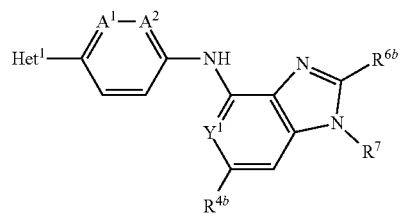
| Co. No. | Pr. | Het¹ | A¹ | A² | Y¹ | R⁴ᵇ | R⁶ᵇ | R⁷ | salt form |
|---|---|---|---|---|---|---|---|---|---|
| 31 | B3 | 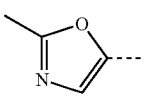 | COCH₃ | CH | N | H | 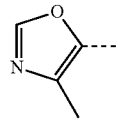 | CH₃ | |
| 32 | Bx | 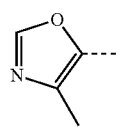 | CH | N | CH | H | 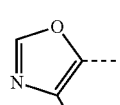 | CH₃ | |
| 33 | Bx | 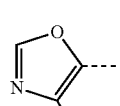 | CH | N | CH | H | 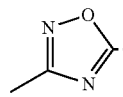 | CH₃ | |
| 34 | B3 | 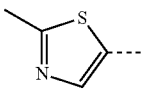 | N | CH | CH | H | 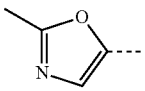 | C(CH₃)₃ | |
| 35 | B3 | | N | CH | CH | H | | CH₃ | |
| 36 | B3 | | COCH₃ | CH | CH | H | | CH₃ | |
| 37 | B3 | | COCH₃ | CH | CH | H | CH₃ | | |
| 53 | B3 | | CH | CH | N | H | | CH₃ | |

TABLE 1-continued
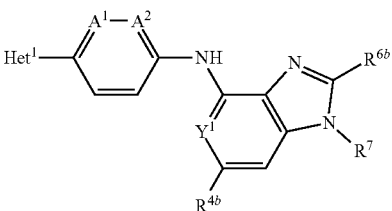
| Co. No. | Pr. | Het¹ | A¹ | A² | Y¹ | R⁴ᵇ | R⁶ᵇ | R⁷ | salt form |
|---|---|---|---|---|---|---|---|---|---|
| 54 | B3 | 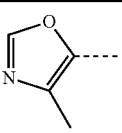 | COCH₃ | CH | N | H | 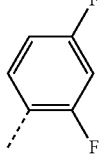 | CH₃ | |
| 55 | B3 | 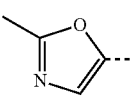 | CF | CH | N | H | 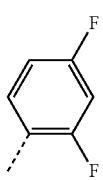 | CH₃ | |
| 56 | B3 | 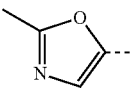 | CH | CH | CH | F | 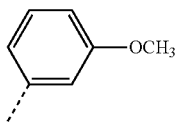 | CH₃ | |
| 58 | B3 | 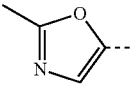 | CH | CH | N | CH₃ | 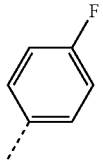 | CH₃ | |
| 59 | B3 | 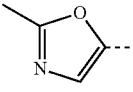 | COCH₃ | CH | N | CH₃ | 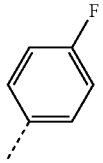 | CH₃ | |
| 61 | B3 | 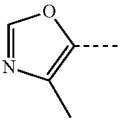 | N | CH | CH | H | 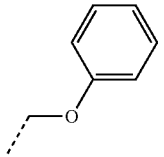 | CH₃ | |
| 62 | B3 | 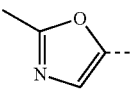 | COCH₃ | CH | CH | H | 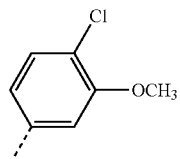 | CH₃ | |
| 63 | B3 | 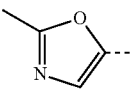 | COCH₃ | CH | CH | H | 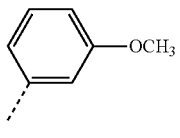 | CH₃ | |

TABLE 1-continued

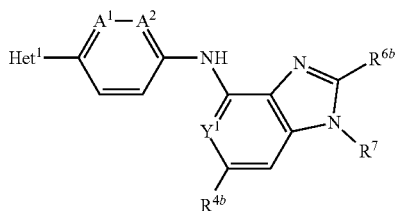

| Co. No. | Pr. | Het¹ | A¹ | A² | Y¹ | R⁴ᵇ | R⁶ᵇ | R⁷ | salt form |
|---|---|---|---|---|---|---|---|---|---|
| 64 | B3 | 2-methyl-oxazol-5-yl | COCH₃ | CH | CH | H | cyclopropylmethyl | C₂H₅ | |
| 65 | B3 | 4-methyl-isoxazol-5-yl | CF | CH | CH | H | 4-fluorophenyl | isopropyl | ·HCl |
| 66 | B3 | 2-methyl-oxazol-5-yl | CF | CH | N | H | cyclopropylmethyl | CH₃ | |
| 67 | B18 | 1-methyl-pyrazol-4-yl | CH | CH | CH | H | 4-fluorophenyl | CH₃ | |
| 68 | B18 | 1-methyl-pyrazol-4-yl | COCH₃ | N | CH | H | 4-fluorophenyl | CH₃ | |
| 69 | B18 | 1-methyl-pyrazol-4-yl | COCH₃ | N | CH | H | 2-fluorophenyl | isopropyl | |
| 70 | B18 | 1-methyl-pyrazol-4-yl | N | CH | CH | H | 4-fluorophenyl | CH₃ | ·2 HCl |
| 71 | B18 | 1-methyl-pyrazol-5-yl | CH | N | CH | H | 4-fluorophenyl | CH₃ | |

TABLE 1-continued
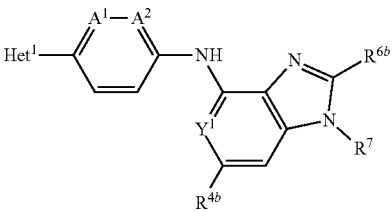
| Co. No. | Pr. | Het¹ | A¹ | A² | Y¹ | R⁴ᵇ | R⁶ᵇ | R⁷ | salt form |
|---|---|---|---|---|---|---|---|---|---|
| 72 | B18 | 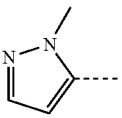 | CH | CH | CH | H | 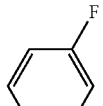 | CH₃ | |
| 73 | B18 | 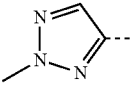 | COCH₃ | CH | CH | H | 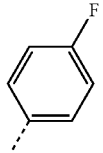 | CH₃ | |
| 74 | B18 | 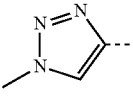 | COCH₃ | CH | CH | H | 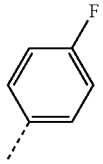 | CH₃ | |
| 75 | B18 | 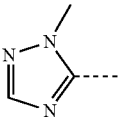 | COCH₃ | CH | CH | H | 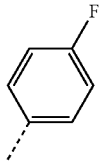 | CH₃ | |
| 76 | B18 | 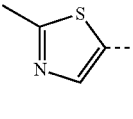 | N | CH | CH | H | 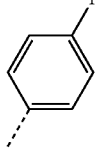 | CH₃ | |
| 77 | B18 | 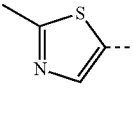 | COCH₃ | CH | CH | H | 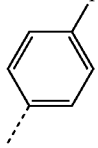 | 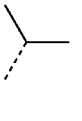 | |
| 78 | B17 | 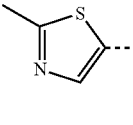 | COCH₃ | CH | N | H | 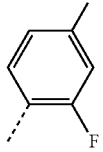 | CH₃ | |
| 79 | B18 | 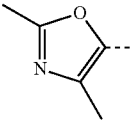 | N | CH | CH | F | 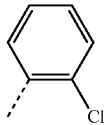 | CH₃ | |

TABLE 1-continued
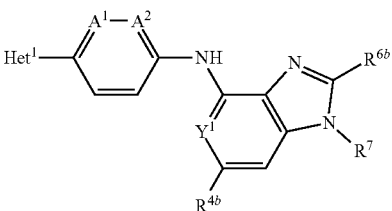
| Co. No. | Pr. | Het¹ | A¹ | A² | Y¹ | R⁴ᵇ | R⁶ᵇ | R⁷ | salt form |
|---|---|---|---|---|---|---|---|---|---|
| 80 | B3 | 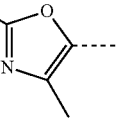 | COCH₃ | CH | CH | H | 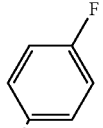 |  | •HCl |
| 81 | B18 | 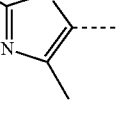 | CH | CH | CH | H | 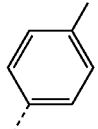 |  | |
| 82 | B18 | 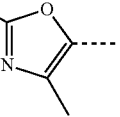 | N | CH | CH | H | 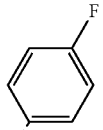 |  | |
| 83 | B18 | 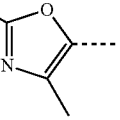 | CH | CH | CH | H | 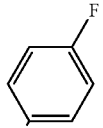 | CH₃ | |
| 84 | B18 | 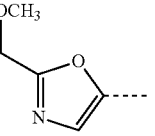 | CH | CH | CH | H | 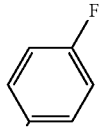 |  | |
| 85 | B17 | 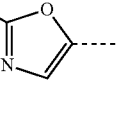 | N | CH | N | H | 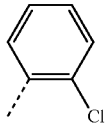 | CH₃ | |
| 86 | B18 | 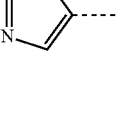 | N | CH | CH | CN | 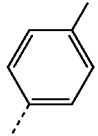 | CH₃ | |
| 87 | B18 | 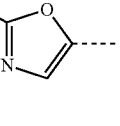 | N | CH | CH | H | 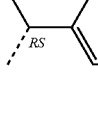 | CH₃ | |

TABLE 1-continued

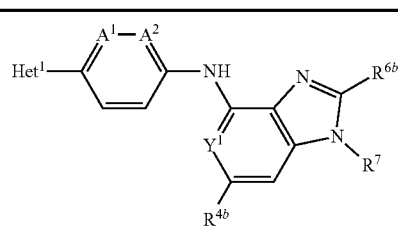

| Co. No. | Pr. | Het¹ | A¹ | A² | Y¹ | R⁴ᵇ | R⁶ᵇ | R⁷ | salt form |
|---|---|---|---|---|---|---|---|---|---|
| 88 | B18 | 2-oxazolyl | N | CH | CH | H | 1-(4-chlorophenyl)cyclopropyl | CH₃ | •2 HCl •H₂O |
| 89 | B18 | 2-oxazolyl | N | CH | CH | F | 4-fluorophenyl | isopropyl | •1.7 HCl •1.6 H₂O. |
| 90 | B18 | 2-oxazolyl | CH | CH | CH | F | pyrrolidin-1-yl | CH₃ | |
| 91 | B17 | 2-oxazolyl | COCH₃ | CH | N | H | 3,3,3-trifluoropropyl | CH₃ | |
| 92 | B17 | 2-oxazolyl | COCH₃ | CH | N | CH₃ | tetrahydropyran-4-yl | CH₃ | |
| 93 | B18 | 2-oxazolyl | COCH₃ | CH | CH | H | tetrahydropyran-4-yl | isopropyl | |
| 94 | B17 | 2-oxazolyl | COCH₃ | CH | N | cyclopropyl | 2,4-difluorophenyl | CH₃ | |
| 95 | B18 | 2-oxazolyl | OCH₃ | CH | CH | OCH₃ | 4-fluorophenyl | CH₃ | |
| 96 | B18 | 2-oxazolyl | CH | CH | CH | H | isopropoxymethyl | CH₃ | |

TABLE 1-continued

| Co. No. | Pr. | Het¹ | A¹ | A² | Y¹ | R⁴ᵇ | R⁶ᵇ | R⁷ | salt form |
|---|---|---|---|---|---|---|---|---|---|
| 97 | B17 | 2-oxazolyl | COCH₃ | CH | N | CH₃ | 3-methoxyphenyl | CH₃ | |
| 98 | B17 | 2-oxazolyl | CH | CH | N | CH₃ | 3-methoxyphenyl | CH₃ | |
| 99 | B18 | 2-oxazolyl | CH | CH | CH | CF₃ | 4-methyloxazol-5-yl | CH₃ | |
| 100 | B18 | 2-oxazolyl | CH | CH | CH | CF₃ | tetrahydropyran-4-yl | CH₃ | |
| 101 | B18 | 2-oxazolyl | N | CH | CH | CF₃ | 4-fluorophenyl | CH₃ | |
| 102 | B17 | 2-oxazolyl | COCH₃ | CH | N | CH₃ | 3-isopropoxyphenyl | CH₃ | |
| 103 | B18 | 2-oxazolyl | N | CH | CH | CN | 3-methoxyphenyl | CH₃ | |
| 104 | B18 | 2-oxazolyl | COCH₃ | CH | CH | F | pyrrolidin-1-yl | CH₃ | |
| 105 | B18 | 2-oxazolyl | N | CH | CH | F | 3-methoxyphenyl | CH₃ | |

TABLE 1-continued

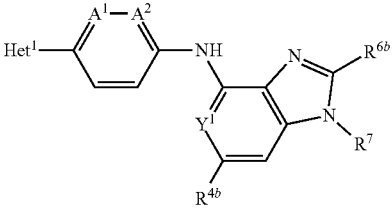

| Co. No. | Pr. | Het¹ | A¹ | A² | Y¹ | R⁴ᵇ | R⁶ᵇ | R⁷ | salt form |
|---|---|---|---|---|---|---|---|---|---|
| 106 | B18 | 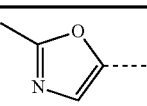 | N | CH | CH | F | 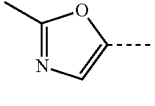 4-F-phenyl | CH₃ | |
| 107 | B18 | 2-methyl-oxazol-5-yl | N | CH | CH | F | 2-Cl-phenyl | CH₃ | |
| 108 | B18 | 2-methyl-oxazol-5-yl | COCH₃ | CH | CH | F | N(CH₃)CH₂CH(CH₃)₂ | CH₃ | •2 HCl •H₂O |
| 109 | B17 | 2-methyl-oxazol-5-yl | CF | CH | N | H | 3-OCH₃-phenyl | CH₃ | |
| 110 | B18 | 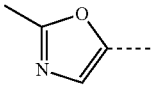 | N | CH | CH | CN | 4-F-phenyl | CH₃ | |
| 111 | B17 | 4-methyl-oxazol-5-yl | N | CH | N | CH₃ | 3-Cl-phenyl | CH₃ | |
| 112 | B18 | 4-methyl-oxazol-5-yl | N | CH | CH | H | 3-Cl-phenyl | isopropyl | •1.5 HCl •2 H₂O |
| 113 | B17 | 4-methyl-oxazol-5-yl | COCH₃ | CH | N | CH₃ | 2-Cl-phenyl | CH₃ | |
| 114 | B18 | 4-methyl-oxazol-5-yl | N | CH | CH | F | 2-Cl-phenyl | CH₃ | |

TABLE 1-continued

| Co. No. | Pr. | Het¹ | A¹ | A² | Y¹ | R⁴ᵇ | R⁶ᵇ | R⁷ | salt form |
|---|---|---|---|---|---|---|---|---|---|
| 115 | B18 | 4-methyloxazol-5-yl | N | CH | CH | H | 5-chlorothiophen-2-yl | isopropyl | |
| 116 | B18 | 4-methyloxazol-5-yl | N | CH | CH | H | 5-chlorothiophen-2-yl | isopropyl | ·2 HCl |
| 117 | B17 | 4-methyloxazol-5-yl | N | CH | N | H | 2-chlorophenyl | CH₃ | |
| 118 | B18 | 4-methyloxazol-5-yl | N | CH | CH | H | 4-fluorophenyl | isopropyl | ·2 HCl |
| 119 | B18 | 4-methyloxazol-5-yl | N | CH | CH | F | 4-fluorophenyl | CH₃ | |
| 120 | B23 | 4-methyloxazol-5-yl | COCH₃ | CH | CH | CH₂NH₂ | 4-fluorophenyl | CH₃ | |
| 121 | B17 | 4-methyloxazol-5-yl | COCH₃ | CH | N | CH₃ | 3-methoxyphenyl | CH₃ | |
| 122 | B18 | 4-methyloxazol-5-yl | COCH₃ | CH | CH | CN | 3-methoxyphenyl | CH₃ | |
| 123 | B18 | 4-methyloxazol-5-yl | COCH₃ | CH | CH | CN | 4-fluorophenyl | CH₃ | |

TABLE 1-continued
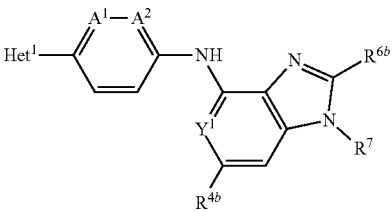
| Co. No. | Pr. | Het¹ | A¹ | A² | Y¹ | R⁴ᵇ | R⁶ᵇ | R⁷ | salt form |
|---|---|---|---|---|---|---|---|---|---|
| 124 | B18 | 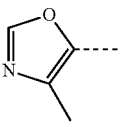 | CH | CH | CH | H | 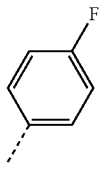 | CH₃ | |
| 125 | B17 | 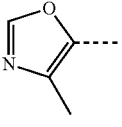 | COCH₃ | CH | N | CH₃ | 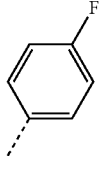 | CH₃ | |
| 126 | B18 | 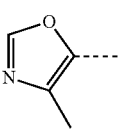 | COCH₃ | CH | CH | CF₃ | 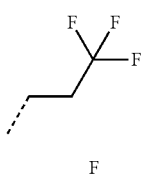 | CH₃ | |
| 127 | B21 | 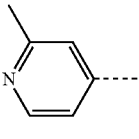 | COCH₃ | CH | N | CH₃ | 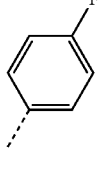 | CH₃ | |
| 128 | B21 | 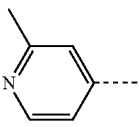 | COCH₃ | CH | CH | H | 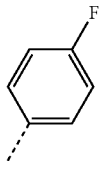 | 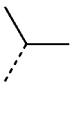 | |
| 129 | B21 | 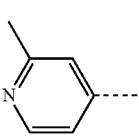 | COCH₃ | N | CH | H | 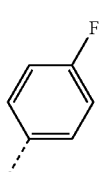 | CH₃ | |
| 130 | B21 | 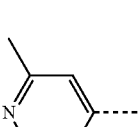 | COCH₃ | N | CH | H | 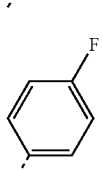 | 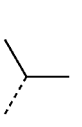 | |
| 131 | B21 | 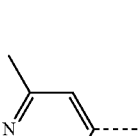 | CH | CH | CH | H | 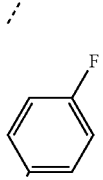 | 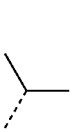 | |

TABLE 1-continued
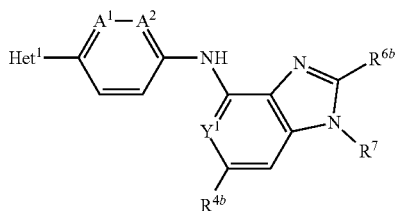
| Co. No. | Pr. | Het¹ | A¹ | A² | Y¹ | R⁴ᵇ | R⁶ᵇ | R⁷ | salt form |
|---|---|---|---|---|---|---|---|---|---|
| 132 | B21 | 2-pyridyl | CH | CH | N | CH₃ | 4-F-phenyl | CH₃ | |
| 133 | B21 | 2-pyridyl | CF | CH | CH | H | 4-F-phenyl | CH₃ | |
| 134 | B17 | 2-pyridyl | N | N | N | CH₃ | 4-F-phenyl | CH₃ | |
| 135 | B18 | 2-pyridyl | N | N | CH | H | 4-F-phenyl | CH₃ | |
| 136 | B21 | 2-pyridyl | CF | CH | N | CH₃ | 4-F-phenyl | CH₃ | |
| 137 | B21 | 2-pyridyl | CF | CH | CH | H | 4-F-phenyl | isopropyl | |
| 138 | B21 | 2-pyridyl | CH | CH | CH | H | 4-F-phenyl | CH₃ | |

TABLE 1-continued
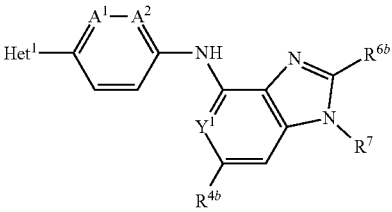
| Co. No. | Pr. | Het¹ | A¹ | A² | Y¹ | R⁴ᵇ | R⁶ᵇ | R⁷ | salt form |
|---|---|---|---|---|---|---|---|---|---|
| 139 | B21 | 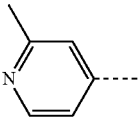 | COCH₃ | CH | CH | H | 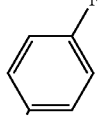 | CH₃ | |
| 140 | B21 | 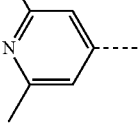 | CH | CH | CH | H | 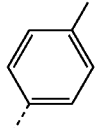 |  | |
| 184 | B21 | 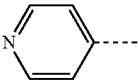 | CH | CH | CH | H | 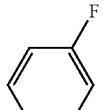 | CH₃ | |
TABLE 2
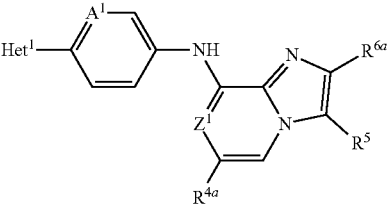
| Co. no. | Pr. | Het¹ | A¹ | Z¹ | R⁴ᵃ | R⁵ | R⁶ᵃ | salt form |
|---|---|---|---|---|---|---|---|---|
| 6 | B6 | 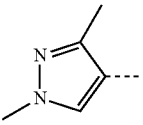 | COCH₃ | CH | H | CH₃ | 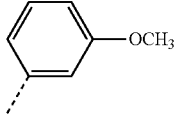 | |
| 38 | A1 | 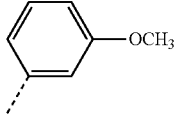 | COCH₃ | CH | H | H | 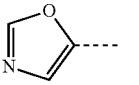 | |
| 39 | B3 | 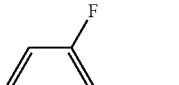 | CH | CH | H | H | 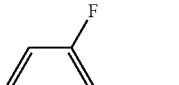 | •2 HCl |

TABLE 2-continued
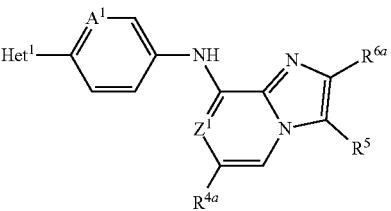
| Co. no. | Pr. | Het¹ | A¹ | Z¹ | R⁴ᵃ | R⁵ | R⁶ᵃ | salt form |
|---|---|---|---|---|---|---|---|---|
| 2 | B2 | 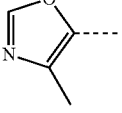 | COCH₃ | CH | H | CH₃ | 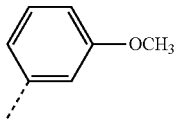 | |
| 40 | B3 | 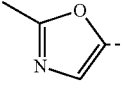 | CH | CH | H | H | 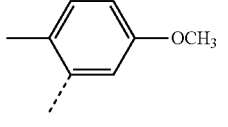 | |
| 41 | B3 | 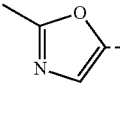 | CF | CH | H | H | 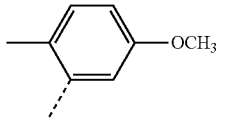 | |
| 42 | B3 | 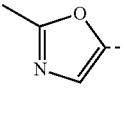 | CH | CH | H | H | 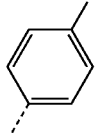 | |
| 3 | B3 | 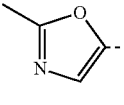 | COCH₃ | CH | H | H | 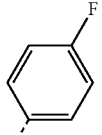 | |
| 1 | B1 | 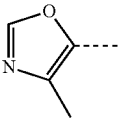 | COCH₃ | CH | H | H | 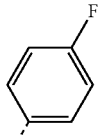 | |
| 43 | B3 | 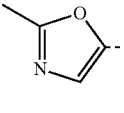 | CH | CH | H | H | 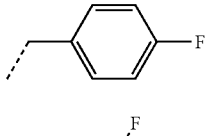 | |
| 44 | B3 | 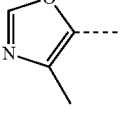 | N | CH | H | H | 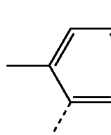 | |
| 45 | B3 | 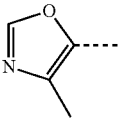 | N | CH | H | H | 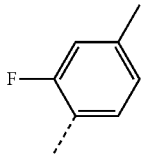 | |

TABLE 2-continued
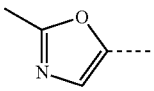
| Co. no. | Pr. | Het¹ | A¹ | Z¹ | R⁴ᵃ | R⁵ | R⁶ᵃ | salt form |
|---|---|---|---|---|---|---|---|---|
| 46 | B3 | 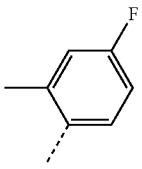 | CH | CH | H | H | 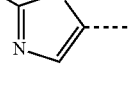 | |
| 47 | B3 | 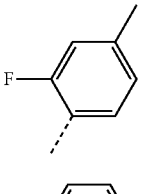 | CH | CH | H | H | 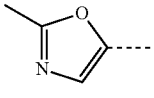 | |
| 48 | B3 | 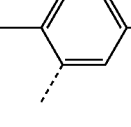 | COCH₃ | CH | H | H | 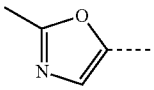 | ·HCl |
| 49 | Bx | 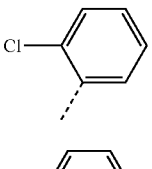 | CH | CH | H | CH₃ | 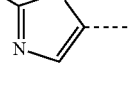 | |
| 50 | B3 | 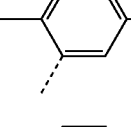 | CH | CH | H | H | 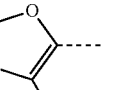 | |
| 51 | B3 | 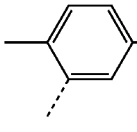 | N | CH | H | H | 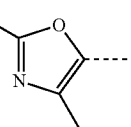 | |
| 8 | B8 | 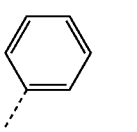 | COCH₃ | CH | H | CH₃ | 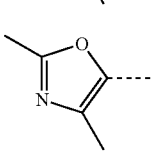 | |
| 7 | B7 | 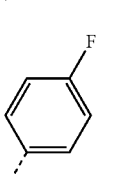 | COCH₃ | CH | H | H | 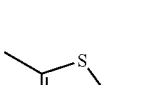 | |
| 4 | B4 | 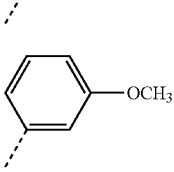 | COCH₃ | CH | H | CH₃ |  | |

TABLE 2-continued
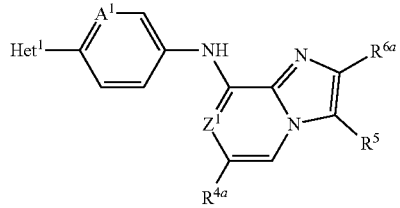
| Co. no. | Pr. | Het¹ | A¹ | Z¹ | R⁴ᵃ | R⁵ | R⁶ᵃ | salt form |
|---|---|---|---|---|---|---|---|---|
| 57 | B24 | 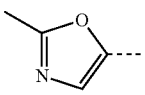 | CH | N | H | H | 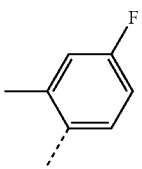 | |
| 60 | B25 | 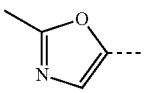 | CH | N | Br | H | 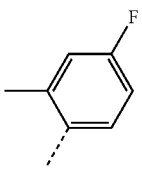 | |
| 52 | B3 | 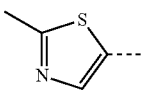 | COCH₃ | CH | H | H | 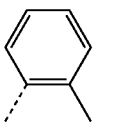 | |
| 5 | B5 | 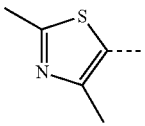 | COCH₃ | CH | H | CH₃ | 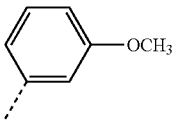 | |
| 141 | B3 | 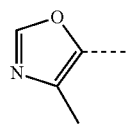 | COCH₃ | CH | CF₃ | H | CH₃ | •2 HCl |
| 142 | B3 | 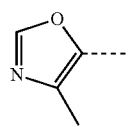 | COCH₃ | CH | CF₃ | CH₃ | CH₃ | |
| 143 | B3 | 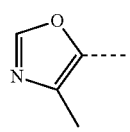 | COCH₃ | CH | CF₃ | H | (C=O)N(CH₃)₂ | |
| 144 | B3 | 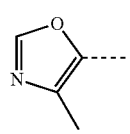 | COCH₃ | CH | H | CH₃ | CH₃ | |
| 145 | B3 | 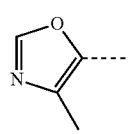 | COCH₃ | CH | CN | H | CH₃ | |

TABLE 2-continued

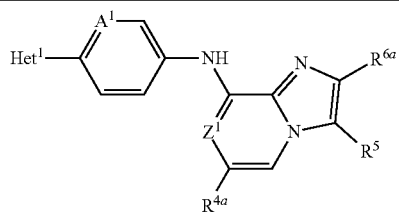

| Co. no. | Pr. | Het¹ | A¹ | Z¹ | R⁴ᵃ | R⁵ | R⁶ᵃ | salt form |
|---|---|---|---|---|---|---|---|---|
| 146 | B3 | 4-methyl-oxazol-5-yl | COCH₃ | CH | CN | H | 4-fluoro-2-methylphenyl | |
| 147 | B3 | 4-methyl-oxazol-5-yl | COCH₃ | CH | F | H | 4-fluoro-2-methylphenyl | •HCl •H₂O |
| 148 | B3 | 4-methyl-oxazol-5-yl | COCH₃ | CH | CF₃ | H | CH₂OCH₂CH₃ | |
| 149 | B23 | 4-methyl-oxazol-5-yl | COCH₃ | CH | CH₃ | H | 4-fluoro-2-methylphenyl | •HCl |
| 150 | B23 | 4-methyl-oxazol-5-yl | COCH₃ | CH | CH₂NH₂ | H | 4-fluoro-2-methylphenyl | |
| 151 | B3 | 4-methyl-oxazol-5-yl | COCH₃ | CH | CN | H | isobutyl | |
| 202 | B3 | 4-methyl-oxazol-5-yl | COCH₃ | CH | CN | H | isobutyl | •2 HCl |
| 152 | B3 | 4-methyl-oxazol-5-yl | CH | CH | H | CH₃ | 3-methoxyphenyl | |
| 153 | B3 | 4-methyl-oxazol-5-yl | COCH₃ | N | cyclopropyl | H | CH₃ | |

TABLE 2-continued

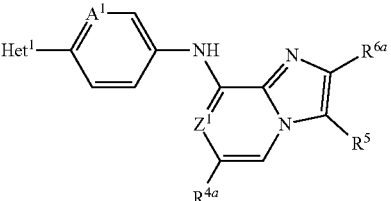

| Co. no. | Pr. | Het¹ | A¹ | Z¹ | R⁴ᵃ | R⁵ | R⁶ᵃ | salt form |
|---|---|---|---|---|---|---|---|---|
| 154 | B3 | 4-methyl-oxazol-5-yl | N | CH | H | H | tetrahydropyran-4-yl | |
| 155 | B3 | 4-methyl-oxazol-5-yl | COCH₃ | CH | H | H | tetrahydropyran-4-yl | •2 HCl |
| 156 | B27a | 4-methyl-oxazol-5-yl | COCH₃ | CH | O (=O) | H | isobutyl | •HCl |
| 157 | B3 | 4-methyl-oxazol-5-yl | COCH₃ | CH | F | H | isobutyl | •HCl |
| 158 | B3 | 4-methyl-oxazol-5-yl | COCH₃ | N | H | H | CH₃ | |
| 159 | B3 | 4-methyl-oxazol-5-yl | COCH₃ | CH | Cl | H | tetrahydropyran-4-yl | •2 HCl |
| 160 | B3 | 4-methyl-oxazol-5-yl | N | CH | H | H | cyclopropyl | |
| 161 | B3 | 4-methyl-oxazol-5-yl | N | CH | H | OCH₃ | 4-fluorophenyl | |
| 162 | B27b | 4-methyl-oxazol-5-yl | COCH₃ | CH | H₃CO-C(=O)- | H | isobutyl | |

TABLE 2-continued

| Co. no. | Pr. | Het¹ | A¹ | Z¹ | R⁴ᵃ | R⁵ | R⁶ᵃ | salt form |
|---|---|---|---|---|---|---|---|---|
| 163 | B3 | 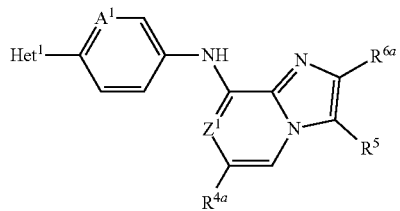 4-methyloxazol-5-yl | COCH₃ | CH | F | H | 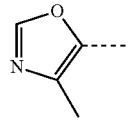 tetrahydropyran-4-yl | |
| 164 | B3 | 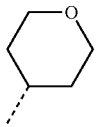 4-methyloxazol-5-yl | N | CH | H | H | 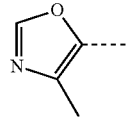 (tetrahydropyran-4-yl)methyl | ·HCl ·0.45 H₂O |
| 165 | B22 | 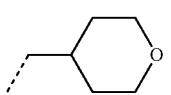 4-methyloxazol-5-yl | COCH₃ | CH | CF₃ | H | (C=O)CH₃ | |
| 166 | B3 | 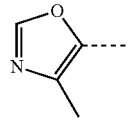 2-methyloxazol-5-yl | CH | CH | H | H | 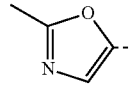 cyclopropyl | |
| 167 | B3 |  2-methyloxazol-5-yl | N | CH | H | CH₃ | 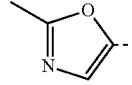 2-(trifluoromethyl)phenyl | |
| 168 | B3 | 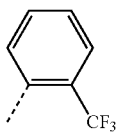 2-methyloxazol-5-yl | COCH₃ | CH | H | CH₂OCH₃ | 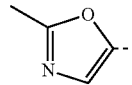 4-fluorophenyl | |
| 169 | B19 | 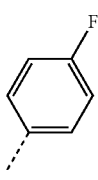 2-methyloxazol-5-yl | COCH₃ | CH | H | (CH₂)₃OCH₃ | 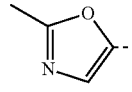 2-(trifluoromethyl)phenyl | |
| 170 | B3 | 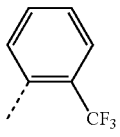 2-methyloxazol-5-yl | COCH₃ | N | CF₃ | H | CH₃ | |
| 171 | B3 | 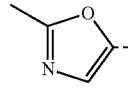 2-methyloxazol-5-yl | N | CH | F | H | 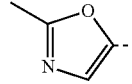 5-fluoro-2-methylphenyl | ·1.2 HCl |
| 172 | B3 | 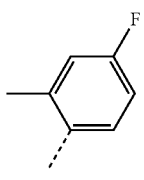 2-methyloxazol-5-yl | N | CH | H | H | CH₃ | |

TABLE 2-continued
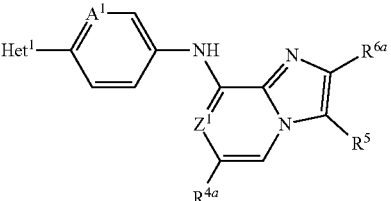
| Co. no. | Pr. | Het¹ | A¹ | Z¹ | R⁴ᵃ | R⁵ | R⁶ᵃ | salt form |
|---|---|---|---|---|---|---|---|---|
| 173 | B3 | 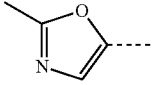 | N | CH | H | CH₃ | 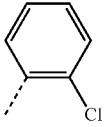 | |
| 174 | B19 | 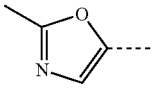 | COCH₃ | CH | H | (CH₂)₂OCH₃ | 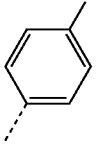 | |
| 175 | B26c | 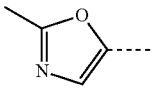 | CH | CH | H |  | 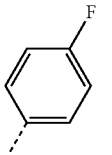 | |
| 176 | B3 | 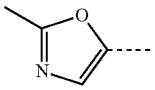 | CH | CH | F | H | 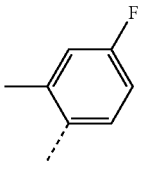 | |
| 177 | B26b | 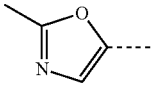 | CH | CH | H |  | 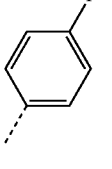 | |
| 178 | B3 | 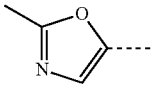 | CH | CH | F | H | 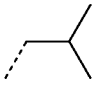 | •2 HCl |
| 179 | B25 | 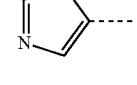 | CH | N | Br | H | CH₃ | |
| 180 | B3 | 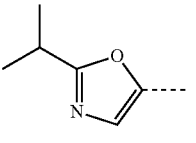 | CH | CH | H | CH₃ | CH₃ | |
| 181 | B3 | 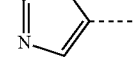 | CF | CH | CF₃ | H | (C=O)N(CH₃)₂ | |

TABLE 2-continued

Structure: Het¹–A¹(benzene ring)–NH–[imidazo[1,2-a]pyridine with Z¹, R⁴ᵃ, R⁵, R⁶ᵃ]

| Co. no. | Pr. | Het¹ | A¹ | Z¹ | R⁴ᵃ | R⁵ | R⁶ᵃ | salt form |
|---|---|---|---|---|---|---|---|---|
| 182 | B21 | 2-methylpyridin-4-yl | CF | CH | H | CH₃ | 2-chlorophenyl | |
| 183 | B21 | 2-methylpyridin-4-yl | CH | CH | H | CH₃ | 2-chlorophenyl | |
| 185 | B26a | 2-methyloxazol-5-yl | CH | CH | H | I | 4-fluorophenyl | |
| 201 | B21 | 2-methylpyridin-4-yl | COCH₃ | CH | H | CH₃ | 2-chlorophenyl | |

TABLE 3

Structure: Het¹–A¹=A²–A⁴ benzene ring–NH–[imidazo-fused ring with Y³, R⁴ᵇ, R⁶ᵇ, R⁷]

| Co. No. | Pr. | Het¹ | A¹ | A² | A⁴ | R⁴ᵇ | Y³ | R⁶ᵇ | R⁷ |
|---|---|---|---|---|---|---|---|---|---|
| 187 | B17 | 2-methyloxazol-5-yl | CF | CH | CH | H | N | 4-fluorophenyl | CH₃ |
| 188 | B20 | 2-methyloxazol-5-yl | CH | N | N | H | CH | 4-fluorophenyl | CH₃ |

TABLE 3-continued
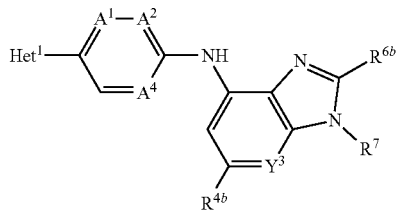
| Co. No. | Pr. | Het¹ | A¹ | A² | A⁴ | R⁴ᵇ | Y³ | R⁶ᵇ | R⁷ |
|---|---|---|---|---|---|---|---|---|---|
| 189 | B18 | 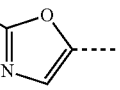 | COCH₃ | CH | CH | CN | N | 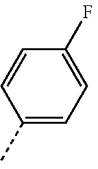 | CH₃ |
| 190 | B26c | 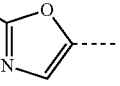 | COCH₃ | CH | CH |  | N | 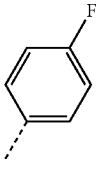 | CH₃ |
| 191 | B17 | 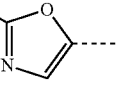 | N | CH | CH |  | N | 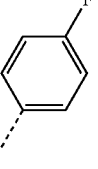 | CH₃ |
| 192 | B17 | 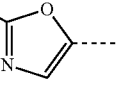 | COCH₃ | CH | CH |  | N | 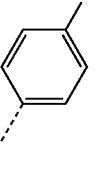 | CH₃ |
| 193 | B17 | 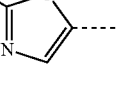 | COCH₃ | CH | CH | CH₃ | N | 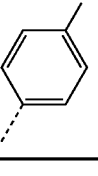 | CH₃ |
TABLE 4
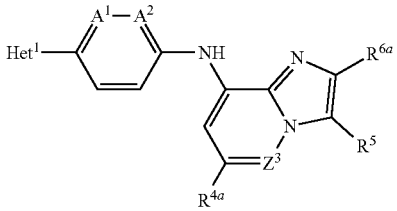
| Co. no. | Pr. | Het¹ | A¹ | A² | R⁴ᵃ | Z³ | R⁵ | R⁶ᵃ |
|---|---|---|---|---|---|---|---|---|
| 194 | B21 | 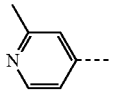 | COCH₃ | N | H | CH | CH₃ | 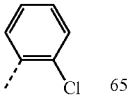 |
| 195 | B3 | 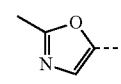 | COCH₃ | CH | CF₃ | N | H | CH₃ |

TABLE 4-continued

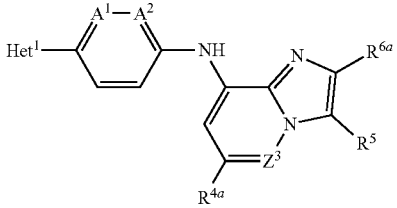

| Co. no. | Pr. | Het¹ | A¹ | A² | R⁴ᵃ | Z³ | R⁵ | R⁶ᵃ |
|---|---|---|---|---|---|---|---|---|
| 196 | B3 |  | COCH₃ | CH | CF₃ | N | H | CH₃ |
| 197 | B24 |  | N | CH | H | N | H |  |
| 198 | B3 | 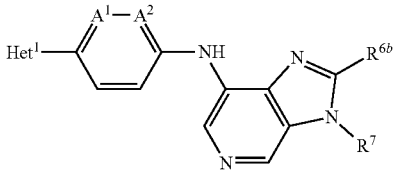 | N | CH | Cl | N | H | 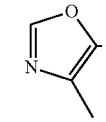 |

TABLE 5

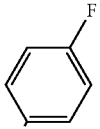

| Co. No. | Pr. | Het¹ | A¹ | A² | R⁶ᵇ | R⁷ |
|---|---|---|---|---|---|---|
| 199 | B18 |  | COCH₃ | CH |  | CH₃ |
| 200 | B18 |  | N | CH |  | CH₃ |
| 186 | B18 |  | COCH₃ | CH |  | CH₃ |

Analytical Part

LCMS

General Procedure A

The LC measurement was performed using an Acquity HPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as the nebulizer gas. Data acquisition was performed with a Waters-Micromass MassLynx-Openlynx data system.

General Procedure B

The HPLC measurement was performed using an Agilent 1100 series liquid chromatography system comprising a binary pump with degasser, an autosampler, a column oven, a UV detector and a column as specified in the respective methods below. Flow from the column was split to a MS spectrometer. The MS detector was configured with an electrospray ionization source. The capillary voltage was 3 kV, the quadrupole temperature was maintained at 100° C. and the desolvation temperature was 300° C. Nitrogen was used as the nebulizer gas. Data acquisition was performed with an Agilent Chemstation data system.

General Procedure C

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

LCMS Method 1

In addition to general procedure A: Reversed phase HPLC (Ultra Performance Liquid Chromatography) was carried out on a bridged ethylsiloxane/silica hybrid (BEH) C18 column (1.7 µm, 2.1×50 mm; Waters Acquity) with a flow rate of 0.8 ml/min. Two mobile phases (25 mM NH₄OAc in H₂O/CH₃CN 95/5; mobile phase B: CH₃CN) were used to run a gradient condition from 95% A and 5% B to 5% A and 95% B in 1.3 minutes (min) and hold for 0.3 min. An injection volume of 0.5 µl was used. Cone voltage was 10 V for positive ionization mode and 20 V for negative ionization mode.

LCMS Method 2

In addition to general procedure A: Reversed phase HPLC was carried out on a BEH C18 column (1.7 µm, 2.1×50 mm; Waters Acquity) with a flow rate of 0.8 ml/min. Two mobile phases (mobile phase A: 0.1% formic acid in H₂O/MeOH 95/5; mobile phase B: MeOH) were used to run a gradient condition from 95% A and 5% B to 5% A and 95% B in 1.3 min and hold for 0.2 min. An injection volume of 0.5 µl was used. Cone voltage was 10 V for positive and 20 V for negative ionization mode.

LCMS Method 3

In addition to general procedure B: Reversed phase HPLC was carried out on a YMC-Pack ODS-AQ C18 column (4.6× 50 mm) with a flow rate of 2.6 ml/min. A gradient run was used from 95% water and 5% CH₃CN to 95% CH₃CN in 4.80 min and was hold for 1.20 min. Mass spectra were acquired by scanning from 100 to 1400. Injection volume was 10 μl. Column temperature was 35° C.

LCMS Method 4

In addition to general procedure C: Column heater was set at 60° C. Reversed phase HPLC was carried out on an Xterra MS C18 column (3.5 μm, 4.6×100 mm) with a flow rate of 1.6 ml/min. Three mobile phases (mobile phase A: 95% 25 mM NH₄OAc+5% CH₃CN; mobile phase B: CH₃CN; mobile phase C: MeOH) were employed to run a gradient condition from 100% A to 50% B and 50% C in 6.5 minutes, to 100% B in 0.5 min and hold these conditions for 1 min and reequilibrate with 100% A for 1.5 minutes. An injection volume of 10 μl was used. Cone voltage was 10 V for positive ionization mode and 20 V for negative ionization mode.

LCMS Method 5

In addition to general procedure C: Column heater was set at 45° C. Reversed phase HPLC was carried out on an Atlantis C18 column (3.5 μm, 4.6×100 mm) with a flow rate of 1.6 ml/min. Two mobile phases (mobile phase A: 70% MeOH+ 30% H₂O; mobile phase B: 0.1% formic acid in H₂O/MeOH 95/5) were employed to run a gradient condition from 100% B to 5% B+95% A in 9 min and hold these conditions for 3 min. An injection volume of 10 μl was used. Cone voltage was 10 V for positive ionization mode and 20 V for negative ionization mode.

LCMS Method 6

In addition to general procedure C: Reversed phase HPLC was carried out on an Xterra MS C18 column (3.5 μm, 4.6× 100 mm) with a flow rate of 1.6 ml/min. Three mobile phases (mobile phase A: 95% 25 mM NH₄OAc+5% CH₃CN; mobile phase B: CH₃CN; mobile phase C: MeOH) were employed to run a gradient condition from 100% A to 1% A, 49% B and 50% C in 6.5 min, to 1% A and 99% B in 1 min and hold these conditions for 1 min and reequilibrate with 100% A for 1.5 min. An injection volume of 10 μl was used. Cone voltage was 10 V for positive and 20 V for negative ionization mode.

LCMS Method 7

In addition to general procedure A: Reversed phase HPLC was carried out on a bridged BEH C18 column (1.7 μm, 2.1×50 mm; Waters Acquity) with a flow rate of 0.8 ml/min. Two mobile phases (25 mM NH₄OAc in H₂O/CH₃CN 95/5; mobile phase B: CH₃CN) were used to run a gradient condition from 95% A and 5% B to 5% A and 95% B in 1.3 min and hold for 0.3 min. An injection volume of 0.5 μl was used. Cone voltage was 30 V for positive and 30 V for negative ionization mode.

Melting Points

For a number of compounds, melting points (m.p.) were determined with a DSC823e (Mettler-Toledo). Melting points were measured with a temperature gradient of 30° C./minute. Maximum temperature was 400° C. Values are peak values.

The results of the analytical measurements are shown in table 6.

TABLE 6

Retention time ($R_t$) in min., [M + H]⁺ peak (protonated molecule), LCMS method and m.p. (melting point in ° C.).
(n.d. means not determined)

| Co. No. | Rt | [M + H]⁺ | LCMS Method | m.p. (° C.) |
|---|---|---|---|---|
| 1 | 1.15 | 415 | 1 | 163.2 |
| 2 | 1.18 | 441 | 1 | n.d. |
| 3 | 1.41 | 415 | 2 | 219.1 |
| 4 | 8.42 | 457 | 5 | n.d. |
| 5 | 1.26 | 471 | 1 | n.d. |
| 6 | 1.16 | 454 | 1 | n.d. |
| 7 | 6.09 | 429 | 4 | n.d. |
| 8 | 1.32 | 425 | 2 | n.d. |
| 9 | 1.33 | 428 | 2 | n.d. |
| 10 | 5.72 | 400 | 4 | 195.4 |
| 11 | 1.08 | 431 | 1 | n.d. |
| 12 | 1.13 | 429 | 1 | n.d. |
| 13 | 1.27 | 428 | 2 | 157.6 |
| 14 | 7.02 | 430 | 5 | 204.9 |
| 15 | 1.23 | 428 | 1 | n.d. |
| 16 | 1.15 | 429 | 1 | 189.0 |
| 17 | 1.13 | 418 | 1 | n.d. |
| 18 | 1.12 | 428 | 1 | 133.4 |
| 19 | 1.54 | 427 | 2 | n.d. |
| 20 | 3.11 | 441 | 3 | n.d. |
| 21 | n.d. | n.d. | — | n.d. |
| 22 | 1.53 | 511 | 2 | n.d. |
| 23 | 1.06 | 400 | 1 | 184.8 |
| 24 | 6.00 | 443 | 4 | 174.1 |
| 25 | 1.27 | 457 | 1 | n.d. |
| 26 | 1.22 | 428 | 1 | n.d. |
| 27 | 1.24 | 458 | 1 | n.d. |
| 28 | 1.46 | 445 | 2 | n.d. |
| 29 | 1.00 | 400 | 1 | n.d. |
| 30 | 1.31 | 497 | 1 | 201.9 |
| 31 | 1.12 | 448 | 1 | 210.1 |
| 32 | 2.95 | 416 | 3 | n.d. |
| 33 | 2.90 | 446 | 3 | n.d. |
| 34 | 1.22 | 442 | 1 | n.d. |
| 35 | 1.07 | 400 | 1 | n.d. |
| 36 | 1.1 | 430 | 1 | n.d. |
| 37 | 1.01 | 409 | 1 | n.d. |
| 38 | 1.16 | 401 | 1 | n.d. |
| 39 | 1.23 | 381 | 1 | n.d. |
| 40 | 1.20 | 411 | 1 | n.d. |
| 41 | n.d. | n.d. | — | n.d. |
| 42 | 1.42 | 385 | 2 | 181.8 |
| 43 | 1.15 | 399 | 1 | n.d. |
| 44 | 1.15 | 400 | 1 | n.d. |
| 45 | 1.21 | 400 | 1 | n.d. |
| 46 | 8.45 | 399 | 5 | 135.3 |
| 47 | 9.55 | 399 | 5 | n.d. |
| 48 | 1.35 | 429 | 2 | n.d. |
| 49 | 6.78 | 415 | 4 | 213.0 |
| 50 | 9.61 | 449 | 5 | 125.5 |
| 51 | 1.28 | 450 | 1 | n.d. |
| 52 | 1.27 | 427 | 1 | n.d. |
| 53 | 1.09 | 418 | 1 | 171.4 |
| 54 | 1.08 | 448 | 1 | 156.8 |
| 55 | 1.14 | 436 | 1 | 204.8 |
| 56 | n.d. | n.d. | — | n.d. |
| 57 | 1.43 | 400 | 2 | n.d. |
| 58 | 1.15 | 414 | 1 | 230.2 |
| 59 | 1.18 | 444 | 1 | 250.8 |
| 60 | 1.53 | 478 | 2 | n.d. |
| 61 | 1.07 | 412 | 1 | 145.1 |
| 62 | 3.73 | 475 | 3 | n.d. |
| 63 | 3.26 | 441 | 3 | n.d. |
| 64 | 2.64 | 403 | 3 | n.d. |
| 65 | 6.63 | 445 | 6 | n.d. |
| 66 | 1.01 | 378 | 7 | 172.5 |
| 67 | 1.09 | 398 | 7 | 195.9 |
| 68 | 1.15 | 429 | 7 | 168.9 |
| 69 | 6.69 | 457 | 6 | 192.8 |
| 70 | 0.96 | 399 | 7 | n.d. |
| 71 | 1.06 | 399 | 7 | 113.5 |
| 72 | 1.13 | 398 | 7 | 146.3 |
| 73 | 6.27 | 429 | 6 | 184.1 |
| 74 | 5.87 | 429 | 6 | 153.3 |
| 75 | 0.99 | 429 | 7 | 224.7 |

TABLE 6-continued

Retention time (R$_t$) in min., [M + H]$^+$ peak (protonated molecule), LCMS method and m.p. (melting point in ° C.). (n.d. means not determined)

| Co. No. | Rt | [M + H]$^+$ | LCMS Method | m.p. (° C.) |
|---|---|---|---|---|
| 76 | 1.07 | 416 | 7 | 147.3 |
| 77 | 1.31 | 473 | 7 | n.d. |
| 78 | 1.15 | 464 | 7 | 122.5 |
| 79 | 1.15 | 448 | 7 | n.d. |
| 80 | 1.25 | 471 | 7 | n.d. |
| 81 | 1.28 | 441 | 7 | n.d. |
| 82 | 1.20 | 442 | 7 | n.d. |
| 83 | 1.17 | 413 | 7 | n.d. |
| 84 | 6.45 | 457 | 6 | 172.5 |
| 85 | 0.97 | 417 | 7 | n.d. |
| 86 | 0.97 | 425 | 7 | 253.6 |
| 87 | 1.14 | 444 | 7 | n.d. |
| 88 | 1.16 | 456 | 7 | n.d. |
| 89 | 1.15 | 446 | 7 | n.d. |
| 90 | 1.12 | 392 | 7 | n.d. |
| 91 | 1.04 | 432 | 7 | 190.7 |
| 92 | 0.99 | 434 | 7 | n.d. |
| 93 | 1.11 | 447 | 7 | 191.6 |
| 94 | 1.27 | 470 | 7 | n.d. |
| 95 | 1.37 | 459 | 2 | n.d. |
| 96 | 1.07 | 377 | 7 | n.d. |
| 97 | 1.19 | 456 | 7 | 183.0 |
| 98 | 1.17 | 426 | 7 | 158.8 |
| 99 | 1.15 | 454 | 7 | 190.1 |
| 100 | 1.12 | 457 | 7 | 204.6 |
| 101 | 1.13 | 468 | 7 | 173.6 |
| 102 | 1.30 | 484 | 7 | n.d. |
| 103 | 1.27 | 437 | 2 | n.d. |
| 104 | 1.14 | 422 | 7 | n.d. |
| 105 | 1.05 | 430 | 7 | n.d. |
| 106 | 1.03 | 418 | 7 | 190.2 |
| 107 | 1.06 | 434 | 7 | 118.3 |
| 108 | 6.83 | 438 | 6 | n.d. |
| 109 | 1.14 | 430 | 7 | 190.4 |
| 110 | 1.03 | 425 | 7 | 230.6 |
| 111 | 1.13 | 431 | 7 | 220.2 |
| 112 | 1.25 | 444 | 7 | n.d. |
| 113 | 1.19 | 460 | 7 | 139.5 |
| 114 | 1.12 | 434 | 7 | n.d. |
| 115 | 1.54 | 450 | 2 | n.d. |
| 116 | 9.50 | 450 | 5 | n.d. |
| 117 | 1.03 | 417 | 7 | 189.2 |
| 118 | 1.17 | 428 | 7 | n.d. |
| 119 | 1.39 | 418 | 2 | 179.6 |
| 120 | 0.79 | 458 | 7 | n.d. |
| 121 | 1.18 | 456 | 7 | 176.2 |
| 122 | 1.10 | 466 | 7 | n.d. |
| 123 | 1.37 | 454 | 2 | 208.9 |
| 124 | 1.15 | 399 | 7 | n.d. |
| 125 | 1.16 | 444 | 7 | 211.0 |
| 126 | 1.20 | 499 | 7 | 180.2 |
| 127 | 1.30 | 454 | 7 | 201.1 |
| 128 | 1.38 | 467 | 7 | n.d. |
| 129 | 1.37 | 440 | 7 | n.d. |
| 130 | 1.45 | 468 | 7 | n.d. |
| 131 | 1.13 | 437 | 2 | n.d. |
| 132 | 0.90 | 424 | 2 | 240.0 |
| 133 | 1.20 | 427 | 7 | n.d. |
| 134 | n.d. | n.d. | n.d. | 258.8 |
| 135 | 0.99 | 411 | 7 | 220.0 |
| 136 | 1.24 | 442 | 7 | 230.5 |
| 137 | 1.31 | 455 | 7 | n.d. |
| 138 | 6.58 | 409 | 6 | 168.9 |
| 139 | 1.17 | 439 | 7 | 163.2 |
| 140 | 1.31 | 451 | 7 | n.d. |
| 141 | 6.20 | 403 | 6 | n.d. |
| 142 | 1.17 | 417 | 7 | n.d. |
| 143 | n.d. | n.d. | — | 201.8 |
| 144 | 0.99 | 349 | 7 | 122.0 |
| 145 | 0.93 | 360 | 7 | 186.6 |
| 146 | 1.21 | 454 | 7 | 195.2 |
| 147 | 1.27 | 447 | 7 | n.d. |
| 148 | 0.91 | 202 | 2 | n.d. |
| 149 | 6.68 | 443 | 6 | n.d. |
| 150 | 0.93 | 458 | 7 | n.d. |
| 151 | 6.27 | 402 | 6 | n.d. |
| 152 | 1.21 | 411 | 7 | 123.7 |
| 153 | 1.44 | 376 | 2 | n.d. |
| 154 | 5.20 | 376 | 6 | n.d. |
| 155 | 5.63 | 405 | 6 | 201.2 |
| 156 | 6.09 | 419 | 6 | n.d. |
| 157 | 6.45 | 395 | 6 | n.d. |
| 158 | 0.92 | 336 | 7 | 263.0 |
| 159 | 1.09 | 439 | 7 | n.d. |
| 160 | 0.82 | 332 | 2 | n.d. |
| 161 | n.d. | n.d. | n.d. | 176.9 |
| 162 | n.d. | n.d. | n.d. | 157.1 |
| 163 | 1.01 | 423 | 7 | 155.2 |
| 164 | 5.41 | 390 | 6 | n.d. |
| 165 | n.d. | n.d. | — | 183.6 |
| 166 | 0.96 | 331 | 2 | n.d. |
| 167 | n.d. | n.d. | n.d. | n.d. |
| 168 | 1.22 | 459 | 7 | 170.8 |
| 169 | 1.27 | 537 | 7 | n.d. |
| 170 | 1.42 | 404 | 2 | 239.8 |
| 171 | 1.12 | 418 | 7 | n.d. |
| 172 | 0.77 | 306 | 7 | n.d. |
| 173 | 6.17 | 415 | 6 | n.d. |
| 174 | 1.24 | 473 | 7 | 163.5 |
| 175 | 1.33 | 427 | 7 | 157.2 |
| 176 | 1.28 | 417 | 7 | n.d. |
| 177 | 1.36 | 425 | 7 | n.d. |
| 178 | 6.64 | 365 | 6 | n.d. |
| 179 | 1.39 | 385 | 2 | 200.1 |
| 180 | 1.15 | 347 | 7 | n.d. |
| 181 | 1.02 | 448 | 7 | n.d. |
| 182 | 1.30 | 443 | 7 | 166.2 |
| 183 | 1.43 | 425 | 7 | 210.8 |
| 184 | 1.14 | 395 | 7 | 230.5 |
| 185 | 1.38 | 511 | 7 | n.d. |
| 186 | 0.93 | 430 | 7 | 254.2 |
| 187 | 1.05 | 418 | 7 | 179.4 |
| 188 | 1.23 | 401 | 2 | n.d. |
| 189 | 1.14 | 455 | 7 | 276.3 |
| 190 | 1.28 | 472 | 7 | 191.7 |
| 191 | 1.13 | 443 | 7 | n.d. |
| 192 | 1.28 | 470 | 7 | n.d. |
| 193 | 1.34 | 444 | 2 | n.d. |
| 194 | 1.44 | 456 | 7 | 175.2 |
| 195 | 1.16 | 404 | 7 | 168.9 |
| 196 | 1.12 | 404 | 7 | 171.5 |
| 197 | 1.14 | 401 | 7 | n.d. |
| 198 | 1.30 | 436 | 7 | 230.1 |
| 199 | 0.91 | 430 | 7 | n.d. |
| 200 | 0.82 | 401 | 7 | 217.5 |
| 201 | 6.92 | 455 | 6 | n.d. |
| 202 | 6.26 | 402 | 6 | n.d. |

NMR

For a number of compounds, $^1$H NMR spectra were recorded on a Bruker DPX-360, on a Bruker DPX-400, or on a Bruker Avance 600 spectrometer with standard pulse sequences, operating at 360, 400 and 600 MHz respectively, using CHLOROFORM-d or DMSO-d$_6$ as solvents. Chemical shifts (δ) are reported in parts per million (ppm) relative to tetramethylsilane (TMS), which was used as internal standard.

Compound 1: $^1$H NMR (360 MHz, DMSO-d$_6$) δ ppm 2.11 (s, 3 H), 3.80 (s, 3 H), 6.81 (t, J=7.1 Hz, 1 H), 7.03-7.13 (m, 2 H), 7.18 (d, J=2.0 Hz, 1 H), 7.28 (d, J=8.4 Hz, 1H), 7.30 (t, J=8.7 Hz, 2 H), 8.02-8.11 (m, 3 H), 8.27 (s, 1 H), 8.39 (s, 1 H), 8.52 (s, 1 H).

Compound 2: $^1$H NMR (360 MHz, DMSO-$d_6$) δ ppm 2.11 (s, 3 H), 2.65 (s, 3 H), 3.80 (s, 3 H), 3.83 (s, 3 H), 6.88 (t, J=7.1 Hz, 1 H), 6.94 (dt, J=5.9, 2.9 Hz, 1 H), 7.05-7.11 (m, 2 H), 7.17 (d, J=2.0 Hz, 1 H), 7.27 (d, J=8.3 Hz, 1 H), 7.37-7.43 (m, 3 H), 7.90 (d, J=6.8 Hz, 1 H), 8.26 (s, 1 H), 8.53 (s, 1 H).

Compound 3: $^1$H NMR (360 MHz, DMSO-$d_6$) δ ppm 2.46 (s, 3 H), 3.92 (s, 3 H), 6.82 (t, J=7.1 Hz, 1 H), 7.06 (d, J=7.5 Hz, 1 H), 7.09 (dd, J=8.5, 2.0 Hz, 1 H), 7.19 (d, J=2.0 Hz, 1 H), 7.24 (s, 1 H), 7.30 (t, J=8.8 Hz, 2 H), 7.56 (d, J=8.4 Hz, 1 H), 8.04-8.09 (m, 3 H), 8.39 (s, 1 H), 8.48 (s, 1 H).

Compound 4: $^1$H NMR (400 MHz, DMSO-$d_6$) δ ppm 2.64 (s, 3 H), 2.65 (s, 3 H), 3.83 (s, 3 H), 3.89 (s, 3 H), 6.87 (t, J=7.1 Hz, 1 H), 6.94 (dt, J=6.4, 2.8 Hz, 1 H), 7.04-7.09 (m, 2 H), 7.18 (d, J=2.2 Hz, 1 H), 7.36-7.44 (m, 3 H), 7.60 (d, J=8.4 Hz, 1 H), 7.88 (d, J=6.7 Hz, 1 H), 7.97 (s, 1 H), 8.45 (s, 1 H).

Compound 5: $^1$H NMR (360 MHz, DMSO-$d_6$) δ ppm 2.22 (s, 3 H), 2.60 (s, 3 H), 2.65 (s, 3 H), 3.77 (s, 3 H), 3.83 (s, 3 H), 6.87 (t, J=7.1 Hz, 1 H), 6.94 (dt, J=5.9, 3.0 Hz, 1H), 7.03-7.10 (m, 2 H), 7.16 (d, J=2.0 Hz, 1 H), 7.20 (d, J=8.3 Hz, 1 H), 7.37-7.43 (m, 3 H), 7.88 (d, J=6.8 Hz, 1 H), 8.46 (s, 1 H).

Compound 6: $^1$H NMR (360 MHz, DMSO-$d_6$) δ ppm 2.14 (s, 3 H), 2.64 (s, 3 H), 3.77 (s, 3 H), 3.78 (s, 3 H), 3.83 (s, 3 H), 6.85 (t, J=7.1 Hz, 1 H), 6.94 (dt, J=6.0, 2.9 Hz, 1H), 7.00 (d, J=7.5 Hz, 1 H), 7.00-7.04 (m, 1 H), 7.12 (d, J=2.1 Hz, 1 H), 7.16 (d, J=8.2 Hz, 1 H), 7.38-7.42 (m, 3 H), 7.65 (s, 1 H), 7.83 (d, J=6.7 Hz, 1 H), 8.25 (s, 1H).

Compound 7: $^1$H NMR (360 MHz, DMSO-$d_6$) δ ppm 2.04 (s, 3 H) 2.38 (s, 3 H) 3.80 (s, 3 H) 6.81 (t, J=7.32 Hz, 1 H) 6.99-7.11 (m, 2 H) 7.16 (d, J=1.83 Hz, 1 H) 7.24 (d, J=8.42 Hz, 1 H) 7.30 (t, J=8.78 Hz, 2 H) 7.99-8.15 (m, 3 H) 8.39 (s, 1 H) 8.48 (s, 1 H).

Compound 8: $^1$H NMR (360 MHz, DMSO-$d_6$) δ ppm 2.04 (s, 3 H), 2.38 (s, 3 H), 2.65 (s, 3 H), 3.79 (s, 3 H), 6.88 (t, J=7.1 Hz, 1 H), 7.04-7.11 (m, 2 H), 7.16 (d, J=2.0 Hz, 1H), 7.24 (d, J=8.3 Hz, 1 H), 7.36 (t, J=7.4 Hz, 1 H), 7.49 (t, J=7.5 Hz, 2 H), 7.86 (d, J=7.7 Hz, 2 H), 7.89 (d, J=6.7 Hz, 1 H), 8.48 (s, 1 H).

Compound 9: $^1$H NMR (360 MHz, CHLOROFORM-d) δ ppm 3.76 (s, 3 H), 3.81 (s, 3H), 3.85 (s, 3 H), 6.24 (d, J=1.9 Hz, 1 H), 6.92 (d, J=2.1 Hz, 1 H), 6.94-7.01 (m, 2 H), 7.14 (s, 1 H), 7.17 (d, J=8.2 Hz, 1 H), 7.22-7.32 (m, 4 H), 7.52 (d, J=1.9 Hz, 1 H), 7.75 (dd, J=8.5, 5.4 Hz, 2 H).

Compound 10: $^1$H NMR (360 MHz, DMSO-$d_6$) δ ppm 2.35 (s, 3 H), 3.86 (s, 3 H), 7.21 (dd, J=8.1, 1.4 Hz, 1 H), 7.25 (t, J=7.8 Hz, 1 H), 7.39 (d, J=8.8 Hz, 1 H), 7.44 (t, J=8.8 Hz, 2 H), 7.81 (dd, J=8.8, 2.5 Hz, 1 H), 7.94 (dd, J=8.6, 5.6 Hz, 2 H), 8.28 (dd, J=7.5, 1.3 Hz, 1 H), 8.32 (s, 1 H), 8.47 (d, J=2.5 Hz, 1 H), 9.22 (s, 1 H).

Compound 11: $^1$H NMR (360 MHz, CHLOROFORM-d) δ ppm 2.24 (s, 3 H), 2.76-2.90 (m, 2 H), 3.10-3.16 (m, 2 H), 3.76 (s, 3 H), 3.85 (s, 3 H), 6.87-6.91 (m, 2 H), 6.97 (dd, J=8.3, 2.1 Hz, 1 H), 6.96 (s, 1 H), 7.20 (t, J=7.7 Hz, 1 H), 7.24 (dd, J=7.9, 1.5 Hz, 1 H), 7.85 (s, 1 H).

Compound 12: $^1$H NMR (360 MHz, DMSO-$d_6$) δ ppm 2.10 (s, 3 H), 3.75 (s, 3 H), 3.86 (s, 3 H), 6.95 (dd, J=8.4, 2.0 Hz, 1 H), 7.06 (d, J=2.0 Hz, 1 H), 7.15-7.26 (m, 4 H), 7.43 (t, J=8.7 Hz, 2 H), 7.92 (dd, J=8.4, 5.4 Hz, 2 H), 8.23 (s, 1 H), 8.53 (s, 1 H).

Compound 13: $^1$H NMR (360 MHz, CHLOROFORM-d) δ ppm 3.84 (s, 3 H), 3.89 (s, 3H), 3.94 (s, 3 H), 6.89-6.93 (m, 2 H), 6.97 (dd, J=8.2, 2.1 Hz, 1 H), 7.07 (s, 1 H), 7.21-7.28 (m, 4 H), 7.45 (d, J=8.2 Hz, 1 H), 7.75 (dd, J=8.6, 5.3 Hz, 2 H), 7.79 (s, 1 H), 7.83 (s, 1 H).

Compound 14: $^1$H NMR (360 MHz, DMSO-$d_6$) δ ppm 2.46 (s, 3 H), 3.86 (s, 3 H), 3.92 (s, 3 H), 7.18 (d, J=5.8 Hz, 1 H), 7.23 (s, 1 H), 7.46 (t, J=8.8 Hz, 2 H), 7.53 (d, J=9.0 Hz, 1 H), 7.93-7.99 (m, 4 H), 8.03 (d, J=5.8 Hz, 1 H), 9.26 (s, 1 H).

Compound 15: $^1$H NMR (360 MHz, DMSO-$d_6$) δ ppm 1.59 (d, J=6.9 Hz, 6 H), 2.47 (s, 3 H), 4.58-4.69 (m, 1 H), 7.20 (t, J=8.1 Hz, 1 H), 7.35 (d, J=8.8 Hz, 1 H), 7.38 (d, J=7.9 Hz, 1 H), 7.39 (s, 1 H), 7.43 (t, J=8.8 Hz, 2 H), 7.74 (dd, J=8.6, 5.5 Hz, 2 H), 7.83 (dd, J=8.8, 2.5 Hz, 1 H), 8.24 (d, J=8.0 Hz, 1 H), 8.52 (d, J=2.4 Hz, 1 H), 9.14 (s, 1 H).

Compound 16: $^1$H NMR (360 MHz, DMSO-$d_6$) δ ppm 2.45 (s, 3 H), 3.86 (s, 3 H), 3.86 (s, 3 H), 6.97 (dd, J=8.5, 2.0 Hz, 1 H), 7.07 (d, J=2.0 Hz, 1 H), 7.14-7.25 (m, 4 H), 7.43 (t, J=8.8 Hz, 2 H), 7.49 (d, J=8.5 Hz, 1 H), 7.92 (dd, J=8.6, 5.5 Hz, 2 H), 8.50 (s, 1 H).

Compound 18: $^1$H NMR (360 MHz, CHLOROFORM-d) δ ppm 1.66 (d, J=6.95 Hz, 6 H) 2.56 (s, 3 H) 4.73 (spt, J=6.92, 6.77 Hz, 1 H) 7.13 (s, 1 H) 7.15-7.22 (m, 3 H) 7.22-7.28 (m, 2 H) 7.40 (s, 1 H) 7.54 (d, J=8.78 Hz, 1 H) 7.62 (dd, J=8.60, 5.31 Hz, 2 H) 7.69 (dd, J=8.60, 2.74 Hz, 1 H) 8.61 (d, J=2.56 Hz, 1 H).

Compound 25: $^1$H NMR (360 MHz, DMSO-$d_6$) δ ppm 1.68 (d, J=6.95 Hz, 6 H) 2.47 (s, 3 H) 3.90 (s, 3 H) 4.71-4.82 (m, 1 H) 6.93 (dd, J=8.42, 1.83 Hz, 1 H) 6.98 (s, 1 H) 7.44-7.52 (m, 2 H) 7.57 (d, J=8.42 Hz, 1 H) 7.61 (t, J=8.96 Hz, 2 H) 7.67 (t, 1 H) 7.95 (dd, J=8.60, 5.31 Hz, 2 H) 9.17 (br. s., 1 H).

Compound 38: $^1$H NMR (360 MHz, DMSO-$d_6$) δ ppm 3.93 (s, 3 H) 6.82 (t, J=7.32 Hz, 1 H) 7.08 (d, J=7.68 Hz, 1 H) 7.11 (dd, J=8.42, 2.20 Hz, 1 H) 7.21 (d, J=2.20 Hz, 1 H) 7.30 (t, J=8.78 Hz, 2 H) 7.40 (s, 1 H) 7.63 (d, J=8.42 Hz, 1 H) 8.01-8.09 (m, 3 H) 8.36 (s, 1 H) 8.40 (s, 1 H) 8.54 (s, 1 H).

Compound 40: $^1$H NMR (360 MHz, CHLOROFORM-d) δ ppm 2.49 (s, 3 H) 2.53 (s, 3 H) 3.88 (s, 3 H) 6.72 (dd, J=7.32, 6.95 Hz, 1 H) 6.85 (dd, J=8.42, 2.93 Hz, 1 H) 6.94 (d, J=6.95 Hz, 1 H) 7.14 (s, 1 H) 7.20 (d, J=8.42 Hz, 1 H) 7.33-7.39 (m, 3 H) 7.51 (d, J=2.56 Hz, 1 H) 7.60 (m, 2 H) 7.69 (s, 1 H) 7.71 (dd, J=6.59, 0.73 Hz, 1 H).

Compound 57: $^1$H NMR (600 MHz, CHLOROFORM-d) δ ppm 2.53 (s, 3 H), 2.53 (s, 3 H), 7.00-7.04 (m, 2 H), 7.15 (s, 1 H), 7.50 (d, J=4.6 Hz, 1 H), 7.60 (d, J=4.6 Hz, 1 H), 7.62 (d, J=8.7 Hz, 2 H), 7.62 (s, 1 H), 7.77 (dd, J=8.1, 6.0 Hz, 1 H), 7.94 (d, J=8.7 Hz, 2 H), 8.20 (s, 1 H).

Compound 60: $^1$H NMR (600 MHz, CHLOROFORM-d) δ ppm 2.52 (s, 3 H), 2.53 (s, 3 H), 6.99-7.05 (m, 2 H), 7.16 (s, 1 H), 7.59 (s, 1 H), 7.64 (d, J=8.5 Hz, 2 H), 7.74 (d, J=7.2 Hz, 1 H), 7.76 (s, 1 H), 7.93 (d, J=8.6 Hz, 2 H), 8.24 (s, 1 H).

Compound 89: $^1$H NMR (360 MHz, DMSO-$d_6$) δ ppm 1.64 (d, J=6.95 Hz, 6 H) 2.52 (s, 3 H) 4.72 (spt, 1 H) 7.18 (dd, J=11.89, 1.65 Hz, 1 H) 7.52-7.64 (m, 4 H) 7.73 (d, J=8.78 Hz, 1 H) 7.87-7.94 (m, 3 H) 8.60 (d, J=2.56 Hz, 1 H) 9.74 (br. s., 1 H).

Compound 95: $^1$H NMR (360 MHz, CHLOROFORM-d) δ ppm 2.52 (s, 3 H) 3.80 (s, 3 H) 3.89 (s, 3 H) 3.94 (s, 3 H) 6.39 (d, J=1.83 Hz, 1 H) 6.87-6.93 (m, 2 H) 7.00 (dd, J=8.42, 2.20 Hz, 1 H) 7.10 (s, 1 H) 7.19-7.28 (m, 2 H) 7.29 (s, 1 H) 7.66 (d, J=8.42 Hz, 1 H) 7.72 (dd, J=8.60, 5.31 Hz, 2 H).

Compound 97: $^1$H NMR (360 MHz, DMSO-$d_6$) δ ppm 2.46 (s, 3 H) 2.54 (s, 3 H) 3.83 (s, 3 H) 3.86 (s, 3 H) 3.94 (s, 3 H) 7.02 (s, 1 H) 7.11-7.17 (m, 1 H) 7.22 (s, 1 H) 7.40-7.46 (m, 2 H) 7.46-7.54 (m, 2 H) 7.77 (dd, J=8.78, 1.83 Hz, 1 H) 8.32 (d, J=1.83 Hz, 1 H) 9.24 (s, 1 H).

Compound 99: $^1$H NMR (600 MHz, CHLOROFORM-d) δ ppm 2.53 (s, 3 H), 2.66 (s, 3 H), 4.03 (s, 3 H), 7.12 (br. s., 1 H), 7.15 (s, 1 H), 7.19 (s, 1 H), 7.36 (d, J=8.5 Hz, 2 H), 7.36 (s, 1 H), 7.62 (d, J=8.5 Hz, 2 H), 8.00 (s, 1 H).

Compound 101: $^1$H NMR (360 MHz, CHLOROFORM-d) δ ppm 2.57 (s, 3 H) 3.91 (s, 3 H) 7.22 (s, 1 H) 7.24-7.33 (m, 2 H) 7.36 (s, 1 H) 7.45 (s, 1 H) 7.61 (d, J=8.78 Hz, 1H) 7.71 (dd, J=8.78, 2.93 Hz, 1 H) 7.77 (dd, J=8.78, 5.12 Hz, 2 H) 8.64 (d, J=2.56 Hz, 1 H).

Compound 106: ¹H NMR (360 MHz, CHLOROFORM-d) δ ppm 2.57 (s, 3 H) 3.81 (s, 3 H) 6.65 (dd, J=8.78, 1.83 Hz, 1 H) 6.90 (dd, J=12.08, 2.20 Hz, 1 H) 7.19 (s, 1 H) 7.25 (t, J=8.23 Hz, 2 H) 7.44 (s, 1 H) 7.58 (d, J=8.78 Hz, 1 H) 7.71-7.78 (m, 3 H) 8.60 (d, J=2.56 Hz, 1 H).

Compound 127: ¹H NMR (400 MHz, DMSO-$d_6$) δ ppm 2.49 (s, 3 H) 2.54 (s, 3 H) 3.81 (s, 3 H) 3.84 (s, 3 H) 7.00 (s, 1 H) 7.31 (d, J=8.48 Hz, 1 H) 7.34 (dd, J=5.05, 1.41 Hz, 1 H) 7.40 (s, 1 H) 7.43 (t, J=8.88 Hz, 2 H) 7.79 (dd, J=8.48, 2.02 Hz, 1 H) 7.94 (dd, J=8.88, 5.65 Hz, 2 H) 8.29 (d, J=2.02 Hz, 1 H) 8.39 (d, J=5.25 Hz, 1 H) 9.19 (s, 1 H).

Compound 129: ¹H NMR (360 MHz, CHLOROFORM-d) δ ppm 2.60 (s, 3 H) 3.85 (s, 3 H) 4.10 (s, 3 H) 6.65 (d, J=8.05 Hz, 1 H) 7.02 (d, J=8.05 Hz, 1 H) 7.22-7.30 (m, 2 H) 7.30-7.37 (m, 2 H) 7.39 (s, 1 H) 7.62 (d, J=8.42 Hz, 1 H) 7.76 (dd, J=8.60, 5.31 Hz, 2 H) 7.91 (s, 1 H) 8.25 (d, J=7.68 Hz, 1 H) 8.48 (d, J=5.12 Hz, 1 H).

Compound 139: ¹H NMR (360 MHz, DMSO-$d_6$) δ ppm 2.48 (s, 3 H) 3.76 (s, 3 H) 3.86 (s, 3 H) 6.98 (dd, J=8.42, 2.20 Hz, 1 H) 7.08 (d, J=2.20 Hz, 1 H) 7.12-7.34 (m, 5 H) 7.37 (s, 1 H) 7.44 (t, J=8.78 Hz, 2 H) 7.93 (dd, J=8.78, 5.49 Hz, 2 H) 8.38 (d, J=5.12 Hz, 1 H) 8.50 (s, 1 H).

Compound 157: ¹H NMR (360 MHz, DMSO-$d_6$) δ ppm 0.96 (d, J=6.59 Hz, 6 H) 2.12 (s, 3 H) 2.13-2.22 (m, 1 H) 2.73 (d, J=6.95 Hz, 2 H) 3.81 (s, 3 H) 7.05 (d, J=8.42, 1.83 Hz, 1 H) 7.09 (d, J=1.83 Hz, 1 H) 7.38 (d, J=8.42 Hz, 1 H) 7.55 (d, J=10.98 Hz, 1H) 8.06 (s, 1 H) 8.30 (s, 1 H) 8.56 (br. s., 1 H) 9.73 (br. s., 1 H).

Compound 167: ¹H NMR (360 MHz, DMSO-$d_6$) δ ppm 2.30 (s, 3 H) 2.49 (s, 3 H) 6.91 (t, J=6.95 Hz, 1 H) 7.03 (d, J=7.32 Hz, 1 H) 7.46 (s, 1 H) 7.54 (d, J=7.32 Hz, 1 H) 7.60 (d, J=8.78 Hz, 1 H) 7.68 (t, J=7.68 Hz, 1 H) 7.76 (t, J=7.68 Hz, 1 H) 7.81 (dd, J=8.78, 2.56 Hz, 1 H) 7.85-7.93 (m, 2 H) 8.65 (d, J=2.56 Hz, 1 H) 8.77 (s, 1 H).

Compound 173: ¹H NMR (360 MHz, CHLOROFORM-d) δ ppm 2.44 (s, 3 H) 2.57 (s, 3 H) 6.82 (t, J=7.14 Hz, 1 H) 6.95 (d, J=6.95 Hz, 1 H) 7.31-7.42 (m, 3 H) 7.44 (s, 1 H) 7.48-7.62 (m, 4 H) 7.69 (dd, J=8.42, 2.56 Hz, 1 H) 8.64 (d, J=2.56 Hz, 1 H).

Compound 186: ¹H NMR (360 MHz, CHLOROFORM-d) δ ppm 2.52 (s, 3 H) 3.94 (s, 3 H) 3.95 (s, 3 H) 6.90 (s, 1 H) 6.92 (d, J=2.20 Hz, 1 H) 6.98 (dd, J=8.42, 2.20 Hz, 1H) 7.27-7.33 (m, 3 H) 7.68 (d, J=8.42 Hz, 1 H) 7.79 (dd, J=8.23, 5.31 Hz, 2 H) 8.45 (s, 1 H) 8.61 (s, 1 H).

Compound 187: ¹H NMR (400 MHz, DMSO-$d_6$) δ ppm 2.49 (s, 3 H), 3.88 (s, 3 H), 7.10 (d, J=5.6 Hz, 1 H), 7.26 (d, J=3.5 Hz, 1 H), 7.33-7.38 (m, 2 H), 7.44 (t, J=8.8 Hz, 2 H), 7.66 (t, J=8.5 Hz, 1 H), 7.98 (dd, J=8.7, 5.5 Hz, 2 H), 8.15 (d, J=5.5 Hz, 1 H), 9.48 (s, 1 H).

Compound 190: ¹H NMR (360 MHz, CHLOROFORM-d) δ ppm 1.35 (d, J=6.95 Hz, 6 H) 2.53 (s, 3 H) 3.10 (spt, J=6.95 Hz, 1 H) 3.93 (s, 3 H) 3.96 (s, 3 H) 6.96 (d, J=1.83 Hz, 1 H) 7.00 (dd, J=8.05, 1.83 Hz, 1 H) 7.04 (s, 1 H) 7.25 (t, J=8.60 Hz, 2 H) 7.32 (s, 1 H) 7.35 (s, 1 H) 7.73 (d, J=8.05 Hz, 1 H) 7.78 (dd, J=8.60, 5.31 Hz, 2 H).

Compound 191: ¹H NMR (360 MHz, CHLOROFORM-d) δ ppm 1.34 (d, J=6.95 Hz, 6 H) 2.58 (s, 3 H) 3.09 (spt, J=6.95 Hz, 1 H) 3.93 (s, 3 H) 6.93 (s, 1 H) 7.25 (t, J=8.42 Hz, 2 H) 7.31 (s, 1 H) 7.48 (s, 1 H) 7.63 (d, J=8.42 Hz, 1 H) 7.70 (dd, J=8.42, 2.56 Hz, 1 H) 7.78 (dd, J=8.42, 5.85 Hz, 2 H) 8.70 (d, J=2.56 Hz, 1 H).

Compound 194: ¹H NMR (360 MHz, CHLOROFORM-d) δ ppm 2.44 (s, 3 H) 2.60 (s, 3 H) 4.11 (s, 3 H) 6.61 (d, J=8.05 Hz, 1 H) 6.90 (t, J=7.14 Hz, 1 H) 7.32-7.43 (m, 4 H) 7.50-7.61 (m, 3 H) 7.63 (d, J=8.05 Hz, 1 H) 8.07 (s, 1 H) 8.23 (d, J=6.95 Hz, 1 H) 8.49 (d, J=5.49 Hz, 1 H).

Compound 195: ¹H NMR (360 MHz, DMSO-$d_6$) δ ppm 2.47 (s, 3 H), 2.49 (s, 3 H), 3.95 (s, 3 H), 6.79 (s, 1 H), 7.15 (dd, J=8.3, 2.0 Hz, 1 H), 7.24 (d, J=2.0 Hz, 1 H), 7.33 (s, 1 H), 7.71 (d, J=8.4 Hz, 1 H), 7.97 (s, 1 H), 10.02 (s, 1 H).

Pharmacology

A) Screening of the Compounds of the Invention for γ-secretase-modulating Activity A1) Method 1

Screening was carried out using SKNBE2 cells carrying the APP 695-wild type, grown in Dulbecco's Modified Eagle's Medium/Nutrient mixture F-12 (DMEM/NUT-mix F-12) (HAM) provided by Gibco (cat no. 31330-38) containing 5% Serum/Fe supplemented with 1% non-essential amino acids. Cells were grown to near confluency.

The screening was performed using the assay as described in Citron et al (1997) Nature Medicine 3: 67. Briefly, cells were plated in a 96-well plate at about $10^5$ cells/ml one day prior to addition of compounds. Compounds were added to the cells in Ultraculture (Lonza, BE12-725F) supplemented with 1% glutamine (Invitrogen, 25030-024) for 18 Hours. The media were assayed by two sandwich ELISAs, for Aβ42 and Aβtotal. Toxicity of the compounds was assayed by WST-1 cell proliferation reagent (Roche, 1 644 807) according to the manufacturer's protocol.

To quantify the amount of Aβ42 in the cell supernatant, commercially available Enzyme-Linked-Immunosorbent-Assay (ELISA) kits were used (Innotest® β-Amyloid$_{(1-42)}$, Innogenetics N.V., Ghent, Belgium). The Aβ42 ELISA was performed essentially according to the manufacturer's protocol. Briefly, the standards (dilutions of synthetic Aβ1-42) were prepared in polypropylene Eppendorf with final concentrations of 8000 down to 3.9 pg/ml (½ dilution step). Samples, standards and blanks (100 µl) were added to the anti-Aβ42-coated plate supplied with the kit (the capture antibody selectively recognizes the C-terminal end of the antigen). The plate was allowed to incubate 3 H at 25° C. in order to allow formation of the antibody-amyloid complex. Following this incubation and subsequent wash steps a selective anti-Aβ-antibody conjugate (biotinylated 3D6) was added and incubated for a minimum of 1 Hour in order to allow formation of the antibody-Amyloid-antibody-complex. After incubation and appropriate wash steps, a Streptavidine-Peroxidase-Conjugate was added, followed 30 minutes later by an addition of 3,3',5,5'-tetramethylbenzidine (TMB)/peroxide mixture, resulting in the conversion of the substrate into a coloured product. This reaction was stopped by the addition of sulfuric acid (0.9 N) and the colour intensity was measured by means of photometry with an ELISA-reader with a 450 nm filter.

To quantify the amount of Aβtotal in the cell supernatant, samples and standards were added to a 6E10-coated plate. The plate was allowed to incubate overnight at 4° C. in order to allow formation of the antibody-amyloid complex. Following this incubation and subsequent wash steps a selective anti-Aβ-antibody conjugate (biotinylated 4G8) was added and incubated for a minimum of 1 Hour in order to allow formation of the antibody-Amyloid-antibody-complex. After incubation and appropriate wash steps, a Streptavidine-Peroxidase-Conjugate was added, followed 30 minutes later by an addition of Quanta Blu fluorogenic peroxidase substrate according to the manufacturer's instructions (Pierce Corp., Rockford, Ill.).

To obtain the values reported in Table 7a, the sigmoidal dose response curves were analysed by computerised curve-fitting, with percent of inhibition plotted against compound concentration. A 4-parameter equation (model 205) in XLfit was used to determine the $IC_{50}$. The top and the bottom of the curve were fixed to 100 and 0, respectively, and the hill slope was fixed to 1. The $IC_{50}$ represents the concentration of a compound that is required for inhibiting a biological effect by 50% (Here, it is the concentration where Aβ peptide level is reduced by 50%).

The $IC_{50}$ values are shown in Table 7a:

| Co. No. | $IC_{50}$ Aβ42 (μM) | $IC_{50}$ Aβtotal (μM) |
|---|---|---|
| 1 | 0.203 | >5 |
| 2 | 0.022 | >3 |
| 3 | 0.196 | >10 |
| 4 | 0.067 | >3 |
| 5 | 0.063 | >3 |
| 6 | 0.077 | >3 |
| 7 | 0.334 | >10 |
| 8 | 0.275 | >5 |
| 9 | 0.399 | >3 |
| 10 | 0.358 | n.d. |
| 11 | 0.072 | n.d. |
| 12 | 0.023 | >1 |
| 13 | 0.065 | >3 |
| 14 | 0.109 | >3 |
| 16 | 0.011 | >3 |
| 19 | 0.049 | >3 |
| 20 | 0.013 | >1 |
| 22 | 0.123 | >3 |
| 23 | 0.417 | >3 |
| 24 | 0.056 | >3 |
| 25 | 0.024 | >3 |
| 29 | 0.029 | >3 |
| 31 | 0.076 | >3 |
| 32 | 0.235 | >10 |
| 33 | 0.102 | >10 |
| 34 | 0.016 | >3 |
| 35 | 0.090 | >3 |
| 36 | 0.328 | >3 |
| 38 | 0.562 | >10 |
| 39 | 0.053 | >3 |
| 40 | 0.011 | >3 |
| 42 | 0.096 | >3 |
| 44 | 0.140 | >10 |
| 45 | 0.848 | >30 |
| 47 | 0.486 | >3 |
| 49 | 0.021 | >3 |
| 50 | 0.038 | >3 |

To obtain the values reported in Table 7b, the data were calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the $IC_{50}$. The values reported in Table 7b are averaged $IC_{50}$ values.

The $IC_{50}$ values are shown in Table 7b (n.d. means not determined):

| Co. No. | $IC_{50}$ Aβ42 (μM) | $IC_{50}$ Aβtotal (μM) |
|---|---|---|
| 66 | >3 | n.d. |
| 179 | >3 | >3 |
| 180 | >3 | >3 |
| 181 | >3 | >3 |
| 55 | 3.02 | >10 |
| 190 | 0.005 | >3 |
| 105 | 0.007 | >3 |
| 16 | 0.009 | >3 |
| 21 | 0.009 | >3 |
| 62 | 0.009 | >3 |
| 173 | 0.009 | >3 |
| 17 | >10 | >3 |
| 106 | 0.010 | >1 |
| 174 | 0.010 | >3 |
| 63 | 0.011 | >3 |
| 40 | 0.012 | >3 |
| 192 | 0.013 | >3 |
| 20 | 0.017 | >1 |
| 107 | 0.018 | >3 |
| 86 | 0.019 | >3 |
| 193 | 0.019 | >3 |
| 2 | 0.020 | >3 |
| 49 | 0.020 | >3 |
| 50 | 0.020 | >3 |
| 121 | 0.020 | >3 |
| 171 | 0.020 | >3 |
| 12 | 0.021 | >3 |
| 97 | 0.021 | >3 |
| 167 | 0.021 | >3 |
| 25 | 0.023 | >3 |
| 95 | 0.023 | >3 |
| 152 | 0.023 | >3 |
| 102 | 0.024 | >3 |
| 119 | 0.025 | >3 |
| 162 | 0.025 | >10 |
| 123 | 0.026 | >1 |
| 19 | 0.028 | >3 |
| 29 | 0.028 | >3 |
| 79 | 0.028 | >3 |
| 112 | 0.028 | >1 |
| 56 | 0.030 | >3 |
| 125 | 0.033 | n.d. |
| 175 | 0.033 | >3 |
| 18 | 0.035 | >3 |
| 30 | 0.035 | >10 |
| 103 | 0.036 | >3 |
| 82 | 0.037 | >3 |
| 122 | 0.038 | >3 |
| 176 | 0.041 | >3 |
| 77 | 0.043 | >3 |
| 169 | 0.045 | >3 |
| 149 | 0.047 | >3 |
| 39 | 0.051 | >3 |
| 124 | 0.051 | >3 |
| 24 | 0.055 | >3 |
| 83 | 0.059 | >3 |
| 4 | 0.063 | >3 |
| 13 | 0.063 | >3 |
| 67 | 0.065 | >3 |
| 85 | 0.066 | >3 |
| 88 | 0.066 | >10 |
| 64 | 0.068 | >3 |
| 11 | 0.071 | n.d. |
| 98 | 0.071 | >3 |
| 51 | 0.072 | >3 |
| 59 | 0.072 | >3 |
| 114 | 0.072 | >3 |
| 70 | 0.076 | >3 |
| 5 | 0.078 | >3 |
| 31 | 0.078 | >3 |
| 157 | 0.081 | >10 |
| 65 | 0.083 | >3 |
| 94 | 0.083 | >3 |
| 110 | 0.083 | >3 |
| 118 | 0.083 | >3 |
| 147 | 0.085 | n.d. |
| 178 | 0.085 | >3 |
| 35 | 0.089 | n.d. |
| 15 | 0.100 | >3 |
| 6 | 0.102 | >3 |
| 14 | 0.105 | >3 |
| 177 | 0.105 | >3 |
| 28 | 0.110 | >3 |
| 34 | 0.110 | >3 |
| 46 | 0.110 | >3 |

-continued

| Co. No. | IC$_{50}$ Aβ42 (μM) | IC$_{50}$ Aβtotal (μM) |
| --- | --- | --- |
| 22 | 0.115 | >3 |
| 42 | 0.123 | >3 |
| 41 | 0.126 | >3 |
| 48 | 0.132 | >10 |
| 108 | 0.132 | >10 |
| 202 | 0.135 | >3 |
| 44 | 0.138 | >10 |
| 160 | 0.138 | >3 |
| 33 | 0.141 | >10 |
| 109 | 0.145 | 2.82 |
| 186 | 0.162 | >10 |
| 52 | 0.166 | >3 |
| 145 | 0.166 | n.d. |
| 3 | 0.178 | >10 |
| 43 | 0.182 | >10 |
| 76 | 0.182 | >3 |
| 195 | 0.195 | >10 |
| 1 | 0.200 | >5 |
| 36 | 0.204 | >3 |
| 126 | 0.214 | n.d. |
| 9 | 0.240 | >3 |
| 58 | 0.240 | >10 |
| 199 | 0.240 | >30 |
| 163 | 0.245 | >10 |
| 87 | 0.251 | >10 |
| 141 | 0.251 | >10 |
| 148 | 0.251 | >10 |
| 78 | 0.275 | >3 |
| 8 | 0.282 | >5 |
| 32 | 0.282 | >10 |
| 165 | 0.288 | >30 |
| 200 | 0.295 | >3 |
| 7 | 0.302 | >10 |
| 120 | 0.324 | >3 |
| 111 | 0.339 | >10 |
| 10 | 0.355 | n.d. |
| 146 | 0.355 | >30 |
| 37 | 0.380 | >3 |
| 155 | 0.389 | 14.79 |
| 23 | 0.398 | >3 |
| 150 | 0.437 | 8.13 |
| 47 | 0.447 | >3 |
| 142 | 0.468 | >10 |
| 144 | 0.468 | 13.80 |
| 54 | 0.490 | >10 |
| 38 | 0.550 | >10 |
| 27 | 0.676 | >3 |
| 196 | 0.676 | >3 |
| 117 | 0.724 | >10 |
| 166 | 0.741 | >3 |
| 45 | 0.813 | >30 |
| 26 | 0.871 | >30 |
| 72 | 0.955 | >3 |
| 61 | 1.071 | >3 |
| 57 | 1.072 | >10 |
| 90 | 1.096 | >3 |
| 75 | 1.148 | >3 |
| 153 | 1.318 | >3 |
| 164 | 1.413 | 9.33 |
| 91 | 1.445 | 66.07 |
| 93 | 1.862 | n.d. |
| 53 | 1.905 | >10 |
| 71 | 1.950 | >3 |
| 154 | 2.042 | >3 |
| 172 | 2.089 | >3 |
| 99 | 2.188 | n.d. |
| 100 | 2.239 | 25.12 |
| 92 | 2.570 | >3 |
| 60 | 3.020 | >3 |
| 170 | 3.548 | n.d. |
| 143 | 9.772 | >30 |

A2) Method 2

Screening was carried out using SKNBE2 cells carrying the APP 695-wild type, grown in Dulbecco's Modified Eagle's Medium/Nutrient mixture F-12 (DMEM/NUT-mix F-12) (HAM) provided by Invitrogen (cat no. 10371-029) containing 5% Serum/Fe supplemented with 1% non-essential amino acids, 1-glutamine 2 mM, Hepes 15 mM, penicillin 50 U/ml (units/ml) en streptomycin 50 μg/ml. Cells were grown to near confluency.

The screening was performed using a modification of the assay as described in Citron et al (1997) Nature Medicine 3: 67. Briefly, cells were plated in a 384-well plate at $10^4$ cells/well in Ultraculture (Lonza, BE12-725F) supplemented with 1% glutamine (Invitrogen, 25030-024), 1% non-essential amino acid (NEAA), penicillin 50 U/ml en streptomycin 50 μg/ml in the presence of test compound at different test concentrations. The cell/compound mixture was incubated overnight at 37° C., 5% $CO_2$. The next day the media were assayed by two sandwich immuno-assays, for Aβ42 and Aβtotal.

Aβtotal and Aβ42 concentrations were quantified in the cell supernatant using the Aphalisa technology (Perkin Elmer). Alphalisa is a sandwich assay using biotinylated antibody attached to streptavidin coated donorbeads and antibody conjugated to acceptor beads. In the presence of antigen, the beads come into close proximity. The excitation of the donor beads provokes the release of singlet oxygen molecules that trigger a cascade of energy transfer in the acceptor beads, resulting in light emission. To quantify the amount of Aβ42 in the cell supernatant, monoclonal antibody specific to the C-terminus of Aβ42 (JRF/cAβ42/26) was coupled to the receptor beads and biotinylated antibody specific to the N-terminus of Aβ (JRF/AβN/25) was used to react with the donor beads. To quantify the amount of Aβtotal in the cell supernatant, monoclonal antibody specific to the N-terminus of Aβ (JRF/AβN/25) was coupled to the receptor beads and biotinylated antibody specific to the mid region of Aβ (biotinylated 4G8) was used to react with the donor beads.

To obtain the values reported in Table 7c, the data were calculated as percentage of the maximum amount of amyloid Beta 42 measured in the absence of the test compound. The sigmoidal dose response curves were analyzed using non-linear regression analysis with percentage of the control plotted against the log concentration of the compound. A 4-parameter equation was used to determine the IC$_{50}$.

The IC$_{50}$ values are shown in Table 7c:

| Co. No. | IC$_{50}$ Aβ42 (μM) | IC$_{50}$ Aβtotal (μM) |
| --- | --- | --- |
| 10 | 1.738 | >10 |
| 11 | 0.363 | >10 |
| 12 | 0.035 | 7.76 |
| 16 | 0.016 | 8.71 |
| 17 | 0.166 | >10 |
| 18 | 0.020 | 6.46 |
| 26 | 0.191 | >10 |
| 35 | 0.214 | >10 |
| 49 | 0.040 | >10 |
| 50 | 0.072 | >10 |
| 65 | 0.117 | >10 |
| 66 | >10 | >10 |
| 68 | 0.018 | >10 |
| 69 | 0.022 | >10 |
| 73 | 0.141 | 5.62 |
| 74 | 7.413 | 4.47 |
| 79 | 0.076 | >10 |
| 80 | 0.049 | >10 |
| 81 | 0.095 | >10 |
| 82 | 0.049 | >10 |
| 84 | 0.112 | >10 |
| 85 | 0.363 | >10 |
| 86 | 0.052 | >10 |

-continued

| Co. No. | IC$_{50}$ Aβ42 (μM) | IC$_{50}$ Aβtotal (μM) |
|---|---|---|
| 87 | 0.288 | 9.12 |
| 88 | 0.058 | 8.91 |
| 89 | 0.019 | 9.77 |
| 93 | 2.754 | >10 |
| 96 | 0.245 | >10 |
| 99 | 7.943 | >10 |
| 101 | 0.046 | >10 |
| 104 | 0.501 | >10 |
| 105 | 0.014 | >10 |
| 106 | 0.024 | >10 |
| 107 | 0.025 | >10 |
| 111 | 0.204 | >10 |
| 113 | 0.066 | 4.90 |
| 116 | 0.072 | >10 |
| 119 | 0.043 | >10 |
| 125 | 0.195 | >10 |
| 126 | 0.741 | n.d. |
| 127 | 0.044 | 3.63 |
| 128 | 0.039 | 9.12 |
| 129 | 0.017 | 5.25 |
| 130 | 0.030 | >10 |
| 131 | 0.028 | >10 |
| 132 | 0.123 | 6.31 |
| 133 | 0.191 | >10 |
| 135 | 0.347 | >10 |
| 136 | 0.112 | >10 |
| 137 | 0.117 | >10 |
| 138 | 0.049 | 7.08 |
| 139 | 0.060 | 6.61 |
| 140 | 0.759 | >10 |
| 145 | 1.047 | 6.31 |
| 147 | 0.468 | n.d. |
| 156 | 0.042 | 8.91 |
| 158 | 1.862 | >10 |
| 159 | 0.269 | >10 |
| 161 | 0.155 | >10 |
| 162 | 0.032 | >10 |
| 163 | 0.158 | >10 |
| 164 | 1.318 | 6.76 |
| 167 | 0.018 | >10 |
| 168 | 0.051 | >10 |
| 170 | 7.413 | >10 |
| 171 | 0.038 | >10 |
| 172 | 0.661 | >10 |
| 173 | 0.007 | >10 |
| 174 | 0.022 | >10 |
| 182 | 0.162 | 7.76 |
| 183 | 0.083 | 8.71 |
| 186 | 0.041 | >10 |
| 187 | 0.062 | >10 |
| 188 | >10 | >10 |
| 189 | 2.399 | >10 |
| 190 | 0.010 | >10 |
| 191 | 0.012 | >10 |
| 194 | 0.017 | ~6.76 |
| 195 | 0.282 | >10 |
| 197 | 0.550 | >10 |
| 198 | 1.175 | 6.76 |
| 201 | 0.045 | >10 |
| 202 | 0.245 | 8.51 |

B) Demonstration of in Vivo Efficacy

Aβ42 lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ42 lowering agents can be administered in any standard form using any standard method. For example, but not limited to, Aβ42 lowering agents can be in the form of liquid, tablets or capsules that are taken orally or by injection. Aβ42 lowering agents can be administered at any dose that is sufficient to significantly reduce levels of Aβ42 in the blood, blood plasma, serum, cerebrospinal fluid (CSF), or brain.

To determine whether acute administration of an Aβ42 lowering agent would reduce Aβ42 levels in vivo, non-transgenic rodents, e.g. mice or rats were used. Alternatively, two to three month old Tg2576 mice expressing APP695 containing the "Swedish" variant can be used or a transgenic mouse model developed by Dr. Fred Van Leuven (K.U.Leuven, Belgium) and co-workers, with neuron-specific expression of a clinical mutant of the human amyloid precursor protein [V717I] (Moechars et al., 1999 J. Biol. Chem. 274, 6483). Young transgenic mice have high levels of Aβ in the brain but no detectable Aβ deposition. At approximately 6-8 months of age, the transgenic mice start to display spontaneous, progressive accumulation of β-amyloid (Aβ) in the brain, eventually resulting in amyloid plaques within the subiculum, hippocampus and cortex. Animals treated with the Aβ42 lowering agent were examined and compared to those untreated or treated with vehicle and brain levels of soluble Aβ42 and total Aβ would be quantitated by standard techniques, for example, using ELISA. Treatment periods varied from hours to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ42 lowering compounds were formulated in 20% of Captisol® (a sulfobutyl ether of β-cyclodextrin) in water or 20% hydroxypropyl β cyclodextrin. The Aβ42 lowering agents were administered as a single oral dose or by any acceptable route of administration to overnight fasted animals. After four hours, the animals were sacrificed and Aβ42 levels were analysed.

Blood was collected by decapitation and exsanguinations in EDTA-treated collection tubes. Blood was centrifuged at 1900 g for 10 min at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains were resuspended in 10 volumes of 0.4% DEA (diethylamine)/50 mM NaCl pH 10 (for non-transgenic animals) or 0.1% 3-[(3-cholamidopropyl)-dimethyl-ammonio]-1-propanesulfonate (CHAPS) in tris buffered saline (TBS) (for transgenic animals) containing protease inhibitors (Roche-11873580001 or 04693159000 per gram of tissue, e.g. for 0.158 g brain, add 1.58 ml of 0.4% DEA. All samples were sonicated for 30 sec on ice at 20% power output (pulse mode). Homogenates were centrifuged at 221.300×g for 50 min. The resulting high speed supernatants were then transferred to fresh tubes and were optionally further purified before the next step. A portion of the supernatant was neutralized with 10% 0.5 M Tris-HCl and this was used to quantify Aβtotal.

The obtained supernatants were purified with Water Oasis HLB reverse phase columns (Waters Corp., Milford, Mass.) to remove non-specific immunoreactive material from the brain lysates prior subsequent Aβ detection. Using a vacuum manifold, all solutions were passed through the columns at a rate of approximately 1 ml per minute, so the vacuum pressure was adjusted accordingly throughout the procedure. Columns were preconditioned with 1 ml of 100% MeOH, before equilibration with 1 ml of H$_2$O. Non-neutralized brain lysates were loaded onto the columns. The loaded samples were then washed twice with the first wash performed with 1 ml of 5% MeOH, and the second wash with 1 ml of 30% MeOH. Finally, the Aβ was eluted from the columns and into 100×30 mm glass tubes, with a solution of 90% MeOH with 2% NH$_4$OH. The eluate was then transferred into 1.5 ml tubes and concentrated in a speed-vac concentrator on high heat for about 1.5-2 H at 70° C. The concentrated Aβ was then resuspended in UltraCULTURE General Purpose Serum-Free Medium (Cambrex Corp., Walkersville, Md.) plus Protease Inhibitors added according to the manufacturers recommendation.

To quantify the amount of Aβ42 in the soluble fraction of the brain homogenates, commercially available Enzyme-Linked-Immunosorbent-Assay (ELISA) kits were used (e.g. Innotest® β-Amyloid$_{(1-42)}$, Innogenetics N.V., Ghent, Belgium). The Aβ42 ELISA was performed using the plate provided with the kit only. Briefly, the standards (a dilution of synthetic Aβ1-42) were prepared in 1.5 ml Eppendorf tube in Ultraculture, with final concentrations ranging from 25000 to 1.5 pg/ml. Samples, standards and blanks (60 µl) were added to the anti-Aβ42-coated plate (the capture antibody selectively recognizes the C-terminal end of the antigen). The plate was allowed to incubate overnight at 4° C. in order to allow formation of the antibody-amyloid complex. Following this incubation and subsequent wash steps a selective anti-Aβ-antibody conjugate (biotinylated detection antibody, e.g., biotinylated 4G8 (Covance Research Products, Dedham, Mass.) was added and incubated for a minimum of 1 H in order to allow formation of the antibody-Amyloid-antibody-complex. After incubation and appropriate wash steps, a Streptavidine-Peroxidase-Conjugate was added, followed 50 min later by an addition of Quanta Blu fluorogenic peroxidase substrate according to the manufacturer's instructions (Pierce Corp., Rockford, Ill.). A kinetic reading was performed every 5 minutes for 30 min (excitation 320/emission 420). To quantify the amount of Aβtotal in the soluble fraction of the brain homogenates, samples and standards were added to JRF/rAβ/2-coated plate. The plate was allowed to incubate overnight at 4° C. in order to allow formation of the antibody-amyloid complex. The ELISA was then performed as for Aβ42 detection.

In this model at least 20% Aβ42 lowering compared to untreated animals would be advantageous.

The results are shown in Table 8:

| Co. No. | Aβ42 (% Ctrl)_Mean | Aβtotal (% Ctrl)_Mean |
|---|---|---|
| 195 | 89 | 99 |
| 2 | 95 | 104 |
| 104 | 110 | 97 |
| 186 | 52 | 82 |
| 97 | 71 | 102 |
| 157 | 77 | 100 |
| 95 | 47 | 88 |
| 10 | 106 | 109 |
| 11 | 91 | 99 |
| 12 | 56 | 101 |
| 13 | 87 | 105 |
| 14 | 78 | 91 |
| 16 | 58 | 95 |
| 17 | 106 | 109 |
| 18 | 54 | 94 |
| 25 | 76 | 96 |
| 30 | 96 | 92 |
| 31 | 91 | 102 |
| 40 | 77 | 102 |
| 41 | 93 | 87 |
| 101 | 77 | 92 |
| 170 | 99 | 99 |
| 105 | 104 | 96 |
| 181 | 104 | 105 |
| 141 | 87 | 89 |
| 63 | 56 | 90 |
| 59 | 97 | 95 |
| 58 | 89 | 105 |
| 54 | 101 | 104 |

C) Effect on the Notch-processing Activity of the γ-secretase-complex

Notch Cell-free Assay

The Notch transmembrane domain is cleaved by gamma secretase to release Notch Intracellular C-terminal Domain (NICD). Notch is a signaling protein which plays a crucial role in developmental processes, and thus compounds are preferred which do not show an effect on the Notch-processing activity of the γ-secretase-complex.

To monitor the effect of compounds on NICD production, a recombinant Notch substrate (N99) was prepared. The Notch substrate, comprised of mouse Notch fragment (V1711-E1809), an N-terminal methionine and a C-terminal FLAG sequence (DYDDDDK), was expressed in E. coli and purified on a column containing an anti-FLAG M2 affinity matrix.

A typical Notch cell-free assay consisted of 0.3-0.5 µM Notch substrate, an enriched preparation of gamma secretase and 1 µM of a test compound (compounds 16, 18 and 106 of the present invention). Controls included a gamma secretase inhibitor (GSI), such as (2S)—N-[2-(3,5-difluorophenyl) acetyl]-L-alanyl-2-phenyl-glycine 1,1-dimethylethyl ester (DAPT) or (2S)-2-hydroxy-3-methyl-N-[(1S)-1-methyl-2-oxo-2-[[(1S)-2,3,4,5-tetrahydro-3-methyl-2-oxo-1H-3-benzazepin-1-yl]amino]ethyl]-butanamide (Semagacestat), and DMSO, the final concentration of DMSO being 1%. Recombinant Notch substrate was pre-treated with 17 µM DTT (1,4-dithiothreitol) and 0.02% SDS (Sodium Dodecyl Sulfate) and heated at 65° C. for 10 min. The mixture of substrate, gamma secretase and compound/DMSO was incubated at 37° C. for 6 to 22 hours (h). Six-hour incubation was sufficient to produce the maximal amount of NICD and the cleaved product remained stable for an additional 16 H. Reaction products were processed for SDS PAGE (Sodium Dodecyl Sulfate-Poly Acrylamide Gel Electrophoresis) and western blotting. Blots were probed with an anti-Flag M2 antibody, followed by LI-COR infrared secondary antibody, and analyzed with the Odyssey Infrared Imaging System (LI-COR® Biosciences).

In the cell-free Notch assay, no test compounds (compounds 16, 18 and 106 of the present invention) inhibited the cleavage of C99 by gamma secretase, whereas the production of NICD was blocked by the control GSI (DAPT or Semagacestat). Thus it was demonstrated that compounds 16, 18 and 106 of the present invention did not show an effect on the Notch-processing activity of the γ-secretase-complex (production of NICD).

Notch Cell-based Assay

The Notch cell-based assay was based on the interaction of Notch and its ligand in a co-culture system and utilized the Dual-Glo Luciferase Assay System (Promega) to monitor NICD production. Two stable cell lines, N2-CHO and DL-CHO, were established to express full-length mouse Notch2 and Delta respectively. Cells that expressed mouse Notch were also transfected with two plasmids, pTP1-Luc and pCMV-RLuc, to express firefly and *Renilla* luciferase. Expression of firefly luciferase was under the control of TP1 promoter that responded to NICD activation. The CMV promoter that drove the expression of *Renilla* luciferase did not respond to NICD activation and therefore was used to control for transfection efficiency and compound toxicity.

N2-CHO cells were seeded at $1 \times 10^5$/well in 24-well plates the day before transfection. On the second day, cells were double transfected with 3 μg/well pTP1-Luc (expressing firefly luciferase) and 0.3 ng/well pCMV-RLuc (expressing *Renilla* luciferase). After 6 H incubation, transfected N2-CHO cells were washed and DL-CHO cells ($2 \times 10^5$ cells/well) were added.

Compounds were pre-mixed with DL-CHO cell suspension in a five-point curve. Typically, compound treatment was performed in duplicate with a serial 1:10 dilution (3 μM-0.3 nM) in DMSO. The final concentration of DMSO in a given culture was 1%. Controls included non-transfected cells and transfected cells treated with a GSI or DMSO only. Luciferase assays were performed after 16 H co-culture and compound treatment.

The luciferase assay was carried out according to manufacture's instructions. Briefly, cells were washed with PBS (Phosphate Buffered Saline), lysed with Passive Lysis Buffer (Promega), and incubated at room temperature for 20 min. Lysates were mixed with Dual-Glo Luciferase Reagent and the firefly luciferase activity was measured by reading the luminescence signal in the EnVision 2101 Multilabel reader. Dual-Glo Stop & Glo Reagent was then added to each well and the *Renilla* luciferase signal was measured.

The results of the Notch cell-based assay were in agreement with those in the cell-free NICD assay. On the basis of luciferase assay readouts, the average $IC_{50}$ values of DAPT and Semagacestat from the Notch cell-based assay were 45 nM and 40 nM respectively, whereas compound 18 of the present invention was found to be non-inhibitory.

D. Composition Examples

"Active ingredient" (a.i.) as used throughout these examples relates to a compound of formula (I), including any stereochemically isomeric form thereof, a pharmaceutically acceptable salt thereof or a solvate thereof; in particular to any one of the exemplified compounds.

Typical examples of recipes for the formulation of the invention are as follows:

1. Tablets

| Active ingredient | 5 to 50 mg |
|---|---|
| Di-calcium phosphate | 20 mg |
| Lactose | 30 mg |
| Talcum | 10 mg |
| Magnesium stearate | 5 mg |
| Potato starch | ad 200 mg |

2. Suspension

An aqueous suspension is prepared for oral administration so that each milliliter contains 1 to 5 mg of active ingredient, 50 mg of sodium carboxymethyl cellulose, 1 mg of sodium benzoate, 500 mg of sorbitol and water ad 1 ml.

3. Injectable

A parenteral composition is prepared by stirring 1.5% (weight/volume) of active ingredient in 0.9% NaCl solution or in 10% by volume propylene glycol in water.

4. Ointment

| Active ingredient | 5 to 1000 mg |
|---|---|
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

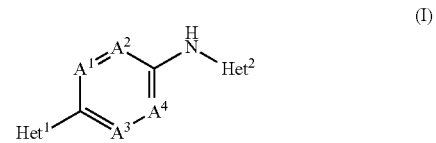

or a stereoisomeric form thereof, wherein $Het^1$ is a 5-membered or 6-membered aromatic heterocycle, having formula (a-1), (a-2), (a-3), (a-4) or (a-5):

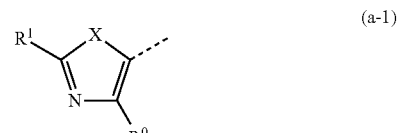

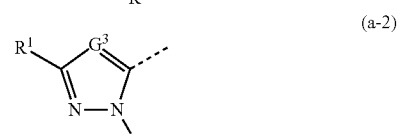

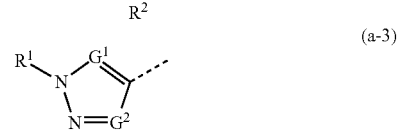

$R^0$ is H or $C_{1-4}$alkyl;
$R^1$ is H, $C_{1-4}$alkyl or $C_{1-4}$alkyloxy$C_{1-4}$alkyl;
$R^2$ is $C_{1-4}$alkyl;
X is O or S;
$G^1$ is CH or N;
$G^2$ is CH, N or C substituted with $C_{1-4}$alkyl;

provided that G¹ and G² are not simultaneously N;
G³ is CH or N;
R¹⁰ᵃ and R¹⁰ᵇ each independently are hydrogen or C₁₋₄alkyl;
A¹ is CR³ or N; wherein R³ is H, halo or C₁₋₄alkyloxy;
A², A³ and A⁴ each independently are CH, CF or N; provided that maximum two of A¹, A², A³ and A⁴ are N;
Het² is a 9-membered bicyclic aromatic heterocycle, having formula (b-2):

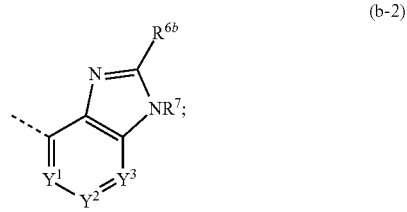

Y¹ is CH;
Y² is CR⁴ᵇ;
Y³ is CH;
R⁴ᵇ is H; halo; C₁₋₄alkyloxy; cyano; cycloC₃₋₇alkyl; or C₁₋₄alkyl optionally substituted with one or more substituents each independently selected from the group consisting of halo and amino;
R⁶ᵇ is C₂₋₆alkyl substituted with one or more halo substituents; C₁₋₆alkyl optionally substituted with one or more substituents each independently selected from the group consisting of piperidinyl, Ar, C₁₋₆alkyloxy, tetrahydropyranyl, cycloC₃₋₇alkyloxy, and cycloC₃₋₇alkyl; cycloC₃₋₇alkyl; cycloC₃₋₇alkyl substituted with one or more phenyl substituents optionally substituted with one or more halo substituents; piperidinyl; morpholinyl; pyrrolidinyl; NR⁸R⁹; tetrahydropyranyl; O—Ar; C₁₋₆alkyloxy; C₁₋₆alkylthio; Ar; CH₂—O—Ar; S—Ar; NCH₃—Ar; or NH—Ar;
wherein each piperidinyl, morpholinyl, and pyrrolidinyl may optionally be substituted with one or more substituents each independently selected from the group consisting of C₁₋₄alkyl, C₂₋₆alkenyl, C₁₋₄alkylcarbonyl, halo, and C₁₋₄alkyloxycarbonyl;
wherein each Ar independently is phenyl optionally substituted with one or more substituents each independently selected from the group consisting of halo, C₁₋₄alkyloxy cyano, NR⁸R⁹, morpholinyl, C₁₋₄alkyl, and C₁₋₄alkyl substituted with one or more halo substituents; pyridinyl optionally substituted with one or more substituents each independently selected from the group consisting of halo, C₁₋₄alkyloxy, cyano, C₁₋₄alkyl, and C₁₋₄alkyl substituted with one or more halo substituents; oxazolyl optionally substituted with one or more C₁₋₄alkyl substituents; or thienyl optionally substituted with one or more halo substituents;
each R⁸ independently is H or C₁₋₄alkyl;
each R⁹ independently is H or C₁₋₄alkyl;
R⁷ is H, C₁₋₆alkyl optionally substituted with one or more substituents each independently selected from the group consisting of halo, phenyl, and C₁₋₄alkyloxy;
or a pharmaceutically acceptable addition salt or a solvate thereof.

2. The compound according to claim 1 or a stereoisomeric form thereof, wherein

Het¹ is a 5-membered aromatic heterocycle, having formula (a-1), (a-2), (a-3) or (a-4);
R⁰ is H or C₁₋₄alkyl;
R¹ is H or C₁₋₄alkyl;
R² is C₁₋₄alkyl;
X is O or S;
G¹ is CH or N; G² is CH, N or C substituted with C₁₋₄alkyl; provided that G¹ and G² are not simultaneously N;
G³ is CH or N;
A¹ is CR³ or N; wherein R³ is H, halo or C₁₋₄alkyloxy;
A², A³ and A⁴ each independently are CH, CF or N; provided that maximum two of A¹, A², A³ and A⁴ are N;
Het² is a 9-membered bicyclic aromatic heterocycle, having formula (b-2):

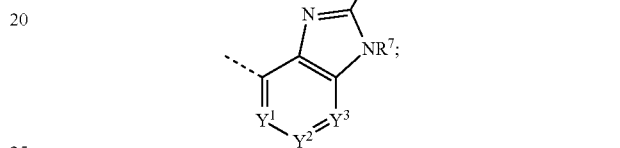

Y¹ is CH or N; Y² is CR⁴ᵇ; Y³ is CH;
R⁴ᵃ is H; halo; C₁₋₄alkyloxy; cyano; or C₁₋₄alkyl optionally substituted with one or more halo substituents;
R⁴ᵇ is H; halo; C₁₋₄alkyloxy; cyano; or C₁₋₄alkyl optionally substituted with one or more halo substituents;
R⁶ᵇ is C₂₋₆alkyl substituted with one or more halo substituents; C₁₋₆alkyl optionally substituted with one or more substituents each independently selected from the group consisting of piperidinyl, Ar, C₁₋₆alkyloxy, tetrahydropyranyl, cycloC₃₋₇alkyloxy, and cycloC₇alkyl; cycloC₃₋₇ alkyl; piperidinyl; morpholinyl; pyrrolidinyl; NR⁸R⁹; tetrahydropyranyl; O—Ar; C₁₋₆alkyloxy; C₁₋₆alkylthio; Ar; CH₂—O—Ar; S—Ar; NCH₃—Ar or NH—Ar;
wherein each piperidinyl, morpholinyl, and pyrrolidinyl may optionally be substituted with one or more substituents each independently selected from the group consisting of C₁₋₄alkyl, C₂₋₆alkenyl, C₁₋₄alkylcarbonyl, halo, and C₁₋₄alkyloxycarbonyl;
wherein each Ar independently is phenyl optionally substituted with one or more substituents each independently selected from the group consisting of halo, C₁₋₄alkyloxy, cyano, NR⁸R⁹, morpholinyl, C₁₋₄alkyl, and C₁₋₄alkyl substituted with one or more halo substituents; or pyridinyl optionally substituted with one or more substituents each independently selected from the group consisting of halo, C₁₋₄alkyloxy, cyano, C₁₋₄alkyl, and C₁₋₄alkyl substituted with one or more halo substituents;
each R⁸ independently is H or C₁₋₄alkyl;
each R⁹ independently is H or C₁₋₄alkyl;
R⁷ is H, C₁₋₆alkyl optionally substituted with one or more substituents each independently selected from the group consisting of halo, phenyl, and C₁₋₄alkyloxy;
or a pharmaceutically acceptable addition salt or a solvate thereof.

3. The compound according to claim 1 or a stereoisomeric form thereof, wherein A¹ is CR³ or N; wherein R³ is H, halo or C₁₋₄alkyloxy;
A², A³ and A⁴ each independently are CH or N; provided that maximum two of A¹, A², A³ and A⁴ are N;

$R^{6b}$ is $C_{2-6}$alkyl substituted with one or more halo substituents; $C_{1-6}$alkyl optionally substituted with one or more substituents each independently selected from the group consisting of Ar, $C_{1-6}$alkyloxy, tetrahydropyranyl, and cyclo$C_{3-7}$alkyl; cyclo$C_{3-7}$alkyl; cyclo$C_{3-7}$alkyl substituted with one phenyl optionally substituted with one or more halo substituents; unsubstituted pyrrolidinyl; $NR^8R^9$; tetrahydropyranyl; Ar; or $CH_2$—O—Ar;

each Ar independently is phenyl optionally substituted with one or more substituents each independently selected from the group consisting of halo, $C_{1-4}$alkyloxy, $C_{1-4}$alkyl, and $C_{1-4}$alkyl substituted with one or more halo substituents; oxazolyl optionally substituted with one or more $C_{1-4}$alkyl substituents; or thienyl optionally substituted with one or more halo substituents;

each $R^8$ independently is $C_{1-4}$alkyl;
each $R^9$ independently is $C_{1-4}$alkyl;
$R^7$ is $C_{1-6}$alkyl optionally substituted with one or more $C_{1-4}$alkyloxy substituents;
or a pharmaceutically acceptable addition salt or a solvate thereof.

4. The compound according to claim 1 or a stereoisomeric form thereof, wherein
Het$^1$ is a 5-membered aromatic heterocycle, having formula (a-1), (a-2), (a-3) or (a-4);
$R^0$ is H or $C_{1-4}$alkyl;
$R^1$ is H or $C_{1-4}$alkyl;
$R^2$ is $C_{1-4}$alkyl;
X is O or S;
$G^1$ is CH;
$G^2$ is CH or C substituted with $C_{1-4}$alkyl;
$G^3$ is CH;
$A^1$ is $CR^3$ or N; wherein $R^3$ is H, halo or $C_{1-4}$alkyloxy;
$A^2$ is CH or N;
$A^3$ and $A^4$ are CH;
Het$^2$ is a 9-membered bicyclic aromatic heterocycle, having formula (b-2);
wherein $Y^1$ is CH; $Y^2$ is $CR^{4b}$; $Y^3$ is CH;
$R^{4b}$ is H, halo or $C_{1-4}$alkyl optionally substituted with one or more halo substituents;
$R^{6b}$ is Ar; $C_{2-6}$alkyl substituted with one or more halo substituents; $C_{1-6}$alkyl optionally substituted with one or more Ar substituents; or $CH_2$—O—Ar;
wherein each Ar independently is phenyl optionally substituted with one or more substituents each independently selected from the group consisting of halo, $C_{1-4}$alkyloxy, $C_{1-4}$alkyl, and $C_{1-4}$alkyl substituted with one or more halo substituents;
$R^7$ is $C_{1-6}$alkyl optionally substituted with one or more $C_{1-4}$alkyloxy substituents;

or a pharmaceutically acceptable addition salt or a solvate thereof.

5. The compound according to claim 1 or a stereoisomeric form thereof, wherein
Het$^1$ is a 5-membered or 6-membered aromatic heterocycle, having formula (a-1) or (a-5);
$R^0$ is H or $C_{1-4}$alkyl;
$R^1$ is H or $C_{1-4}$alkyl;
X is O;
$R^{10a}$ and $R^{10b}$ each independently are hydrogen or $C_{1-4}$alkyl;
$A^1$ is $CR^3$ or N; wherein $R^3$ is $C_{1-4}$alkyloxy;
$A^2$, $A^3$ and $A^4$ are CH;
Het$^2$ is a 9-membered bicyclic aromatic heterocycle, having formula (b-2);
$Y^1$ and $Y^3$ are CH;
$Y^2$ is $CR^{4b}$; $R^{4b}$ is H or $C_{1-4}$alkyloxy; in particular H or methoxy;
$R^{6b}$ is phenyl optionally substituted with one or more halo substituents;
$R^7$ is $C_{1-6}$alkyl;
or a pharmaceutically acceptable addition salt or a solvate thereof.

6. The compound according to claim 5, wherein Het$^1$ has formula (a-1).

7. The compound according to claim 1, wherein the compound is
2-(4-fluorophenyl)-1-(1-methylethyl)-N-[6-(2-methyl-5-oxazolyl)-3-pyridinyl]-1H-benzimidazol-4-amine,
6-fluoro-N-[3-methoxy-4-(4-methyl-5-oxazolyl)phenyl]-2-(2-methylpropyl)-imidazo[1,2-a]pyridin-8-amine .HCl,
2-(4-fluorophenyl)-6-methoxy-N-[3-methoxy-4-(2-methyl-5-oxazolyl)phenyl]-1-methyl-1H-benzimidazol-4-amine,
2-(4-fluorophenyl)-N-[3-methoxy-4-(4-methyl-5-oxazolyl)phenyl]-1-methyl-1H-benzimidazol-4-amine, or
2-(4-fluorophenyl)-N-[3-methoxy-4-(2-methyl-4-pyridinyl)phenyl]-1-(1-methylethyl)-1H-benzimidazol-4-amine,
including any stereochemically isomeric form thereof or a pharmaceutically acceptable addition salt or a solvate thereof.

8. The compound according to claim 1, wherein the compound is 2-(4-fluorophenyl)-1-(1-methylethyl)-N-[6-(2-methyl-5-oxazolyl)-3-pyridinyl]-1H-benzimidazol-4-amine.

9. A pharmaceutical composition comprising a pharmaceutically acceptable carrier and, as active ingredient, a therapeutically effective amount of a compound as defined in any one of claims 1 to 8.

* * * * *

UNITED STATES PATENT AND TRADEMARK OFFICE
CERTIFICATE OF CORRECTION

| | | |
|---|---|---|
| PATENT NO. | : 8,946,426 B2 | Page 1 of 1 |
| APPLICATION NO. | : 13/144554 | |
| DATED | : February 3, 2015 | |
| INVENTOR(S) | : Henricus Jacobus Maria Gijsen et al. | |

It is certified that error appears in the above-identified patent and that said Letters Patent is hereby corrected as shown below:

In the claims

At COL. 176 (Claim 2), line 27, delete "or N" so that the phrase will read -- $Y^1$ is CH; --

Signed and Sealed this
Seventeenth Day of November, 2015

Michelle K. Lee
*Director of the United States Patent and Trademark Office*